(12) United States Patent
Wang et al.

(10) Patent No.: US 6,531,315 B1
(45) Date of Patent: Mar. 11, 2003

(54) COMPOSITIONS AND METHODS FOR THE THERAPY AND DIAGNOSIS OF LUNG CANCER

(75) Inventors: Tongtong Wang, Medina, WA (US); Liqun Fan, Bellevue, WA (US); Michael D. Kalos, Seattle, WA (US); Chaitanya S. Bangur, Seattle, WA (US); Nancy A. Hosken, Seattle, WA (US); Gary R. Fanger, Mill Creek, WA (US); Samuel X. Li, Redmond, WA (US); Aijun Wang, Issaquah, WA (US); Yasir A. W. Skeiky, Bellevue, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/606,421

(22) Filed: Jun. 28, 2000

Related U.S. Application Data

(63) Continuation-in-part of application No. 09/542,615, filed on Apr. 4, 2000, which is a continuation-in-part of application No. 09/510,376, filed on Feb. 22, 2000, which is a continuation-in-part of application No. 09/480,884, filed on Jan. 10, 2000, which is a continuation-in-part of application No. 09/476,496, filed on Dec. 30, 1999, which is a continuation-in-part of application No. 09/466,396, filed on Dec. 17, 1999, which is a continuation-in-part of application No. 09/285,479, filed on Apr. 2, 1999, which is a continuation of application No. PCT/US99/05798, filed on Mar. 17, 1999, which is a continuation-in-part of application No. 09/221,107, filed on Dec. 22, 1998, which is a continuation-in-part of application No. 09/123,912, filed on Jul. 27, 1998, now Pat. No. 6,312,695, which is a continuation-in-part of application No. 09/040,802, filed on Mar. 18, 1998, now abandoned.

(51) Int. Cl.[7] .............................. C12N 5/08; C12N 5/06; A61K 39/00
(52) U.S. Cl. ................. 435/372.3; 435/326; 424/184.1; 424/185.11
(58) Field of Search .......................... 424/184.1, 185.1; 530/300, 350; 435/372.3, 326

(56) References Cited

U.S. PATENT DOCUMENTS

| | | | |
|---|---|---|---|
| 5,705,159 A | 1/1998 | Irie et al. | 424/185.1 |
| 5,783,422 A | 7/1998 | Suminami et al. | 435/69.3 |
| 6,297,364 B1 | 10/2001 | Chen et al. | 536/23.1 |

FOREIGN PATENT DOCUMENTS

| | | |
|---|---|---|
| EP | 0695760 A1 | 2/1996 |
| WO | WO 91/18926 | 12/1991 |
| WO | WO 94/06929 | 3/1994 |
| WO | WO 95/21862 | 8/1995 |
| WO | WO96/02552 | 2/1996 |
| WO | WO 96/28473 | 9/1996 |
| WO | WO96/30389 | 10/1996 |
| WO | WO 97/07244 | 2/1997 |
| WO | WO 98/35985 | 8/1998 |
| WO | WO 98/46788 | 10/1998 |
| WO | WO 99/38973 | 8/1999 |
| WO | WO 99/47674 | 9/1999 |

OTHER PUBLICATIONS

Kaye et al., A single amino acid substitution results in a retinoblastoma protein defective in phosphorlation and oncoprotein binding, Sep. 1990, Proc. Natl. Acad. Sci., pp. 6922–6926.*
Rudinger, Characteristic of the amino acids as components of a peptide hormone sequence, 1976, Peptide Hormones, pp. 1–7.*
Brass et al., "Translation initiation factor eIF–4gamma is encoded by an amplified gene and induces an immune response in squamous cell lung carcinoma," *Human Molecular Genetics*, 6(1): 33–39, 1997.
Database EMBLest17 Accession No. AA340797:EST46165 Fetal kidney II Homo sapiens cDNA 3' end, Apr. 18, 1997.
Database EMBLest17 Accession NO. W22264:Human retina cDNATsp–509I–cleaved sublibrary Homo sapiens cDNA not directional, May 9, 1996.
Finch et al., "Identification of a cloned sequence activated during multi–stage carcinogenesis in mouse skin," *Carcinogenesis*, 12(8):1519–1522, Aug. 1991.
Gerhold and Caskey, "It's the genes! EST access to human genome content," *BioEssays* 18(12):973–981, 1996.
Russell and Barton, "Structural features can be unconserved in proteins with similar folds," *J. Mol. Biol.* 244:332–350, 1994.
Wells and Peitsch, "The chemokine information source: identification and characterization of novel chemokines using the WorldWideWeb and expressed sequence tag databases," *Journal of Leukocyte Biology* 61:545–550, May 1997.
Baldi et al., "Differential expression of Rb2/p130 and p107 in normal human tissues and in primary lung cancer," *Clinical Cancer Research* 3(10):1691–1697, Oct. 1997.
Database EMBL Nucleotide and Protein Sequence, Accession No. AI468638, Mar. 17, 1999.
Davidson et al., "Lung tumours immunoreative for parathyroid hormone related peptide: analysis of serum calcium levels and tumour type," *Journal of Pathology* 178:398–401, Jan. 1996.

(List continued on next page.)

Primary Examiner—Scott D. Priebe
Assistant Examiner—Shin-Lin Chen
(74) Attorney, Agent, or Firm—Seed Intellectual Property Law Group PLLC

(57) ABSTRACT

Compositions and methods for the therapy and diagnosis of cancer, such as lung cancer, are disclosed. Compositions may comprise one or more lung tumor proteins, immunogenic portions thereof, or polynucleotides that encode such portions. Alternatively, a therapeutic composition may comprise an antigen presenting cell that expresses a lung tumor protein, or a T cell that is specific for cells expressing such a protein. Such compositions may be used, for example, for the prevention and treatment of diseases such as lung cancer. Diagnostic methods based on detecting a lung tumor protein, or mRNA encoding such a protein, in a sample are also provided.

6 Claims, No Drawings

OTHER PUBLICATIONS

Hara et al., "Characterization of cell phenotype by a novel cDNA library subtraction system: expression of CD8α in a mast cell–derived interleukin–4–dependent cell line," *Blood* 84(1):189–199, Jul. 1, 1994.

Henderson et al., "Identification of lung tumor antigens for cancer immunotherapy: immunological and molecular approaches," *Immunological Investigation* 29(2):87–91, May 2000.

Hogan et al., "The peptide recognized by HLA–A68.2–restricted, squamous cell carcinoma of the lung–specific cytotoxic T lymphocytes in derived from a mutated elongation factor 2 gene," *Cancer Research* 58(22):5144–5150, Nov. 1998.

Hu et al., "A small proline–rich protein, spr1: specific marker for squamous lung carcinoma," *Lung Cancer* 20:25–30, 1998.

Lelievre et al., "Structural properties of chimeric peptides containing a T–cell epitope linked to a fusion peptide and their importance for in vivo induction of cytotoxic T–cell responses," *European Journal of Biochemistry* 249(3):895–904, 1997.

Marshall and Hodgson, "DNA chips: an array of possibilities," *Nature Biotechnology* 16:27 Jan. 31, 1998.

Pastor et al., "Diagnostic value of SCC, CEA and CYFRA 21.1 in lung cancer: a Bayesian analysis," *Eur. Respir J.* 10(3):603–609, Mar. 1997.

Rammensee et al., "MHC ligands and peptide motifs: first listing," *Immunogenetics* 41:178–228, 1995.

Ramsay, G., "DNA chips: state–of–the art," *Nature Biotechnology* 16:40–44, Jan. 1998.

Ruppert et al., "Prominent role of secondary anchor residues in peptide binding to HLA–A2.1 molecules," *Cell* 74:929–937, Sep. 10, 1993.

Skeiky et al., "Cloning, expression and immunological evaluation of two putative secreted serine protease antigens of Mycobacterium tuberculosis," *Infection and Immunity* 67(8):3998–4007, Aug. 1999.

Theobald et al., "Targeting p53 as a general tumor antigen," *Proc. Natl. Acad. Sci. USA* 92:11993–11997, Dec. 1995.

Visseren et al., "Identification of HLA–A *0201–restricted CTL epitopes encoded by the tumor–specific MAGE–2 gene product," *International Journal of Cancer* 73(1):125–130, 1997.

Wang et al., "Identification of genes differentially over–expressed in lung squamous cell carcinoma using combination of cDNA subtraction and microarray analysis," *Oncogene* 19(12):1519–1528, Mar. 16, 2000.

GenBank Accession No. AF043977, Jun. 23, 1999.

GenBank Accession No. U85946, Jul. 30, 1999.

Geneseq Accession No. AAZ24653, Dec. 7, 1999.

Gruber et al., "Molecular cloning and transmembrane structure of hCLCA2 from human lung, trachea, and mammary gland," *Am. J. Physiol.* 276(Cell Physiol 45):C1261–C1270, 1999.

Guo et al., "Identification and characterization of homologues of the Exocyst component Sec10p," *FEBS Letters* 404(2–3):135–139, 1997.

Geneseq Accession No. AAC66035, Feb. 21, 2001.

Geneseq Accession NO. AAZ36150, Dec. 7, 1999.

Jolly, D., "Viral vector systems for gene therapy," *Cancer Gene Therapy* 1(1):51–64, 1994.

* cited by examiner

SEQUENCE LISTING

```
<160> NUMBER OF SEQ ID NOS: 358

<210> SEQ ID NO 1
<211> LENGTH: 315
<212> TYPE: DNA
<213> ORGANISM: Homo sapien
<220> FEATURE:
<221> NAME/KEY: misc_feature
<222> LOCATION: (1)...(315)
<223> OTHER INFORMATION: n = A,T,C or G

<400> SEQUENCE: 1
gcagagacag actggtggtt gaacctggag gtgccaaaaa agccagctgc gggcccagga      60
cagctgccgt gagactcccg atgtcacagg cagtctgtgt ggttacagcg cccctcagtg     120
ttcatctcca gcagagacaa cggaggaggc tcccaccagg acggttctca ttatttatat     180
gttaatatgt ttgtaaactc atgtacagtt ttttttgggg gggaagcaat gggaanggta     240
naaattacaa atagaatcat ttgctgtaat ccttaaatgg caaacggtca ggccacgtga     300
aaaaaaaaaa aaaaa                                                       315

<210> SEQ ID NO 2
<211> LENGTH: 380
<212> TYPE: DNA
<213> ORGANISM: Homo sapien

<400> SEQUENCE: 2
atttaggctt aagattttgt ttaccettgt tactaaggag caaattagta ttaaagtata      60
atatatataa acaaatacaa aaagttttga gtggttcagc tttttattt tttttaatgg     120 cataacttttt aacaacactg ctctgtaatg ggttgaactg tggtactcag actgagataa     180
ctgaaatgag tggatgtata gtgttattgc ataattatcc cactatgaag caaagggact     240
ggataaattc ccagtctaga ttattagcct ttgttaacca tcaagcacct agaagaagaa     300
ttattggaaa ttttgtcctc tgtaactggc actttggggt gtgacttatc ttttgccttt     360
gtaaaaaaaa aaaaaaaaa                                                   380

<210> SEQ ID NO 3
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G
```

<400> SEQUENCE: 3

```
ttgtaagtat acaattttag aaaggattaa atgttattga tcattttact gaatactgca      60
catcctcacc atacaccatc cactttccaa taacatttaa tcctttctaa aattgtaagt     120
atacaattgt actttctttg gattttcata acaaatatac catagactgt taattttatt     180
gaagtttcct taatggaatg agtcattttt gtcttgtgct tttgaggtta cctttgcttt     240
gacttccaac aatttgatca tatagtgttg agctgtggaa atctttaagt ttattctata     300
gcaataattt ctattnnnag annccnggnn naaaannann annaaa                    346
```

<210> SEQ ID NO 4
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 4

```
actagtctca ttactccaga attatgctct tgtacctgtg tggctgggtt tcttagtcgt      60
tggtttggtt tggttttttg aactggtatg tagggtggtt cacagttcta atgtaagcac     120
tctcttctcc aagttgtgct tgtggggac aatcattctt tgaacattag agaggaaggc      180
agttcaagct gttgaaaaga ctattgctta ttttttgtttt taaagaccta cttgacgtca     240
tgtggacagt gcacgtgcct tacgctacat cttgttttct aggaagaagg ggatgcnggg     300
aaggantggg tgctttgtga tggataaaac gnctaaataa cacacccttta cattttgaaa    360
aaaacaaaac aa                                                         372
```

<210> SEQ ID NO 5
<211> LENGTH: 698
<212> TYPE: DNA
<213> ORGANISM: Homo sapien
<220> FEATURE:
<221> NAME/KEY: misc_feature
<222> LOCATION: (1)...(698)
<223> OTHER INFORMATION: n = A,T,C or G

<400> SEQUENCE: 5

```
actagtanga tagaaacact gtgtcccgag agtaaggaga gaagctacta ttgattagag      60
cctaacccag gttaactgca agaagaggcg ggatactttc agctttccat gtaactgtat     120
gcataaagcc aatgtagtcc agtttctaag atcatgttcc aagctaactg aatcccactt     180
caatacacac tcatgaactc ctgatggaac aataacaggc ccaagcctgt ggtatgatgt     240
gcacacttgc tagactcaga aaaatacta ctctcataaa tgggtgggag tattttgggt       300
gacaacctac tttgcttggc tgagtgaagg aatgatattc atatnttcat ttattccatg     360
gacatttagt tagtgctttt tataccag gcatgatgct gagtgacact cttgtgtata        420
tntccaaatn ttngtncngt cgctgcacat atctgaaatc ctatattaag antttcccaa     480
natgangtcc ctggtttttc cacgccactt gatcngtcaa ngatctcacc tctgtntgtc     540
ctaaaaccnt ctnctnnang gttagacngg acctctcttc tcccttcccg aanaataag      600
tgtgngaaga nanccncncn cccccctncn tncnncctng ccngctnnnc cncntgtngg     660
gggngccgcc ccgcgggggg gaccccccn ttttcccc                              698
```

<210> SEQ ID NO 6

<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 6

```
actagtcaaa aatgctaaaa taatttggga gaaatatttt tttaagtagt gttatagttt      60
catgtttatc ttttattatg tnttgtgaag ttgtgtcttt tcactaatta cctatactat     120
gccaatattt ccttatatct atccataaca tttatactac atttgtaaga gaatatgcac     180
gtgaaactta acactttata aggtaaaaat gaggtttcca agatttaata atctgatcaa     240
gttcttgtta tttccaaata gaatggactt ggtctgttaa ggggctaagg gagaagaaga     300
agataaggtt aaaagttgtt aatgaccaaa cattctaaaa gaaatgcaaa aaaaaattta     360
ttttcaagcc ttcgaactat ttaaggaaag caaaatcatt tcctanatgc atatcatttg     420
tgaganttc tcantaatat cctgaatcat tcatttcagc tnaggcttca tgttgactcg     480
atatgtcatc tagggaaagt ctatttcatg gtccaaacct gttgccatag ttggtnaggc     540
tttccttaa ntgtgaanta ttnacangaa attttctctt tnanagttct tnatagggtt     600
agggggtgtgg gaaaagcttc taacaatctg tagtgttncg tgttatctgt ncagaaccan     660
aatnacggat cgnangaagg actgggtcta tttacangaa cgaatnatct ngttnnntgt     720
gtnnncaact ccngggagcc                                                 740
```

<210> SEQ ID NO 7
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 7

```
gctggggagc tcggcatggc ggtccccgct gcagccatgg ggccctcggc gttgggccag      60
agcggccccg gctcgatggc cccgtggtgc tcagtgagca gcggcccgtc gcgctacgtg     120
cttgggatgc aggagctgtt ccggggccac agcaagaccg cgagttcctg gcgcacagcg     180
ccaaggtgca ctcggtggcc tggagttgcg acgggcgtcg cctacctcgg ggtcttcgac     240
aagacgccac gtcttcttgc tgganaanga ccgttggtca agaaaacaa ttatcgggga      300
catggggata gtgtggacca ctttgttggc atccaagtaa tcctgaccta tttgttacgg     360
cgtctggaga taaaaccatt cgcatctggg atgtgaggac tacaaaatgc attgccactg     420
tgaacactaa aggggagaac attaatatct gctggantcc tgatgggcan accattgctg     480
tagcnacaag gatgatgtgg tgactttatt gatgccaaga acccgttc caaagcaaaa      540
aaacanttcc aanttcgaag tcaccnaaat ctcctggaac aatgaacatn aatatntct      600
tcctgacaat ggnccttggg tgtntcacat cctcagctnc cccaaaactg aancctgtnc     660
natccacccc                                                            670
```

<210> SEQ ID NO 8
<211> LENGTH: 689
<212> TYPE: DNA
<213> ORGANISM: Homo sapien
<220> FEATURE:
<221> NAME/KEY: misc_feature
<222> LOCATION: (1)...(689)
<223> OTHER INFORMATION: n = A,T,C or G

<400> SEQUENCE: 8

```
actagtatct aggaatgaac agtaaaagag gagcagttgg ctacttgatt acaacagagt      60
aaatgaagta ctggatttgg gaaaacctgg ttttattaga acatatggaa tgaaagccta     120
cacctagcat tgcctactta gccccctgaa ttaacagagc ccaattgaga caaacccctg     180
gcaacaggaa attcaaggga gaaaagtaa gcaacttggg ctaggatgag ctgactccct      240
tagagcaaag ganagacagc ccccattacc aaataccatt tttgcctggg gcttgtgcag     300
ctggcagtgt tcctgcccca gcatggcacc ttatngtttt gatagcaact tcgttgaatt     360
ttcaccaact tattacttga aattataata tagcctgtcc gtttgctgtn ccaggctgt      420
gatatatntt cctagtggtt tgactttnaa ataaatnag gtttantttt ctcccccnn       480
cnntnctncc nntcnctcnn cnntccccc cnctcngtcc tccnnnnttn ggggggccn       540
ccccncggn ggaccccct ttggtccctt agtggaggtt natggcccct ggnnttatcc       600
nggccntann tttccccgtn nnaaatgntt cccctccca ntcccnccac ctcaanccgg      660
aagcctaagt ttntaccctg ggggtcccc                                        689
```

<210> SEQ ID NO 9
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 9

```
gtccactctc ctttgagtgt actgtcttac tgtgcactct gttttcaac tttctagata      60
taaaaatgc ttgttctata gtggagtaag agctcacaca cccaaggcag caagataact     120
gaaaaaagcg aggcttttt gccaccttgg taaaggccag ttcactgcta tagaactgct     180
ataagcctga agggaagtag ctatgagact ttccattttt cttagttctc ccaataggct    240
ccttcatgga aaaaggcttc ctgtaataat tttcacctaa tgaattagca gtgtgattat    300
ttctgaaata agagacaaat tgggccgcag agtcttcctg tgatttaaaa taaacaaccc    360
aaagttttgt ttggtcttca ccaaaggaca tactctaggg ggtatgttgt tgaagacatt    420
caaaaacatt agctgttctg tctttcaatt tcaagttatt ttggagactg cctccatgtg    480
agttaattac tttgctctgg aactagcatt attgtcatta tcatcacatt ctgtcatcat    540
catctgaata atattgtgga tttccccctc tgcttgcatc ttcttttgac tcctctggga    600
anaaatgtca aaaaaaagg tcgatctact cngcaaggnc catctaatca ctgcgctgga    660
aggacccnct gccc                                                       674
```

<210> SEQ ID NO 10
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 10

```
actagtctgc tgatagaaag cactatacat cctattgttt ctttctttcc aaaatcagcc     60
```

-continued

```
ttctgtctgt aacaaaaatg tactttatag agatggagga aaaggtctaa tactacatag    120
ccttaagtgt ttctgtcatt gttcaagtgt attttctgta acagaaacat atttggaatg    180
tttttctttt ccccttataa attgtaattc ctgaaatact gctgctttaa aaagtcccac    240
tgtcagatta tattatctaa caattgaata ttgtaaatat acttgtctta cctctcaata    300
aaagggtact tttctattan nnagnngnnn gnnnnataaa anaaaa                   346
```

<210> SEQ ID NO 11
<211> LENGTH: 602
<212> TYPE: DNA
<213> ORGANISM: Homo sapien

<400> SEQUENCE: 11

```
actagtaaaa agcagcattg ccaaataatc cctaattttc cactaaaaat ataatgaaat     60
gatgttaagc tttttgaaaa gtttaggtta aacctactgt tgttagatta atgtatttgt    120
tgcttccctt tatctggaat gtggcattag ctttttttatt ttaaccctct ttaattctta   180
ttcaattcca tgacttaagg ttggagagct aaacactggg attttttggat aacagactga   240 cagttttgca taattataat cggcattgta catagaaagg atatggctac cttttgttaa    300
atctgcactt tctaaatatc aaaaaaggga aatgaagtta taaatcaatt tttgtataat    360
ctgtttgaaa catgagtttt atttgcttaa tattagggct ttgccccttt tctgtaagtc    420
tcttgggatc ctgtgtagaa ctgttctcat taaacaccaa acagttaagt ccattctctg    480
gtactagcta caaattcggt ttcatattct acttaacaat ttaaataaac tgaaatattt    540
ctagatggtc tacttctgtt catataaaaa caaaacttga tttccaaaaa aaaaaaaaaa    600
aa                                                                   602
```

<210> SEQ ID NO 12
<211> LENGTH: 685
<212> TYPE: DNA
<213> ORGANISM: Homo sapien
<220> FEATURE:
<221> NAME/KEY: misc_feature
<222> LOCATION: (1)...(685)
<223> OTHER INFORMATION: n = A,T,C or G

<400> SEQUENCE: 12

```
actagtcctg tgaaagtaca actgaaggca gaaagtgtta ggattttgca tctaatgttc     60
attatcatgg tattgatgga cctaagaaaa taaaaattag actaagcccc caaataagct    120
gcatgcattt gtaacatgat tagtagattt gaatatatag atgtagtatn ttgggtatct    180
aggtgtttta tcattatgta aaggaattaa agtaaaggac tttgtagttg tttttattaa    240
atatgcatat agtagagtgc aaaaatatag caaaaatana aactaaaggt agaaaagcat    300
tttagatatg ccttaatnta nnaactgtgc caggtggccc tcggaataga tgccaggcag    360
agaccagtgc ctgggtggtg cctcccttg tctgccccc tgaagaactt ccctcacgtg    420
angtagtgcc ctcgtaggtg tcacgtggan tantgggang aggccgnncn gtnanaagaa    480
ancanngtga nagtttcncc gtngangcng aactgtccct gngccnnnac gctcccanaa    540
cntntccaat ngacaatcga gtttccnnnc tccngnaacc tngccgnnnn cnngccnnc    600 cantntgnta acccgcgcc cggatcgctc tcnnntcgtt ctcncncnaa ngggntttcn    660
cnnccgccgt ncnnccccg cnncc                                          685
```

<210> SEQ ID NO 13
<211> LENGTH: 694

```
<212> TYPE: DNA
<213> ORGANISM: Homo sapien
<220> FEATURE:
<221> NAME/KEY: misc_feature
<222> LOCATION: (1)...(694)
<223> OTHER INFORMATION: n = A,T,C or G

<400> SEQUENCE: 13
cactagtcac tcattagcgt tttcaatagg gctcttaagt ccagtagatt acgggtagtc      60
agttgacgaa gatctggttt acaagaacta attaaatgtt tcattgcatt tttgtaagaa     120
cagaataatt ttataaaatg tttgtagttt ataattgccg aaaataattt aaagacactt    180
tttctctgtg tgtgcaaatg tgtgtttgtg atccatttttt tttttttttt taggacacct   240
gtttactagc tagctttaca atatgccaaa aaaggatttc tccctgaccc catccgtggt    300
tcaccctctt ttcccccccat gcttttttgcc ctagtttata acaaaggaat gatgatgatt  360 taaaagtag ttctgtatct tcagtatctt ggtcttccag aaccctctgg ttgggaaggg     420
gatcattttt tactggtcat ttcccttttgg agtgtactac tttaacagat ggaaagaact   480
cattggccat ggaaacagcc gangtgttgg gagccagcag tgcatggcac cgtccggcat    540
ctggcntgat tggtctggct gccgtcattg tcagcacagt gccatgggac atggggaana   600
ctgactgcac ngccaatggt tttcatgaag aatacngcat ncncngtgat cacgtnancc   660
angacgctat gggggncana gggccanttg cttc                                694

<210> SEQ ID NO 14
<211> LENGTH: 679
<212> TYPE: DNA
<213> ORGANISM: Homo sapien
<220> FEATURE:
<221> NAME/KEY: misc_feature
<222> LOCATION: (1)...(679)
<223> OTHER INFORMATION: n = A,T,C or G

<400> SEQUENCE: 14
cagccgcctg catctgtatc cagcgccang tcccgccagt cccagctgcg cgcgcccccc      60
agtcccgnac ccgttcggcc cangctnagt tagncctcac catnccggtc aaaggangca   120
ccaagtgcat caaatacctg cngtncggat ntaaattcat cttctggctt gccgggattg   180
ctgtccntgc cattggacta nggctccgat ncgactctca gaccanganc atcttcganc  240
naganactaa tnatnattnt tccagcttct acacaggagt ctatattctg atcggatccg   300
gcnccctcnt gatgctggtg ggcttcctga gctgctgcgg ggctgtgcaa gagtcccant   360
gcatgctggg actgttcttc ggcttcntct tggtgatatn cgccattgaa atacctgcgg   420
ccatctgggg atattccact ncgatnatgt gattaaggaa ntccacggag ttttacaagg    480
acacgtacaa cnacctgaaa accnnggatg anccccaccg ggaancnctg aangccatcc   540
actatgcgtt gaactgcaat ggtttggctg gggnccttga acaatttaat cncatacatc    600
tggccccann aaaggacntn ctcgannect tcnccgtgna attcngttct gatnccatca    660
cagaagtctc gaacaatcc                                                 679

<210> SEQ ID NO 15
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G
```

```
<400> SEQUENCE: 15
actagtggat aaaggccagg gatgctgctc aacctcctac catgtacagg gacgtctccc      60
cattacaact acccaatccg aagtgtcaac tgtgtcagga ctaanaaacc ctggttttga     120
ttaaaaaagg gcctgaaaaa aggggagcca caaatctgtc tgcttcctca cnttantcnt     180
tggcaaatna gcattctgtc tcnttggctg cngcctcanc ncaaaaaanc ngaactcnat     240
cnggcccagg aatacatctc ncaatnaacn aaattganca aggcnntggg aaatgccnga     300
tgggattatc ntccgcttgt tgancttcta agtttcnttc ccttcattcn accctgccag     360
ccnagttctg ttagaaaaat gccngaattc naacnccggt tttcntactc ngaatttaga     420
tctncanaaa cttcctggcc acnattcnaa ttnanggnca cgnacanatn ccttccatna     480
ancncacccc acntttgana gccangacaa tgactgcntn aantgaaggc ntgaaggaan     540
aactttgaaa ggaaaaaaaa ctttgtttcc ggcccttcc aacncttctg tgttnancac      600
tgccttctng naaccctgga agcccngnga cagtgttaca tgttgttcta nnaaacngac     660
ncttnaatnt cnatcttccc nanaacgatt ncncc                                695

<210> SEQ ID NO 16
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G

<400> SEQUENCE: 16
cgccgaagca gcagcgcagg ttgtccccgt ttcccctccc ccttcccttc tccggttgcc      60
ttcccgggcc ccttacactc cacagtcccg gtcccgccat gtcccagaaa caagaagaag     120
agaaccctgc ggaggagacc ggcgaggaga agcaggacac gcaggagaaa gaaggtattc     180
tgcctgagag agctgaagag gcaaagctaa aggccaaata cccaagccta ggacaaaagc     240
ctggaggctc cgacttcctc atgaagagac tccagaaagg gcaaaagtac tttgactcng     300
gagactacaa catggccaaa gccaacatga agaataagca gctgccaagt gcangaccag     360
acaagaacct ggtgactggt gatcacatcc cacccaca ggatctgccc agagaaagtc       420
ctcgctcgtc accagcaagc ttgcgggtgg ccaagttgaa tgatgctgcc ggggctctgc     480
canatctgag acgcttccct ccctgcccca cccgggtcct gtgctggctc ctgcccttcc     540
tgcttttgca gccanggggtc aggaagtggc ncnggtngtg gctggaaagc aaaacccttt    600
cctgttggtg tcccacccat ggagcccctg gggcgagccc angaacttga nccttttttgt    660
tntcttncc                                                             669

<210> SEQ ID NO 17
<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 17
gcaagatatg gacaactaag tgagaaggta atnctctact gctctagntn ctccnggcnn      60
gacgcgctga ggagannnac gctggcccan ctgccggcca cacacgggga tcntggtnat     120
gcctgcccan gggancccca ncnctcggan cccatntcac accgnnccn tncgcccacn      180
```

―continued

| | |
|---|---|
| ncctggctcn cncngcccng nccagctcnc gnccccctcc gccnnnctcn ttnncntctc | 240 |
| cncnccctcc ncnacnacct cctacccncg gctccctccc cagccccccc ccgcaanccT | 300 |
| ccacnacncc ntcnncncga ancnccnctc gcnctcngcc ccngcccccT gcccccCgcc | 360 |
| cncnacnncg cgntcccccg cgcncgcngc ctcnccccct cccacnacag ncncacccgc | 420 |
| agncacgcnc tccgcccnct gacgcccCnn cccgccgcgc tcaccttcat ggnccnacng | 480 |
| ccccgctcnc nccnctgcnc gccgncnggg cgccccgccc cnnccgngtn ccncncgnng | 540 |
| ccccngcngn angcngtgcg cnncangncc gngccgnncn ncaccctccg nccnccgccc | 600 |
| cgcccgctgg gggctcccgc cncgcggntc antccccncc cntncgccca ctntccgntc | 660 |
| cnncnctcnc gctcngcgcn cgcccncccnc ccccccc | 697 |

<210> SEQ ID NO 18
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 18

| | |
|---|---|
| ctcgtgtgaa gggtgcagta cctaagccgg agcggggtag aggcgggccg gcaccccctt | 60 |
| ctgacctcca gtgccgccgg cctcaagatc agacatggcc cagaacttga acgacttggc | 120 |
| gggacggctg cccgccgggc cccggggcat gggcacggcc ctgaagctgt tgctgggggc | 180 |
| cggcgccgtg gcctacggtg tgcgcgaatc tgtgttcacc gtggaaggcg ggcncagagc | 240 |
| catcttcttc aatcggatcg gtggagtgca caggacacta tcctgggccg anggccttca | 300 |
| cttcaggatc cttggttcca gtaccccanc atctatgaca ttcgggccag acctcgaaaa | 360 |
| aatctcctcc ctacaggctc caaagaccta cagatggtga atatctccct gcgagtgttg | 420 |
| tctcgaccaa tgctcangaa cttcctaaca tgttccancg cctaagggct ggactacnaa | 480 |
| gaacgantgt tgccgtccat tgtcacgaag tgctcaagaa tttnggtggc caagttcaat | 540 |
| gnccctcacnn ctgatcncccc agcgggggcca agttanccct ggttgatccc cggggganctg | 600 |
| acnnaaaagg gccaaggact tccccctcatc ctggataatg tggccntcac aaagctcaac | 660 |
| tttanccacc | 670 |

<210> SEQ ID NO 19
<211> LENGTH: 606
<212> TYPE: DNA
<213> ORGANISM: Homo sapien
<220> FEATURE:
<221> NAME/KEY: misc_feature
<222> LOCATION: (1)...(606)
<223> OTHER INFORMATION: n = A,T,C or G

<400> SEQUENCE: 19

| | |
|---|---|
| actagtgcca acctcagctc ccaggccagt tctctgaatg tcgaggagtt ccaggatctc | 60 |
| tggcctcagt tgtccttggt tattgatggg ggacaaattg gggatggcca gagccccgag | 120 |
| tgtcgccttg gctcaactgt ggttgatttg tctgtgcccg gaaagtttgg catcattcgt | 180 |
| ccaggctgtg ccctggaaag tactacagcc atcctccaac agaagtacgg actgctcccc | 240 |
| tcacatgcgt cctacctgtg aaactctggg aagcaggaag gccaagacc tggtgctgga | 300 |
| tactatgtgt ctgtccactg acgactgtca aggcctcatt tgcagaggcc accggagcta | 360 |

```
gggcactagc ctgactttta aggcagtgtg tctttctgag cactgtagac caagcccttg      420
gagctgctgg tttagccttg cacctgggga aaggatgtat ttatttgtat tttcatatat      480
cagccaaaag ctgaatggaa aagttnagaa cattcctagg tggccttatt ctaataagtt      540
tcttctgtct gttttgtttt tcaattgaaa agttattaaa taacagattt agaatctagt      600
gagacc                                                                 606
```

<210> SEQ ID NO 20
<211> LENGTH: 449
<212> TYPE: DNA
<213> ORGANISM: Homo sapien

<400> SEQUENCE: 20

```
actagtaaac aacagcagca gaaacatcag tatcagcagc gtcgccagca ggagaatatg       60
cagcgccaga gccgaggaga accccgctc cctgaggagg acctgtccaa actcttcaaa      120
ccaccacagc cgcctgccag gatggactcg ctgctcattg caggccagat aaacacttac      180
tgccagaaca tcaaggagtt cactgcccaa aacttaggca agctcttcat ggcccaggct      240
cttcaagaat acaacaacta agaaaaggaa gtttccagaa aagaagttaa catgaactct      300
tgaagtcaca ccagggcaac tcttggaaga aatatatttg catattgaaa agcacagagg      360
atttctttag tgtcattgcc gattttggct ataacagtgt ctttctagcc ataataaaat      420
aaaacaaaat cttgactgct tgctcaaaa                                        449
```

<210> SEQ ID NO 21
<211> LENGTH: 409
<212> TYPE: DNA
<213> ORGANISM: Homo sapien

<400> SEQUENCE: 21

```
tatcaatcaa ctggtgaata attaaacaat gtgtggtgtg atcatacaaa gggtaccact       60
caatgataaa aggaacaagc tgcctatatg tggaacaaca tggatgcatt tcagaaactt      120
tatgttgagt gaaagaacaa acacggagaa catactatgt ggttctcttt atgtaacatt      180
acagaaataa aaacagaggc aaccaccttt gaggcagtat ggagtgagat agactggaaa      240
aaggaaggaa ggaaactcta cgctgatgga aatgtctgtg tcttcattgg gtggtagtta      300
tgtggggata tacatttgtc aaaatttatt gaactatata ctaaagaact ctgcatttta      360
ttgggatgta aataatacct caattaaaaa gacaaaaaaa aaaaaaaaa                  409
```

<210> SEQ ID NO 22
<211> LENGTH: 649
<212> TYPE: DNA
<213> ORGANISM: Homo sapien
<220> FEATURE:
<221> NAME/KEY: misc_feature
<222> LOCATION: (1)...(649)
<223> OTHER INFORMATION: n = A,T,C or G

<400> SEQUENCE: 22

```
acaattttca ttatcttaag cacattgtac atttctacag aacctgtgat tattctcgca       60
tgataaggat ggtacttgca tatggtgaat tactactgtt gacagtttcc gcagaaatcc      120
tatttcagtg gaccaacatt gtggcatggc agcaaatgcc aacattttgt ggaatagcag      180
caaatctaca agagccctg gttggttttt cgttttgttt tctttgtttt ttccccttc       240 tcctgaatca gcagggatgg aangagggta gggaagttat gaattactcc ttccagtagt      300
agctctgaag tgtcacattt aatatcagtt tttttttaaac atgattctag ttnaatgtag      360
```

```
aagagagaag aaagaggaag tgttcacttt tttaatacac tgatttagaa atttgatgtc    420
ttatatcagt agttctgagg tattgatagc ttgctttatt tctgccttta cgttgacagt    480
gttgaagcag ggtgaataac tagggcata  tatatttttt ttttttgtaa gctgtttcat    540
gatgttttct ttggaatttc cggataagtt caggaaaaca tctgcatgtt gttatctagt    600
ctgaagttcn tatccatctc attacaacaa aaacnccccag aacggnttg               649
```

<210> SEQ ID NO 23
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G

<400> SEQUENCE: 23

```
actagtgccg tactggctga atccctgca  ggaccaggaa gagaaccagt tcagactttg     60
tactctcagt caccagctct ggaattagat aaattccttg aagatgtcag gaatgggatc    120
tatcctctga cagcctttgg gctgcctcgg ccccagcagc cacagcagga ggaggtgaca    180
tcacctgtcg tgccccctc  tgtcaagact ccgacacctg aaccagctga ggtggagact    240
cgcaaggtgg tgctgatgca gtgcaacatt gagtcggtgg aggagggagt caaacaccac    300
ctgacacttc tgctgaagtt ggaggacaaa ctgaaccggc acctgagctg tgacctgatg    360
ccaaatgaga atatccccga gttggcggct gagctggtgc agctgggctt cattagtgag    420
gctgaccaga gccggttgac ttctctgcta gaagagactt gaacaagttc aattttgcca    480
ggaacagtac cctcaactca gccgctgtca ccgtctcctc ttagagctca ctcgggccag    540
gccctgatct gcgctgtggc tgtcctggac gtgctgcacc ctctgtcctt cccccagtc    600 agtattacct gtgaagccct tccctccttt attattcagg anggctgggg gggctccttg    660 nttctaacc                                                           669
```

<210> SEQ ID NO 24
<211> LENGTH: 442
<212> TYPE: DNA
<213> ORGANISM: Homo sapien

<400> SEQUENCE: 24

```
actagtacca tcttgacaga ggatacatgc tcccaaaacg tttgttacca cacttaaaaa     60
tcactgccat cattaagcat cagtttcaaa attatagcca ttcatgattt acttttcca    120 gatgactatc attattctag tcctttgaat ttgtaagggg aaaaaaaca aaaacaaaaa    180 cttacgatgc acttttctcc agcacatcag atttcaaatt gaaattaaa  gacatgctat    240 ggtaatgcac ttgctagtac tacacacttt ggtacaacaa aaaacagagg caagaaacaa    300
cggaaagaga aaagccttcc tttgttggcc cttaaactga gtcaagatct gaaatgtaga    360
gatgatctct gacgatacct gtatgttctt attgtgtaaa taaaattgct ggtatgaaat    420
gacctaaaaa aaaaaaaaga aa                                            442
```

<210> SEQ ID NO 25
<211> LENGTH: 656
<212> TYPE: DNA
<213> ORGANISM: Homo sapien
<220> FEATURE:
<221> NAME/KEY: misc_feature
<222> LOCATION: (1)...(656)

<223> OTHER INFORMATION: n = A,T,C or G

<400> SEQUENCE: 25

| | | | | | |
|---|---|---|---|---|---|
| tgcaagtacc | acacactgtt | tgaattttgc | acaaaaagtg | actgtaggat | caggtgatag | 60 |
| ccccggaatg | tacagtgtct | tggtgcacca | agatgccttc | taaaggctga | catagcttgg | 120 |
| accctaatgg | ggcagagagt | atagcccttag | cccagtggtg | acatgaccac | tcccctttggg | 180 |
| aggcctgagg | tagaggggag | tggtatgtgt | tttctcagtg | gaagcagcac | atgagtgggt | 240 |
| gacaggatgt | tagataaagg | ctctagttag | ggtgtcattg | tcattgaga | gactgacaca | 300 |
| ctcctagcag | ctggtaaagg | ggtgctggan | gccatggagg | anctctagaa | acattagcat | 360 |
| gggctgatct | gattacttcc | tggcatcccg | ctcacttta | tgggaagtct | tattagangg | 420 |
| atgggacagt | tttccatatc | cttgctgtgg | agctctggaa | cactctctaa | atttccctct | 480 |
| attaaaaatc | actgccctaa | ctacacttcc | tccttgaagg | aatagaaatg | gaactttctc | 540 |
| tgacatantt | cttggcatgg | ggagccagcc | acaaatgana | atctgaacgt | gtccaggttt | 600 |
| ctcctganac | tcatctacat | agaattggtt | aaaccctccc | ttggaataag | gaaaaa | 656 |

<210> SEQ ID NO 26
<211> LENGTH: 434
<212> TYPE: DNA
<213> ORGANISM: Homo sapien
<220> FEATURE:
<221> NAME/KEY: misc_feature
<222> LOCATION: (1)...(434)
<223> OTHER INFORMATION: n = A,T,C or G

<400> SEQUENCE: 26

| | | | | | |
|---|---|---|---|---|---|
| actagttcag | actgccacgc | caaccccaga | aaataccccca | catgccagaa | aagtgaagtc | 60 |
| ctaggtgttt | ccatctatgt | ttcaatctgt | ccatctacca | ggcctcgcga | taaaaacaaa | 120 |
| acaaaaaaac | gctgccaggt | tttagaagca | gttctggtct | caaaaccatc | aggatcctgc | 180 |
| caccagggtt | cttttgaaat | agtaccacat | gtaaaaggga | atttggcttt | cacttcatct | 240 |
| aataactgaa | ttgtcaggct | ttgattgata | attgtagaaa | taagtagcct | tctgttgtgg | 300 |
| gaataagtta | taatcagtat | tcatctcttt | gttttttgtc | actcttttct | ctctaattgt | 360 |
| gtcatttgta | ctgtttgaaa | aatatttctt | ctatnaaatt | aaactaacct | gccttaaaaa | 420 |
| aaaaaaaaaa | aaaa | | | | | 434 |

<210> SEQ ID NO 27
<211> LENGTH: 654
<212> TYPE: DNA
<213> ORGANISM: Homo sapien
<220> FEATURE:
<221> NAME/KEY: misc_feature
<222> LOCATION: (1)...(654)
<223> OTHER INFORMATION: n = A,T,C or G

<400> SEQUENCE: 27

| | | | | | |
|---|---|---|---|---|---|
| actagtccaa | cacagtcaga | aacattgttt | tgaatcctct | gtaaaccaag | gcattaatct | 60 |
| taataaacca | ggatccattt | aggtaccact | tgatataaaa | aggatatcca | taatgaatat | 120 |
| tttatactgc | atcctttaca | ttagccacta | aatacgttat | tgcttgatga | agacctttca | 180 |
| cagaatccta | tggattgcag | catttcactt | ggctacttca | tacccatgcc | ttaaagaggg | 240 |
| gcagtttctc | aaaagcagaa | acatgccgcc | agttctcaag | ttttcctcct | aactccattt | 300 |
| gaatgtaagg | gcagctggcc | cccaatgtgg | ggaggtccga | acattttctg | aattcccatt | 360 |
| ttcttgttcg | cggctaaatg | acagtttctg | tcattactta | gattccgatc | tttcccaaag | 420 |

| | |
|---|---|
| gtgttgattt acaaagaggc cagctaatag cagaaatcat gaccctgaaa gagagatgaa | 480 |
| attcaagctg tgagccaggc agganctcag tatggcaaag gtcttgagaa tcngccattt | 540 |
| ggtacaaaaa aaattttaaa gcntttatgt tataccatgg aaccatagaa anggcaaggg | 600 |
| aattgttaag aanaatttta agtgtccaga cccanaanga aaaaaaaaaa aaaa | 654 |

<210> SEQ ID NO 28
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 28

| | |
|---|---|
| cgtgtgcaca tactgggagg atttccacag ctgcacggtc acagcccttta cggattgcca | 60 |
| ggaaggggcg aaagatatgt gggataaact gagaaaagaa nccaaaaacc tcaacatcca | 120 |
| aggcagctta ttcgaactct gcggcagcgg caacggggcg gcgggggtccc tgctcccggc | 180 |
| gttcccggtg ctcctggtgt ctctctcggc agctttagcg acctgncttt ccttctgagc | 240 |
| gtggggccag ctcccccccgc ggcgcccacc cacnctcact ccatgctccc ggaaatcgag | 300 |
| aggaagatca ttagttcttt ggggacgttn gtgattctct gtgatgctga aaaacactca | 360 |
| tatagggaat gtgggaaatc ctganctctt tnttatntcg tntgatttct tgtgttttat | 420 |
| ttgccaaaat gttaccaatc agtgaccaac cnagcacagc caaaaatcgg acntcngctt | 480 |
| tagtccgtct tcacacacag aataagaaaa cggcaaaccc accccacttt tnantttnat | 540 |
| tattactaan ttttttctgt tgggcaaaag aatctcagga acngccctgg ggccnccgta | 600 |
| ctanagttaa ccnagctagt tncatgaaaa atgatgggct ccnccctcaat gggaaagcca | 660 |
| agaaaaagnc | 670 |

<210> SEQ ID NO 29
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 29

| | |
|---|---|
| actagtcctc cacagcctgt gaatccccct agacctttca agcatagtga gcggagaaga | 60 |
| agatctcagc gtttagccac cttacccatg cctgatgatt ctgtagaaaa ggtttcttct | 120 |
| ccctctccag ccactgatgg gaaagtattc tccatcagtt ctcaaaatca gcaagaatct | 180 |
| tcagtaccag aggtgcctga tgttgcacat ttgccacttg agaagctggg accctgtctc | 240 |
| cctcttgact taagtcgtgg ttcagaagtt acagcaccgg tagcctcaga ttcctcttac | 300 |
| cgtaatgaat gtcccagggc agaaaaagag gatacncaga tgcttccaaa tccttcttcc | 360 |
| aaagcaatag ctgatgggaa gaggagctcc agcagcagca ggaatatcga aaacagaaaa | 420 |
| aaaagtgaaa ttgggaagac aaaagctcaa cagcatttgg taaggagaaa aganaagatg | 480 |
| aggaaggaag agagaagaga gacnaagatc nctacggacc gnnncggaag aagaagaagn | 540 |
| aaaaaanaaa a | 551 |

<210> SEQ ID NO 30

<211> LENGTH: 684
<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 30

| | | | | | |
|---|---|---|---|---|---|
| actagttcta | tctggaaaaa | gcccggttg | aagaagctg | tggagagtgc | gtgtgcaatg | 60 |
| cgagactcat | ttcttggaag | catccctggc | aaaaatgcag | ctgagtacaa | ggttatcact | 120 |
| gtgatagaac | ctggactgct | ttttgagata | atagagatgc | tgcagtctga | agagacttcc | 180 |
| agcacctctc | agttgaatga | attaatgatg | gcttctgagt | caactttact | ggctcaggaa | 240 |
| ccacgagaga | tgactgcaga | tgtaatcgag | cttaaaggga | aattcctcat | caacttagaa | 300 |
| ggtggtgata | ttcgtgaaga | gtcttcctat | aaagtaattg | tcatgccgac | tacgaaagaa | 360 |
| aaatgccccc | gttgttggaa | gtatacagcg | ggagtcttca | gatacactgt | gtcctcgatg | 420 |
| tgcagaagtt | gtcagtggga | aaatagtatt | acagctcac | tcgagcaaga | accctcctga | 480 |
| cagtactggg | ctagaagttt | ggatggatta | tttacaatat | aggaaagaaa | gccaagaatt | 540 |
| aggtnatgag | tggatgagta | atggtggan | gatggggaat | tcaaatcaga | attatggaag | 600 |
| aagttnttcc | tgttactata | gaaaggaatt | atgtttattt | acatgcagaa | aatatanatg | 660 |
| tgtggtgtgt | accgtggatg | gaan | | | | 684 |

<210> SEQ ID NO 31
<211> LENGTH: 654
<212> TYPE: DNA
<213> ORGANISM: Homo sapien
<220> FEATURE:
<221> NAME/KEY: misc_feature
<222> LOCATION: (1)...(654)
<223> OTHER INFORMATION: n = A,T,C or G

<400> SEQUENCE: 31

| | | | | | |
|---|---|---|---|---|---|
| gcgcagaaaa | ggaaccaata | tttcagaaac | aagcttaata | ggaacagctg | cctgtacatc | 60 |
| aacatcttct | cagaatgacc | cagaagttat | catcgtggga | gctggcgtgc | ttggctctgc | 120 |
| tttggcagct | gtgctttcca | gagatggaag | aaaggtgaca | gtcattgaga | gagacttaaa | 180 |
| agagcctgac | agaatagttg | gagaattcct | gcagccgggt | ggttatcatg | ttctcaaaga | 240 |
| ccttggtctt | ggagatacag | tggaaggtct | tgatgcccag | gttgtaaatg | gttacatgat | 300 |
| tcatgatcag | ggaaagcaaa | tcagangttc | agattcctta | ccctctgtca | gaaaacaatc | 360 |
| aagtgcagag | tggaagagct | ttccatcacg | gaagattcat | catgagtctc | cggaaagcag | 420 |
| ctatggcaga | gcccaatgca | aagtttattg | aaggtgttgt | gttacagtta | ttagaggaag | 480 |
| atgatgttgt | gatgggagtt | cagtacaagg | ataaagagac | tggagatat | caaggaactc | 540 |
| catgctccac | tgactgttgt | tgcagatggg | cttttctcca | anttcaggaa | aagcctggtc | 600 |
| tcaataaagt | ttctgtatca | ctcatttggt | tggcttctta | tgaagaatgc | nccc | 654 |

<210> SEQ ID NO 32
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 32

```
actagtgaag aaaagaaat tctgatacgg gacaaaaatg ctcttcaaaa catcattctt    60
tatcacctga caccaggagt tttcattgga aaaggatttg aacctggtgt tactaacatt   120
ttaaagacca cacaaggaag caaaatcttt ctgaaagaag taaatgatac acttctggtg   180
aatgaattga aatcaaaaga atctgacatc atgacaacaa atggtgtaat tcatgttgta   240
gataaactcc tctatccagc agacacacct gttggaaatg atcaactgct ggaaatactt   300
aataaattaa tcaaatacat ccaaattaag tttgttcgtg gtagcacctt caaagaaatc   360
cccgtgactg tctatnagcc aattattaaa aaatacacca aaatcattga tgggagtgcc   420
tgtgggaaat aactgaaaaa gagaccgaga agaacgaatc attacaggtc ctgaaataaa   480
atacctagga tttctactgg aggtggagaa acagaagaac tctgaagaaa ttgttacaag   540
aagangtccc aaggtcacca aattcattga aggtggtgat ggtctttatt tgaagatgaa   600
gaaattaaaa gacgcttcag ggagacnccc catgaaggaa ttgccagcca caaaaaaatt   660
cagggattag aaa                                                      673
```

<210> SEQ ID NO 33
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 33

```
actagttatt tactttcctc cgcttcagaa ggttttttcag actgagagcc taagcatact    60
ggatctgttg tttcttttgg gtctcacctc atcagtgtgc atagtggcag aaattataaa   120
gaaggttgaa aggagcaggg aaaagatcca gaagcatgtt agttcgacat catcatcttt   180
tcttgaagta tgatgcatat tgcattattt tatttgcaaa ctaggaattg cagtctgagg   240
atcatttaga agggcaagtt caagaggata tgaagatttg agaacttttt aactattcat   300
tgactaaaaa tgaacattaa tgttnaagac ttaagacttt aacctgctgg cagtcccaaa   360
tgaaattatg caactttgat atcatattcc ttgatttaaa ttgggctttt gtgattgant   420
gaaactttat aaagcatatg gtcagttatt tnattaaaaa ggcaaaacct gaaccacctt   480
ctgcacttaa agaagtctaa cagtacaaat acctatctat cttagatgga tntatttntt   540
tntattttta aatattgtac tatttatggt nggtggggct ttcttactaa tacacaaatn   600
aatttatcat ttcaanggca ttctatttgg gtttagaagt tgattccaag nantgcatat   660
ttcgctactg tnt                                                      673
```

<210> SEQ ID NO 34
<211> LENGTH: 684
<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 34

```
actagtttat tcaagaaaag aacttactga ttcctctgtt cctaaagcaa gagtggcagg    60
tgatcagggc tggtgtagca tccggttcct ttagtgcagc taactgcatt tgtcactgat   120
gaccaaggag gaaatcacta agacatttga gaagcagtgg tatgaacgtt cttggacaag   180
```

```
ccacagttct gagccttaac cctgtagttt gcacacaaga acgagctcca cctcccttc      240 ttcaggagga atctgtgcgg atagattggc tggacttttc aatggttctg ggttgcaagt      300
gggcactgtt atggctgggt atggagcgga cagccccagg aatcagagcc tcagcccggc      360
tgcctggttg gaaggtacag gtgttcagca ccttcggaaa aagggcataa agtngtgggg      420
gacaattctc agtccaagaa gaatgcattg accattgctg gctatttgct tncctagtan      480
gaattggatn cattttttgac cangatnntt ctnctatgct ttnttgcaat gaaatcaaat      540
cccgcattat ctacaagtgg tatgaagtcc tgcnnccccc agagaggctg ttcaggcnat      600
gtcttccaag ggcagggtgg gttacaccat tttacctccc ctctcccccc agattatgna      660
cncagaagga atttntttcc tccc                                            684

<210> SEQ ID NO 35
<211> LENGTH: 614
<212> TYPE: DNA
<213> ORGANISM: Homo sapien
<220> FEATURE:
<221> NAME/KEY: misc_feature
<222> LOCATION: (1)...(614)
<223> OTHER INFORMATION: n = A,T,C or G

<400> SEQUENCE: 35
actagtccaa cgcgttngcn aatattcccc tggtagccta cttccttacc cccgaatatt       60
ggtaagatcg agcaatggct tcaggacatg ggttctcttc cctgtgatc attcaagtgc      120 tcactgcatg aagactggct tgtctcagtg tntcaacctc accagggctg tctcttggtc      180
cacacctcgc tccctgttag tgccgtatga cagcccccat canatgacct tggccaagtc      240
acggtttctc tgtggtcaat gttggtnggc tgattggtgg aaagtanggt ggaccaaagg      300
aagncncgtg agcagncanc nccagttctg caccagcagc gcctccgtcc tactnggtg      360 ttccngtttc tcctggccct gngtgggcta nggcctgatt cgggaanatg cctttgcang      420
gaaggganga taantgggat ctaccaattg attctggcaa aacnatntct aagattnttn      480
tgctttatgt gggnacana tctanctctc atttnntgct gnanatnaca ccctactcgt      540
gntcgancnc gtcttcgatt ttcgganaca cnccantnaa tactggcgtt ctgttgttaa      600
aaaaaaaaaa aaaa                                                       614

<210> SEQ ID NO 36
<211> LENGTH: 686
<212> TYPE: DNA
<213> ORGANISM: Homo sapien
<220> FEATURE:
<221> NAME/KEY: misc_feature
<222> LOCATION: (1)...(686)
<223> OTHER INFORMATION: n = A,T,C or G

<400> SEQUENCE: 36
gtggctggcc cggttctccg cttctcccca tcccctactt tcctccctcc ctcccttcc       60 ctccctcgtc gactgttgct tgctggtcgc agactccctg accctcccct cacccctccc      120
taacctcggt gccaccggat tgcccttctt ttcctgttgc ccagcccagc cctagtgtca      180
gggcgggggc ctggagcagc ccgaggcact gcagcagaag ananaaaaga cacgacnaac      240
ctcagctcgc cagtccggtc gctngcttcc cgccgcatgg caatnagaca dacgccgctc      300
acctgctctg ggcacacgcg acccgtggtt gatttggcct tcagtggcat caccccttatg      360 ggtatttctt aatcagcgct tgcaaagatg gttaacctat gctacgccag ggagatacag      420
gagactggat tggaacattt ttggggtcta aaggtctgtt tggggtgcaa cactgaataa      480
```

```
ggatgccacc aaagcagcta cagcagctgc agatttcaca gcccaagtgt gggatgctgt    540
ctcagganat naattgataa cctggctcat aacacattgt caagaatgtg gatttcccca    600
ggatattatt atttgtttac cggggganag gataactgtt tcncntattt taattgaaca    660
aactnaaaca aaanctaagg aaatcc                                         686
```

<210> SEQ ID NO 37
<211> LENGTH: 681
<212> TYPE: DNA
<213> ORGANISM: Homo sapien
<220> FEATURE:
<221> NAME/KEY: misc_feature
<222> LOCATION: (1)...(681)
<223> OTHER INFORMATION: n = A,T,C or G

<400> SEQUENCE: 37

```
gagacanacn naacgtcang agaanaaaag angcatggaa cacaanccag gcncgatggc     60
caccttccca ccagcancca gcgcccccca gcngccccca ngccggang accangactc    120 cancctgnat caatctganc tctattcctg gcccatncct acctcggagg tggangccgn    180
aaaggtcgca cnnncagaga agctgctgcc ancaccancc gccccnnccc tgncgggctn    240
nataggaaac tggtgaccnn gctgcanaat tcatacagga gcacgcgang ggcacnnnct    300
cacactgagt tnnngatgan gcctnaccan ggacctnccc cagcnnattg anncnggac    360 tgcggaggaa ggaagacccc gnacnggatc ctggccggcn tgccaccccc caccccctag    420
gattatnccc cttgactgag tctctgaggg gctacccgaa cccgcctcca ttccctacca    480
natnntgctc natcgggact gacangctgg ggatnggagg ggctatcccc cancatcccc    540
tnanaccaac agcnacngan natngggggct ccccnggggtc ggngcaacnc tcctncaccc    600
cggcgcnggc cttcggtgnt gtcctccntc aacnaattcc naaanggcgg gcccccnngt    660
ggactcctcn ttgttccctc c                                              681
```

<210> SEQ ID NO 38
<211> LENGTH: 687
<212> TYPE: DNA
<213> ORGANISM: Homo sapien
<220> FEATURE:
<221> NAME/KEY: misc_feature
<222> LOCATION: (1)...(687)
<223> OTHER INFORMATION: n = A,T,C or G

<400> SEQUENCE: 38

```
canaaaaaaa aaaacatggc cgaaaccagn aagctgcgcg atggcgccac ggcccctctt     60
ctcccggcct gtgtccggaa ggtttccctc cgaggcgccc cggctcccgc aagcggagga    120
gagggcggga cntgccgggg ccggagctca naggccctgg ggccgctctg ctctcccgcc    180
atcgcaaggg cggcgctaac ctnaggcctc cccgcaaagg tccccnangc ggnggcggcg    240
gggggctgtg anaaccgcaa aaanaacgct gggcgcgcng cgaacccgtc cacccccgcg    300
aaggananac ttccacagan gcagcgtttc cacagcccan agccacnttt ctagggtgat    360 gcacccccagt aagttcctgn cggggaagct caccgctgtc aaaaaanctc ttcgctccac    420
cggcgcacna agggganggan ggcangangc tgccgcccgc acaggtcatc tgatcacgtc    480
gcccgcccta ntctgctttt gtgaatctcc actttgttca accccacccg ccgttctctc    540
ctccttgcgc cttcctctna ccttaanaac cagcttcctc tacccnatng tanttnctct    600
gcncnngtng aaattaattc ggtccnccgg aacctcttnc ctgtggcaac tgctnaaaga    660
```

| aactgctgtt ctgnttactg cngtccc | 687 |

<210> SEQ ID NO 39
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 39

| actagtctgg cctacaatag tgtgattcat gtaggacttc tttcatcaat tcaaaacccc | 60 |
| tagaaaaacg tatacagatt atataagtag ggataagatt tctaacatttt ctgggctctc | 120 |
| tgacccctgc gctagactgt ggaaagggag tattattata gtatacaaca ctgctgttgc | 180 |
| cttattagtt ataacatgat aggtgctgaa ttgtgattca caatttaaaa acactgtaat | 240 |
| ccaaactttt ttttttaact gtagatcatg catgtgaatg ttaatgttaa tttgttcaan | 300 |
| gttgttatgg gtagaaaaaa ccacatgcct taaaatttta aaaagcaggg cccaaactta | 360 |
| ttagtttaaa attaggggta tgtttccagt ttgttattaa ntggttatag ctctgtttag | 420 |
| aanaaatcna ngaacangat ttngaaantt aagntgacat tatttnccag tgacttgtta | 480 |
| atttgaaatc anacacggca ccttccgttt tggtnctatt ggnntttgaa tccaancngg | 540 |
| ntccaaatct tnttggaaac ngtccnttta acttttttac nanatcttat tttttttattt | 600 |
| tggaatggcc ctatttaang ttaaaagggg ggggnnccac naccattcnt gaataaaact | 660 |
| naatatatat ccttggtccc ccaaaattta aggng | 695 |

<210> SEQ ID NO 40
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 40

| actagtagtc agttgggagt ggttgctata ccttgacttc atttatatga atttccactt | 60 |
| tattaaataa tagaaaagaa atcccggtg cttgcagtag agttatagga cattctatgc | 120 |
| ttacagaaaa tatagccatg attgaaatca aatagtaaag gctgttctgg cttttttatct | 180 |
| tcttagctca tcttaaataa gtagtacact tgggatgcag tgcgtctgaa gtgctaatca | 240 |
| gttgtaacaa tagcacaaat cgaacttagg atgtgtttct tctcttctgt gtttcgattt | 300 |
| tgatcaattc tttaattttg ggaacctata atacagtttt cctattcttg gagataaaaa | 360 |
| ttaaatggat cactgatatt taagtcattc tgcttctcat ctnaatattc catattctgt | 420 |
| attagganaa antacctccc agcacagccc cctctcaaac cccacccaaa accaagcatt | 480 |
| tggaatgagt ctcctttatt tccgaantgt ggatggtata acccatatcn ctccaatttc | 540 |
| tgnttgggtt gggtattaat ttgaactgtg catgaaaagn ggnaatcttt nctttgggtc | 600 |
| aaantttncc ggttaatttg nctngncaaa tccaatttnc tttaagggtg tctttataaa | 660 |
| atttgctatt cngg | 674 |

<210> SEQ ID NO 41
<211> LENGTH: 657
<212> TYPE: DNA
<213> ORGANISM: Homo sapien
<220> FEATURE:
<221> NAME/KEY: misc_feature
<222> LOCATION: (1)...(657)
<223> OTHER INFORMATION: n = A,T,C or G

<400> SEQUENCE: 41

| | | | | | |
|---|---|---|---|---|---|
| gaaacatgca | agtaccacac | actgtttgaa | ttttgcacaa | aaagtgactg | tagggatcag | 60 |
| gtgatagccc | cggaatgtac | agtgtcttgg | tgcaccaaga | tgccttctaa | aggctgacat | 120 |
| accttgggac | cctaatgggg | cagagagtat | agccctagcc | cagtggtgac | atgaccactc | 180 |
| cctttgggag | gctgaagtta | aagggaatgg | tatgtgtttt | ctcatggaag | cagcacatga | 240 |
| atnggtnaca | ngatgttaaa | ntaaggntct | antttgggtg | tcttgtcatt | tgaaaaantg | 300 |
| acacactcct | ancanctggt | aaagggggtgc | tggaagccat | ggaagaactc | taaaaacatt | 360 |
| agcatgggct | gatctgatta | cttcctggca | tcccgctcac | ttttatggga | agtcttatta | 420 |
| naaggatggg | ananttttcc | atatccttgc | tgttggaact | ctggaacact | ctctaaattt | 480 |
| ccctctatta | aaaatcactg | nccttactac | acttcctcct | tganggaata | gaaatggacc | 540 |
| tttctctgac | ttagttcttg | gcatggganc | cagcccaaat | taaaatctga | cttntccggt | 600 |
| ttctccngaa | ctcacctact | tgaattggta | aaacctcctt | tggaattagn | aaaaacc | 657 |

<210> SEQ ID NO 42
<211> LENGTH: 389
<212> TYPE: DNA
<213> ORGANISM: Homo sapien
<220> FEATURE:
<221> NAME/KEY: misc_feature
<222> LOCATION: (1)...(389)
<223> OTHER INFORMATION: n = A,T,C or G

<400> SEQUENCE: 42

| | | | | | |
|---|---|---|---|---|---|
| actagtgctg | aggaatgtaa | acaagtttgc | tgggccttgc | gagacttcac | caggttgttt | 60 |
| cgatagctca | cactcctgca | ctgtgcctgt | cacccaggaa | tgtctttttt | aattagaaga | 120 |
| caggaagaaa | acaaaaacca | gactgtgtcc | cacaatcaga | aacctccgtt | gtggcagang | 180 |
| ggccttcacc | gccaccaggg | tgtcccgcca | gacagggaga | gactccagcc | ttctgaggcc | 240 |
| atcctgaaga | attcctgttt | ggggggttgtg | aaggaaaatc | accggatttt | aaaaagatgc | 300 |
| tgttgcctgc | ccgcgtngtn | gggaagggac | tggtttcctg | gtgaatttct | taaaagaaaa | 360 |
| atattttaag | ttaagaaaaa | aaaaaaaaa | | | | 389 |

<210> SEQ ID NO 43
<211> LENGTH: 279
<212> TYPE: DNA
<213> ORGANISM: Homo sapien

<400> SEQUENCE: 43

| | | | | | |
|---|---|---|---|---|---|
| actagtgaca | agctcctggt | cttgagatgt | cttctcgtta | aggagatggg | cctttttggag | 60 |
| gtaaaggata | aaatgaatga | gttctgtcat | gattcactat | tctagaactt | gcatgacctt | 120 |
| tactgtgtta | gctctttgaa | tgttcttgaa | attttagact | ttcttttgtaa | acaaataata | 180 |
| tgtccttatc | attgtataaa | agctgttatg | tgcaacagtg | tggagatcct | tgtctgattt | 240 |
| aataaaatac | ttaaacactg | aaaaaaaaaa | aaaaaaaaa | | | 279 |

<210> SEQ ID NO 44
<211> LENGTH: 449
<212> TYPE: DNA
<213> ORGANISM: Homo sapien
<220> FEATURE:

```
<221> NAME/KEY: misc_feature
<222> LOCATION: (1)...(449)
<223> OTHER INFORMATION: n = A,T,C or G

<400> SEQUENCE: 44
actagtagca tcttttctac aacgttaaaa ttgcagaagt agcttatcat taaaaaacaa      60
caacaacaac aataacaata atcctaagt gtaaatcagt tattctaccc cctaccaagg      120
atatcagcct gttttttccc ttttttctcc tgggaataat tgtgggcttc ttcccaaatt    180
tctacagcct ctttcctctt ctcatgcttg agcttcctg tttgcacgca tgcgttgtgc    240
aagantgggc tgtttngctt ggantncggt ccnagtggaa ncatgctttc ccttgttact    300
gttggaagaa actcaaacct tcnaccccta ggtgttncca ttttgtcaag tcatcactgt    360
atttttgtac tggcattaac aaaaaaagaa atnaaatatt gttccattaa actttaataa    420
aactttaaaa gggaaaaaaa aaaaaaaaa                                       449

<210> SEQ ID NO 45
<211> LENGTH: 559
<212> TYPE: DNA
<213> ORGANISM: Homo sapien
<220> FEATURE:
<221> NAME/KEY: misc_feature
<222> LOCATION: (1)...(559)
<223> OTHER INFORMATION: n = A,T,C or G

<400> SEQUENCE: 45
actagtgtgg gggaatcacg gacacttaaa gtcaatctgc gaaataattc ttttattaca     60
cactcactga agttttttgag tcccagagag ccattctatg tcaaacattc caagtactct    120
ttgagagccc agcattacat caacatgccc gtgcagttca aaccgaagtc cgcaggcaaa    180
tttgaagctt tgcttgtcat tcaaacagat gaaggcaaga gtattgctat tcgactaatt    240
ggtgaagctc ttgaaaaaaa ttnactagaa tacttttttgt gttaagttaa ttacataagt    300 tgtatttttgt taactttatc tttctacact acaattatgc ttttgtatat atattttgta    360
tgatggatat ctataattgt agattttgtt tttacaagct aatactgaag actcgactga    420
aatattatgt atctagccca tagtattgta cttaacttttt acagggtgaa aaaaaaattc    480
tgtgtttgca ttgattatga tattctgaat aaatatggga atatattttta atgtgggtaa    540 aaaaaaaaaa aaaaaggaa                                                  559

<210> SEQ ID NO 46
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 46
actagttcta gtaccatggc tgtcatagat gcaaccatta tattccattt agtttcttcc     60
tcaggttccc taacaattgt ttgaaactga atatatatgt ttatgtatgt gtgtgtgttc    120
actgtcatgt atatggtgta tatgggatgt gtgcagtttt cagttatata tatattcata    180
tatacatatg catatatatg tataatatac atatatacat gcatacactt gtataatata    240
catatatata cacatatatg cacacatatn atcactgagt tccaaagtga gtctttattt    300
ggggcaattg tattctctcc ctctgtctgc tcactgggcc tttgcaagac atagcaattg    360
cttgatttcc tttggataag agtcttatct tcggcactct tgactctagc cttaacttta    420
```

```
gatttctatt ccagaatacc tctcatatct atcttaaaac ctaaganggg taaagangtc      480
ataagattgt agtatgaaag antttgctta gttaaattat atctcaggaa actcattcat      540
ctacaaatta aattgtaaaa tgatggtttg ttgtatctga aaaaatgttt agaacaagaa      600
atgtaactgg gtacctgtta tatcaaagaa cctcnattta ttaagtctcc tcatagccan      660
atccttatat ngccctctct gacctgantt aatananact tgaataatga atagttaatt      720
taggnttggg c                                                          731
```

```
<210> SEQ ID NO 47
<211> LENGTH: 640
<212> TYPE: DNA
<213> ORGANISM: Homo sapien
<220> FEATURE:
<221> NAME/KEY: misc_feature
<222> LOCATION: (1)...(640)
<223> OTHER INFORMATION: n = A,T,C or G

<400> SEQUENCE: 47
```

```
tgcgngccgg tttggcccctt ctttgtanga cactttcatc cgccctgaaa tcttcccgat      60
cgttaataac tcctcaggtc cctgcctgca cagggttttt tcttanttty ttgcctaaca     120
gtacaccaaa tgtgacatcc tttcaccaat atngattnct tcataccaca tcntcnatgg     180
anacgactnc aacaatttt tgatnacccn aaanactggg ggctnnaana agtacantct     240
ggagcagcat ggacctgtcn gcnactaang gaacaaanagt nntgaacatt tacacaacct     300
ttggtatgtc ttactgaaag anagaaacat gcttctnncc ctagaccacg aggncaaccg     360
caganattgc caatgccaag tccgagcggt tagatcaggt aatacattcc atggatgcat     420
tacatacntt gtccccgaaa nanaagatgc cctaanggct tcttcanact ggtccngaaa     480
acanctacac ctggtgcttg ganaacanac tctttggaag atcatctggc acaagttccc     540
cccagtgggt tttnccttgg cacctanctt accanatcna ttcggaancc attctttgcc     600
ntggcnttnt nttgggacca ntcttctcac aactgnaccc                            640
```

```
<210> SEQ ID NO 48
<211> LENGTH: 257
<212> TYPE: DNA
<213> ORGANISM: Homo sapien

<400> SEQUENCE: 48
```

```
actagtatat gaaaatgtaa atatcacttg tgtactcaaa caaagttgg tcttaagctt        60 ccaccttgag cagccttgga aacctaacct gcctctttta gcataatcac attttctaaa      120
tgattttctt tgttcctgaa aaagtgattt gtattagttt tacatttgtt ttttggaaga     180
ttatatttgt atatgtatca tcataaaata tttaaataaa aagtatcttt agagtgaaaa      240
aaaaaaaaaa aaaaaaa                                                    257
```

```
<210> SEQ ID NO 49
<211> LENGTH: 652
<212> TYPE: DNA
<213> ORGANISM: Homo sapien
<220> FEATURE:
<221> NAME/KEY: misc_feature
<222> LOCATION: (1)...(652)
<223> OTHER INFORMATION: n = A,T,C or G

<400> SEQUENCE: 49
```

```
actagttcag atgagtggct gctgaagggg ccccccttgtc attttcatta taacccaatt      60
```

```
tccacttatt tgaactctta agtcataaat gtataatgac ttatgaatta gcacagttaa      120
gttgacacta gaaactgccc atttctgtat tacactatca aataggaaac attggaaaga      180
tggggaaaaa aatcttattt taaaatggct tagaaagttt tcagattact ttgaaaattc      240
taaacttctt tctgtttcca aaacttgaaa atatgtagat ggactcatgc attaagactg      300
ttttcaaagc tttcctcaca ttttaaagt gtgattttcc ttttaatata catatttatt      360
ttctttaaag cagctatatc ccaacccatg actttggaga tatacctatn aaaccaatat      420
aacagcangg ttattgaagc agctttctca aatgttgctt cagatgtgca agttgcaaat      480
tttattgtat ttgtanaata caatttttgt tttaaactgt atttcaatct atttctccaa      540
gatgcttttc atatagagtg aaatatccca ngataactgc ttctgtgtcg tcgcatttga      600
cgcataactg cacaaatgaa cagtgtatac ctcttggttg tgcattnacc cc             652

<210> SEQ ID NO 50
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 50
ttgcgctttg atttttttag ggcttgtgcc ctgtttcact tatagggtct agaatgcttg       60
tgttgagtaa aaaggagatg cccaatattc aaagctgcta atgttctct ttgccataaa      120 gactccgtgt aactgtgtga acacttggga tttttctcct ctgtcccgag gtcgtcgtct      180
gctttctttt ttggttcctt tctagaagat tgagaaatgc atatgacagg ctgagancac      240
ctccccaaac acacaagctc tcagccacan gcagcttctc cacagcccca gcttcgcaca      300
ggctcctgga nggctgcctg ggggaggcag acatgggagt gccaaggtgg ccagatggtt      360
ccaggactac aatgtcttta tttttaactg tttgccactg ctgccctcac ccctgcccgg      420
ctctggagta ccgtctgccc canacaagtg ggantgaaat gggggtgggg gggaacactg      480
attcccantt agggggtgcc taactgaaca gtagggatan aaggtgtgaa cctgngaant      540
gcttttataa attatnttcc ttgttanatt tattttttaa tttaatctct gttnaactgc      600
ccngggaaaa gggaaaaaa aaaaaaaat tctntttaaa cacatgaaca                  650

<210> SEQ ID NO 51
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 51
tggcgtgcaa ccagggtagc tgaagtttgg gtctgggact ggagattggc cattaggcct       60
cctganattc cagctcccct tccaccaagcc cagtcttgct acgtggcaca gggcaaacct     120
gactcccttt gggcctcagt ttcccctccc cttcatgana tgaaagaat actacttttt      180 cttgttggtc taacnttgct ggacncaaag tgtngtcatt attgttgtat tgggtgatgt      240
gtncaaaact gcagaagctc actgcctatg agaggaanta agagagatag tggatganag      300
ggacanaagg agtcattatt tggtatagat ccacccntcc caacctttct ctcctcagtc      360 cctgcnccctc atgntctgg tntggtgagt cctttgtgcc accanccatc atgctttgca      420
```

| ttgctgccat cctgggaagg gggtgnatcg tctcacaact tgttgtcatc gtttganatg | 480 |
| catgctttct tnatnaaaca aanaaannaa tgtttgacag ngtttaaaat aaaaaanaaa | 540 |
| caaaa | 545 |

<210> SEQ ID NO 52
<211> LENGTH: 678
<212> TYPE: DNA
<213> ORGANISM: Homo sapien
<220> FEATURE:
<221> NAME/KEY: misc_feature
<222> LOCATION: (1)...(678)
<223> OTHER INFORMATION: n = A,T,C or G

<400> SEQUENCE: 52

| actagtagaa gaactttgcc gcttttgtgc ctctcacagg cgcctaaagt cattgccatg | 60 |
| ggaggaagac gatttggggg gggaggggggg ggggcangg tccgtggggc tttccctant | 120 |
| ntatctccat ntccantgnn cnntgtcgcc tcttccctcg tcncattnga anttantccc | 180 |
| tggncccnn ncctctccn nctncncct cccccctccg ncncctccnn cttttttntan | 240 |
| ncttccccat ctccntcccc cctnanngtc ccaacnccgn cagcaatnnc ncacttnctc | 300 |
| nctcncncc tccnnccgtt cttctnttct cnacntntnc ncnnntnccn tgccnntnaa | 360 |
| annctctccc cnctgcaanc gattctctcc ctccncnnan ctntccactc cntncttctc | 420 |
| ncncgctcct nttcntcnnc ccacctctcn ccttcgnccc cantacnctc nccnccttn | 480 |
| cgnntcnttn nnntcctcnn accnccncc tccttcncc cctcttctcc ccggtntntc | 540 |
| tctctccccnc nncncnncct cnncccntcc nngcgnccnt ttccgccccn cnccnccntt | 600 |
| ccttcntcnc cantccatcn cntntnccat nctnccctncc nctcacnccc gctnccccn | 660 |
| ntctctttca cacngtcc | 678 |

<210> SEQ ID NO 53
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 53

| tgaagatcct ggtgtcgcca tgggccgccg ccccgcccgt tgttaccggt attgtaagaa | 60 |
| caagccgtac ccaaagtctc gcttctgccg aggtgtccct gatgccaaaa ttcgcatttt | 120 |
| tgacctgggg cggaaaaang caaaantgga tgagtctccg ctttgtggcc acatggtgtc | 180 |
| agatcaatat gagcagctgt cctctgaagc cctgnangct gcccgaattt gtgccaataa | 240 |
| gtacatggta aaaagtngtg gcnaagatgc ttccatatcc gggtgcggnt ccaccccttc | 300 |
| cacgtcatcc gcatcaacaa gatgttgtcc tgtgctgggg ctgacaggct cccaacaggc | 360 |
| atgcgaagtg cctttggaaa acccanggca ctgtggccag ggttcacatt gggccaattn | 420 |
| atcatgttca tccgcaccaa ctgcagaaca angaacntgt naattnaagc cctgcccagg | 480 |
| gncaanttca aatttcccgg cc | 502 |

<210> SEQ ID NO 54
<211> LENGTH: 494
<212> TYPE: DNA
<213> ORGANISM: Homo sapien
<220> FEATURE:

<221> NAME/KEY: misc_feature
<222> LOCATION: (1)...(494)
<223> OTHER INFORMATION: n = A,T,C or G

<400> SEQUENCE: 54

| | | | | | |
|---|---|---|---|---|---|
| actagtccaa | gaaaaatatg | cttaatgtat | attacaaagg | ctttgtatat | gttaacctgt | 60 |
| tttaatgcca | aaagtttgct | ttgtccacaa | tttccttaag | acctcttcag | aaagggattt | 120 |
| gtttgcctta | atgaatactg | ttgggaaaaa | acacagtata | atgagtgaaa | agggcagaag | 180 |
| caagaaattt | ctacatctta | gcgactccaa | gaagaatgag | tatccacatt | tagatggcac | 240 |
| attatgagga | ctttaatctt | tccttaaaca | caataatgtt | ttcttttttc | ttttattcac | 300 |
| atgatttcta | agtatatttt | tcatgcagga | cagttttca | accttgatgt | acagtgactg | 360 |
| tgttaaattt | ttctttcagt | ggcaacctct | ataatcttta | aaatatggtg | agcatcttgt | 420 |
| ctgttttgaa | ngggatatga | cnatnaatct | atcagatggg | aaatcctgtt | tccaagttag | 480 |
| aaaaaaaaaa | aaaa | | | | | 494 |

<210> SEQ ID NO 55
<211> LENGTH: 606
<212> TYPE: DNA
<213> ORGANISM: Homo sapien
<220> FEATURE:
<221> NAME/KEY: misc_feature
<222> LOCATION: (1)...(606)
<223> OTHER INFORMATION: n = A,T,C or G

<400> SEQUENCE: 55

| | | | | | |
|---|---|---|---|---|---|
| actagtaaaa | agcagcattg | ccaaataatc | cctaattttc | cactaaaaat | ataatgaaat | 60 |
| gatgttaagc | ttttgaaaa | gtttaggtta | aacctactgt | tgttagatta | atgtatttgt | 120 |
| tgcttcccttt | tatctggaat | gtggcattag | ctttttttatt | ttaaccctct | ttaattctta | 180 |
| ttcaattcca | tgacttaagg | ttggagagct | aaacactggg | attttttggat | aacagactga | 240 |
| cagttttgca | taattataat | cggcattgta | catagaaagg | atatggctac | cttttgttaa | 300 |
| atctgcactt | tctaaatatc | aaaaaaggga | atgaagtat | aaatcaattt | ttgtataatc | 360 |
| tgtttgaaac | atganttta | tttgcttaat | attanggctt | tgcccttttc | tgttagtctc | 420 |
| ttgggatcct | gtgtaaaact | gttctcatta | acaccaaac | agttaagtcc | attctctggt | 480 |
| actagctaca | aattccgttt | catattctac | ntaacaattt | aaattaactg | aaatatttct | 540 |
| anatggtcta | cttctgtcnt | ataaaaacna | aacttgantt | nccaaaaaaa | aaaaaaaaa | 600 |
| aaaaaa | | | | | | 606 |

<210> SEQ ID NO 56
<211> LENGTH: 183
<212> TYPE: DNA
<213> ORGANISM: Homo sapien

<400> SEQUENCE: 56

| | | | | | |
|---|---|---|---|---|---|
| actagtatat | ttaaacttac | aggcttattt | gtaatgtaaa | ccaccatttt | aatgtactgt | 60 |
| aattaacatg | gttataatac | gtacaatcct | tccctcatcc | catcacacaa | cttttttttgt | 120 |
| gtgtgataaa | ctgattttgg | tttgcaataa | aaccttgaaa | ataaaaaaaa | aaaaaaaaa | 180 |
| aaa | | | | | | 183 |

<210> SEQ ID NO 57
<211> LENGTH: 622
<212> TYPE: DNA
<213> ORGANISM: Homo sapien

```
<220> FEATURE:
<221> NAME/KEY: misc_feature
<222> LOCATION: (1)...(622)
<223> OTHER INFORMATION: n = A,T,C or G

<400> SEQUENCE: 57
actagtcact actgtcttct ccttgtagct aatcaatcaa tattcttccc ttgcctgtgg    60
gcagtggaga gtgctgctgg gtgtacgctg cacctgccca ctgagttggg gaaagaggat   120
aatcagtgag cactgttctg ctcagagctc ctgatctacc ccaccccta ggatccagga    180 ctgggtcaaa gctgcatgaa accaggccct ggcagcaacc tggaatggc tggaggtggg    240 agagaacctg acttctcttt ccctctccct cctccaacat tactggaact ctatcctgtt   300
agggatcttc tgagcttgtt tccctgctgg gtgggacaga agacaaagga aagggaggg    360 tctacaanaa gcagcccttc tttgtcctct ggggttaatg agcttgacct ananttcatg   420
gaganaccan aagcctctga ttttttaattt ccntnaaatg tttgaagtnt atatntacat  480
atatatattt ctttnaatnt ttgagtcttt gatatgtctt aaaatccant ccctctgccn   540
gaaacctgaa ttaaaaccat gaanaaaaat gtttnccttta aagatgttan taattaattg  600
aaacttgaaa aaaaaaaaaa aa                                           622

<210> SEQ ID NO 58
<211> LENGTH: 433
<212> TYPE: DNA
<213> ORGANISM: Homo sapien

<400> SEQUENCE: 58
gaacaaattc tgattggtta tgtaccgtca aaagacttga agaaatttca tgattttgca    60
gtgtggaagc gttgaaaatt gaaagttact gcttttccac ttgctcatat agtaaaggga   120
tcctttcagc tgccagtgtt gaataatgta tcatccagag tgatgttatc tgtgacagtc   180
accagcttta agctgaacca ttttatgaat accaaataaa tagacctctt gtactgaaaa   240
catatttgtg actttaatcg tgctgcttgg atagaaatat ttttactggt tcttctgaat   300
tgacagtaaa cctgtccatt atgaatggcc tactgttcta ttatttgttt tgacttgaat   360
ttatccacca aagacttcat ttgtgtatca tcaataaagt tgtatgtttc aactgaaaaa   420
aaaaaaaaaa aaa                                                     433

<210> SEQ ID NO 59
<211> LENGTH: 649
<212> TYPE: DNA
<213> ORGANISM: Homo sapien
<220> FEATURE:
<221> NAME/KEY: misc_feature
<222> LOCATION: (1)...(649)
<223> OTHER INFORMATION: n = A,T,C or G

<400> SEQUENCE: 59
actagttatt atctgacttt cnggttataa tcattctaat gagtgtgaag tagcctctgg    60
tgtcatttgg atttgcattt ctctgatgag tgatgctatc aagcaccttt gctggtgctg   120
ttggccatat gtgtatgttc cctggagaag tgtctgtgct gagccttggc ccactttta   180 attaggcgtn tgtctttta ttactgagtt gtaaganttc tttatatatt ctggattcta   240
gacccttatc agatacatgg tttgcaaata ttttctccca ttctgtgggt tgtgttttca   300
ctttatcgat aatgtcctta gacatataat aaatttgtat tttaaaagtg acttgatttg   360
ggctgtgcaa ggtgggctca cgcttgtaat cccagcactt tgggagactg aggtgggtgg   420
```

```
atcatatgan gangctagga gttcgaggtc agcctggcca gcatagcgaa aacttgtctc      480
tacnaaaaat acaaaaatta gtcaggcatg gtggtgcacg tctgtaatac cagcttctca      540
ggangctgan gcacaaggat cacttgaacc ccagaangaa gangttgcag tganctgaag      600
atcatgccag ggcaacaaaa atgagaactt gtttaaaaaa aaaaaaaaa                  649
```

<210> SEQ ID NO 60
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 60

```
actagttcag gccttccagt tcactgacaa acatggggaa gtgtgcccag ctggctggaa      60
acctggcagt gataccatca agcctgatgt ccaaaagagc aaagaatatt tctccaagca     120
gaagtgagcg ctgggctgtt ttagtgccag gctgcggtgg gcagccatga gaacaaaacc     180
tcttctgtat tttttttttc cattagtana acacaagact cngattcagc cgaattgtgg     240
tgtcttacaa ggcagggctt tcctacaggg ggtggganaaa acagcctttc ttcctttggt    300
aggaatggcc tgagttggcg ttgtgggcag gctactggtt tgtatgatgt attagtagag     360
caacccatta atcttttgta gtttgtatna aacttganct gagaccttaa acaaaaaaaa    420
aaa                                                                  423
```

<210> SEQ ID NO 61
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 61

```
cgggactgga atgtaaagtg aagttcggag ctctgagcac gggctcttcc cgccgggtcc      60
tccctcccca gacccagag ggagaggccc accccgccca gccccgcccc agcccctgct      120
caggtctgag tatggctggg agtcggggc cacaggcctc tagctgtgct gctcaagaag      180
actggatcag ggtanctaca agtggccggg ccttgccttt gggattctac cctgttccta     240
atttggtgtt ggggtgcggg gtccctggcc cccttttcca cactncctcc ctccngacag     300
caacctccct tggggcaatt gggcctggnt ctccncccgn tgttgcnacc cttttgttggt   360 ttaaggncctt taaaaatgtt annttttccc ntgccngggt taaaaaagga aaaaactnaa   420
aaa                                                                  423
```

<210> SEQ ID NO 62
<211> LENGTH: 683
<212> TYPE: DNA
<213> ORGANISM: Homo sapien
<220> FEATURE:
<221> NAME/KEY: misc_feature
<222> LOCATION: (1)...(683)
<223> OTHER INFORMATION: n = A,T,C or G

<400> SEQUENCE: 62

```
gctggagagg ggtacggact ttcttggagt tgtcccaggt tggaatgaga ctgaactcaa       60
gaagagaccc taagagactg gggaatggtt cctgccttca ggaaagtgaa agacgcttag     120
```

| | |
|---|---|
| gctgtcaaca cttaaaggaa gtccccttga agcccagagt ggacagacta gacccattga | 180 |
| tggggccact ggccatggtc cgtggacaag acattccngt gggccatggc acaccggggg | 240 |
| ggatcaaaat gtgtacttgt ggggtctcgc cccttgccaa aaccaaacca ntcccactcc | 300 |
| tgtcnttgga ctttcttccc attccctcct ccccaaatgc acttcccctc ctccctctgc | 360 |
| ccctcctgtg tttttggaat tctgtttccc tcaaaattgt taattttta nttttngacc | 420 |
| atgaacttat gtttggggtc nangttcccc ttnccaatgc atactaatat attaatggtt | 480 |
| atttattttt gaaatatttt ttaatgaact tggaaaaaat tnntggaatt tccttncttc | 540 |
| cnttttnttt ggggggggtg gggggntggg ttaaaattt tttggaancc cnatnggaaa | 600 |
| ttnttacttg gggccccct naaaaaantn anttccaatt cttnnatngc ccctnttccn | 660 |
| ctaaaaaaaa ananannaaa aan | 683 |

<210> SEQ ID NO 63
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 63

| | |
|---|---|
| actagtcata aagggtgtgc gcgtcttcga cgtggcggtc ttggcgccac tgctgcgaga | 60 |
| cccggccctg gacctcaagg tcatccactt ggtgcgtgat ccccgcgcgg tggcgagttc | 120 |
| acggatccgc tcgcgccacg gcctcatccg tgagagccta caggtggtgc gcagccgaga | 180 |
| ccgcgagctc accgcatgcc cttcttggag gccgcgggcc acaagcttgg cgcccanaaa | 240 |
| gaaggcgtng gggccccgca aantaccacg ctctgggcgc tatggaangt cctcttgcaa | 300 |
| taatattggt tnaaaanctg canaanagcc cctgcanccc cctgaactgg gntgcagggc | 360 |
| cncttaccctn gtttggntgc ggttacaaag aacctgttttn ggaaaacccct nccnaaaacc | 420 |
| ttccgggaaa attntncaaa tttttnttgg ggaattnttg ggtaaacccc ccnaaaatgg | 480 |
| gaaacnttt tgccctnnaa antaaaccat tnggttccgg gggcccccc ncaaaaccct | 540 |
| tttttnttt tttntgcccc cantnnccc ccggggcccc tttttttngg ggaaaaccc | 600 |
| cccccctncc nananttta aaagggnggg anaattttn nttncccccc gggncccccn | 660 |
| ggngntaaaa nggtttcncc ccccgagggg gngggggnnnc ctcnnaaacc cntntcnnna | 720 |
| ccncnttttn n | 731 |

<210> SEQ ID NO 64
<211> LENGTH: 313
<212> TYPE: DNA
<213> ORGANISM: Homo sapien
<220> FEATURE:
<221> NAME/KEY: misc_feature
<222> LOCATION: (1)...(313)
<223> OTHER INFORMATION: n = A,T,C or G

<400> SEQUENCE: 64

| | |
|---|---|
| actagttgtg caaaccacga ctgaagaaag acgaaaagtg ggaataact tgcaacgtct | 60 |
| gttagagatg gttgctacac atgttgggtc tgtagagaaa catcttgagg agcagattgc | 120 |
| taaagttgat agagaatatg aagaatgcat gtcagaagat ctctcggaaa atattaaaga | 180 |
| gattagagat aagtatgaga agaaagctac tctaattaag tcttctgaag aatgaagatn | 240 |

-continued

| | |
|---|---|
| aaatgttgat catgtatata tatccatagt gaataaaatt gtctcagtaa agttgtaaaa | 300 |
| aaaaaaaaaa aaa | 313 |

<210> SEQ ID NO 65
<211> LENGTH: 420
<212> TYPE: DNA
<213> ORGANISM: Homo sapien
<220> FEATURE:
<221> NAME/KEY: misc_feature
<222> LOCATION: (1)...(420)
<223> OTHER INFORMATION: n = A,T,C or G

<400> SEQUENCE: 65

| | |
|---|---|
| actagttccc tggcaggcaa gggcttccaa ctgaggcagt gcatgtgtgg cagagagagg | 60 |
| caggaagctg gcagtggcag cttctgtgtc tagggagggg tgtggctccc tccttccctg | 120 |
| tctgggaggt tggagggaag aatctaggcc ttagcttgcc ctcctgccac ccttcccctt | 180 |
| gtagatactg ccttaacact ccctcctctc tcagctgtgg ctgccaccca agccaggttt | 240 |
| ctccgtgctc actaatttat ttccaggaaa ggtgtgtgga agacatgagc cgtgtataat | 300 |
| atttgtttta acattttcat tgcaagtatt gaccatcatc cttggttgtg tatcgttgta | 360 |
| acacaaatta atgatattaa aaagcatcca aacaaagccn annnnnaana nnannngaaa | 420 |

<210> SEQ ID NO 66
<211> LENGTH: 676
<212> TYPE: DNA
<213> ORGANISM: Homo sapien
<220> FEATURE:
<221> NAME/KEY: misc_feature
<222> LOCATION: (1)...(676)
<223> OTHER INFORMATION: n = A,T,C or G

<400> SEQUENCE: 66

| | |
|---|---|
| actagtttcc tatgatcatt aaactcattc tcagggttaa gaaaggaatg taaatttctg | 60 |
| cctcaatttg tacttcatca ataagttttt gaagagtgca gattttttagt caggtcttaa | 120 |
| aaataaactc acaaatctgg atgcatttct aaattctgca aatgtttcct ggggtgactt | 180 |
| aacaaggaat aatcccacaa tataccctagc tacctaatac atggagctgg ggctcaaccc | 240 |
| actgttttta aggatttgcg cttacttgtg gctgaggaaa aataagtagt tccgagggaa | 300 |
| gtagttttta aatgtgagct tatagatngg aaacagaata tcaacttaat tatggaaatt | 360 |
| gttagaaacc tgttctcttg ttatctgaat cttgattgca attactattg tactggatag | 420 |
| actccagccc attgcaaagt ctcagatatc ttanctgtgt agttgaattc cttggaaatt | 480 |
| cttttttaaga aaaattgga gtttnaaaga aataaacccc tttgttaaat gaagcttggc | 540 |
| tttttggtga aaaanaatca tcccgcaggg cttattgttt aaaaanggaa ttttaagcct | 600 |
| ccctggaaaa anttgttaat taaatgggga aaatgntggg naaaaattat ccgttagggt | 660 |
| ttaaagggaa aactta | 676 |

<210> SEQ ID NO 67
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 67

| | |
|---|---|
| caccattaaa gctgcttacc aagaacttcc ccagcatttt gacttccttg tttgatagct | 60 |

```
gaattgtgag caggtgatag aagagccttt ctagttgaac atacagataa tttgctgaat    120
acattccatt taatgaaggg gttacatctg ttacgaagct actaagaagg agcaagagca    180 tagggaaaa aaatctgatc agaacgcatc aaactcacat gtgcccctc tactacaaac      240 agattgtagt gctgtggtgg tttattccgt tgtgcagaac ttgcaagctg agtcactaaa    300
cccaaagaga ggaaattata ggttagttaa acattgtaat cccaggaact aagtttaatt    360 cactttgaa gtgttttgtt ttttatttt ggtttgtctg atttactttg ggggaaaang      420
ctaaaaaaaa agggatatca atctctaatt cagtgcccac taaagttgt ccctaaaaag     480 tctttactgg aanttatggg acttttaag ctccaggtnt tttggtcctc caaattaacc     540
ttgcatgggc cccttaaaat tgttgaangg cattcctgcc tctaagtttg gggaaaattc    600
ccccnttttn aaaatttgga                                                620
```

```
<210> SEQ ID NO 68
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 68
actagtagct ggtacataat cactgaggag ctatttctta acatgctttt atagaccatg     60
ctaatgctag accagtattt aagggctaat ctcacacctc cttagctgta agagtctggc    120
ttagaacaga cctctctgtg caataacttg tggccactgg aaatccctgg gccggcattt    180 gtattgggt tgcaatgact cccaagggcc aaaagagtta aaggcacgac tgggatttct    240
tctgagactg tggtgaaact ccttccaagg ctgaggggt cagtangtgc tctgggaggg    300
actcggcacc actttgatat tcaacaagcc acttgaagcc caattataaa attgttattt    360
tacagctgat ggaactcaat ttgaaccttc aaaactttgt tagtttatcc tattatattg    420
ttaaacctaa ttacatttgt ctagcattgg atttggttcc tgtngcatat gttttttcn    480 cctatgtgct cccctcccc nnatcttaat ttaaaccnca attttgcnat tcnccnnnnn     540
nannnannna a                                                          551
```

```
<210> SEQ ID NO 69
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 69
cagaaatgga aagcagagtt ttcatttctg tttataaacg tctccaaaca aaatggaaa      60 gcagagtttt cattaaatcc ttttaccttt tttttttctt ggtaatcccc tcaaataaca    120
gtatgtggga tattgaatgt taagggata ttttttttcta ttatttttat aattgtacaa    180
aattaagcaa atgttaaaag ttttatatgc tttattaatg ttttcaaaag gtatnataca    240
tgtgatacat ttttaagct tcagttgctt gtcttctggt actttctgtt atgggctttt     300
ggggagccan aaaccaatct acnatctctt tttgtttgcc aggacatgca ataaaattta    360
aaaaataaat aaaaactatt nagaaattga aaaaaa                              396
```

<210> SEQ ID NO 70
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 70

| | | | | | |
|---|---|---|---|---|---|
| actagtgcaa | aagcaaatat | aaacatcgaa | aaggcgttcc | tcacgttagc | tgaagatatc | 60 |
| cttcgaaaga | cccctgtaaa | agagcccaac | agtgaaaatg | tagatatcag | cagtggagga | 120 |
| ggcgtgacag | gctggaagag | caatgctgc | tgagcattct | cctgttccat | cagttgccat | 180 |
| ccactacccc | gttttctctt | cttgctgcaa | aataaaccac | tctgtccatt | tttaactcta | 240 |
| aacagatatt | tttgtttctc | atcttaacta | tccaagccac | ctattttatt | tgttctttca | 300 |
| tctgtgactg | cttgctgact | ttatcataat | tttcttcaaa | caaaaaatg | tatagaaaaa | 360 |
| tcatgtctgt | gacttcattt | ttaaatgnta | cttgctcagc | tcaactgcat | ttcagttgtt | 420 |
| ttatagtcca | gttcttatca | acattnaaac | ctatngcaat | catttcaaat | ctattctgca | 480 |
| aattgtataa | gaataaaagt | tagaatttaa | caattaaaaa | aaaaaaaaaa | aaaaaa | 536 |

<210> SEQ ID NO 71
<211> LENGTH: 865
<212> TYPE: DNA
<213> ORGANISM: Homo sapien
<220> FEATURE:
<221> NAME/KEY: misc_feature
<222> LOCATION: (1)...(865)
<223> OTHER INFORMATION: n = A,T,C or G

<400> SEQUENCE: 71

| | | | | | |
|---|---|---|---|---|---|
| gacaaagcgt | taggagaaga | anagaggcag | ggaanactnc | ccaggcacga | tggccncctt | 60 |
| cccaccagca | accagcgccc | cccaccagcc | cccaggcccg | gacgacgaag | actccatcct | 120 |
| ggattaatct | nacctctntc | gcctgnccca | ttcctacctc | ggaggtggag | gccggaaagg | 180 |
| tcncaccaag | aganaanctg | ctgccaacac | caaccgcccc | agccctggcg | ggcacganag | 240 |
| gaaactggtg | accaatctgc | agaattctna | gaggaanaag | cnaggggccc | cgcgctnaga | 300 |
| cagagctgga | tatgangcca | gaccatggac | nctacnccn | ncaatncana | cgggactgcg | 360 |
| gaagatggan | gaccncgac | nngatcaggc | cngctnncca | nccccccacc | cctatgaatt | 420 |
| attcccgctg | aangaatctc | tganngctt | ccannaaagc | gcctcccnc | cnaacgnaan | 480 |
| tncaacatng | ggattananng | ctgggaactg | naagggcaa | ancctnnaat | atccccagaa | 540 |
| acaanctctc | ccnaanaaac | tggggcncct | catnggtggn | accaactatt | aactaaaccg | 600 |
| cacgccaagn | aantataaaa | gggggcccc | tccncggnng | accccctttt | gtcccttaat | 660 |
| ganggttatc | cnccttgcgt | accatggtnc | ccnnttctgt | ntgnatgttt | ccnctcccct | 720 |
| ccncctatnt | cnagccgaac | tcnnatttnc | ccggggggtgc | natcnantng | tncnccttn | 780 |
| ttngttgncc | cngcccttc | cgncggaacn | cgtttccccg | ttantaacgg | cacccggggn | 840 |
| aagggtgntt | ggcccccctcc | ctccc | | | | 865 |

<210> SEQ ID NO 72
<211> LENGTH: 560
<212> TYPE: DNA
<213> ORGANISM: Homo sapien
<220> FEATURE:
<221> NAME/KEY: misc_feature

```
<222> LOCATION: (1)...(560)
<223> OTHER INFORMATION: n = A,T,C or G

<400> SEQUENCE: 72
cctggacttg tcttggttcc agaacctgac gacccggcga cggcgacgtc tcttttgact      60
aaaagacagt gtccagtgct ccngcctagg agtctacggg gaccgcctcc cgcgccgcca     120
ccatgcccaa cttctctggc aactggaaaa tcatccgatc ggaaaacttc gangaattgc     180
tcnaantgct gggggtgaat gtgatgctna ngaanattgc tgtggctgca gcgtccaagc     240
cagcagtgga gatcnaacag gagggagaca ctttctacat caaaacctcc accaccgtgc     300
gcaccacaaa gattaacttc nnngttgggg aggantttga ggancaaact gtggatngga     360
ngcctgtnaa aacctggtga atgggagaa tganaataaa atggtctgtg ancanaaact      420
cctgaaagga gaaggccccc anaactcctg gaccngaaaa actgacccnc cnatnggga     480 actgatnctt gaaccctgaa cgggcgggat ganccttttt tnttgccncc naangggttc     540
tttccntttc cccaaaaaaa                                                 560

<210> SEQ ID NO 73
<211> LENGTH: 379
<212> TYPE: DNA
<213> ORGANISM: Homo sapien
<220> FEATURE:
<221> NAME/KEY: misc_feature
<222> LOCATION: (1)...(379)
<223> OTHER INFORMATION: n = A,T,C or G

<400> SEQUENCE: 73
ctggggancc ggcggtnngc nccatntcnn gncgcgaagg tggcaataaa aanccnctga     60
aaccgcncaa naaacatgcc naagatatgg acgaggaaga tngngctttc nngnacaanc    120
gnanngagga acanaacaaa ctcnangagc tctcaagcta atgccgcggg gaaggggccc    180
ttggccacnn gtgaattaa gaaatctggc aaanngtann tgttccttgt gcctnangag     240
ataagngacc cttttatttca tctgtattta aacctctctn ttccctgnca taacttcttt    300
tnccacgtan agntggaant anttgttgtc ttggactgtt gtncatttta gannaaactt    360
ttgttcaaaa aaaaaataa                                                 379

<210> SEQ ID NO 74
<211> LENGTH: 437
<212> TYPE: DNA
<213> ORGANISM: Homo sapien
<220> FEATURE:
<221> NAME/KEY: misc_feature
<222> LOCATION: (1)...(437)
<223> OTHER INFORMATION: n = A,T,C or G

<400> SEQUENCE: 74
actagttcag actgccacgc caaccccaga aaatacccca catgccagaa aagtgaagtc     60
ctaggtgttt ccatctatgt ttcaatctgt ccatctacca ggcctcgcga taaaaacaaa    120
acaaaaaaac gctgccaggt tttanaagca gttctggtct caaaaccatc aggatcctgc    180
caccagggtt cttttgaaat agtaccacat gtaaaaggga atttggcttt cacttcatct    240
aatcactgaa ttgtcaggct ttgattgata attgtagaaa taagtagcct tctgttgtgg    300
gaataagtta taatcagtat tcatctcttt gttttttgtc actcttttct ctctnattgt    360
gtcatttgta ctgtttgaaa atatttcttt ctataaaatt aaactaacct gccttaaaaa    420
aaaaaaaaaa aaaaaaa                                                  437
```

<210> SEQ ID NO 75
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 75

| | | | | | |
|---|---|---|---|---|---|
| ctccgtcgcc | gccaagatga | tgtgcgggc | gccctccgcc | acgcagccgg | ccaccgccga | 60 |
| gacccagcac | atcgccgacc | aggtgaggtc | ccagcttgaa | gagaaagaaa | acaagaagtt | 120 |
| ccctgtgttt | aaggccgtgt | cattcaagag | ccaggtggtc | gcggggacaa | actacttcat | 180 |
| caaggtgcac | gtcggcgacg | aggacttcgt | acacctgcga | gtgttccaat | ctctccctca | 240 |
| tgaaaacaag | cccttgacct | tatctaacta | ccagaccaac | aaagccaagc | atgatgagct | 300 |
| gacctatttc | tgatcctgac | tttggacaag | gcccttcagc | cagaagactg | acaaagtcat | 360 |
| cctccgtcta | ccagagcgtg | cacttgtgat | cctaaaataa | gcttcatctc | cgggctgtgc | 420 |
| ccttggggtg | aaggggcan | gatctgcact | gcttttgcat | ttctcttcct | aaatttcatt | 480 |
| gtgttgattc | tttccttcca | ataggtgatc | ttnattactt | tcagaatatt | ttccaaatna | 540 |
| gatatatttt | naaaatcctt | aaaaaaaaaa | aaaaaaaa |   | | 579 |

<210> SEQ ID NO 76
<211> LENGTH: 666
<212> TYPE: DNA
<213> ORGANISM: Homo sapien
<220> FEATURE:
<221> NAME/KEY: misc_feature
<222> LOCATION: (1)...(666)
<223> OTHER INFORMATION: n = A,T,C or G

<400> SEQUENCE: 76

| | | | | | |
|---|---|---|---|---|---|
| gtttatccta | tctctccaac | cagattgtca | gctccttgag | ggcaagagcc | acagtatatt | 60 |
| tccctgtttc | ttccacagtg | cctaataata | ctgtggaact | aggttttaat | aattttttaa | 120 |
| ttgatgttgt | tatgggcagg | atggcaacca | gaccattgtc | tcagagcagg | tgctggctct | 180 |
| ttcctggcta | ctccatgttg | gctagcctct | ggtaacctct | tacttattat | cttcaggaca | 240 |
| ctcactacag | ggaccaggga | tgatgcaaca | tccttgtctt | tttatgacag | gatgtttgct | 300 |
| cagcttctcc | aacaataaaa | agcacgtggt | aaaacacttg | cggatattct | ggactgtttt | 360 |
| taaaaaatat | acagtttacc | gaaaatcata | ttatcttaca | atgaaaagga | ntttatagat | 420 |
| cagccagtga | acaaccttttt | cccaccatac | aaaaattcct | tttcccgaan | gaaaanggct | 480 |
| ttctcaataa | ncctcacttt | cttaanatct | tacaagatag | ccccganatc | ttatcgaaac | 540 |
| tcattttagg | caaatatgan | ttttattgtn | cgttacttgt | ttcaaaattt | ggtattgtga | 600 |
| atatcaatta | ccaccccat | ctcccatgaa | anaaanggga | aanggtgaan | ttcntaancg | 660 |
| cttaaa |   |   |   |   | | 666 |

<210> SEQ ID NO 77
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 77

| | |
|---|---|
| ctgcagcccg ggggatccac taatctacca nggttatttg gcagctaatt ctanatttgg | 60 |
| atcattgccc aaagttgcac ttgctggtct cttgggattt ggccttggaa aggtatcata | 120 |
| catanganta tgccanaata aattccattt ttttgaaaat canctccntg gggctggttt | 180 |
| tggtccacag cataacangc actgcctcct tacctgtgag gaatgcaaaa taaagcatgg | 240 |
| attaagtgag aagggagact ctcagccttc agcttcctaa attctgtgtc tgtgactttc | 300 |
| gaagtttttt aaacctctga atttgtacac atttaaaatt tcaagtgtac tttaaaataa | 360 |
| aatacttcta atgggaacaa aaaaaaaaaa aaaaaa | 396 |

<210> SEQ ID NO 78
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 78

| | |
|---|---|
| gcatcctagc cgccgactca cacaaggcag gtgggtgagg aaatccagag ttgccatgga | 60 |
| gaaaattcca gtgtcagcat tcttgctcct tgtggccctc tcctacactc tggccagaga | 120 |
| taccacagtc aaacctggag ccaaaaagga cacaaggac tctcgaccca aactgcccca | 180 |
| gaccctctcc agaggttggg gtgaccaact catctggact cagacatatg aagaagctct | 240 |
| atataaatcc aagacaagca caaaccctt gatgattatt catcacttgg atgagtgccc | 300 |
| acacagtcna gctttaaaga aagtgtttgc tgaaaataaa gaaatccaga aattggcaga | 360 |
| gcagtttgtc ctcctcaatc tggtttatga aacaactgac aaacacctt ctcctgatgg | 420 |
| ccagtatgtc ccaggattat gtttgttgac ccatctctga cagttgaagc cgatatcctg | 480 |
| ggaagatatt cnaaccgtct ctatgcttac aaactgcaga tacgctctgt tgcttgacac | 540 |
| atgaaaaagc tctcaagttg ctnaaaatga attgtaagaa aaaaaatctc cagccttctg | 600 |
| tctgtcggct tgaaaattga aaccagaaaa atgtgaaaaa tggctattgt ggaacanatn | 660 |
| gacacctgat taggttttgg ttatgttcac cactatttt aanaaaanan nttttaaaat | 720 |
| ttggttcaat tntcttttn aaacaatntg tttctacntt gnganctgat ttctaaaaaa | 780 |
| aataatnttt ggc | 793 |

<210> SEQ ID NO 79
<211> LENGTH: 456
<212> TYPE: DNA
<213> ORGANISM: Homo sapien
<220> FEATURE:
<221> NAME/KEY: misc_feature
<222> LOCATION: (1)...(456)
<223> OTHER INFORMATION: n = A,T,C or G

<400> SEQUENCE: 79

| | |
|---|---|
| actagtatgg ggtgggaggc cccaccttc tcccctaggc gctgttcttg ctccaaaggg | 60 |
| ctccgtggag agggactggc agagctgang ccacctgggg ctgggatcc cactcttctt | 120 |
| gcagctgttg agcgcaccta accactggtc atgccccac cctgctctc cgcacccgct | 180 |
| tcctcccgac cccangacca ggctacttct cccctcctct tgcctccctc ctgcccctgc | 240 |
| tgcctctgat cgtangaatt gangantgtc ccgccttgtg gctganaatg gacagtggca | 300 |
| ggggctggaa atgggtgtgt gtgtgtgtgt gtgtgtgtgt gtgtgtgtgt gcnccccccc | 360 |

| | |
|---|---|
| tgcaagaccg agattgaggg aaancatgtc tgctgggtgt gaccatgttt cctctccata | 420 |
| aantncccct gtgacnctca naaaaaaaaa aaaaaa | 456 |

<210> SEQ ID NO 80
<211> LENGTH: 284
<212> TYPE: DNA
<213> ORGANISM: Homo sapien
<220> FEATURE:
<221> NAME/KEY: misc_feature
<222> LOCATION: (1)...(284)
<223> OTHER INFORMATION: n = A,T,C or G

<400> SEQUENCE: 80

| | |
|---|---|
| ctttgtacct ctagaaaaga taggtattgt gtcatgaaac ttgagtttaa attttatata | 60 |
| taaaactaaa agtaatgctc actttagcaa cacatactaa aattggaacc atactgagaa | 120 |
| gaatagcatg acctccgtgc aaacaggaca agcaaatttg tgatgtgttg attaaaaaga | 180 |
| aataaataaa tgtgtatatg tgtaacttgt atgtttatgt ggaatacaga ttgggaaata | 240 |
| aaatgtattt cttactgtga aaaaaaaaaa aaaaaaaaaa aana | 284 |

<210> SEQ ID NO 81
<211> LENGTH: 671
<212> TYPE: DNA
<213> ORGANISM: Homo sapien
<220> FEATURE:
<221> NAME/KEY: misc_feature
<222> LOCATION: (1)...(671)
<223> OTHER INFORMATION: n = A,T,C or G

<400> SEQUENCE: 81

| | |
|---|---|
| gccaccaaca ttccaagcta ccctgggtac ctttgtgcag tagaagctag tgagcatgtg | 60 |
| agcaagcggt gtgcacacgg agactcatcg ttataattta ctatctgcca agagtagaaa | 120 |
| gaaaggctgg ggatatttgg gttggcttgg ttttgatttt ttgcttgttt gtttgttttg | 180 |
| tactaaaaca gtattatctt ttgaatatcg tagggacata agtatataca tgttatccaa | 240 |
| tcaagatggc tagaatggtg cctttctgag tgtctaaaac ttgacacccc tggtaaatct | 300 |
| ttcaacacac ttccactgcc tgcgtaatga agttttgatt cattttttaac cactggaatt | 360 |
| tttcaatgcc gtcattttca gttagatnat tttgcactttt gagattaaaa tgccatgtct | 420 |
| atttgattag tcttattttt ttattttttac aggcttatca gtctcactgt ggctgtcat | 480 |
| tgtgacaaag tcaaataaac ccccnaggac aacacacagt atgggatcac atattgtttg | 540 |
| acattaagct ttggccaaaa aatgttgcat gtgttttacc tcgacttgct aaatcaatan | 600 |
| canaaaggct ggctnataat gttggtggtg aaataattaa tnantaacca aaaaaaaaan | 660 |
| aaaaaaaaaa a | 671 |

<210> SEQ ID NO 82
<211> LENGTH: 217
<212> TYPE: DNA
<213> ORGANISM: Homo sapien
<220> FEATURE:
<221> NAME/KEY: misc_feature
<222> LOCATION: (1)...(217)
<223> OTHER INFORMATION: n = A,T,C or G

<400> SEQUENCE: 82

| | |
|---|---|
| ctgcagatgt ttcttgaatg ctttgtcaaa ttaanaaagt taaagtgcaa taatgtttga | 60 |
| agacaataag tggtggtgta tcttgttttct aataagataa actttttttgt ctttgcttta | 120 |
| tcttattagg gagttgtatg tcagtgtata aaacatactg tgtggtataa caggcttaat | 180 |

```
aaattcttta aaaggaaaaa aaaaaaaaaa aaaaaaa                                    217
```

<210> SEQ ID NO 83
<211> LENGTH: 460
<212> TYPE: DNA
<213> ORGANISM: Homo sapien
<220> FEATURE:
<221> NAME/KEY: misc_feature
<222> LOCATION: (1)...(460)
<223> OTHER INFORMATION: n = A,T,C or G

<400> SEQUENCE: 83

```
cgcgagtggg agcaccagga tctcgggctc ggaacgagac tgcacggatt gttttaagaa            60
aatggcagac aaaccagaca tgggggaaat cgccagcttc gatnaggcca agctgaanaa          120
aacggagacg caggagaaga acaccctgcc gaccaaagag accattgagc angagaagcg          180
gagtgaaatt tcctaagatc ctggaggatt tcctaccccc gtcctcttcg agaccccagt          240
cgtgatgtgg aggaagagcc acctgcaaga tggacacgag ccacaagctg cactgtgaac          300
ctgggcactc cgcgccgatg ccaccggcct gtgggtctct gaaggacccc ccccaatcg           360
gactgccaaa ttctccggtt tgccccggga tattatacaa nattatttgt atgaataatg          420
annataaaac acacctcgtg gcancaaana aaaaaaaaa                                 460
```

<210> SEQ ID NO 84
<211> LENGTH: 323
<212> TYPE: DNA
<213> ORGANISM: Homo sapien
<220> FEATURE:
<221> NAME/KEY: misc_feature
<222> LOCATION: (1)...(323)
<223> OTHER INFORMATION: n = A,T,C or G

<400> SEQUENCE: 84

```
tggtggatct tggctctgtg gagctgctgg gacgggatct aaaagactat tctggaagct           60
gtggtccaan gcattttgct ggcttaacgg gtcccggaac aaaggacacc agctctctaa         120
aattgaagtt tacccganat aacaatcttt tgggcagaga tgcctatttt aacaaacncc         180
gtccctgcgc aacaacnaac aatctctggg aaataccggc catgaactg ctgtctcaat          240
cnancatctc tctagctgac cgatcatatc gtcccagatt actacanatc ataataattg         300
atttcctgta naaaaaaaaa aaa                                                  323
```

<210> SEQ ID NO 85
<211> LENGTH: 771
<212> TYPE: DNA
<213> ORGANISM: Homo sapien
<220> FEATURE:
<221> NAME/KEY: misc_feature
<222> LOCATION: (1)...(771)
<223> OTHER INFORMATION: n = A,T,C or G

<400> SEQUENCE: 85

```
aaactgggta ctcaacactg agcagatctg ttctttgagc taaaaccat gtgctgtacc           60
aanagtttgc tcctggctgc tttgatgtca gtgctgctac tccacctctg cggcgaatca         120
gaagcaagca actttgactg ctgtcttgga tacacagacc gtattcttca tcctaaattt         180
attgtgggct tcacacggca gctggccaat gaaggctgtg acatcaatgc tatcatcttt         240
cacacaaaga aaaagttgtc tgtgtgcgca aatccaaaac agacttgggt gaaatatatt         300
gtgcgtctcc tcagtaaaaa agtcaagaac atgtaaaaac tgtggctttt ctggaatgga         360
```

-continued

| | |
|---|---|
| attggacata gcccaagaac agaaagaact tgctggggtt ggaggtttca cttgcacatc | 420 |
| atggangqtt tagtgcttat ctttatttgtg cctcctggac ttgtccaatt natgaagtta | 480 |
| atcatattgc atcatantttt gctttgttta acatcacatt naaattaaac tgtatttttat | 540 |
| gttatttata gctntaggtt ttctgtgttt aactttttat acnaantttc ctaaactatt | 600 |
| ttggtntant gcaanttaaa aattatattt gggggggaa taaatattgg antttctgca | 660 |
| gccacaagct ttttttaaaa aaccantaca nccnngttaa atggtnggtc ccnaatggtt | 720 |
| tttgcttttn antagaaaat ttnttagaac natttgaaaa aaaaaaaaa a | 771 |

<210> SEQ ID NO 86
<211> LENGTH: 628
<212> TYPE: DNA
<213> ORGANISM: Homo sapien
<220> FEATURE:
<221> NAME/KEY: misc_feature
<222> LOCATION: (1)...(628)
<223> OTHER INFORMATION: n = A,T,C or G

<400> SEQUENCE: 86

| | |
|---|---|
| actagtttgc tttacatttt tgaaaagtat tattttttgtc caagtgctta tcaactaaac | 60 |
| cttgtgttag gtaagaatgg aatttattaa gtgaatcagt gtgacccttc ttgtcataag | 120 |
| attatcttaa agctgaagcc aaaatatgct tcaaagaaaa angactttat tgttcattgt | 180 |
| agttcataca ttcaaagcat ctgaactgta gtttctatag caagccaatt acatccataa | 240 |
| gtggagaaag aaatagatta atgtcnaagt atgattggtg gagggagcaa ggttgaagat | 300 |
| aatctggggt tgaaattttc tagttttcat tctgtacatt tttagttnga catcagattt | 360 |
| gaaatattaa tgtttacctt tcaatgtgtg gtatcagctg gactcantaa caccccttc | 420 |
| ttccctnggg gatggggaat ggattattgg aaaatggaaa gaaaaagta cttaaagcct | 480 |
| tccttttcnca gtttctggct cctaccctac tgattttancc agaataagaa aacattttat | 540 |
| catcntctgc tttattccca ttaatnaant tttgatgaat aaatctgctt ttatgcnnac | 600 |
| ccaaggaatt nagtggnttc ntcnttgt | 628 |

<210> SEQ ID NO 87
<211> LENGTH: 518
<212> TYPE: DNA
<213> ORGANISM: Homo sapien
<220> FEATURE:
<221> NAME/KEY: misc_feature
<222> LOCATION: (1)...(518)
<223> OTHER INFORMATION: n = A,T,C or G

<400> SEQUENCE: 87

| | |
|---|---|
| tttttttatt tttttagaga gtagttcagc ttttatttat aaatttattg cctgttttat | 60 |
| tataacaaca ttatactgtt tatggtttaa tacatatggt tcaaaatgta taatacatca | 120 |
| agtagtacag ttttaaaatt ttatgcttaa aacaagtttt gtgtaaaaaa tgcagataca | 180 |
| ttttacatgg caaatcaatt tttaagtcat cctaaaaatt gatttttttt tgaaatttaa | 240 |
| aaacacattt aatttcaatt tctctcttat ataacccttta ttactatagc atggtttcca | 300 |
| ctacagttta acaatgcagc aaaattccca tttcacggta aattgggttt taagcggcaa | 360 |
| ggttaaaatg ctttgaggat cctnaatacc ctttgaactt caaatgaagg ttatggttgt | 420 |
| naatttaacc ctcatgccat aagcagaagc acaagtttag ctgcattttg ctctaaactg | 480 |
| taaaancgag ccccccgttg aaaaagcaaa agggaccc | 518 |

<210> SEQ ID NO 88
<211> LENGTH: 1844
<212> TYPE: DNA
<213> ORGANISM: Homo sapien

<400> SEQUENCE: 88

| | | | | | |
|---|---|---|---|---|---|
| gagacagtga | atcctagtat | caaaggattt | ttggcctcag | aaaaagttgt | tgattatttt | 60 |
| tattttattt | tattttcga | gactccgtct | caaaaaaaaa | aaaaaaaaa | agaatcacaa | 120 |
| ggtatttgct | aaagcatttt | gagctgcttg | gaaaaaggga | agtagttgca | gtagagtttc | 180 |
| ttccatcttc | ttggtgctgg | gaagccatat | atgtgtcttt | tactcaagct | aagggggtata | 240 |
| agcttatgtg | ttgaatttgc | tacatctata | tttcacatat | tctcacaata | agagaattt | 300 |
| gaaatagaaa | tatcatagaa | catttaagaa | agtttagtat | aaataatatt | ttgtgtgttt | 360 |
| taatcccttt | gaagggatct | atccaaagaa | aatattttac | actgagctcc | ttcctacacg | 420 |
| tctcagtaac | agatcctgtg | ttagtctttg | aaaatagctc | attttttaaa | tgtcagtgag | 480 |
| tagatgtagc | atacatatga | tgtataatga | cgtgtattat | gttaacaatg | tctgcagatt | 540 |
| ttgtaggaat | acaaaacatg | gccttttta | taagcaaaac | gggccaatga | ctagaataac | 600 |
| acatagggca | atctgtgaat | atgtattata | agcagcattc | cagaaaagta | gttggtgaaa | 660 |
| taattttcaa | gtcaaaaagg | gatatggaaa | gggaattatg | agtaacctct | atttttaag | 720 |
| ccttgctttt | aaattaaacg | ctacagccat | ttaagccttg | aggataataa | agcttgagag | 780 |
| taataatgtt | aggttagcaa | aggtttagat | gtatcacttc | atgcatgcta | ccatgatagt | 840 |
| aatgcagctc | ttcgagtcat | ttctggtcat | tcaagatatt | cacccttttg | cccatagaaa | 900 |
| gcaccctacc | tcacctgctt | actgacattg | tcttagctga | tcacaagatc | attatcagcc | 960 |
| tccattattc | cttactgtat | ataaaataca | gagttttata | ttttcctttc | ttcgttttc | 1020 |
| accatattca | aaacctaaat | ttgttttttgc | agatggaatg | caaagtaatc | aagtgttcgt | 1080 |
| gctttcacct | agaagggtgt | ggtcctgaag | gaaagaggtc | cctaaatatc | ccccacctg | 1140 |
| ggtgctcctc | cttccctggt | accctgacta | ccagaagtca | ggtgctagag | cagctggaga | 1200 |
| agtgcagcag | cctgtgcttc | cacagatggg | ggtgctgctg | caacaaggct | ttcaatgtgc | 1260 |
| ccatcttagg | gggagaagct | agatcctgtg | cagcagcctg | gtaagtcctg | aggaggttcc | 1320 |
| attgctcttc | ctgctgctgt | cctttgcttc | tcaacggggc | tcgctctaca | gtctagagca | 1380 |
| catgcagcta | acttgtgcct | ctgcttatgc | atgagggtta | aattaacaac | cataaccttc | 1440 |
| atttgaagtt | caaggtgta | ttcaggatcc | tcaaagcatt | ttaaccttgc | cgcttaaaac | 1500 |
| ccaatttacc | gtgaaatggg | aattttgctg | cattgttaaa | ctgtagtgga | aaccatgcta | 1560 |
| tagtaataaa | ggttatataa | gagagaaatt | gaaattaaat | gtgttttaa | atttcaaaaa | 1620 |
| aaaatcaatc | tttaggatga | cttaaaaatt | gatttgccat | gtaaaatgta | tctgcatttt | 1680 |
| ttacacaaaa | cttgttttaa | gcataaaatt | ttaaaactgt | actacttgat | gtattataca | 1740 |
| ttttgaacca | tatgtattaa | accataaaca | gtataatgtt | gttataataa | aacaggcaat | 1800 |
| aaatttataa | ataaaagctg | aaaaaaaaaa | aaaaaaaaa | aaaa | | 1844 |

<210> SEQ ID NO 89
<211> LENGTH: 523
<212> TYPE: DNA
<213> ORGANISM: Homo sapien
<220> FEATURE:
<221> NAME/KEY: misc_feature
<222> LOCATION: (1)...(523)
<223> OTHER INFORMATION: n = A,T,C or G

<400> SEQUENCE: 89

| | | | | | |
|---|---|---|---|---|---|
| tttttttttt | tttttttagt | caatccacat | ttattgatca | cttattatgt | accaggcact | 60 |
| gggataaaga | tgactgttag | tcactcacag | taaggaagaa | actagcaaa | taagacgatt | 120 |
| acaatatgat | gtagaaaatg | ctaagccaga | gatatagaaa | ggtcctattg | ggtccttctg | 180 |
| tcaccttgtc | tttccacatc | cctacccttc | acaggccttc | cctccagctt | cctgcccccg | 240 |
| ctccccactg | cagatcccct | gggattttgc | ctagagctaa | acgagganat | gggcccctg | 300 |
| gccctggcat | gacttgaacc | caaccacaga | ctgggaaagg | gagcctttcg | anagtggatc | 360 |
| actttgatna | gaaaacacat | agggaattga | agagaaantc | cccaaatggc | cacccgtgct | 420 |
| ggtgctcaag | aaaagtttgc | agaatggata | aatgaaggat | caagggaatt | aatanatgaa | 480 |
| taattgaatg | gtggctcaat | aagaatgact | ncnttgaatg | acc | | 523 |

<210> SEQ ID NO 90
<211> LENGTH: 604
<212> TYPE: DNA
<213> ORGANISM: Homo sapien
<220> FEATURE:
<221> NAME/KEY: misc_feature
<222> LOCATION: (1)...(604)
<223> OTHER INFORMATION: n = A,T,C or G

<400> SEQUENCE: 90

| | | | | | |
|---|---|---|---|---|---|
| ccagtgtggt | ggaatgcaaa | gattaccccg | gaagctttcg | agaagctggg | attccctgca | 60 |
| gcaaaggaaa | tagccaatat | gtgtcgtttc | tatgaaatga | agccagaccg | agatgtcaat | 120 |
| ctcacccacc | aactaaatcc | caaagtcaaa | agcttcagcc | agtttatctc | agagaaccag | 180 |
| gggagccttc | aagggcatgt | agaaaatcag | ctgttcagat | aggcctctgc | accacacagc | 240 |
| ctctttcctc | tctgatccttt | ttcctcttta | cggcacaaca | ttcatgtttg | acagaacatg | 300 |
| ctggaatgca | attgtttgca | acaccgaagg | atttcctgcg | gtcgcctctt | cagtaggaag | 360 |
| cactgcattg | gtgataggac | acggtaattt | gattcacatt | taacttgcta | gttagtgata | 420 |
| aggggtggta | cacctgtttg | gtaaaatgag | aagcctcgga | aacttgggag | cttctctcct | 480 |
| accactaatg | gggagggcag | attattactg | ggatttctcc | tggggtgaat | taatttcaag | 540 |
| ccctaattgc | tgaaattccc | ctnggcaggc | tccagttttc | tcaactgcat | tgcaaaattc | 600 |
| cccc | | | | | | 604 |

<210> SEQ ID NO 91
<211> LENGTH: 858
<212> TYPE: DNA
<213> ORGANISM: Homo sapien
<220> FEATURE:
<221> NAME/KEY: misc_feature
<222> LOCATION: (1)...(858)
<223> OTHER INFORMATION: n = A,T,C or G

<400> SEQUENCE: 91

| | | | | | |
|---|---|---|---|---|---|
| tttttttttt | ttttttttta | tgattattat | ttttttatt | gatctttaca | tcctcagtgt | 60 |
| tggcagagtt | tctgatgctt | aataaacatt | tgttctgatc | agataagtgg | aaaaaattgt | 120 |
| catttcctta | ttcaagccat | gcttttctgt | gatattctga | tcctagttga | acatacagaa | 180 |
| ataaatgtct | aaaacagcac | ctcgattctc | gtctataaca | ggactaagtt | cactgtgatc | 240 |
| ttaaataagc | ttggctaaaa | tgggacatga | gtggaggtag | tcacacttca | gcgaagaaag | 300 |
| agaatctcct | gtataatctc | accaggagat | tcaacgaatt | ccaccacact | ggactagtgg | 360 |
| atccccgggg | ctgcaggaat | tcgatatcaa | gcttatcgat | accgtcgacc | tcgagggggg | 420 |

```
gcccggtacc caattcgccc tatagtgagt cgtattacgc gcgctcactg gccgtcgttt    480
tacaacgtcg tgactgggaa accctggcg ttacccaact taatcgcctt gcagcacatc    540
cccctttcgc cagctggcgt aatagcgaan agcccgcacc gatcgccctt ncaacagttg    600
cgcagcctga atggcgaatg ggacgcgccc tgtagcggcg cattaaagcg cggcnggggtg    660 tggnggntcc cccacgtgac cgntacactt ggcagcgcct tacgccggtc nttcgctttc    720
ttccctccct ttctcgcacc gttcgccggg tttccccgnn agctnttaat cggggnctc    780 cctttanggg tncnaattaa nggnttacng gaccttngan cccaaaaact ttgattaggg    840
ggaaggtccc cgaagggg                                                  858

<210> SEQ ID NO 92
<211> LENGTH: 585
<212> TYPE: DNA
<213> ORGANISM: Homo sapien
<220> FEATURE:
<221> NAME/KEY: misc_feature
<222> LOCATION: (1)...(585)
<223> OTHER INFORMATION: n = A,T,C or G

<400> SEQUENCE: 92
gttgaatctc ctggtgagat tatacaggag attctctttc ttcgctgaag tgtgactacc     60
tccactcatg tcccatttta gccaagctta tttaagatca cagtgaactt agtcctgtta    120
tagacgagaa tcgaggtgct gttttagaca tttatttctg tatgttcaac taggatcaga    180
atatcacaga aaagcatggc ttgaataagg aaatgacaat tttttccact tatctgatca    240
gaacaaatgt ttattaagca tcagaaactc tgccaacact gaggatgtaa agatcaataa    300
aaaaaataat aatcatnann naaanannan nngaagggcg gccgccaccg cggtggagct    360
ccagcttttg ttccctttag tgagggttaa ttgcgcgctt ggcgttaatc atggtcatag    420
ctgtttcctg tgtgaaattg ttatccggct cacaattccn cncaacatac gagccgggaa    480
gcntnangtg taaaagcctg ggggtgccta attgagtgag ctnactcaca ttaattgngt    540
tgcgctccac ttgcccgctt ttccantccg ggaaacctgt tcgnc                   585

<210> SEQ ID NO 93
<211> LENGTH: 567
<212> TYPE: DNA
<213> ORGANISM: Homo sapien
<220> FEATURE:
<221> NAME/KEY: misc_feature
<222> LOCATION: (1)...(567)
<223> OTHER INFORMATION: n = A,T,C or G

<400> SEQUENCE: 93
cggcagtgtt gctgtctgcg tgtccacctt ggaatctggc tgaactggct gggaggacca     60
agactgcggc tggggtgggc anggaaggga accgggggct gctgtgaagg atcttggaac    120
ttccctgtac ccaccttccc cttgcttcat gtttgtanag gaaccttgtg ccggccaagc    180
ccagtttcct tgtgtgatac actaatgtat ttgctttttt tgggaaatan anaaaaatca    240
attaaattgc tantgtttct ttgaannnnn nnnnnnnnnn nnnnnnnggg ggggncgccc    300
ccncggngga aacnccccct tttgttccct ttaattgaaa ggttaattng cncncntggc    360
gttaanccnt gggccaaanc tngttncccg tgntgaaatt gttatccccc tcccaaattc    420 cccccennce ttccaaaccc ggaaanccct annntgttna ncccgggggg gttgcctaan    480
ngnaattnaa ccnaacccce ntttaaatng nntttgcncn ccacnngccc cncttteccea    540
```

-continued

```
nttcggggaa aaccctntcc gtgccca                                          567
```

<210> SEQ ID NO 94
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 94

```
actagtcaaa aatgctaaaa taatttggga gaaatatttt ttaagtagt gttatagttt        60
catgtttatc ttttattatg ttttgtgaag ttgtgtcttt tcactaatta cctatactat      120
gccaatattt ccttatatct atccataaca tttatactac atttgtaana naatatgcac      180
gtgaaactta cactttata aggtaaaaat gaggtttcca anatttaata atctgatcaa       240
gttcttgtta tttccaaata gaatggactt ggtctgttaa gggctaagga gaagaggaag      300
ataaggttaa aagttgttaa tgaccaaaca ttctaaaaga aatgcaaaaa aaagtttat      360
tttcaagcct tcgaactatt taaggaaagc aaaatcattt cctaaatgca tatcatttgt      420
gagaatttct cattaatatc ctgaatcatt catttcacta aggctcatgt tnactccgat      480
atgtctctaa gaaagtacta tttcatggtc caaacctggt tgccatantt gggtaaaggc      540
tttcccttaa gtgtgaaant atttaaaatg aaatttttcct cttttttaaaa attctttana    600
agggttaagg gtgttgggga                                                  620
```

<210> SEQ ID NO 95
<211> LENGTH: 470
<212> TYPE: DNA
<213> ORGANISM: Homo sapien
<220> FEATURE:
<221> NAME/KEY: misc_feature
<222> LOCATION: (1)...(470)
<223> OTHER INFORMATION: n = A,T,C or G

<400> SEQUENCE: 95

```
ctcgaccttc tctgcacagc ggatgaaccc tgagcagctg aagaccagaa aagccactat       60
nactttntgc ttaattcang agcttacang attcttcaaa gagtgngtcc agcatccttt      120
gaaacatgag ttcttaccag cagaagcaga cctttacccc accacctcag cttcaacagc      180
agcaggtgaa acaacccatc cagcctccac ctnaggaaat atttgttccc acaaccaagg      240
agccatgcca ctcaaaggtt ccacaacctg naaacacaaa nattccagag ccaggctgta      300
ccaaggtccc tgagccaggg ctgtaccaan gtccctgagc caggttgtac caangtccct      360
gagccaggat gtaccaaggt ccctgancca ggttgtccaa ggtccctgag ccaggctaca      420
ccaagggcct gngccaggca gcatcaangt ccctgaccaa ggcttatcaa                  470
```

<210> SEQ ID NO 96
<211> LENGTH: 660
<212> TYPE: DNA
<213> ORGANISM: Homo sapien
<220> FEATURE:
<221> NAME/KEY: misc_feature
<222> LOCATION: (1)...(660)
<223> OTHER INFORMATION: n = A,T,C or G

<400> SEQUENCE: 96

```
tttttttttt tttttttttt ggaattaaaa gcaatttaat gagggcagag caggaaacat       60
gcatttcttt tcattcgaat cttcagatga accctgagca gccgaagacc agaaaagcca      120
```

```
tgaagacttt ctgcttaatt caggggctta caggattctt cagagtgtgt gtgaacaaaa    180
gctttatagt acgtattttt aggatacaaa taagagagag actatggctt ggggtgagaa    240
tgtactgatt acaaggtcta cagacaatta agacacagaa acagatggga agagggtgnc    300
cagcatctgg nggttggctt ctcaagggct tgtctgtgca ccaaattact tctgcttggn    360
cttctgctga gctgggcctg gagtgaccgt tgaaggacat ggctctggta cctttgtgta    420
gcctgncaca ggaactttgg tgtatccttg ctcaggaact ttgatggcac ctggctcagg    480
aaacttgatg aagccttggt caagggacct tgatgcttgc tggctcaggg accttggngn    540 anctgggct canggacctt tgncncaacc ttggcttcaa gggaccttg gnacatcctg     600 gcnnagggac ccttgggncc aaccctgggc ttnagggacc ctttggntnc nanccttggc    660
```

<210> SEQ ID NO 97
<211> LENGTH: 441
<212> TYPE: DNA
<213> ORGANISM: Homo sapien
<220> FEATURE:
<221> NAME/KEY: misc_feature
<222> LOCATION: (1)...(441)
<223> OTHER INFORMATION: n = A,T,C or G

<400> SEQUENCE: 97

```
gggaccatac anagtattcc tctcttcaca ccaggaccag ccactgttgc agcatgagtt     60
cccagcagca gaagcagccc tgcatcccac cccctcagct tcagcagcag caggtgaaac    120
agccttgcca gcctccacct caggaaccat gcatcccaa aaccaaggag ccctgccacc     180
ccaaggtgcc tgagccctgc caccccaaag tgcctgagcc ctgccagccc aaggttccag    240
agccatgcca ccccaaggtg cctgagccct gcccttcaat agtcactcca gcaccagccc    300 agcagaaanac caagcagaag taatgtggtc cacagccatg cccttgagga gccggccacc    360
agatgctgaa tcccctatcc cattctgtgt atgagtccca tttgccttgc aattagcatt    420
ctgtctcccc caaaaaaaaa a                                               441
```

<210> SEQ ID NO 98
<211> LENGTH: 600
<212> TYPE: DNA
<213> ORGANISM: Homo sapien
<220> FEATURE:
<221> NAME/KEY: misc_feature
<222> LOCATION: (1)...(600)
<223> OTHER INFORMATION: n = A,T,C or G

<400> SEQUENCE: 98

```
gtattcctct cttcacacca ggaccagcca ctgttgcagc atgagttccc agcagcagaa     60
gcagccctgc atcccacccc ctcagcttca gcagcagcag gtgaaacagc cttgccagcc    120
tccacctcag gaaccatgca tccccaaaac caaggagccc tgccacccca aggtgcctga    180
gccctgccac cccaaagtgc ctgagccctg ccagcccaag gttccagagc catgccaccc    240
caaggtgcct gagccctgcc cttcaatagt cactccagca ccagcccagc agaanaccaa    300
gcagaagtaa tgtggtccac agccatgccc ttgaggagcc ggccaccana tgctgaatcc    360
cctatcccat tctgtgtatg agtcccattt gccttgcaat tagcattctg tctccccaa     420 aaaagaatgt gctatgaagc tttctttcct acacactctg agtctctgaa tgaagctgaa    480
ggtcttaant acaganctag ttttcagctg ctcagaattc tctgaagaaa agatttaaga    540
tgaaaggcaa atgattcagc tccttattac cccattaaat tcnctttcaa ttccaaaaaa    600
```

<210> SEQ ID NO 99
<211> LENGTH: 667
<212> TYPE: DNA
<213> ORGANISM: Homo sapien
<220> FEATURE:
<221> NAME/KEY: misc_feature
<222> LOCATION: (1)...(667)
<223> OTHER INFORMATION: n = A,T,C or G

<400> SEQUENCE: 99

| | | | | | |
|---|---|---|---|---|---|
| actagtgact | gagttcctgg | caaagaaatt | tgacctggac | cagttgataa | ctcatgtttt | 60 |
| accatttaaa | aaaatcagtg | aaggatttga | gctgctcaat | tcaggacaaa | gcattcgaac | 120 |
| ggtcctgacg | ttttgagatc | caaagtggca | ggaggtctgt | gttgtcatgg | tgaactggag | 180 |
| tttctcttgt | gagagttccc | tcatctgaaa | tcatgtatct | gtctcacaaa | tacaagcata | 240 |
| agtagaagat | ttgttgaaga | catagaaccc | ttataaagaa | ttattaacct | ttataaacat | 300 |
| ttaaagtctt | gtgagcacct | gggaattagt | ataataacaa | tgttnatatt | tttgatttac | 360 |
| attttgtaag | gctataattg | tatcttttaa | gaaaacatac | cttggatttc | tatgttgaaa | 420 |
| tggagatttt | taagagtttt | aaccagctgc | tgcagatata | ttactcaaaa | cagatatagc | 480 |
| gtataaagat | atagtaaatg | catctcctag | agtaatattc | acttaacaca | ttggaaacta | 540 |
| ttatttttta | gatttgaata | tnaatgttat | tttttaaaca | cttgttatga | gttacttggg | 600 |
| attacatttt | gaaatcagtt | cattccatga | tgcanattac | tgggattaga | ttaagaaaga | 660 |
| cggaaaa | | | | | | 667 |

<210> SEQ ID NO 100
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 100

| | | | | | |
|---|---|---|---|---|---|
| gttttgtttg | taagatgatc | acagtcatgt | tacactgatc | taaaggacat | atatataacc | 60 |
| ctttaaaaaa | aaaatcactg | cctcattctt | atttcaagat | gaatttctat | acagactaga | 120 |
| tgttttctg | aagatcaatt | agacattttg | aaaatgattt | aaagtgtttt | ccttaatgtt | 180 |
| ctctgaaaac | aagtttcttt | tgtagtttta | accaaaaaag | tgcccttttt | gtcactggat | 240 |
| tctcctagca | ttcatgattt | ttttttcata | caatgaaatt | aaaattgcta | aaatcatgga | 300 |
| ctggctttct | ggttggattt | caggtaagat | gtgtttaagg | ccagagcttt | tctcagtatt | 360 |
| tgattttttt | ccccaatatt | tgattttta | aaaatataca | catnggtgct | gcatttatat | 420 |
| ctgctggttt | aaaattctgt | catatttcac | ttctagccctt | ttagttatgg | caaatcatat | 480 |
| tttactttta | cttaaagcat | ttggtnattt | ggantatctg | gttctannct | aaaaaaanta | 540 |
| attctatnaa | ttgaatttt | ggtactcnnc | catatttgga | tcc | | 583 |

<210> SEQ ID NO 101
<211> LENGTH: 592
<212> TYPE: DNA
<213> ORGANISM: Homo sapien
<220> FEATURE:
<221> NAME/KEY: misc_feature
<222> LOCATION: (1)...(592)
<223> OTHER INFORMATION: n = A,T,C or G

<400> SEQUENCE: 101

```
gtggagacgt acaaagagca gccgctcaag acacctggga agaaaaagaa aggcaagccc      60
gggaaacgca aggagcagga aaagaaaaaa cggcgaactc gctctgcctg gttagactct     120
ggagtgactg ggagtgggct agaaggggac cacctgtctg acacctccac aacgtcgctg     180
gagctcgatt cacggaggca ttgaaatttt cagcaganac cttccaagga catattgcag     240
gattctgtaa tagtgaacat atggaaagta ttagaaatat ttattgtctg taaatactgt     300
aaatgcattg gaataaaact gtctccccca ttgctctatg aaactgcaca ttggtcattg     360
tgaatatttt ttttttgcc aaggctaatc caattattat tatcacattt accataattt      420
attttgtcca ttgatgtatt tattttgtaa atgtatcttg gtgctgctga atttctatat     480
tttttgtaca taatgcnttt anatatacct atcaagtttg ttgataaatg acncaatgaa     540
gtgncncnan ttggnggttg aatttaatga atgcctaatt ttattatccc aa             592
```

<210> SEQ ID NO 102
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 102

```
cgtcctaagc acttagacta catcagggaa gaacacagac cacatccctg tcctcatgcg      60
gcttatgttt tctggaagaa agtggagacc nagtccttgg ctttagggct ccccggctgg     120
gggctgtgca ntccggtcag ggcgggaagg gaaatgcacc gctgcatgtg aacttacagc     180
ccaggcggat gccccttccc ttagcactac ctggcctcct gcatcccctc gcctcatgtt     240
cctcccacct tcaaanaatg aanaacccca tgggcccagc cccttgccct ggggaaccaa     300
ggcagccttc caaaactcag gggctgaagc anactattag ggcaggggct gactttgggt     360
gacactgccc attccctctc agggcagctc angtcacccn ggnctcttga acccagcctg     420
ttcctttgaa aagggcaaa actgaaaagg gcttttccta naaaagaaa aaccagggaa       480 ctttgccagg gcttcnntnt taccaaaacn ncttctcnng gatttttaat tccccattng     540
gcctccactt accnggggcn atgccccaaa attaanaatt tcccatc                   587
```

<210> SEQ ID NO 103
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 103

```
anaggactgg ccctacntgc tctctctcgt cctacctatc aatgcccaac atggcagaac      60
ctgcanccct tggncactgc anatggaaac ctctcagtgt cttgacatca ccctaccent     120 gcggtgggtc tccaccacaa ccactttgac tctgtggtcc ctgnanggtg gnttctcctg     180
actggcagga tggaccttan ccacatatc cctctgttcc ctctgctnag anaaagaatt      240
cccttaacat gatataatcc acccatgcaa ntngctactg gcccagctac catttaccat     300
ttgcctacag aatttcattc agtctacact ttggcattct ctctggcgat agagtgtggc     360
tgggctgacc gcaaaaggtg ccttacacac tggcccccac cctcaaccgt tgacncatca    420
```

```
gangcttgcc tcctccttct gattnncccc catgttggat atcagggtgc tcnagggatt    480
ggaaaagaaa caaaac                                                    496
```

<210> SEQ ID NO 104
<211> LENGTH: 575
<212> TYPE: DNA
<213> ORGANISM: Homo sapien
<220> FEATURE:
<221> NAME/KEY: misc_feature
<222> LOCATION: (1)...(575)
<223> OTHER INFORMATION: n = A,T,C or G

<400> SEQUENCE: 104

```
gcacctgctc tcaatccnnc tctcaccatg atcctccgcc tgcanaaact cctctgccaa     60
ctatggangt ggtttcnggg gtggctcttg ccaactggga agaagccgtg gtgtctctac    120
ctgttcaact cngtttgtgt ctgggggatc aactngggc tatggaagcg gctnaactgt    180
tgttttggtg aagggctgg taattggctt tgggaagtng cttatngaag ttggcctngg    240
gaagttgcta ttgaaagtng ccntggaagt ngntttggtg gggggttttg ctggtggcct    300
ttgttnaatt tgggtgcttt gtnaatggcg gcccctcnc ctgggcaatg aaaaaaatca    360
ccnatgcngn aaacctcnac nnaacagcct gggcttccct cacctcgaaa aagttgctc    420 ccccccaaa aaaggncaan cccctcaann tggaangttg aaaaaatcct cgaatgggga    480
ncccnaaaac aaaaanccc ccntttcccn gnaanggggg aaataccncc cccccactta    540
cnaaaaccct tntaaaaaac cccccgggaa aaaaa                              575
```

<210> SEQ ID NO 105
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 105

```
cactagtagg atagaaacac tgtgtcccga gagtaaggag agaagctact attgattaga     60
gcctaaccca ggttaactgc aagaagaggc gggatacttt cagctttcca tgtaactgta    120
tgcataaagc caatgtagtc cagtttctaa gatcatgttc caagctaact gaatcccact    180
tcaatacaca ctcatgaact cctgatgaa caataacagg cccaagcctg tggtatgatg    240
tgcacacttg ctagactcan aaaaatact actctcataa atgggtggga gtattttggt    300
gacaacctac tttgcttggc tgagtgaagg aatgatattc atatattcat ttattccatg    360
gacatttagt tagtgctttt tatataccag gcatgatgct gagtgacact cttgtgtata    420
tttccaaatt tttgtacagt cgctgcacat atttgaaatc atatattaag acttccaaaa    480
aatgaagtcc ctggttttc atggcaactt gatcagtaaa ggattcncct ctgtttggta    540
cttaaaacat ctactatatn gttnanatga aattccttt cccncctcc cgaaaaaana    600 aagtggtggg gaaaaaaaa                                                 619
```

<210> SEQ ID NO 106
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 106

```
cattggtnct ttcatttgct ntggaagtgt nnatctctaa cagtggacaa agttcccngt      60
gccttaaact ctgtnacact tttgggaant gaaaanttng tantatgata ggttattctg     120
angtanagat gttctggata ccattanatn tgcccccngt gtcagaggct catattgtgt     180
tatgtaaatg gtatntcatt cgctactatn antcaattng aaatanggtc tttgggttat     240
gaatantnng cagcncanct nanangctgt ctgtngtatt cattgtggtc atagcacctc     300
acancattgt aacctcnatc nagtgagaca nactagnaan ttcctagtga tggctcanga    360
ttccaaatgg nctcatntcn aatgtttaaa agttanttaa gtgtaagaaa tacagactgg    420
atgttccacc aactagtacc tgtaatgacn ggcctgtccc aacacatctc ccttttccat    480
gactgtggta ncccgcatcg gaaaaa                                          506
```

<210> SEQ ID NO 107
<211> LENGTH: 452
<212> TYPE: DNA
<213> ORGANISM: Homo sapien
<220> FEATURE:
<221> NAME/KEY: misc_feature
<222> LOCATION: (1)...(452)
<223> OTHER INFORMATION: n = A,T,C or G

<400> SEQUENCE: 107

```
gttgagtctg tactaaacag taagatatct caatgaacca taaattcaac tttgtaaaaa     60
tcttttgaag catagataat attgttggt aaatgtttct tttgtttggt aaatgtttct    120
tttaaagacc ctcctattct ataaaactct gcatgtagag gcttgtttac ctttctctct    180
ctaaggttta caataggagt ggtgatttga aaaatataaa attatgagat tggttttcct    240
gtggcataaa ttgcatcact gtatcatttt cttttttaac cggtaagant ttcagttttgt   300
tggaaagtaa ctgtganaac ccagtttccc gtccatctcc cttagggact acccatagaa    360
catgaaaagg tccccacnga agcaagaaga taagtctttc atggctgctg gttgcttaaa    420
ccactttaaa accaaaaaat tccccttgga aa                                   452
```

<210> SEQ ID NO 108
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 108

```
atcttcttcc cttaattagt tnttatttat ntattaaatt ttattgcatg tcctggcaaa     60
caaaagaga ttgtagattg gcttctggct ccccaaaagc ccataacaga aagtaccaca    120
agaccncaac tgaagcttaa aaaatctatc acatgtataa taccttnga agaacattaa    180
tanagcatat aaaactttta acatntgctt aatgttgtnc aattataaaa ntaatngaaa   240
aaaatgtccc tttaacatnc aatatcccac atagtgttat ttnagggat taccnngnaa   300
naaaaaaagg gtagaaggga tttaatgaaa actctgccttn ccatttctgt ttanaaacgt    360
ctccagaaca aaaacttntc aantctttca gctaaccgca tttgagctna ggccactcaa    420
aaactccatt agcccacttt tctaanggtc tctanagctt actaanccttt ttgaccccttt   480
accctggnta ctcctgccct ca                                              502
```

<210> SEQ ID NO 109
<211> LENGTH: 1308
<212> TYPE: DNA
<213> ORGANISM: Homo sapien

<400> SEQUENCE: 109

```
acccgaggtc tcgctaaaat catcatggat tcacttggcg ccgtcagcac tcgacttggg      60
tttgatcttt tcaaagagct gaagaaaaca aatgatggca acatcttctt ttcccctgtg     120
ggcatcttga ctgcaattgg catggtcctc ctggggaccc gaggagccac cgcttcccag     180
ttggaggagg tgtttcactc tgaaaaagag acgaagagct caagaataaa ggctgaagaa     240
aaagaggtga ttgagaacac agaagcagta catcaacaat tccaaaagtt tttgactgaa     300
ataagcaaac tcactaatga ttatgaactg aacataacca acaggctgtt tggagaaaaa     360
acatacctct tccttcaaaa atacttagat tatgttgaaa aatattatca tgcatctctg     420
gaacctgttg attttgtaaa tgcagccgat gaaagtcgaa agaagattaa ttcctgggtt     480
gaaagcaaaa caaatgaaaa aatcaaggac ttgttcccag atggctctat tagtagctct     540
accaagctgg tgctggtgaa catggtttat tttaaagggc aatgggacag ggagtttaag     600
aaagaaaata ctaaggaaga gaaattttgg atgaataaga gcacaagtaa atctgtacag     660
atgatgacac agagccattc ctttagcttc actttcctgg aggacttgca ggccaaaatt     720
ctagggattc catataaaaa caacgaccta agcatgtttg tgcttctgcc caacgacatc     780
gatggcctgg agaagataat agataaaata agtcctgaga aattggtaga gtggactagt     840
ccagggcata tggaagaaag aaaggtgaat ctgcacttgc cccggtttga ggtggaggac     900
agttacgatc tagaggcggt cctggctgcc atggggatgg cgatgccttc agtgagcac      960
aaagccgact actcgggaat gtcgtcaggc tccgggttgt acgcccagaa gttcctgcac    1020
agttcctttg tggcagtaac tgaggaaggc accgaggctg cagctgccac tggcataggc    1080
tttactgtca catccgcccc aggtcatgaa atgttcact gcaatcatcc cttcctgttc     1140
ttcatcaggc acaatgaatc caacagcatc ctcttcttcg gcagattttc ttctccttaa    1200
gatgatcgtt gccatggcat tgctgctttt agcaaaaaac aactaccagt gttactcata    1260
tgattatgaa aatcgtccat tctttttaaat ggtggctcac ttgcattt                1308
```

<210> SEQ ID NO 110
<211> LENGTH: 391
<212> TYPE: PRT
<213> ORGANISM: Homo sapien

<400> SEQUENCE: 110

```
Met Asp Ser Leu Gly Ala Val Ser Thr Arg Leu Gly Phe Asp Leu Phe
  1               5                  10                  15

Lys Glu Leu Lys Lys Thr Asn Asp Gly Asn Ile Phe Phe Ser Pro Val
             20                  25                  30

Gly Ile Leu Thr Ala Ile Gly Met Val Leu Leu Gly Thr Arg Gly Ala
         35                  40                  45

Thr Ala Ser Gln Leu Glu Glu Val Phe His Ser Glu Lys Glu Thr Lys
     50                  55                  60

Ser Ser Arg Ile Lys Ala Glu Glu Lys Glu Val Ile Glu Asn Thr Glu
 65                  70                  75                  80

Ala Val His Gln Gln Phe Gln Lys Phe Leu Thr Glu Ile Ser Lys Leu
                 85                  90                  95

Thr Asn Asp Tyr Glu Leu Asn Ile Thr Asn Arg Leu Phe Gly Glu Lys
```

```
                100                 105                 110
Thr Tyr Leu Phe Leu Gln Lys Tyr Leu Asp Tyr Val Glu Lys Tyr Tyr
            115                 120                 125

His Ala Ser Leu Glu Pro Val Asp Phe Val Asn Ala Ala Asp Glu Ser
    130                 135                 140

Arg Lys Lys Ile Asn Ser Trp Val Glu Ser Lys Thr Asn Glu Lys Ile
145                 150                 155                 160

Lys Asp Leu Phe Pro Asp Gly Ser Ile Ser Ser Thr Lys Leu Val
                165                 170                 175

Leu Val Asn Met Val Tyr Phe Lys Gly Gln Trp Asp Arg Glu Phe Lys
                180                 185                 190

Lys Glu Asn Thr Lys Glu Glu Lys Phe Trp Met Asn Lys Ser Thr Ser
            195                 200                 205

Lys Ser Val Gln Met Met Thr Gln Ser His Ser Phe Ser Phe Thr Phe
    210                 215                 220

Leu Glu Asp Leu Gln Ala Lys Ile Leu Gly Ile Pro Tyr Lys Asn Asn
225                 230                 235                 240

Asp Leu Ser Met Phe Val Leu Leu Pro Asn Asp Ile Asp Gly Leu Glu
                245                 250                 255

Lys Ile Ile Asp Lys Ile Ser Pro Glu Lys Leu Val Glu Trp Thr Ser
                260                 265                 270

Pro Gly His Met Glu Glu Arg Lys Val Asn Leu His Leu Pro Arg Phe
            275                 280                 285

Glu Val Glu Asp Ser Tyr Asp Leu Glu Ala Val Leu Ala Ala Met Gly
    290                 295                 300

Met Gly Asp Ala Phe Ser Glu His Lys Ala Asp Tyr Ser Gly Met Ser
305                 310                 315                 320

Ser Gly Ser Gly Leu Tyr Ala Gln Lys Phe Leu His Ser Ser Phe Val
                325                 330                 335

Ala Val Thr Glu Glu Gly Thr Glu Ala Ala Ala Thr Gly Ile Gly
                340                 345                 350

Phe Thr Val Thr Ser Ala Pro Gly His Glu Asn Val His Cys Asn His
                355                 360                 365

Pro Phe Leu Phe Phe Ile Arg His Asn Glu Ser Asn Ser Ile Leu Phe
    370                 375                 380

Phe Gly Arg Phe Ser Ser Pro
385                 390

<210> SEQ ID NO 111
<211> LENGTH: 1419
<212> TYPE: DNA
<213> ORGANISM: Homo sapien

<400> SEQUENCE: 111
ggagaactat aaattaagga tcccagctac ttaattgact tatgcttcct agttcgttgc      60
ccagccacca ccgtctctcc aaaaacccga ggtctcgcta aaatcatcat ggattcactt    120
ggcgccgtca gcactcgact tgggtttgat cttttcaaag agctgaagaa aacaaatgat    180
ggcaacatct tcttttcccc tgtgggcatc ttgactgcaa ttggcatggt cctcctgggg    240
acccgaggag ccaccgcttc ccagttggag gaggtgtttc actctgaaaa agagacgaag    300
agctcaagaa taaaggctga agaaaaagag gtggtaagaa taaaggctga aggaaaagag    360
attgagaaca cagaagcagt acatcaacaa ttccaaaagt ttttgactga ataagcaaa    420 ctcactaatg attatgaact gaacataacc aacaggctgt ttggagaaaa aacataccctc   480
```

```
ttccttcaaa aatacttaga ttatgttgaa aatattatc atgcatctct ggaacctgtt    540
gattttgtaa atgcagccga tgaaagtcga agaagatta attcctgggt tgaaagcaaa    600
acaaatgaaa aaatcaagga cttgttccca gatggctcta ttagtagctc taccaagctg    660
gtgctggtga acatggttta ttttaaaggg caatgggaca gggagtttaa gaaagaaaat    720
actaaggaag agaaattttg gatgaataag agcacaagta aatctgtaca gatgatgaca    780
cagagccatt cctttagctt cactttcctg gaggacttgc aggccaaaat tctagggatt    840
ccatataaaa acaacgacct aagcatgttt gtgcttctgc ccaacgacat cgatggcctg    900
gagaagataa tagataaaat aagtcctgag aaattggtag agtggactag tccagggcat    960
atggaagaaa gaaaggtgaa tctgcacttg ccccggtttg aggtggagga cagttacgat   1020
ctagaggcgg tcctggctgc catggggatg ggcgatgcct tcagtgagca aaagccgac    1080 tactcgggaa tgtcgtcagg ctccggggttg tacgcccaga agttcctgca cagttccttt   1140
gtggcagtaa ctgaggaagg caccgaggct gcagctgcca ctggcatagg ctttactgtc   1200
acatccgccc caggtcatga aaatgttcac tgcaatcatc ccttcctgtt cttcatcagg   1260
cacaatgaat ccaacagcat cctcttcttc ggcagatttt cttctcctta agatgatcgt   1320
tgccatggca ttgctgcttt tagcaaaaaa caactaccag tgttactcat atgattatga   1380
aaatcgtcca ttcttttaaa tggtggctca cttgcattt                         1419
```

<210> SEQ ID NO 112
<211> LENGTH: 400
<212> TYPE: PRT
<213> ORGANISM: Homo sapien

<400> SEQUENCE: 112

```
Met Asp Ser Leu Gly Ala Val Ser Thr Arg Leu Gly Phe Asp Leu Phe
 1               5                  10                  15

Lys Glu Leu Lys Lys Thr Asn Asp Gly Asn Ile Phe Phe Ser Pro Val
            20                  25                  30

Gly Ile Leu Thr Ala Ile Gly Met Val Leu Leu Gly Thr Arg Gly Ala
        35                  40                  45

Thr Ala Ser Gln Leu Glu Glu Val Phe His Ser Glu Lys Glu Thr Lys
    50                  55                  60

Ser Ser Arg Ile Lys Ala Glu Lys Glu Val Val Arg Ile Lys Ala
65                  70                  75                  80

Glu Gly Lys Glu Ile Glu Asn Thr Glu Ala Val His Gln Gln Phe Gln
                85                  90                  95

Lys Phe Leu Thr Glu Ile Ser Lys Leu Thr Asn Asp Tyr Glu Leu Asn
            100                 105                 110

Ile Thr Asn Arg Leu Phe Gly Glu Lys Thr Tyr Leu Phe Leu Gln Lys
        115                 120                 125

Tyr Leu Asp Tyr Val Glu Lys Tyr Tyr His Ala Ser Leu Glu Pro Val
    130                 135                 140

Asp Phe Val Asn Ala Ala Asp Glu Ser Arg Lys Lys Ile Asn Ser Trp
145                 150                 155                 160

Val Glu Ser Lys Thr Asn Glu Lys Ile Lys Asp Leu Phe Pro Asp Gly
                165                 170                 175

Ser Ile Ser Ser Ser Thr Lys Leu Val Leu Val Asn Met Val Tyr Phe
            180                 185                 190

Lys Gly Gln Trp Asp Arg Glu Phe Lys Lys Glu Asn Thr Lys Glu Glu
        195                 200                 205
```

```
Lys Phe Trp Met Asn Lys Ser Thr Ser Lys Ser Val Gln Met Met Thr
    210                 215                 220
Gln Ser His Ser Phe Ser Phe Thr Phe Leu Glu Asp Leu Gln Ala Lys
225                 230                 235                 240
Ile Leu Gly Ile Pro Tyr Lys Asn Asn Asp Leu Ser Met Phe Val Leu
                245                 250                 255
Leu Pro Asn Asp Ile Asp Gly Leu Glu Lys Ile Ile Asp Lys Ile Ser
            260                 265                 270
Pro Glu Lys Leu Val Glu Trp Thr Ser Pro Gly His Met Glu Glu Arg
        275                 280                 285
Lys Val Asn Leu His Leu Pro Arg Phe Glu Val Glu Asp Ser Tyr Asp
290                 295                 300
Leu Glu Ala Val Leu Ala Ala Met Gly Met Gly Asp Ala Phe Ser Glu
305                 310                 315                 320
His Lys Ala Asp Tyr Ser Gly Met Ser Ser Gly Ser Gly Leu Tyr Ala
                325                 330                 335
Gln Lys Phe Leu His Ser Ser Phe Val Ala Val Thr Glu Glu Gly Thr
            340                 345                 350
Glu Ala Ala Ala Thr Gly Ile Gly Phe Thr Val Thr Ser Ala Pro
        355                 360                 365
Gly His Glu Asn Val His Cys Asn His Pro Phe Leu Phe Ile Arg
370                 375                 380
His Asn Glu Ser Asn Ser Ile Leu Phe Phe Gly Arg Phe Ser Ser Pro
385                 390                 395                 400
```

<210> SEQ ID NO 113
<211> LENGTH: 957
<212> TYPE: DNA
<213> ORGANISM: Homo sapien

<400> SEQUENCE: 113

```
ctcgaccttc tctgcacagc ggatgaaccc tgagcagctg aagaccagaa aagccactat    60
gactttctgc ttaattcagg agcttacagg attcttcaaa gagtgtgtcc agcatccttt   120
gaaacatgag ttcttaccag cagaagcaga cctttacccc accacctcag cttcaacagc   180
agcaggtgaa acaacccagc cagcctccac ctcaggaaat atttgttccc acaaccaagg   240
agccatgcca ctcaaaggtt ccacaacctg gaaacacaaa gattccgaga ccaggctgta   300
ccaaggtccc tgagccaggc tgtaccaagg tccctgagcc aggttgtacc aaggtccctg   360
agccaggatg taccaaggtc cctgagccag gttgtaccaa ggtccctgag ccaggctaca   420
ccaaggtccc tgagccaggc agcatcaagg tccctgacca aggcttcatc aagtttcctg   480
agccaggtgc catcaaagtt cctgagcaag atacaccaa agttcctgtg ccaggctaca    540
caaaggtacc agagccatgt ccttcaacgg tcactccagg cccagctcag cagaagacca   600
agcagaagta atttggtgca cagacaagcc cttgagaagc caaccaccag atgctggaca   660
ccctcttccc atctgtttct gtgtcttaat tgtctgtaga ccttgtaatc agtacattct   720
cacccccaagc catagtctct ctcttatttg tatcctaaaa atacggtact ataaagcttt   780
tgttcacaca cactctgaag aatcctgtaa gcccctgaat taagcagaaa gtcttcatgg   840
cttttctggt cttcggctgc tcagggttca tctgaagatt cgaatgaaaa gaaatgcatg   900
tttcctgctc tgccctcatt aaattgcttt taattccaaa aaaaaaaaaa aaaaaaa      957
```

<210> SEQ ID NO 114

```
<211> LENGTH: 161
<212> TYPE: PRT
<213> ORGANISM: Homo sapien

<400> SEQUENCE: 114

Met Ser Ser Tyr Gln Gln Lys Gln Thr Phe Thr Pro Pro Gln Leu
1               5                   10                  15

Gln Gln Gln Gln Val Lys Gln Pro Ser Gln Pro Pro Gln Glu Ile
            20                  25                  30

Phe Val Pro Thr Thr Lys Glu Pro Cys His Ser Lys Val Pro Gln Pro
                35                  40                  45

Gly Asn Thr Lys Ile Pro Glu Pro Gly Cys Thr Lys Val Pro Glu Pro
            50                  55                  60

Gly Cys Thr Lys Val Pro Glu Pro Gly Cys Thr Lys Val Pro Glu Pro
65                  70                  75                  80

Gly Cys Thr Lys Val Pro Glu Pro Gly Cys Thr Lys Val Pro Glu Pro
                85                  90                  95

Gly Tyr Thr Lys Val Pro Glu Pro Gly Ser Ile Lys Val Pro Asp Gln
                100                 105                 110

Gly Phe Ile Lys Phe Pro Glu Pro Gly Ala Ile Lys Val Pro Glu Gln
            115                 120                 125

Gly Tyr Thr Lys Val Pro Val Pro Gly Tyr Thr Lys Val Pro Glu Pro
            130                 135                 140

Cys Pro Ser Thr Val Thr Pro Gly Pro Ala Gln Gln Lys Thr Lys Gln
145                 150                 155                 160

Lys

<210> SEQ ID NO 115
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 115
cattggtnct ttcatttgct ntggaagtgt nnatctctaa cagtggacaa agttcccngt      60
gccttaaact ctgtnacact tttgggaant gaaaanttng tantatgata ggttattctg     120
angtanagat gttctggata ccattanatn tgcccccngt gtcagaggct catattgtgt     180
tatgtaaatg gtatntcatt cgctactatn antcaattng aaatanggtc tttgggttat    240
gaatantnng cagcncanct nanangctgt ctgtngtatt cattgtggtc atagcacctc    300
acancattgt aacctcnatc nagtgagaca nactagnaan ttcctagtga tggctcanga    360
ttccaaatgg nctcatntcn aatgtttaaa agttanttaa gtgtaagaaa tacagactgg    420
atgttccacc aactagtacc tgtaatgacn ggcctgtccc aacacatctc ccttttccat    480
gactgtggta ncccgcatcg aaaaa                                          506

<210> SEQ ID NO 116
<211> LENGTH: 3079
<212> TYPE: DNA
<213> ORGANISM: Homo sapien

<400> SEQUENCE: 116
ggatccccgg gtttcctaaa ccccccacag agtcctgccc aggccaaaga gcaaggaaaa      60
ggtcaaaggg cagaaaaaat gctgagttag gaggagctat ggaaggataa acctggcctt    120
```

-continued

```
aaagaggtca aagtggttta tagggggcgc tgagggcttc ccacattctc tggcctaaac      180
cttgcaggca gatctgccca gtgggctctg ggatagctgt gccttccctta acaaaaaaat     240 tgtgcacaaa aggatgaaac tctatttttcc ctctagcaca taaccaagaa tataaggcta    300
cagattgcct ttcccagagg gaaaaccctg cagcaacctg ctgcctggaa aagtgtaaga    360
gcagatcact ggggaatcgt ttgcccccccg ctgatggaca gcttcccaa gctccaaggg    420 caggtgctca gcatgtaccg tactgggatg ttgtcaata ctcctggtcc tgtaagagtc     480
ccaggacact gccatgccaa tgcccccctca gttcctggca tccttttttgg gctgctcaca    540 gccccagcct ctatggtgaa gacatacttg ctagcagcgt caccaacttg ttgccaagag     600
atcagtgctc gaaggcaagg ttatttctaa ctgagcagag cctgccagga agaaagcgtt     660
tgcaccccac accactgtgc aggtgtgacc ggtgagctca cagctgcccc ccaggcatgc     720
ccagcccact taatcatcac agctcgacag ctctctcgcc cagcccagtt ctggaaggga     780
taaaaagggg catcaccgtt cctgggtaac agagccacct tctgcgtcct gctgagctct    840
gttctctcca gcacctccca acccactagt gcctggttct cttgctccac caggaacaag     900
ccaccatgtc tcgccagtca agtgtgtctt ccggagcggg gggcagtcgt agcttcagca    960
ccgcctctgc catcaccccg tctgtctccc gcaccagctt cacctccgtg tcccggtccg    1020
ggggtggcgg tggtggtggc ttcggcaggg tcagccttgc gggtgcttgt ggagtgggtg    1080
gctatggcag ccggagcctc tacaacctgg ggggctccaa gaggatatcc atcagcacta    1140
gtggtggcag cttcaggaac cggtttggtg ctggtgctgg aggcggctat ggctttggag    1200
gtggtgccga tagtggattt ggtttcggcg gtggagctgg tggtggcttt gggctcggtg    1260
gcggagctgg cttttggaggt ggcttcggtg gccctggctt tcctgtctgc cctcctggag    1320
gtatccaaga ggtcactgtc aaccagagtc tcctgactcc cctcaacctg caaatcgacc    1380
ccagcatcca gagggtgagg accgaggagc gcgagcagat caagaccctc aacaataagt    1440
ttgcctcctt catcgacaag gtgcggttcc tggagcagca gaacaaggtt ctggaaacaa    1500
agtggaccct gctgcaggag cagggcacca agactgtgag gcagaacctg agccgttgt    1560 tcgagcagta catcaacaac ctcaggaggc agctggacag catcgtgggg gaacggggcc    1620
gcctggactc agagctgaga aacatgcagg acctggtgga agacttcaag aacaagtatg    1680
aggatgaaat caacaagcgt accactgctg agaatgagtt tgtgatgctg aagaaggatg    1740
tagatgctgc ctacatgaac aaggtggagc tgaggccaa ggttgatgca ctgatggatg    1800
agattaactt catgaagatg ttctttgatg cggagctgtc ccagatgcag acgcatgtct    1860
ctgacacctc agtggtcctc tccatggaca acaaccgcaa cctggacctg gatagcatca    1920
tcgctgaggt caaggcccag tatgaggaga ttgccaaccg cagccggaca gaagccgagt    1980
cctggtatca gaccaagtat gaggagctgc agcagacagc tggccggcat ggcgatgacc    2040
tccgcaacac caagcatgag atctctgaga tgaaccggat gatccagagg ctgagagccg    2100
agattgacaa tgtcaagaaa cagtgcgcca atctgcagaa cgccattgcg gatgccgagc    2160
agcgtgggga gctggccctc aaggatgcca ggaacaagct ggccgagctg gaggaggccc    2220
tgcagaaggc caagcaggac atggcccggc tgctgcgtga gtaccaggag ctcatgaaca    2280
ccaagctggc cctggacgtg gagatcgcca cttaccgcaa gctgctggag ggcgaggaat    2340
gcagactcag tggagaagga gttggaccag tcaacatctc tgttgtcaca agcagtgttt    2400
cctctggata tggcagtggc agtggctatg gcggtggcct cggtggaggt cttggcggcg    2460
```

-continued

```
gcctcggtgg aggtcttgcc ggaggtagca gtggaagcta ctactccagc agcagtgggg    2520
gtgtcggcct aggtggtggg ctcagtgtgg ggggctctgg cttcagtgca agcagtagcc    2580
gagggctggg ggtgggcttt ggcagtgncg ggggtagcag ctccagcgtc aaatttgtct    2640
ccaccacctc ctcctcccgg aagagcttca agagctaaga acctgctgca agtcactgcc    2700
ttccaagtgc agcaacccag cccatggaga ttgcctcttc taggcagttg ctcaagccat    2760 gtttatcct tttctggaga gtagtctaga ccaagccaat tgcagaacca cattctttgg    2820
ttcccaggag agccccattc ccagcccctg gtctcccgtg ccgcagttct atattctgct    2880
tcaaatcagc cttcaggttt cccacagcat ggcccctgct gacacgagaa cccaaagttt    2940
tcccaaatct aaatcatcaa aacagaatcc cacccccaat cccaaatttt gttttggttc    3000
taactacctc cagaatgtgt tcaataaaat gttttataat ataagctggt gtgcagaatt    3060
gttttttttt tctacccaa                                                 3079
```

<210> SEQ ID NO 117
<211> LENGTH: 6921
<212> TYPE: DNA
<213> ORGANISM: Homo sapien

<400> SEQUENCE: 117

```
gaattctgac tgtccactca aaacttctat tccgatcaaa gctatctgtg actacagaca      60
aattgagata accatttaca aagacgatga atgtgttttg gcgaataact ctcatcgtgc     120
taaatggaag gtcattagtc ctactgggaa tgaggctatg gtcccatctg tgtgcttcac     180
cgttcctcca ccaaacaaag aagcggtgga ccttgccaac agaattgagc aacagtatca     240
gaatgtcctg actctttggc atgagtctca cataaacatg aagagtgtag tatcctggca     300
ttatctcatc aatgaaattg atagaattcg agctagcaat gtggcttcaa taagacaat     360 gctacctggt gaacatcagc aagttctaag taatctacaa tctcgttttg aagattttct     420
ggaagatagc caggaatccc aagtcttttc aggctcagat ataacacaac tggaaaagga     480
ggttaatgta tgtaagcagt attatcaaga acttcttaaa tctgcagaaa gagaggagca     540
agaggaatca gtttataatc tctacatctc tgaagttcga acattagac ttcggttaga     600 gaactgtgaa gatcggctga ttagacagat tcgaactccc ctggaaagag atgatttgca     660
tgaaagtgtg ttcagaatca cagaacagga gaaactaaag aaagagctgg aacgacttaa     720
agatgatttg ggaacaatca caaataagtg tgaggagttt ttcagtcaag cagcagcctc     780
ttcatcagtc cctacccctac gatcagagct taatgtggtc cttcagaaca tgaaccaagt     840
ctattctatg tcttccactt acatagataa gttgaaaact gttaacttgg tgttaaaaaa     900
cactcaagct gcagaagccc tcgtaaaact ctatgaaact aaactgtgtg aagaagaagc     960
agttatagct gacaagaata atattgagaa tctaataagt actttaaagc aatggagatc    1020
tgaagtagat gaaagagac aggtattcca tgccttagag gatgagttgc agaaagctaa    1080
agccatcagt gatgaaatgt ttaaaacgta taagaacgg gaccttgatt ttgactggca    1140
caaagaaaaa gcagatcaat tagttgaaag gtggcaaaat gttcatgtgc agattgacaa    1200
caggttacgg gacttagagg gcattggcaa atcactgaag tactacagag acacttacca    1260
tcctttagat gattggatcc agcaggttga aactactcag agaaagattc aggaaaatca    1320
gcctgaaaat agtaaaaccc tagccacaca gttgaatcaa cagaagatgc tggtgtccga    1380
aatagaaatg aaacagagca aaatggacga gtgtcaaaaa tatgcagaac agtactcagc    1440
tacagtgaag gactatgaat tacaaacaat gacctaccgg gccatggtag attcacaaca    1500
```

-continued

```
aaaatctcca gtgaaacgcc gaagaatgca gagttcagca gatctcatta ttcaagagtt   1560
catggaccta aggactcgat atactgccct ggtcactctc atgacacaat atattaaatt   1620
tgctggtgat tcattgaaga ggctggaaga ggaggagatt aaaaggtgta aggagacttc   1680
tgaacatggg gcatattcag atctgcttca gcgtcagaag gcaacagtgc ttgagaatag   1740
caaacttaca ggaaagataa gtgagttgga agaatggta gctgaactaa agaaacaaaa    1800
gtcccgagta gaggaagaac ttccgaaggt cagggaggct gcagaaaatg aattgagaaa   1860
gcagcagaga aatgtagaag atatctctct gcagaagata agggctgaaa gtgaagccaa   1920
gcagtaccgc agggaacttg aaaccattgt gagagagaag gaagccgctg aaagagaact   1980
ggagcgggtg aggcagctca ccatagaggc cgaggctaaa agagctgccg tggaagagaa   2040
cctcctgaat tttcgcaatc agttggagga aaacaccttt accagacgaa cactggaaga   2100
tcatcttaaa agaaagatt taagtctcaa tgatttggag caacaaaaaa ataaattaat    2160
ggaagaatta agaagaaga gagacaatga ggaagaactc ttgaagctga taaagcagat    2220
ggaaaaagac cttgcatttc agaaacaggt agcagagaaa cagttgaaag aaaagcagaa   2280
aattgaattg gaagcaagaa gaaaaataac tgaaattcag tatacatgta gagaaaatgc   2340
attgccagtg tgtccgatca cacaggctac atcatgcagg gcagtaacgg gtctccagca   2400
agaacatgac aagcagaaag cagaagaact caaacagcag gtagatgaac taacagctgc   2460
caatagaaag gctgaacaag acatgagaga gctgacatat gaacttaatg ccctccagct   2520
tgaaaaaacg tcatctgagg aaaaggctcg tttgctaaaa gataaactag atgaaacaaa   2580
taatacactc agatgcctta agttggagct ggaaggaag gatcaggcgg agaaagggta    2640
ttctcaacaa ctcagagagc ttggtaggca attgaatcaa accacaggta agctgaaga    2700 agccatgcaa gaagctagtg atctcaagaa aataaagcgc aattatcagt tagaattaga   2760
atctcttaat catgaaaaag ggaaactaca agagaagta gacagaatca aagggcaca    2820 tgctgtagct gagaagaata ttcagcattt aaattcacaa attcattctt ttcgagatga   2880
gaaagaatta gaaagactac aaatctgcca gagaaaatca gatcatctaa aagaacaatt   2940
tgagaaaagc catgagcagt tgcttcaaaa tatcaaagct gaaaagaaa ataatgataa    3000 aatccaaagg ctcaatgaag aattggagaa aagtaatgag tgtgcagaga tgctaaaaca   3060
aaaagtagag gagcttacta ggcagaataa tgaaaccaaa ttaatgatgc agagaattca   3120
ggcagaatca gagaatatag ttttagagaa acaaactatc cagcaaagat gtgaagcact   3180
gaaaattcag gcagatggtt ttaaagatca gctacgcagc acaaatgaac acttgcataa   3240
acagacaaaa acagagcagg attttcaaag aaaaattaaa tgcctagaag aagacctggc   3300
gaaaagtcaa aatttggtaa gtgaatttaa gcaaaagtgt gaccaacaga acattatcat   3360
ccagaatacc aagaaagaag ttagaaatct gaatgcggaa ctgaatgctt ccaaagaaga   3420
gaagcgacgc ggggagcaga agttcagct acaacaagct caggtgcaag agttaaataa    3480
caggttgaaa aaagtacaag acgaattaca cttaaagacc atagaggagc agatgaccca   3540
cagaaagatg gttctgtttc aggaagaatc tggtaaattc aaacaatcag cagaggagtt   3600
tcggaagaag atgaaaaat taatggagtc caaagtcatc actgaaaatg atatttcagg   3660
cattaggctt gactttgtgt ctcttcaaca agaaaactct agagcccaag aaaatgctaa   3720
gctttgtgaa acaaacatta aagaacttga aagacagctt caacagtatc gtgaacaaat   3780
gcagcaaggg cagcacatgg aagcaaatca ttaccaaaaa tgtcagaaac ttgaggatga   3840
```

```
gctgatagcc cagaagcgtg aggttgaaaa cctgaagcaa aaaatggacc aacagatcaa    3900
agagcatgaa catcaattag ttttgctcca gtgtgaaatt caaaaaaaga gcacagccaa    3960
agactgtacc ttcaaaccag attttgagat gacagtgaag gagtgccagc actctggaga    4020
gctgtcctct agaaacactg gacaccttca cccaacaccc agatcccctc tgttgagatg    4080
gactcaagaa ccacagccat tggaagagaa gtggcagcat cgggttgttg aacagatacc    4140
caaagaagtc caattccagc caccagggc tccactcgag aaagagaaaa gccagcagtg    4200
ttactctgag tacttttctc agacaagcac cgagttacga ataacttttg atgagacaaa    4260
ccccattaca agactgtctg aaattgagaa gataagagac caagccctga acaattctag    4320
accacctgtt aggtatcaag ataacgcatg tgaaatggaa ctggtgaagg ttttgacacc    4380
cttagagata gctaagaaca agcagtatga tatgcataca gaagtcacaa cattaaaaca    4440
agaaaagaac ccagttccca gtgctgaaga atggatgctt gaagggtgca gagcatctgg    4500
tggactcaag aaagggggatt tccttaagaa gggcttagaa ccagagacct tccagaactt    4560
tgatggtgat catgcatgtt cagtcaggga tgatgaattt aaattccaag gcttaggca    4620 cactgtgact gccaggcagt tggtggaagc taagcttctg gacatgagaa caattgagca    4680
gctgcgactc ggtcttaaga ctgttgaaga agttcagaaa actcttaaca gtttctgac    4740 gaaagccacc tcaattgcag ggctttacct agaatctaca aaagaaaaga tttcatttgc    4800
ctcagcggcc gagagaatca taatagacaa aatggtggct ttggcatttt tagaagctca    4860
ggctgcaaca ggttttataa ttgatcccat ttcaggtcag acatattctg ttgaagatgc    4920
agttcttaaa ggagttgttg accccgaatt cagaattagg cttcttgagg cagagaaggc    4980
agctgtggga tattcttatt cttctaagac attgtcagtg tttcaagcta tggaaaatag    5040
aatgcttgac agacaaaaag gtaaacatat cttggaagcc cagattgcca gtgggggtgt    5100
cattgaccct gtgagaggca ttcgtgttcc tccagaaatt gctctgcagc aggggttgtt    5160
gaataatgcc atcttacagt ttttacatga gccatccagc aacacaagag ttttccctaa    5220
tcccaataac aagcaagctc tgtattactc agaattactg cgaatgtgtg tatttgatgt    5280
agagtcccaa tgctttctgt ttccatttgg ggagaggaac atttccaatc tcaatgtcaa    5340
gaaaacacat agaatttctg tagtagatac taaaacagga tcagaattga ccgtgtatga    5400
ggctttccag agaaacctga ttgagaaaag tatatatctt gaactttcag ggcagcaata    5460
tcagtggaag gaagctatgt tttttgaatc ctatgggcat tcttctcata tgctgactga    5520
tactaaaaca ggattacact tcaatattaa tgaggctata gagcagggaa caattgacaa    5580
agccttggtc aaaaagtatc aggaaggcct catcacactt acagaacttg ctgattcttt    5640
gctgagccgg ttagtcccca agaaagattt gcacagtcct gttgcagggt attggctgac    5700
tgctagtggg gaaaggatct ctgtactaaa agcctcccgt agaaatttgg ttgatcggat    5760
tactgccctc cgatgccttg aagcccaagt cagtacaggg ggcataattg atcctcttac    5820
tggcaaaaag taccgggtgg ccgaagcttt gcatagaggc ctggttgatg aggggttttgc    5880 ccagcagctg cgacagtgtg aattagtaat cacagggatt ggccatccca tcactaacaa    5940
aatgatgtca gtggtggaag ctgtgaatgc aaatattata aataaggaaa tgggaatccg    6000
atgtttggaa tttcagtact tgacaggagg gttgatagag ccacaggttc actctcggtt    6060
atcaatagaa gaggctctcc aagtaggtat tatagatgtc ctcattgcca caaaactcaa    6120
agatcaaaag tcatatgtca gaaatataat atgccctcag acaaaaagaa agttgacata    6180
taaagaagcc ttagaaaaag ctgattttga tttccacaca ggacttaaac tgttagaagt    6240
```

```
atctgagccc ctgatgacag gaatttctag cctctactat tcttcctaat gggacatgtt      6300
taaataactg tgcaaggggt gatgcaggct ggttcatgcc actttttcag agtatgatga      6360
tatcggctac atatgcagtc tgtgaattat gtaacatact ctatttcttg agggctgcaa      6420
attgctaagt gctcaaaata gagtaagttt taaattgaaa attacataag atttaatgcc      6480
cttcaaatgg tttcatttag ccttgagaat ggttttttga aacttggcca cactaaaatg      6540
tttttttttt tttacgtaga atgtgggata aacttgatga actccaagtt cacagtgtca      6600
tttcttcaga actccccttc attgaatagt gatcatttat taaatgataa attgcactcg      6660
ctgaaagagc acgtcatgaa gcaccatgga atcaaagaga aagatataaa ttcgttccca      6720
cagccttcaa gctgcagtgt tttagattgc ttcaaaaaat gaaaagtttt tgcctttttc      6780
gatatagtga ccttctttgc atattaaaat gtttaccaca atgtcccatt tctagttaag      6840
tcttcgcact tgaaagctaa cattatgaat attatgtgtt ggaggagggg aaggattttc      6900
ttcattctgt gtattttccg g                                                6921
```

```
<210> SEQ ID NO 118
<211> LENGTH: 946
<212> TYPE: DNA
<213> ORGANISM: Homo sapien

<400> SEQUENCE: 118
cttctgactg ggctcaggct gacaggtaga gctcaccatg gcttcttgtg tccttgtccc       60
ctccccatca cagctgtggt gcagtccacc gtctccagtg gctatggcgg tgccagtggt      120
gtcggcagtg gcttaggcct gggtggagga agcagctact cctatggcag tggtcttggc      180
gttggaggtg gcttcagttc cagcagtggc agagccattg ggggtggcct cagctctgtt      240
ggaggcggca gttccaccat caagtacacc accacctcct cctccagcag gaagagctat      300
aagcactaaa gtgcgtctgc tagctctcgg tcccacagtc ctcaggcccc tctctggctg      360
cagagccctc tcctcaggtt gcctgtcctc tcctggcctc cagtcccccc tgctgtccca      420
ggtagagctg gggatgaatg cttagtgccc tcacttcttc tctctctctc tataccatct      480
gagcacccat tgctcaccat cagatcaacc tctgatttta catcatgatg taatcaccac      540
tggagcttca ctgttactaa attattaatt tcttgcctcc agtgttctat ctctgaggct      600
gagcattata agaaaatgac ctctgctcct tttcattgca gaaaattgcc aggggcttat      660
ttcagaacaa cttccactta ctttccactg gctctcaaac tctctaactt ataagtgttg      720
tgaaccccca cccaggcagt atccatgaaa gcacaagtga ctagtcctat gatgtacaaa      780
gcctgtatct ctgtgatgat ttctgtgctc ttcactgttt gcaattgcta aataaagcag      840
atttataata catatattct tttactttgc cttgctttgg ggccaaagtt ttgggcttaa      900
acttttttat ctgataagtg aatagttgtt tttaaaagat aatcta                    946
```

```
<210> SEQ ID NO 119
<211> LENGTH: 8948
<212> TYPE: DNA
<213> ORGANISM: Homo sapien

<400> SEQUENCE: 119
tcaacagccc ctgctccttg ggcccctcca tgccatgccg taatctctcc cacccgacca       60
acaccaacac ccagctccga cgcagctcct ctgcgccctt gccgccctcc gagccacagc      120
tttcctcccg ctcctgcccc cggcccgtcg ccgtctccgc gctcgcagcg gcctcgggag      180
```

-continued

```
ggcccaggta gcgagcagcg acctcgcgag ccttccgcac tcccgcccgg ttccccggcc      240
gtccgcctat ccttggcccc ctccgctttc tccgcgccgg cccgcctcgc ttatgcctcg      300
gcgctgagcc gctctcccga ttgcccgccg acatgagctg caacgaggc tcccacccgc       360 ggatcaacac tctgggccgc atgatccgcg ccgagtctgg cccggacctg cgctacgagg      420
tgaccagcgg cggcggggc accagcagga tgtactattc tcggcgcggc gtgatcaccg       480
accagaactc ggacggctac tgtcaaaccg gcacgatgtc caggcaccag aaccagaaca      540
ccatccagga gctgctgcag aactgctccg actgcttgat gcgagcagag ctcatcgtgc      600
agcctgaatt gaagtatgga gatggaatac aactgactcg gagtcgagaa ttggatgagt      660
gttttgccca ggccaatgac caaatggaaa tcctcgacag cttgatcaga gagatgcggc      720
agatgggcca gccctgtgat gcttaccaga aaggcttct tcagctccaa gagcaaatgc       780
gagcccttta taaagccatc agtgtccctc gagtccgcag ggccagctcc aagggtggtg      840
gaggctacac ttgtcagagt ggctctggct gggatgagtt caccaaacat gtcaccagtg      900
aatgtttggg gtggatgagg cagcaaaggg cggagatgga catggtggcc tggggtgtgg      960
acctggcctc agtggagcag cacattaaca gccaccgggg catccacaac tccatcggcg     1020
actatcgctg gcagctggac aaaatcaaag ccgacctgcg cgagaaatct gcgatctacc     1080
agttggagga ggagtatgaa aacctgctga agcgtccttt tgagaggatg gatcacctgc     1140
gacagctgca gaacatcatt caggccacgt ccagggagat catgtggatc aatgactgcg     1200
aggaggagga gctgctgtac gactggagcg acaagaacac caacatcgct cagaaacagg     1260
aggccttctc catacgcatg agtcaactgg aagttaaaga aaagagctc aataagctga      1320 aacaagaaag tgaccaactt gtcctcaatc agcatccagc ttcagacaaa attgaggcct     1380
atatggacac tctgcagacg cagtggagtt ggattcttca gatcaccaag tgcattgatg     1440
ttcatctgaa agaaaatgct gcctactttc agttttttga agaggcgcag tctactgaag     1500
catacctgaa ggggctccag gactccatca ggaagaagta cccctgcgac aagaacatgc     1560
ccctgcagca cctgctggaa cagatcaagg agctggagaa agaacgagag aaaatccttg     1620
aatacaagcg tcaggtgcag aacttggtaa acaagtctaa gaagattgta cagctgaagc     1680
ctcgtaaccc agactacaga agcaataaac ccattattct cagagctctc tgtgactaca     1740
aacaagatca gaaaatcgtg cataaggggg atgagtgtat cctgaaggac aacaacgagc     1800
gcagcaagtg gtacgtgacg ggcccgggag gcgttgacat gcttgttccc tctgtggggc     1860
tgatcatccc tcctccgaac ccactggccg tggacctctc ttgcaagatt gagcagtact     1920
acgaagccat cttggctctg tggaaccagc tctacatcaa catgaagagc ctggtgtcct     1980
ggcactactg catgattgac atagagaaga tcagggccat gacaatcgcc aagctgaaaa     2040
caatgcggca ggaagattac atgaagacga tagccgacct tgagttacat taccaagagt     2100
tcatcagaaa tagccaaggc tcagagatgt ttggagatga tgacaagcgg aaaatacagt     2160
ctcagttcac cgatgcccag aagcattacc agaccctggt cattcagctc cctggctatc     2220
cccagcacca gacagtgacc acaactgaaa tcactcatca tggaacctgc caagatgtca     2280
accataataa agtaattgaa accaacagag aaaatgacaa gcaagaaaca tggatgctga     2340
tggagctgca gaagattcgc aggcagatag agcactgcga gggcaggatg actctcaaaa     2400
acctccctct agcagaccag gggtcttctc accacatcac agtgaaaatt aacgagctta     2460
agagtgtgca gaatgattca caagcaattg ctgaggttc caaccagctt aaagatatgc      2520
ttgccaactt cagaggttct gaaaagtact gctatttaca gaatgaagta tttggactat     2580
```

```
ttcagaaact ggaaaatatc aatggtgtta cagatggcta cttaaatagc ttatgcacag    2640
taagggcact gctccaggct attctccaaa cagaagacat gttaaaggtt tatgaagcca    2700
ggctcactga ggaggaaact gtctgcctgg acctggataa agtggaagct taccgctgtg    2760
gactgaagaa aataaaaaat gacttgaact tgaagaagtc gttgttggcc actatgaaga    2820
cagaactaca gaaagcccag cagatccact ctcagacttc acagcagtat ccactttatg    2880
atctggactt gggcaagttc ggtgaaaaag tcacacagct gacagaccgc tggcaaagga    2940
tagataaaca gatcgacttt agattatggg acctggagaa acaaatcaag caattgagga    3000
attatcgtga taactatcag gctttctgca gtggctcta tgatcgtaaa cgccgccagg    3060
attccttaga atccatgaaa tttggagatt ccaacacagt catgcggttt ttgaatgagc    3120
agaagaactt gcacagtgaa atatctggca acgagacaa atcagaggaa gtacaaaaaa    3180
ttgctgaact ttgcgccaat tcaattaagg attatgagct ccagctggcc tcatacacct    3240
caggactgga aactctgctg aacatacca tcaagaggac catgattcag tccccttctg    3300
gggtgattct gcaagaggct gcagatgttc atgctcggta cattgaacta cttacaagat    3360
ctggagacta ttacaggttc ttaagtgaga tgctgaagag tttggaagat ctgaagctga    3420
aaaataccaa gatcgaagtt ttggaagagg agctcagact ggcccgagat gccaactcgg    3480
aaaactgtaa taagaacaaa ttcctggatc agaacctgca gaaataccag gcagagtgtt    3540
cccagttcaa agcgaagctt gcgagcctgg aggagctgaa gagacaggct gagctggatg    3600
ggaagtcggc taagcaaaat ctagacaagt gctacggcca ataaaagaa ctcaatgaga    3660 agatcacccg actgacttat gagattgaag atgaaaagag aagaagaaaa tctgtggaag    3720
acagatttga ccaacagaag aatgactatg accaactgca gaaagcaagg caatgtgaaa    3780
aggagaacct tggttggcag aaattagagt ctgagaaagc catcaaggag aaggagtacg    3840
agattgaaag gttgagggtt ctactgcagg aagaaggcac ccggaagaga gaatatgaaa    3900
atgagctggc aaaggtaaga aaccactata tgaggagat gagtaattta aggaacaagt    3960
atgaaacaga gattaacatt acgaagacca ccatcaagga gatatccatg caaaaagagg    4020
atgattccaa aaatcttaga aaccagcttg atagactttc aagggaaaat cgagatctga    4080
aggatgaaat tgtcaggctc aatgacagca tcttgcaggc cactgagcag cgaaggcgag    4140
ctgaagaaaa cgcccttcag caaaaggcct gtggctctga taatgcag aagaagcagc    4200 atctggagat agaactgaag caggtcatgc agcagcgctc tgaggacaat gcccggcaca    4260
agcagtccct ggaggaggct gccaagacca ttcaggacaa aaataaggag atcgagagac    4320
tcaaagctga gtttcaggag gaggccaagc gccgctggga atatgaaaat gaactgagta    4380
aggtaagaaa caattatgat gaggagatca ttagcttaaa aaatcagttt gagaccgaga    4440
tcaacatcac caagaccacc atccaccagc tcaccatgca gaaggaagag gataccagtg    4500
gctaccgggc tcagatagac aatctcaccc gagaaaacag gagcttatct gaagaaataa    4560
agaggctgaa gaacactcta acccagacca cagagaatct caggagggtg gaagaagaca    4620
tccaacagca aaaggccact ggctctgagg tgtctcagag gaaacagcag ctggaggttg    4680
agctgagaca agtcactcag atgcgaacag aggagagcgt aagatataag caatctcttg    4740
atgatgctgc caaaccatc caggataaaa acaaggagat agaaaggtta aacaactga    4800 tcgacaaaga aacaaatgac cggaaatgcc tggaagatga aaacgcgaga ttacaaaggg    4860
tccagtatga cctgcagaaa gcaaacagta gtgcgacgga gacaataaac aaactgaagg    4920
```

```
ttcaggagca agaactgaca cgcctgagga tcgactatga aagggtttcc caggagagga    4980
ctgtgaagga ccaggatatc acgcggttcc agaactctct gaaagagctg cagctgcaga    5040
agcagaaggt ggaagaggag ctgaatcggc tgaagaggac cgcgtcagaa gactcctgca    5100
agaggaagaa gctggaggaa gagctggaag gcatgaggag gtcgctgaag gagcaagcca    5160
tcaaaatcac caacctgacc cagcagctgg agcaggcatc cattgttaag aagaggagtg    5220
aggatgacct ccggcagcag agggacgtgc tggatggcca cctgagggaa aagcagagga    5280
cccaggaaga gctgaggagg ctctcttctg aggtcgaggc cctgaggcgg cagttactcc    5340
aggaacagga aagtgtcaaa caagctcact tgaggaatga gcatttccag aaggcgatag    5400
aagataaaag cagaagctta aatgaaagca aaatagaaat tgagaggctg cagtctctca    5460
cagagaacct gaccaaggag cacttgatgt tagaagaaga actgcggaac ctgaggctgg    5520
agtacgatga cctgaggaga ggacgaagcg aagcggacag tgataaaaat gcaaccatct    5580
tggaactaag gagccagctg cagatcagca acaaccggac cctggaactg caggggctga    5640
ttaatgattt acagagagag agggaaaatt tgagacagga aattgagaaa ttccaaaagc    5700
aggctttaga ggcatctaat aggattcagg aatcaaagaa tcagtgtact caggtggtac    5760
aggaaagaga gagccttctg gtgaaaatca aagtcctgga gcaagacaag gcaaggctgc    5820
agaggctgga ggatgagctg aatcgtgcaa aatcaactct agaggcagaa accagggtga    5880
aacagcgcct ggagtgtgag aaacagcaaa ttcagaatga cctgaatcag tggaagactc    5940
aatattcccg caaggaggag gctattagga agatagaatc ggaaagagaa aagagtgaga    6000
gagagaagaa cagtcttagg agtgagatcg aaagactcca agcagagatc aagagaattg    6060
aagagaggtg caggcgtaag ctggaggatt ctaccaggga gacacagtca cagttagaaa    6120
cagaacgctc ccgatatcag agggagattg ataaactcag acagcgccca tatgggtccc    6180
atcgagagac ccagactgag tgtgagtgga ccgttgacac ctccaagctg gtgtttgatg    6240
ggctgaggaa gaaggtgaca gcaatgcagc tctatgagtg tcagctgatc gacaaaacaa    6300
ccttggacaa actattgaag gggaagaagt cagtggaaga gttgcttct gaaatccagc     6360
cattccttcg gggtgcagga tctatcgctg gagcatctgc ttctcctaag gaaaaatact    6420
ctttggtaga ggccaagaga aagaaattaa tcagcccaga atccacagtc atgcttctgg    6480
aggcccaggc agctacaggt ggtataattg atccccatcg gaatgagaag ctgactgtcg    6540
acagtgccat agctcgggac ctcattgact tcgatgaccg tcagcagata tatgcagcag    6600
aaaaagctat cactggtttt gatgatccat tttcaggcaa gacagtatct gtttcagaag    6660
ccatcaagaa aaatttgatt gatagagaaa ccggaatgcg cctgctggaa gcccagattg    6720
cttcaggggg tgtagtagac cctgtgaaca gtgtcttttt gccaaaagat gtcgccttgg    6780
cccgggggct gattgataga gatttgtatc gatccctgaa tgatcccga gatagtcaga    6840
aaaactttgt ggatccagtc accaaaaaga aggtcagtta cgtgcagctg aaggaacggt    6900
gcagaatcga accacatact ggtctgctct tgctttcagt acagaagaga agcatgtcct    6960
tccaaggaat cagacaacct gtgaccgtca ctgagctagt agattctggt atattgagac    7020
cgtccactgt caatgaactg gaatctggtc agatttctta tgacgaggtt ggtgagagaa    7080
ttaaggactt cctccagggt tcaagctgca tagcaggcat atacaatgag accacaaaac    7140
agaagcttgg catttatgag gccatgaaaa ttggcttagt ccgacctggt actgctctgg    7200
agttgctgga agcccaagca gctactggct ttatagtgga tcctgttagc aacttgaggt    7260
taccagtgga ggaagcctac aagagaggtc tggtgggcat tgagttcaaa gagaagctcc    7320
```

-continued

| | |
|---|---|
| tgtctgcaga acgagctgtc actgggtata atgatcctga aacaggaaac atcatctctt | 7380 |
| tgttccaagc catgaataag gaactcatcg aaaagggcca cggtattcgc ttattagaag | 7440 |
| cacagatcgc aaccgggggg atcattgacc caaaggagag ccatcgttta ccagttgaca | 7500 |
| tagcatataa gagggctat ttcaatgagg aactcagtga gattctctca gatccaagtg | 7560 |
| atgataccaa aggatttttt gacccaaca ctgaagaaaa tcttacctat ctgcaactaa | 7620 |
| aagaaagatg cattaaggat gaggaaacag ggctctgtct tctgcctctg aagaaaaga | 7680 |
| agaaacaggt gcagacatca caaagaata ccctcaggaa gcgtagagtg gtcatagttg | 7740 |
| acccagaaac caataaagaa atgtctgttc aggaggccta caagaagggc ctaattgatt | 7800 |
| atgaaaccttt caagaactg tgtgagcagg aatgtgaatg ggaagaaata accatcacgg | 7860 |
| gatcagatgg ctccaccagg gtggtcctgg tagatagaaa gacaggcagt cagtatgata | 7920 |
| ttcaagatgc tattgacaag ggccttgttg acaggaagtt ctttgatcag taccgatccg | 7980 |
| gcagcctcag cctcactcaa tttgctgaca tgatctcctt gaaaaatggt gtcggcacca | 8040 |
| gcagcagcat gggcagtggt gtcagcgatg atgttttttag cagctcccga catgaatcag | 8100 |
| taagtaagat ttccaccata tccagcgtca ggaattaaac cataaggagc agctcttttt | 8160 |
| cagacaccct ggaagaatcg agccccattg cagccatctt tgacacagaa aacctggaga | 8220 |
| aaatctccat tacagaaggt atagagcggg gcatcgttga cagcatcacg ggtcagaggc | 8280 |
| ttctggaggc tcaggcctgc acaggtggca tcatccaccc aaccacgggc cagaagctgt | 8340 |
| cacttcagga cgcagtctcc cagggtgtga ttgaccaaga catggccacc agcgtgaagc | 8400 |
| ctgctcagaa agccttcata ggcttcgagg gtgtgaaggg aaagaagaag atgtcagcag | 8460 |
| cagaggcagt gaaagaaaaa tggctcccgt atgaggctgg ccagcgcttc ctggagttcc | 8520 |
| agtacctcac gggaggtctt gttgacccgg aagtgcatgg gaggataagc accgaagaag | 8580 |
| ccatccggaa ggggttcata gatggccgcg ccgcacagag gctgcaagac accagcagct | 8640 |
| atgccaaaat cctgacctgc cccaaaacca aattaaaaat atcctataag gatgccataa | 8700 |
| atcgctccat ggtagaagat atcactgggc tgcgccttct ggaagccgcc tccgtgtcgt | 8760 |
| ccaagggctt acccagccct tacaacatgt cttcggctcc ggggtcccgc tccggctccc | 8820 |
| gctcgggatc tcgctccgga tctcgctccg ggtcccgcag tgggtcccgg agaggaagct | 8880 |
| ttgacgccac agggaattct tcctactctt attcctactc atttagcagt agttctattg | 8940 |
| ggcactag | 8948 |

<210> SEQ ID NO 120
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 120

| | |
|---|---|
| cgtcctaagc acttagacta catcagggaa gaacacagac cacatccctg tcctcatgcg | 60 |
| gcttatgttt tctggaagaa agtggagacc nagtccttgg ctttagggct ccccggctgg | 120 |
| gggctgtgca ntccggtcag ggcgggaagg gaaatgcacc gctgcatgtg aacttacagc | 180 |
| ccaggcggat gccccttccc ttagcactac ctggcctcct gcatccctc gcctcatgtt | 240 |
| cctcccacct tcaaanaatg aanaacccca tgggcccagc cccttgccct ggggaaccaa | 300 |

-continued

| | |
|---|---|
| ggcagccttc caaaactcag gggctgaagc anactattag gcaggggct gactttgggt | 360 |
| gacactgccc attccctctc agggcagctc angtcacccn ggnctcttga acccagcctg | 420 |
| ttcctttgaa aaagggcaaa actgaaaagg gcttttccta naaaaagaaa aaccagggaa | 480 |
| ctttgccagg gcttcnntnt taccaaaacn ncttctcnng gatttttaat tccccattng | 540 |
| gcctccactt accngggggcn atgccccaaa attaanaatt tcccatc | 587 |

<210> SEQ ID NO 121
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 121

| | |
|---|---|
| cactagtagg atagaaacac tgtgtcccga gagtaaggag agaagctact attgattaga | 60 |
| gcctaaccca ggttaactgc aagaagaggc gggatacttt cagcttttcca tgtaactgta | 120 |
| tgcataaagc caatgtagtc cagtttctaa gatcatgttc caagctaact gaatcccact | 180 |
| tcaatacaca ctcatgaact cctgatgaaa caataacagg cccaagcctg tggtatgatg | 240 |
| tgcacacttg ctagactcan aaaaaatact actctcataa atgggtggga gtattttggt | 300 |
| gacaacctac tttgcttggc tgagtgaagg aatgatattc atatattcat ttattccatg | 360 |
| gacatttagt tagtgctttt tatataccag gcatgatgct gagtgacact cttgtgtata | 420 |
| tttccaaatt tttgtacagt cgctgcacat atttgaaatc atatattaag acttccaaaa | 480 |
| aatgaagtcc ctggtttttc atggcaactt gatcagtaaa ggattcncct ctgtttggta | 540 |
| cttaaaacat ctactatatn gttnanatga aattccttt ccccnnctcc cgaaaaaana | 600 |
| aagtggtggg gaaaaaaaa | 619 |

<210> SEQ ID NO 122
<211> LENGTH: 1475
<212> TYPE: DNA
<213> ORGANISM: Homo sapien

<400> SEQUENCE: 122

| | |
|---|---|
| tccacctgtc cccgcagcgc cggctcgcgc cctcctgccg cagccaccga gccgccgtct | 60 |
| agcgccccga cctcgccacc atgagagccc tgctggcgcg cctgcttctc tgcgtcctgg | 120 |
| tcgtgagcga ctccaaaggc agcaatgaac ttcatcaagt tccatcgaac tgtgactgtc | 180 |
| taaatggaga acatgtgtg tccaacaagt acttctccaa cattcactgg tgcaactgcc | 240 |
| caaagaaatt cggagggcag cactgtgaaa tagataagtc aaaaacctgc tatgagggga | 300 |
| atggtcactt ttaccgagga aaggccagca ctgacaccat gggccggccc tgcctgccct | 360 |
| ggaactctgc cactgtcctt cagcaaacgt accatgccca cagatctgat gctcttcagc | 420 |
| tgggcctggg gaaacataat tactgcagga acccagacaa ccggaggcga ccctggtgct | 480 |
| atgtgcaggt gggcctaaag ccgcttgtcc aagagtgcat ggtgcatgac tgcgcagatg | 540 |
| gaaaaaagcc ctcctctcct ccagaagaat taaaatttca gtgtggccaa aagactctga | 600 |
| ggccccgctt taagattatt gggggagaat tcaccaccat cgagaaccag ccctggtttg | 660 |
| cggccatcta caggaggcac cgggggggct ctgtcaccta cgtgtgtgga ggcagcctca | 720 |
| tcagcccttg ctgggtgatc agcgccacac actgcttcat tgattaccca agaaggagg | 780 |
| actacatcgt ctacctgggt cgctcaaggc ttaactccaa cacgcaaggg gagatgaagt | 840 |

-continued

```
ttgaggtgga aaacctcatc ctacacaagg actacagcgc tgacacgctt gctcaccaca      900
acgacattgc cttgctgaag atccgttcca aggagggcag gtgtgcgcag ccatcccgga      960
ctatacagac catctgcctg ccctcgatgt ataacgatcc ccagtttggc acaagctgtg     1020
agatcactgg ctttggaaaa gagaattcta ccgactatct ctatccggag cagctgaaga     1080
tgactgttgt gaagctgatt tcccaccggg agtgtcagca gccccactac tacggctctg     1140
aagtcaccac caaaatgctg tgtgctgctg acccacagtg gaaaacagat tcctgccagg     1200
gagactcagg gggacccctc gtctgttccc tccaaggccg catgactttg actggaattg     1260
tgagctgggg ccgtggatgt gccctgaagg acaagccagg cgtctacacg agagtctcac     1320
acttcttacc ctggatccgc agtcacacca aggaagagaa tggcctggcc ctctgagggt     1380
ccccagggag gaaacgggca ccacccgctt tcttgctggt tgtcattttt gcagtagagt     1440
catctccatc agctgtaaga agagactggg aagat                                1475

<210> SEQ ID NO 123
<211> LENGTH: 2294
<212> TYPE: DNA
<213> ORGANISM: Homo sapien

<400> SEQUENCE: 123
cagcgccggc tcgcgccctc ctgccgcagc caccgagccg ccgtctagcg ccccgacctc       60
gccaccatga gagccctgct ggcgcgcctg cttctctgcg tcctggtcgt gagcgactcc      120
aaaggcagca atgaacttca tcaagttcca tcgaactgtg actgtctaaa tggaggaaca      180
tgtgtgtcca acaagtactt ctccaacatt cactggtgca actgcccaaa gaaattcgga      240
gggcagcact gtgaaataga taagtcaaaa acctgctatg aggggaatgg tcacttttac      300
cgaggaaagg ccagcactga caccatgggc cggccctgcc tgccctggaa ctctgccact      360
gtccttcagc aaacgtacca tgcccacaga tctgatgctc ttcagctggg cctggggaaa      420
cataattact gcaggaaccc agacaaccgg aggcgaccct ggtgctatgt gcaggtgggc      480
ctaaagccgc ttgtccaaga gtgcatggtg catgactgcg cagatggaaa aaagccctcc      540
tctcctccag aagaattaaa atttcagtgt ggccaaaaga ctctgaggcc ccgctttaag      600
attattgggg gagaattcac caccatcgag aaccagccct ggtttgcggc catctacagg      660
aggcaccggg gggctctgt cacctacgtg tgtggaggca gcctcatcag cccttgctgg      720
gtgatcagcg ccacacactg cttcattgat tacccaaaga aggaggacta catcgtctac      780
ctgggtcgct caaggcttaa ctccaacacg caagggagat gaagtttga ggtggaaaac      840 ctaatcctac acaaggacta cagcgctgac acgcttgctc accacaacga cattgccttg      900
ctgaagatcc gttccaagga gggcaggtgt gcgcagccat cccggactat acagaccatc      960
tgcctgcccc gatgtataa cgatcccag tttggcacaa gctgtgagat cactggcttt     1020
ggaaaagaga attctaccga ctatctctat ccggagcagc tgaaaatgac tgttgtgaag     1080
ctgatttccc accgggagtg tcagcagccc cactactacg gctctgaagt caccaccaaa     1140
atgctgtgtg ctgctgaccc acagtggaaa acagattcct gccagggaga ctcagggga     1200 cccctcgtct gttccctcca aggccgcatg actttgactg gaattgtgag ctgggccgt     1260 ggatgtgccc tgaaggacaa gccaggcgtc tacacgagag tctcacactt cttaccctgg     1320
atccgcagtc acaccaagga agagaatggc ctggccctct gagggtcccc agggaggaaa     1380
cgggcaccac ccgctttctt gctggttgct attttgcagt agagtcatct ccatcagctg     1440
```

-continued

| | |
|---|---|
| taagaagagc tgggaatata ggctctgcac agatggattt gcctgtgcca ccaccagggc | 1500 |
| gaacgacaat agctttaccc tcaggcatag gcctgggtgc tggctgccca gacccctctg | 1560 |
| gccaggatgg aggggtggtc ctgactcaac atgttactga ccagcaactt gtcttttct | 1620 |
| ggactgaagc ctgcaggagt taaaaagggc agggcatctc ctgtgcatgg gctcgaaggg | 1680 |
| agagccagct cccccgaccg gtgggcattt gtgaggccca tggttgagaa atgaataatt | 1740 |
| tcccaattag gaagtgtaag cagctgaggt ctcttgaggg agcttagcca atgtgggagc | 1800 |
| agcggtttgg ggagcagaga cactaacgac ttcagggcag ggctctgata ttccatgaat | 1860 |
| gtatcaggaa atatatatgt gtgtgtatgt ttgcacactt gtgtgtgggc tgtgagtgta | 1920 |
| agtgtgagta agagctggtg tctgattgtt aagtctaaat atttccttaa actgtgtgga | 1980 |
| ctgtgatgcc acacagagtg gtctttctgg agaggttata ggtcactcct ggggcctctt | 2040 |
| gggtccccca cgtgacagtg cctgggaatg tattattctg cagcatgacc tgtgaccagc | 2100 |
| actgtctcag tttcactttc acatagatgt ccctttcttg gccagttatc ccttcctttt | 2160 |
| agcctagttc atccaatcct cactgggtgg ggtgaggacc actcctgtac actgaatatt | 2220 |
| tatatttcac tatttttatt tatatttttg taattttaaa taaaagtgat caataaaatg | 2280 |
| tgattttct gatg | 2294 |

<210> SEQ ID NO 124
<211> LENGTH: 956
<212> TYPE: DNA
<213> ORGANISM: Homo sapien

<400> SEQUENCE: 124

| | |
|---|---|
| gatgagttcc gcaccaagtt tgagacagac caggccctgc gcctgagtgt ggaggccgac | 60 |
| atcaatggcc tgcgcagggt gctggatgag ctgaccctgg ccagagccga cctggagatg | 120 |
| cagattgaga acctcaagga ggagctggcc tacctgaaga gaaccacga ggaggagatg | 180 |
| aacgccctgc gaggccaggt gggtggtgag atcaatgtgg agatggacgc tgccccaggc | 240 |
| gtggacctga gccgcatcct caacgagatg cgtgaccagt atgagaagat ggcagagaag | 300 |
| aaccgcaagg atgccgagga ttggttcttc agcaagacag aggaactgaa ccgcgaggtg | 360 |
| gccaccaaca gtgagctggt gcagagtggc aagagtgaga tctcggagct ccggcgcacc | 420 |
| atgcaggcct tggagataga gctgcagtcc cagctcagca tgaaagcatc cctggagggc | 480 |
| aacctggcgg agacagagaa ccgctactgc gtgcagctgt cccagatcca ggggctgatt | 540 |
| ggcagcgtgg aggagcagct ggcccagctt cgctgcgaga tggagcagca gaaccaggaa | 600 |
| tacaaaatcc tgctggatgt gaagacgcgg ctggagcagg agattgccac ctaccgccgc | 660 |
| ctgctggagg gagaggatgc ccacctgact cagtacaaga agaaccggt gaccacccgt | 720 |
| caggtgcgta ccattgtgga agaggtccag gatggcaagg tcatctcctc ccgcgagcag | 780 |
| gtccaccaga ccacccgctg aggactcagc taccccggcc ggccacccag gaggcaggga | 840 |
| cgcagccgcc ccatctgccc cacagtctcc ggcctctcca gcctcagccc cctgcttcag | 900 |
| tcccttcccc atgcttcctt gcctgatgac aataaaagct tgttgactca gctatg | 956 |

<210> SEQ ID NO 125
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 125

```
aaattatata tagtgnttca gctcccattg tggtgttcat agtcttctag gaacagataa    60
acttaagtat tcaattcact cttggcattt tttctttaat ataggctttt tagcctattt   120
ttggaaaact gcttttcttc tgagaacctt attctgaatg tcatcaactt taccaaacct   180
tctaagtcca gagctaactt agtactgttt aagttactat tgactgaatt ttcttcattt   240
tctgtttagc cagtgttacc aaggtaagct ggggaatgaa gtataccaac ttctttcaga   300
gcattttagg acattatggc agctttagaa ggctgtcttt tttctagcca agggagagcc   360
agcgcaggtt ttggatacta gagaaagtca tttgcttgta ctattgccat tttagaaagc   420
tctgatgtga attcaaattt tacctctgtt acttaaagcc aacaatttta aggcagtagt   480
tttact                                                              486
```

<210> SEQ ID NO 126
<211> LENGTH: 3552
<212> TYPE: DNA
<213> ORGANISM: Homo sapien

<400> SEQUENCE: 126

```
cggcaggcag gtctcgtctc ggcaccctcc cggcgcccgc gttctcctgg ccctgcccgg    60
catcccgatg gccgccgctg ggccccggcg ctccgtgcgc ggagccgtct gcctgcatct   120
gctgctgacc ctcgtgatct tcagtcgtgc tggtgaagcc tgcaaaaagg tgatacttaa   180
tgtaccttct aaactagagg cagacaaaat aattggcaga gttaatttgg aagagtgctt   240
caggtctgca gacctcatcc ggtcaagtga tcctgatttc agagttctaa atgatgggtc   300
agtgtacaca gccagggctg ttgcgctgtc tgataagaaa agatcattta ccatatggct   360
ttctgacaaa aggaaacaga cacagaaaga ggttactgtg ctgctagaac atcagaagaa   420
ggtatcgaag acaagacaca ctagagaaac tgttctcagg cgtgccaaga ggagatgggc   480
acctattcct tgctctatgc aagagaattc cttgggccct ttcccattgt ttcttcaaca   540
agttgaatct gatgcagcac agaactatac tgtcttctac tcaataagtg gacgtggagt   600
tgataaagaa cctttaaatt tgttttatat agaaagagac actggaaatc tattttgcac   660
tcggcctgtg gatcgtgaag aatatgatgt ttttgatttg attgcttatg cgtcaactgc   720
agatggatat tcagcagatc tgcccctccc actacccatc agggtagagg atgaaaatga   780
caaccaccct gttttcacag aagcaattta aattttgaa gttttggaaa gtagtagacc   840
tggtactaca gtgggggtgg tttgtgccac agacagagat gaaccggaca caatgcatac   900
gcgcctgaaa tacagcattt tgcagcagac accaaggtca cctgggctct tttctgtgca   960
tcccagcaca ggcgtaatca ccacagtctc tcattatttg gacagagagg ttgtagacaa  1020
gtactcattg ataatgaaag tacaagacat ggatggccag ttttttggat tgataggcac  1080
atcaacttgt atcataacag taacagattc aaatgataat gcacccactt tcagacaaaa  1140
tgcttatgaa gcatttgtag aggaaaatgc attcaatgtg gaaatcttac gaataccatt  1200
agaagataag gatttaatta acactgccaa ttggagagtc aattttacca ttttaaaggg  1260
aaatgaaaat ggacatttca aaatcagcac agacaaagaa actaatgaag gtgttctttc  1320
tgttgtaaag ccactgaatt atgaagaaaa ccgtcaagtg aacctggaaa ttggagtaaa  1380
caatgaagcg ccatttgcta gagatattcc cagagtgaca gccttgaaca gagccttggt  1440
tacagttcat gtgagggatc tggatgaggg gcctgaatgc actcctgcag cccaatatgt  1500
```

-continued

```
gcggattaaa gaaaacttag cagtggggtc aaagatcaac ggctataagg catatgaccc    1560
cgaaaataga aatggcaatg gtttaaggta caaaaaattg catgatccta aaggttggat    1620
caccattgat gaaatttcag ggtcaatcat aacttccaaa atcctggata gggaggttga    1680
aactcccaaa aatgagttgt ataatattac agtcctggca atagacaaag atgatagatc    1740
atgtactgga acacttgctg tgaacattga agatgtaaat gataatccac cagaaatact    1800
tcaagaatat gtagtcattt gcaaaccaaa atgggggtat accgacattt tagctgttga    1860
tcctgatgaa cctgtccatg gagctccatt ttatttcagt ttgcccaata cttctcccaga    1920 aatcagtaga ctgtggagcc tcaccaaagt taatgataca gctgcccgtc tttcatatca    1980
gaaaaatgct ggatttcaag aatataccat tcctattact gtaaaagaca gggccggcca    2040
agctgcaaca aaattattga gagttaatct gtgtgaatgt actcatccaa ctcagtgtcg    2100
tgcgacttca aggagtacag gagtaatact tggaaaatgg gcaatccttg caatattact    2160
gggtatagca ctgctctttt ctgtattgct aactttagta tgtggagttt ttggtgcaac    2220
taaagggaaa cgttttcctg aagatttagc acagcaaaac ttaattatat caaacacaga    2280
agcacctgga gacgatagag tgtgctctgc caatggattt atgacccaaa ctaccaacaa    2340
ctctagccaa ggttttttgtg gtactatggg atcaggaatg aaaaatggag ggcaggaaac    2400
cattgaaatg atgaaaggag gaaaccagac cttggaatcc tgccgggggg ctgggcatca    2460 tcatacccctg gactcctgca gggaggaca cacggaggtg gacaactgca gatacactta    2520
ctcggagtgg cacagttta ctcaacccccg tctcggtgaa aaattgcatc gatgtaatca    2580
gaatgaagac cgcatgccat cccaagatta tgtcctcact tataactatg agggaagagg    2640
atctccagct ggttctgtgg gctgctgcag tgaaaagcag gaagagatg gccttgactt    2700 tttaaataat ttggaaccca aatttattac attagcagaa gcatgcacaa agagataatg    2760
tcacagtgct acaattaggt ctttgtcaga cattctggag gtttccaaaa ataatattgt    2820
aaagttcaat ttcaacatgt atgtatatga tgattttttt ctcaattttg aattatgcta    2880
ctcaccaatt tatattttta aagcaagttg ttgcttatct tttccaaaaa gtgaaaaatg    2940
ttaaaacaga caactggtaa atctcaaact ccagcactgg aattaaggtc tctaaagcat    3000
ctgctctttt ttttttttac agatatttta gtaataaaata tgctggataa atattagtcc    3060
aacaatagct aagttatgct aatatcacat tattatgtat tcactttaag tgatagttta    3120
aaaaataaac aagaaatatt gagtatcact atgtgaagaa agttttggaa agaaacaat    3180 gaagactgaa ttaaattaaa aatgttgcag ctcataaaga attggactca cccctactgc    3240
actaccaaat tcatttgact ttggaggcaa aatgtgttga agtgccctat gaagtagcaa    3300
ttttctatag gaatatagtt ggaaataaat gtgtgtgtgt atattattat taatcaatgc    3360
aatatttaaa tgaaatgaga acaaagagga aaatggtaaa aacttgaaat gaggctgggg    3420
tatagtttgt cctacaatag aaaaaagaga gagcttccta ggcctgggct cttaaatgct    3480
gcattataac tgagtctatg aggaaatagt tcctgtccaa tttgtgtaat ttgtttaaaa    3540
ttgtaaataa at                                                        3552
```

<210> SEQ ID NO 127
<211> LENGTH: 754
<212> TYPE: DNA
<213> ORGANISM: Homo sapien

<400> SEQUENCE: 127

```
ttttttttt ttgtcattgt tcattgattt taatgagaaa gctaagagag gaaataagta      60
```

```
gcctttcaaa ggtcacacag aagtaagtga cagatccagg attcatatcc aagcattctg      120
gctctagtgt ccatgcttct caaccattat gacccaatat tcaaccaaat caatactgaa      180
ggacacgtga aatgtatccg gtattttact attacaaaca aaaatccaat gaacattctt      240
gaagacatac acaaaaataa tggttacaat agaagttact ggaattgaaa ttttggttca      300
acctatatta aaatgtaagg cttttgatat agctaataga ttttgaaat gatcagtctt       360 aacgtttgta ggggagcaca ctcctgcatg gggaaaagat tcactgtgaa gcacagagca      420
cctttatggt tggatcatct tgtcattaaa gttcaggcgt tatctatcct gtaagtggca      480
gaatcaagac tgcaatatcg cctgcttttc ttttttaactc atgttttccc ttgactacac     540
tggtcctcaa agtaaaaccc ctgtgtcagt gtactattca tggaatactc tgcaattata     600
accaccttct aatactttta atacccaatc aaaatttatt atacatatgt atcatagata     660
ctcatctgta aagctgtgct tcaaaatagt gatctcttcc caacattaca atatatatta     720
atgatgtcga acctgcccgg gcggccgctc gaag                                  754

<210> SEQ ID NO 128
<211> LENGTH: 374
<212> TYPE: DNA
<213> ORGANISM: Homo sapien

<400> SEQUENCE: 128
aggttttgat taaaaaggca aatgatttta ttgttcgata atcttttaaa aaaataagag       60
gaaggagtaa aattaaagat gaaagatgat ttttatttcc ttgtgacctc tatatccccc     120
ttcccctgcc cttggtaagt aactcttgat ggagaaagga ttaaagactc ttatttaacc    180
aaaaaacaga gccagctaat catttccaaa ggttagtatc tccctgctga cctcttcttt     240
ggtttaattg aataaaacta tatgttcata tatgttattaa aacaactcag aataacatct    300
tttcttcctt agttaaggca ttataagggc tatactatca tccataataa ccaaggcaat    360
aacttaaaaa gctg                                                       374

<210> SEQ ID NO 129
<211> LENGTH: 546
<212> TYPE: DNA
<213> ORGANISM: Homo sapien

<400> SEQUENCE: 129
agtgtgatgg atatctgcag aattcgggct aagcgtggtc gcggcccgag gtctggaact       60
tcccagcacy tgaaaaggag cctcctgagc tgactcggct aaagcccccac tttcgctcct    120 cctcatttct gcctactgat ttccttggag cattcatctg aatattaccg tttgctgtgt    180
aacctggtac atacatagca tgactccctg gaatagagtg ggctggggtg cttatgctgg    240
gagagtgatt gacatgcact ttcaagctat atctaccatt tgcagcaaag gagaaaaaat    300
acctcgagta aattccatca tttttttataa catcagcacc tgctccatca tcaaggagtc    360
tcagcgtaac aggatctcca gtctctggct caactgtggc agtgacagtg gcattaagaa    420
tgggataaaa tccctgtttc acattggcat aaatcatcac aggatgagga aaatggaggc    480
tgtctctttc cacaaaggct tccacagtgg ctgggggcac agacctgccc gggcggccgc    540
tcgaaa                                                                546

<210> SEQ ID NO 130
<211> LENGTH: 5156
<212> TYPE: DNA
```

<213> ORGANISM: Homo sapien

<400> SEQUENCE: 130

```
accaaccgag gcgccgggca gcgacccctg cagcggagac agagactgag cggcccggca        60
ccgccatgcc tgcgctctgg ctgggctgct gcctctgctt gtcgctcctc ctgcccgcag       120
cccgggccac ctccaggagg gaagtctgtg attgcaatgg gaagtccagg cagtgtatct       180
ttgatcggga acttcacaga caaactggta atggattccg ctgcctcaac tgcaatgaca       240
acactgatgg cattcactgc gagaagtgca agaatggctt ttaccggcac agagaaaggg       300
accgctgttt gccctgcaat tgtaactcca aaggttctct tagtgctcga tgtgacaact       360
ccggacggtg cagctgtaaa ccaggtgtga caggagccag atgcgaccga tgtctgccag       420
gcttccacat gctcacggat gcggggtgca cccaagacca gagactgcta gactccaagt       480
gtgactgtga cccagctggc atcgcagggc cctgtgacgc gggccgctgt gtctgcaagc       540
cagctgtcac tggagaacgc tgtgataggt gtcgatcagg ttactataat ctggatgggg       600
ggaaccctga gggctgtacc cagtgtttct gctatgggca ttcagccagc tgccgcagct       660
ctgcagaata cagtgtccat aagatcacct ctacctttca tcaagatgtt gatggctgga       720
aggctgtcca acgaaatggg tctcctgcaa agctccaatg gtcacagcgc catcaagatg       780
tgtttagctc agcccaacga ctagaccctg tctattttgt ggctcctgcc aaatttcttg       840
ggaatcaaca ggtgagctat ggtcaaagcc tgtcctttga ctaccgtgtg acagaggag        900
gcagacaccc atctgcccat gatgtgattc tggaaggtgc tggtctacgg atcacagctc       960
ccttgatgcc acttggcaag acactgcctt gtgggctcac caagacttac acattcaggt      1020
taaatgagca tccaagcaat aattggagcc cccagctgag ttactttgag tatcgaaggt      1080
tactgcggaa tctcacagcc ctccgcatcc gagctacata tggagaatac agtactgggt      1140
acattgacaa tgtgaccctg atttcagccc gccctgtctc tggagcccca gcaccctggg      1200
ttgaacagtg tatatgtcct gttgggtaca gggggcaatt ctgccaggat tgtgcttctg      1260
gctacaagag agattcagcg agactggggc cttttggcac ctgtattcct tgtaactgtc      1320
aaggggagg ggcctgtgat ccagacacag gagattgtta ttcaggggat gagaatcctg       1380
acattgagtg tgctgactgc ccaattggtt tctacaacga tccgcacgac ccccgcagct      1440
gcaagccatg tccctgtcat aacgggttca gctgctcagt gatgccggag acggaggagg      1500
tggtgtgcaa taactgccct cccggggtca ccggtgcccg ctgtgagctc tgtgctgatg      1560
gctactttgg ggaccccttt ggtgaacatg gcccagtgag gccttgtcag ccctgtcaat      1620
gcaacaacaa tgtggacccc agtgcctctg ggaattgtga ccggctgaca ggcaggtgtt      1680
tgaagtgtat ccacaacaca gccggcatct actgcgacca gtgcaaagca ggctacttcg      1740
gggacccatt ggctcccaac ccagcagaca agtgtcgagc ttgcaactgt aaccccatgg      1800
gctcagagcc tgtaggatgt cgaagtgatg gcacctgtgt ttgcaagcca ggatttggtg      1860
gccccaactg tgagcatgga gcattcagct gtccagcttg ctataatcaa gtgaagattc      1920
agatggatca gtttatgcag cagcttcaga gaatggaggc cctgatttca aaggctcagg      1980
gtggtgatgg agtagtacct gatacagagc tggaaggcag gatgcagcag gctgagcagg      2040
cccttcagga cattctgaga gatgcccaga tttcagaagg tgctagcaga tcccttggtc      2100
tccagttggc caaggtgagg agccaagaga cagctacca gagccgcctg gatgacctca      2160
agatgactgt ggaaagagtt cgggctctgg gaagtcagta ccagaaccga gttcgggata      2220
ctcacaggct catcactcag atgcagctga gcctggcaga aagtgaagct tccttgggaa      2280
```

```
acactaacat tcctgcctca gaccactacg tggggccaaa tggctttaaa agtctggctc    2340
aggaggccac aagattagca gaaagccacg ttgagtcagc cagtaacatg gagcaactga    2400
caagggaaac tgaggactat tccaaacaag ccctctcact ggtgcgcaag gccctgcatg    2460
aaggagtcgg aagcggaagc ggtagcccgg acggtgctgt ggtgcaaggg cttgtggaaa    2520
aattggagaa aaccaagtcc ctggcccagc agttgacaag ggaggccact caagcggaaa    2580
ttgaagcaga taggtcttat cagcacagtc tccgcctcct ggattcagtg tctcggcttc    2640
agggagtcag tgatcagtcc tttcaggtgg aagaagcaaa gaggatcaaa caaaaagcgg    2700
attcactctc aagcctggta accaggcata tggatgagtt caagcgtaca cagaagaatc    2760
tgggaaactg gaaagaagaa gcacagcagc tcttacagaa tggaaaaagt gggagagaga    2820
aatcagatca gctgctttcc cgtgccaatc ttgctaaaag cagagcacaa gaagcactga    2880
gtatgggcaa tgccactttt tatgaagttg agagcatcct taaaaacctc agagagtttg    2940
acctgcaggt ggacaacaga aaagcagaag ctgaagaagc catgaagaga ctctcctaca    3000
tcagccagaa ggtttcagat gccagtgaca agacccagca agcagaaaga gccctgggga    3060
gcgctgctgc tgatgcacag agggcaaaga atggggccgg ggaggccctg aaatctcca    3120 gtgagattga acaggagatt gggagtctga acttggaagc caatgtgaca gcagatggag    3180
ccttggccat ggaaaaggga ctggcctctc tgaagagtga gatgagggaa gtggaaggag    3240
agctggaaag gaaggagctg gagtttgaca cgaatatgga tgcagtacag atggtgatta    3300
cagaagccca gaaggttgat accagagcca agaacgctgg ggttacaatc caagacacac    3360 tcaaacatt agacggcctc ctgcatctga tggaccagcc tctcagtgta gatgaagagg    3420
ggctggtctt actggagcag aagctttccc gagccaagac ccagatcaac agccaactgc    3480
ggcccatgat gtcagagctg aagagaggg cacgtcagca gaggggccac ctccattgc    3540 tggagacaag catagatggg attctggctg atgtgaagaa cttggagaac attagggaca    3600
acctgccccc aggctgctac aatacccagg ctcttgagca acagtgaagc tgccataaat    3660
atttctcaac tgaggttctt gggatacaga tctcagggct cgggagccat gtcatgtgag    3720
tgggtgggat ggggacattt gaacatgttt aatgggtatg ctcaggtcaa ctgacctgac    3780
cccattcctg atcccatggc caggtggttg tcttattgca ccatactcct tgcttcctga    3840
tgctgggcaa tgaggcagat agcactgggt gtgagaatga tcaaggatct ggaccccaaa    3900
gaatagactg gatggaaaga caaactgcac aggcagatgt ttgcctcata atagtcgtaa    3960
gtggagtcct ggaatttgga caagtgctgt tgggatatag tcaacttatt ctttgagtaa    4020
tgtgactaaa ggaaaaaact ttgactttgc ccaggcatga aattcttcct aatgtcagaa    4080
cagagtgcaa cccagtcaca ctgtggccag taaaatacta ttgcctcata ttgtcctctg    4140
caagcttctt gctgatcaga gttcctccta cttacaaccc agggtgtgaa catgttctcc    4200
attttcaagc tggaagaagt gagcagtgtt ggagtgagga cctgtaaggc aggcccattc    4260
agagctatgg tgcttgctgg tgcctgccac cttcaagttc tggacctggg catgacatcc    4320 tttctttaa tgatgccatg gcaacttaga gattgcattt ttattaaagc atttcctacc    4380
agcaaagcaa atgttgggaa agtatttact ttttcggttt caaagtgata gaaagtgtg    4440 gcttgggcat tgaaagaggt aaaattctct agatttatta gtcctaattc aatcctactt    4500
ttagaacacc aaaaatgatg cgcatcaatg tattttatct tattttctca atctcctctc    4560
tctttcctcc acccataata agagaatgtt cctactcaca cttcagctgg gtcacatcca    4620
```

```
tccctccatt catccttcca tccatctttc catccattac ctccatccat ccttccaaca    4680
tatatttatt gagtacctac tgtgtgccag ggctggtgg gacagtggtg acatagtctc     4740
tgccctcata gagttgattg tctagtgagg aagacaagca tttttaaaaa ataaatttaa    4800
acttacaaac tttgtttgtc acaagtggtg tttattgcaa taaccgcttg gtttgcaacc    4860
tctttgctca acagaacata tgttcaaga ccctcccatg ggggcacttg agttttggca     4920
aggctgacag agctctgggt tgtgcacatt tctttgcatt ccagctgtca ctctgtgcct    4980
ttctacaact gattgcaaca gactgttgag ttatgataac accagtggga attgctggag    5040
gaaccagagg cacttccacc ttggctggga agactatggt gctgccttgc ttctgtattt    5100
ccttggattt tcctgaaagt gttttaaat aaagaacaat tgttagaaaa aaaaaa         5156
```

<210> SEQ ID NO 131
<211> LENGTH: 671
<212> TYPE: DNA
<213> ORGANISM: Homo sapien

<400> SEQUENCE: 131

```
aggtctggag ggcccacagc cggatgtggg acaccgggaa aaagtggtca tagcacacat     60
ttttgcatcc cggttgcagt gtgttgcaga cgaagtcctc ttgctcgtca ccccacactt    120
cctgggcagc caycacgagg atcatgactc ggaaaataaa gatgactgtg atccacacct    180
tcccgatgct ggtggagtgt tgttgacac ccccgatgaa agtgtgcagc gtccccaat     240 ccattgcgct ggtttatccc tgagtcctgt ttccaacgac tgccagtgtt tcagacccaa    300
agaatgaggg caagatccct ctgcgagggt ttcagacctc cttctcctac cccactggag    360
tgcctagaag ccaatgggtg cacagtgatg atacgaatgt caatctttgc tcggtcagtg    420
aggatgtcgc ctggaatatt caaattgaat tacagatgca tgaagagggc gtacaagtta    480 gaattttct ttcgccatac agaaattgtt tagccagatc ttctgtactt cttttccttc     540 cctgacccctt cctgctcccc aggaagggag gtcagccccg tttgcaaaac acaggatgcc    600
cgtgacaccg gagacaggtc ttcttcaccg acaggaagtg ccttctggtg cctgcacgtt    660
ttaactgcta t                                                          671
```

<210> SEQ ID NO 132
<211> LENGTH: 590
<212> TYPE: DNA
<213> ORGANISM: Homo sapien

<400> SEQUENCE: 132

```
ctgaatggaa aagcttatgg ctctgtgatg atattagtga ccagcggaga tgataagctt     60
cttggcaatt gcttacccac tgtgctcagc agtggttcaa caattcactc cattgccctg    120
ggttcatctg cagcccccaaa tctggaggaa ttatcacgtc ttacaggagg tttaaagttc    180
tttgttccag atatatcaaa ctccaatagc atgattgatg ctttcagtag aatttcctct    240
ggaactggag acattttcca gcaacatatt cagcttgaaa gtacaggtga aaatgtcaaa    300
cctcaccatc aattgaaaaa cacagtgact gtggataata ctgtgggcaa cgacactatg    360
tttctagtta cgtggcaggc cagtggtcct cctgagatta tattatttga tcctgatgga    420
cgaaaatact acacaaataa ttttatcacc aatctaactt ttcggacagc tagtctttgg    480
attccaggaa cagctaagcc tgggcactgg acttacaccc tgaacaatac ccatcattct    540
ctgcaagccc tgaaagtgac agtgacctct cgcgcctcca actcagacct                 590
```

```
<210> SEQ ID NO 133
<211> LENGTH: 581
<212> TYPE: DNA
<213> ORGANISM: Homo sapien

<400> SEQUENCE: 133
aggtcctgtc cgggggcact gagaactccc tctggaattc ttgggggtg ttggggagag       60 actgtgggcc tggagataaa acttgtctcc tctaccacca ccctgtaccc tagcctgcac      120
ctgtcctcat ctctgcaaag ttcagcttcc ttccccaggt ctctgtgcac tctgtcttgg      180
atgctctggg gagctcatgg gtggaggagt ctccaccaga gggaggctca ggggactggt      240
tgggccaggg atgaatattt gagggataaa aattgtgtaa agccaaaga attggtagta       300 gggggagaac agagaggagc tgggctatgg gaaatgattt gaataatgga gctgggaata      360
tggctggata tctggtacta aaaaaggggtc tttaagaacc tacttcctaa tctcttcccc     420
aatccaaacc atagctgtct gtccagtgct ctcttcctgc ctccagctct gccccaggct      480
cctcctagac tctgtccctg ggctagggca ggggaggagg gagagcaggg ttgggggaga     540
ggctgaggag agtgtgacat gtggggagag gaccagacct c                          581

<210> SEQ ID NO 134
<211> LENGTH: 4797
<212> TYPE: DNA
<213> ORGANISM: Homo sapien
<220> FEATURE:
<221> NAME/KEY: misc_feature
<222> LOCATION: (1)...(4797)
<223> OTHER INFORMATION: n = A,T,C or G

<400> SEQUENCE: 134
cctgggacca aagtgctgcc cagagctgag ggtcctggag ccacatgaga aggcttctcc       60
ctgtgtacct gtgcagcaca gggtagggtg agtccactca gctgtctagg agaggaccca      120
ggagcagcag agacncgcca agcctttact cataccatat tctgatcctt ttccagcaaa      180
ttgtggctac taatttgccc cctgaagatc aagatggctc tggggatgac tctgacaact      240
tctccggctc aggtgcaggt gaggttgtca tggggggcccc ccccacccaa gacggcaaca    300
ggtcatgcct gggggcagtg gtcaggcagt ctcctgtgtt tactgagcat gtactgagtg      360
caccctgcct gccctgtctc cacccagctg gctccaaagg gcaatgctga ggagaggaat      420
ggggtcgtga gctgctgtta aggagagctc atgcttggag gtgaggtgaa ggctgtgagc     480
tccagaaggc cccagggcgc nctgctgcac gcaggctcat attcactagg aatagcttta      540
ctcactaaga aacctctgga accccttca gaaggttatt tgactcctga gcctctattt       600
tctcatctgc aaaatgggaa taataccttg acctgataag cttgtggagc tgtaaggcag      660
cacagagcca gctgggtgt agctcttcca tccaagctcc cttccttact tccccttttcc      720 tgtggggact gggggagaga agtccctgag ctggaggtgg tcaggaaagc ttcacagagg      780
aggtggctct tgagtggacc tcaggaagag gggtgagaga gctaaggaag gaggctgagg      840
tcatccctgg ggaagtgacc tagcggaggc ctgagagctg caaggtagga tatctgttgt       900
tggaagtgtc tgttgttgga agtgggggcc tttttttcag ggagggtggg gccagagaag      960
tgtgtgccct gggataagta ggataaccac agtagttatg cccctaaggg atgcccaccc     1020 caccctgtg gtcacagaaa agctttccca ggtggcctag gcacctgtct cgtggctcca      1080
gagacaggct gcacctgaca cacacaatgg aaggacagct ctccttgtcc attttccaag     1140
gagcttagcc tcagctgcct tgtccaggta ctagcctccc tcatagcctg agcttggcca     1200
```

-continued

```
gcccaggtgc tctggagcct ccccgaccc acccaacaca ctctgcttct ggtcctcccc    1260
accccccacc tccccaacac actctgcttc tggtcctgca ggtgctttgc aagatatcac    1320
cttgtcacag cagaccccct ccacttggaa ggacacgcag ctcctgacgg ctattcccac    1380
gtctccagaa cccaccggcc tggaggctac agctgcctcc acctccaccc tgccggctgg    1440 agagggccc aaggagggag aggctgtagt cctgccagaa gtggagcctg gcctcaccgc    1500
ccgggagcag gaggccaccc cccgacccag ggagaccaca cagctcccga ccactcatca    1560
ggcctcaacg accacagcca ccgggccca ggagcccgcc acctcccacc cccacaggga    1620
catgcagcct ggccaccatg agacctcaac ccctgcagga cccagccaag ctgaccttca    1680
cactccccac acagaggatg gaggtccttc tgccaccgag agggctgctg aggatggagc    1740
ctccagtcag ctcccagcag cagagggctc tggggagcag gtgagtggcc tctgcattcc    1800
ttgggaaatt gagtgggttg gtcctaatgc ctggcacttg gcaggcccta cacctgtgcc    1860
ctgcgcgatc tcgtattcct caccaggaag acagggcaca ggggccgcct tcccctaccc    1920
ccagggcctc gcagagcagg acagactaac tatgagatca gagcagaagc acccttaaag    1980
atcacccaag agagggctcc caaactcaca atccaaactt gcagccctcg tcgaagagtg    2040
aacgttatac cagtcatttt atttatagct tcgtggattt acgcttacac taaatagtct    2100
gctattcata caaaatgtgt gctttgtatc acttttgtg atatccatgc catggtccag    2160
ccagggtccg gagttgatgt ggcaagaagg cctggctttc gggccctgtg cgatcctggt    2220
ttgggtgcat ctgagtgggt ggtggcaaag atcaggagg caggagctgc ttctgggtct    2280
gtagtggagc tggttgctgc tgctggcggt gacctggcca acccaatctg cccctgccct    2340
cccacaggac ttcacctttg aaacctcggg ggagaatacg gctgtagtgg ccgtggagcc    2400
tgaccgccgg aaccagtccc cagtggatca gggggccacg ggggcctcac agggcctcct    2460
ggacaggaaa gaggtgctgg gagtgagtt ttctttcagg ggggtagttt ggggtgaatt    2520
gctgctgtgg ggtcagggtg gggctgacca cagccaaggc cactgctttg ggagggtctg    2580
cacgagagcc caaggagccg ctgagctgag ctggccccgt ctacctgccc tagggtcat    2640 tgccggaggc ctcgtggggc tcatcttgc tgtgtgcctg gtgggtttca tgctgtaccg    2700
catgaagaag aaggacgaag gcagctactc cttggaggag ccgaaacaag ccaacggcgg    2760
ggcctaccag aagcccacca aacaggagga attctatgcc tgacgcggga gccatgcgcc    2820
ccctccgccc tgccactcac taggccccca cttgcctctt ccttgaagaa ctgcaggccc    2880
tggcctcccc tgccaccagg ccacctcccc agcattccag cccctctggt cgctcctgcc    2940
cacggagtcg tgggtgtgct gggagctcca ctctgcttct ctgacttctg cctggagact    3000
tagggcacca ggggtttctc gcataggacc tttccaccac agccagcacc tggcatcgca    3060
ccattctgac tcggtttctc caaactgaag cagcctctcc ccaggtccag ctctggaggg    3120
gagggggatc cgactgcttt ggacctaaat ggcctcatgt ggctggaaga tcctgcgggt    3180
ggggcttggg gctcacacac ctgtagcact tactggtagg accaagcatc ttgggggggt    3240
ggccgctgag tggcagggga caggagtcac tttgtttcgt ggggaggtct aatctagata    3300
tcgacttgtt tttgcacatg tttcctctag ttctttgttc atagcccagt agaccttgtt    3360
acttctgagg taagttaagt aagttgattc ggtatccccc catcttgctt ccctaatcta    3420
tggtcgggag acagcatcag ggttaagaag actttttttt ttttttttaa actaggagaa    3480
ccaaatctgg aagccaaaat gtaggcttag tttgtgtgtt gtctcttgag tttgtcgctc    3540
atgtgtgcaa cagggtatgg actatctgtc tggtggcccc gttctggtgg tctgttggca    3600
```

```
ggctggccag tccaggctgc cgtggggccg ccgcctcttt caagcagtcg tgcctgtgtc    3660
catgcgctca gggccatgct gaggcctggg ccgctgccac gttggagaag cccgtgtgag    3720
aagtgaatgc tgggactcag ccttcagaca gagaggacta tagggagggc ggcaggggcc    3780
tggagatcct cctgcaggct cacgcccgtc tcctgtggc gccgtctcca ggggctgctt     3840
cctcctggaa attgacgagg ggtgtcttgg gcagagctgg ctctgagcgc ctccatccaa    3900
ggccaggttc tccgttagct cctgtggccc caccctgggc cctgggctgg aatcaggaat    3960
attttccaaa gagtgatagt cttttgcttt tggcaaaact ctacttaatc caatgggttt    4020
ttccctgtac agtagatttt ccaaatgtaa taaactttaa tataaagtag tctgtgaatg    4080
ccactgcctt cgcttcttgc ctctgtgctg tgtgtgacgt gaccggactt ttctgcaaac    4140
accaacatgt tgggaaactt ggctcgaatc tctgtgcctt cgtctttccc atggggaggg    4200
attctggttc cagggtccct ctgtgtattt gcttttttgt tttggctgaa attctcctgg    4260
aggtcggtag gttcagccaa ggttttataa ggctgatgtc aatttctgtg ttgccaagct    4320
ccaagcccat cttctaaatg gcaaaggaag gtggatggcc ccagcacagc ttgacctgag    4380
gctgtggtca cagcggaggt gtggagccga ggcctacccc ncagacacct tggacatcct    4440
cctcccaccc ggctgcagag gccagannnc agcccaggt cctgcactta cttgcttatt     4500
tgacaacgtt tcagcgactc cgttggccac tccgagagtg ggccagtctg tggatcagag    4560
atgcaccacc aagccaaggg aacctgtgtc cggtattcga tactgcgact ttctgcctgg    4620
agtgtatgac tgcacatgac tcgggggtgg ggaaaggggt cggctgacca tgctcatctg    4680
ctggtccgtg ggacggtncc caagccagag gtgggttcat ttgtgtaacg acaataaacg    4740
gtacttgtca tttcgggcaa cggctgctgt ggtggtggtt gagtctcttc ttggcct      4797

<210> SEQ ID NO 135
<211> LENGTH: 2856
<212> TYPE: DNA
<213> ORGANISM: Homo sapien

<400> SEQUENCE: 135
tagtcgcggg tccccgagtg agcacgccag ggagcaggag accaaacgac gggggtcgga     60
gtcagagtcg cagtgggagt ccccggaccg gagcacgagc ctgagcggga gagcgccgct    120
cgcacgcccg tcgccacccg cgtacccggc gcagccagag ccaccagcgc agcgctgcca    180
tggagcccag cagcaagaag ctgacgggtc gcctcatgct ggctgtggga ggagcagtgc    240
ttggctccct gcagtttggc tacaacactg gagtcatcaa tgcccccag aaggtgatcg     300 aggagttcta caaccagaca tgggtccacc gctatgggga gagcatcctg cccaccacgc    360
tcaccacgct ctggtccctc tcagtggcca tcttttctgt tgggggcatg attggctcct    420
tctctgtggg ccttttcgtt aaccgctttg gccggcggaa ttcaatgctg atgatgaacc    480
tgctggcctt cgtgtccgcc gtgctcatgg gcttctcgaa actgggcaag tcctttgaga    540
tgctgatcct gggccgcttc atcatcggtg tgtactgcgg cctgaccaca ggcttcgtgc    600
ccatgtatgt gggtgaagtg tcacccacag cctttcgtgg ggccctgggc accctgcacc    660
agctgggcat cgtcgtcggc atcctcatcg cccaggtgtt cggcctggac tccatcatgg    720
gcaacaagga cctgtggccc ctgctgctga gcatcatctt catcccggcc ctgctgcagt    780
gcatcgtgct gcccttctgc cccgagagtc ccgcttcct gctcatcaac cgcaacgagg     840
agaaccgggc caagagtgtg ctaaagaagc tgcgcgggac agctgacgtg acccatgacc    900
```

```
tgcaggagat gaaggaagag agtcggcaga tgatgcggga gaagaaggtc accatcctgg    960
agctgttccg ctcccccgcc taccgccagc ccatcctcat cgctgtggtg ctgcagctgt   1020
cccagcagct gtctggcatc aacgctgtct tctattactc cacgagcatc ttcgagaagg   1080
cgggggtgca gcagcctgtg tatgccacca ttggctccgg tatcgtcaac acggccttca   1140
ctgtcgtgtc gctgtttgtg gtggagcgag caggccggcg gaccctgcac ctcataggcc   1200
tcgctggcat ggcgggttgt gccatactca tgaccatcgc gctagcactg ctggagcagc   1260
taccctggat gtcctatctg agcatcgtgg ccatctttgg ctttgtggcc ttctttgaag   1320
tgggtcctgg ccccatccca tggttcatcg tggctgaact cttcagccag ggtccacgtc   1380
cagctgccat tgccgttgca ggcttctcca actggacctc aaatttcatt gtgggcatgt   1440
gcttccagta tgtggagcaa ctgtgtggtc cctacgtctt catcatcttc actgtgctcc   1500
tggttctgtt cttcatcttc acctacttca agttcctga gactaaaggc cggaccttcg    1560
atgagatcgc ttccggcttc cggcagggg gagccagcca aagtgataag acacccgagg    1620
agctgttcca tcccctgggg gctgattccc aagtgtgagt cgccccagat caccagcccg   1680
gcctgctccc agcagcccta aggatctctc aggagcacag gcagctggat gagacttcca   1740
aacctgacag atgtcagccg agccgggcct gggctccttt ctccagcca gcaatgatgt    1800
ccagaagaat attcaggact taacggctcc aggattttaa caaaagcaag actgttgctc   1860
aaatctattc agacaagcaa caggttttat aatttttta ttactgatttt tgttatttttt   1920
atatcagcct gagtctcctg tgcccacatc ccaggcttca ccctgaatgg ttccatgcct   1980
gagggtggag actaagccct gtcgagacac ttgccttctt cacccagcta atctgtaggg   2040
ctggacctat gtcctaagga cacactaatc gaactatgaa ctacaaagct tctatcccag   2100
gaggtggcta tggccacccg ttctgctggc ctggatctcc ccactctagg ggtcaggctc   2160
cattaggatt tgccccttcc catctcttcc tacccaacca ctcaaattaa tctttctta    2220
cctgagacca gttgggagca ctggagtgca gggaggagag gggaagggcc agtctgggct   2280
gccgggttct agtctccttt gcactgaggg ccacactatt accatgagaa gagggcctgt   2340
gggagcctgc aaactcactg ctcaagaaga catggagact cctgccctgt tgtgtataga   2400
tgcaagatat ttatatatat ttttggttgt caatattaaa tacagacact aagttatagt   2460
atatctggac aagccaactt gtaaatacac cacctcactc ctgttactta cctaaacaga   2520
tataaatggc tggttttag aaacatggtt ttgaaatgct tgtggattga gggtaggagg    2580
tttggatggg agtgagacag aagtaagtgg ggttgcaacc actgcaacgg cttagacttc   2640
gactcaggat ccagtccctt acacgtacct ctcatcagtg tcctcttgct caaaaatctg   2700
tttgatccct gttacccaga gaatatatac attctttatc ttgacattca aggcatttct   2760
atcacatatt tgatagttgg tgttcaaaaa aacactagtt ttgtgccagc cgtgatgctc   2820
aggcttgaaa tcgcattatt ttgaatgtga agggaa                             2856
```

<210> SEQ ID NO 136
<211> LENGTH: 356
<212> TYPE: DNA
<213> ORGANISM: Homo sapien

<400> SEQUENCE: 136

```
ggtggagcca aatgaagaaa atgaagatga aagagacaga cacctcagtt tttctggatc     60
aggcattgat gatgatgaag attttatctc cagcaccatt tcaaccacac cacgggcttt    120
tgaccacaca aaacagaacc aggactggac tcagtggaac ccaagccatt caaatccgga    180
```

```
agtgctactt cagacaacca caaggatgac tgatgtagac agaaatggca ccactgctta      240
tgaaggaaac tggaacccag aagcacaccc tcccctcatt caccatgagc atcatgagga      300
agaagagacc ccacattcta caagcacaat ccaggcaact cctagtagta caacgg          356
```

<210> SEQ ID NO 137
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 137

```
gcaggtggag aagacatttt attgttcctg gggtctctgg aggcccattg gtggggctgg      60
gtcactggct gccccggaa  cagggcgctg ctccatggct ctgcttgtgg tagtctgtgg      120
ctatgtctcc cagcaaggac agaaactcag aaaaatcaat cttcttatcc tcattcttgt      180
cctttttctc aaagacatcg gcgaggtaat ttgtgcccct tttacctcgg ccgcgacca       240 cgctaaggcc aaanttccag acanayggcc gggccggtnc natagggan  cccaacttgg      300 ggacccaaac tctggcgcgg aaacacangg gcataagctt gnttcctgtg gggaaa          356
```

<210> SEQ ID NO 138
<211> LENGTH: 353
<212> TYPE: DNA
<213> ORGANISM: Homo sapien

<400> SEQUENCE: 138

```
aggtccagtc ctccacttgg cctgatgaga gtggggagtg gcaagggacg tttctcctgc      60
aatagacact tagatttctc tcttgtggga agaaaccacc tgtccatcca ctgactcttc      120
tacattgatg tggaaattgc tgctgctacc accacctcct gaagaggctt ccctgatgcc      180
aatgccagcc atcttggcat cctggccctc gagcaggctg cggtaagtag cgatctcctg      240
ctccagccgt gtctttatgt caagcagcat cttgtactcc tggttctgag cctccatctc      300
gcatcggagc tcactcagac ctcgsccgsg mssmcgctam gccgaattcc agc             353
```

<210> SEQ ID NO 139
<211> LENGTH: 371
<212> TYPE: DNA
<213> ORGANISM: Homo sapien

<400> SEQUENCE: 139

```
agcgtggtcg cggccgaggt ccatccgaag caagattgca gatggcagtg tgaagagaga      60
agacatattc tacacttcaa agctttggtg caattcccat cgaccagagt tggtccgacc      120
agccttggaa aggtcactga aaaatcttca attggattat gttgacctct accttattca      180
ttttccagtg tctgtaaagc caggtgagga agtgatccca aaagatgaaa atggaaaaat      240
actatttgac acagtggatc tctgtgccac gtgggaggcc gtggagaagt gtaaagatgc      300
aggattggac ctgcccgggc ggccgctcga aagccgaatt ccagcacact ggcggccgtt      360
actagtggat c                                                          371
```

<210> SEQ ID NO 140
<211> LENGTH: 370
<212> TYPE: DNA
<213> ORGANISM: Homo sapien

```
<400> SEQUENCE: 140
tagcgtggtc gcggccgagg tccatctccc tttgggaact aggggctgc tggtgggaaa      60
tgggagccag ggcagatgtt gcattccttt gtgtccctgt aaatgtggga ctacaagaag    120
aggagctgcc tgagtggtac tttctcttcc tggtaatcct ctggcccagc ctcatggcag    180
aatagaggta ttttaggct attttgtaa tatggcttct ggtcaaaatc cctgtgtagc      240
tgaattccca agccctgcat tgtacagccc cccactcccc tcaccaccta ataaaggaat    300
agttaacact caaaaaaaaa aaaaaacctg cccgggcggc cgctcgaaag ccgaattcca    360
gcacactggc                                                            370

<210> SEQ ID NO 141
<211> LENGTH: 371
<212> TYPE: DNA
<213> ORGANISM: Homo sapien

<400> SEQUENCE: 141
tagcgtggtc gcggccgagg tcctctgtgc tgcctgtcac agcccgatgg taccagcgca      60
gggtgtaggc agtgcaggag ccctcatcca gtggcaggga acaggggtca tcactatccc    120
aaggagcttc aggtcctgg tactcctcca cagaatactc ggagtattca gagtactcat     180
catcctcagg gggtacccgc tcttcctcct ctgcatgaga gacgcggagc acaggcacag    240
catggagctg ggagccggca gtgtctgcag cataactagg gagggtcgt gatccagatg     300
cgatgaactg gccctggcag gcacagtgct gactcatctc ttggcgacct gcccgggcgg    360
ccgctcgaag c                                                          371

<210> SEQ ID NO 142
<211> LENGTH: 343
<212> TYPE: DNA
<213> ORGANISM: Homo sapien

<400> SEQUENCE: 142
gcgttttgag gccaatggtg taaaggaaa tatcttcaca taaaaactag atggaagcat       60
tgtcagaaac ctctttgtga tgtttgcttt caactcacag agttgaacat tccttttcat    120
agagcagttt tgaaacactc ttttgtagaa tttgcaagcg gatgattgga tcgctatgag    180
gtcttcattg gaaacgggat acctttacat aaaaactaga cagtagcatt ctcagaaatt    240
tctttgggat gtgggcattc aacccacaga ggagaacttc atttgataga gcagttttga    300
aacaccctttt ttgtagaatc tacaggtgga catttagagt gct                     343

<210> SEQ ID NO 143
<211> LENGTH: 354
<212> TYPE: DNA
<213> ORGANISM: Homo sapien

<400> SEQUENCE: 143
aggtctgatg gcagaaaaac tcagactgtc tgcaacttta cagatggtgc attggttcag      60
catcaggagt gggatgggaa ggaaagcaca ataacaagaa aattgaaaga tgggaaatta    120
gtggtggagt gtgtcatgaa caatgtcacc tgtactcgga tctatgaaaa agtagaataa    180
aaattccatc atcactttgg acaggagtta attaagagaa tgaccaagct cagttcaatg    240
agcaaatctc catactgttt cttctttttt ttttcatta ctgtgttcaa ttatctttat     300
cataaacatt ttacatgcag ctatttcaaa gtgtgttgga ttaattagga tcat          354
```

<210> SEQ ID NO 144
<211> LENGTH: 353
<212> TYPE: DNA
<213> ORGANISM: Homo sapien

<400> SEQUENCE: 144

| ggtcaaggac ctgggggacc cccaggtcca gcagccacat gattctgcag cagacaggga | 60 |
| cctagagcac atctggatct cagccccacc cctggcaacc tgcctgccta gagaactccc | 120 |
| aagatgacag actaagtagg attctgccat ttagaataat tctggtatcc tgggcgttgc | 180 |
| gttaagttgc ttaactttca ttctgtctta cgatagtctt cagaggtggg aacagatgaa | 240 |
| gaaaccatgc cccagagaag gttaagtgac ttcctctttta tggagccagt gttccaacct | 300 |
| aggtttgcct gataccagac ctgtggcccc acctcccatg caggtctctg tgg | 353 |

<210> SEQ ID NO 145
<211> LENGTH: 371
<212> TYPE: DNA
<213> ORGANISM: Homo sapien

<400> SEQUENCE: 145

| caggtctgtc ataaactggt ctggagtttc tgacgactcc ttgttcacca aatgcaccat | 60 |
| ttcctgagac ttgctggcct ctccgttgag tccacttggc tttctgtcct ccacagctcc | 120 |
| attgccactg ttgatcacta gctttttctt ctgcccacac cttcttcgac tgttgactgc | 180 |
| aatgcaaact gcaagaatca agccaaggc caagagggat gccaagatga tcagccattc | 240 |
| tggaatttgg ggtgtcctta taggaccaga ggttgtgttt gctccacctt cttgactccc | 300 |
| atgtgagacc tcggccgcga ccacgctaag ccgaattcca gcacactggc ggcccgttac | 360 |
| tagtggatcc g | 371 |

<210> SEQ ID NO 146
<211> LENGTH: 355
<212> TYPE: DNA
<213> ORGANISM: Homo sapien

<400> SEQUENCE: 146

| ggtcctccgt cctcttccca gaggtgtcgg ggcttggccc cagcctccat cttcgtctct | 60 |
| caggatggcg agtagcagcg gctccaaggc tgaattcatt gtcggaggga aatataaact | 120 |
| ggtacgaaag atcgggtctg gctccttcgg ggacatctat ttggcgatca acatcaccaa | 180 |
| cggcgaggaa gtggcagtga agctagaatc tcagaaggcc aggcatcccc agttgctgta | 240 |
| cgagagcaag ctctataaga ttcttcaagg tggggttggc atcccccaca tacggtggta | 300 |
| tggtcaggaa aaagactaca atgtactagt catggatctt ctgggaccta gcctc | 355 |

<210> SEQ ID NO 147
<211> LENGTH: 355
<212> TYPE: DNA
<213> ORGANISM: Homo sapien

<400> SEQUENCE: 147

| ggtctgttac aaaatgaaga cagacaacac aacatttact ctgtggagat atcctactca | 60 |
| tactatgcac gtgctgtgat tttgaacata actcgtccca aaaacttgtc acgatcatcc | 120 |
| tgactttttta ggttggctga tccatcaatc ttgcactcaa ctgttacttc tttcccagtg | 180 |
| ttgttaggag caaagctgac ctgaacagca accaatggct gtagataccc aacatgcagt | 240 |
| ttttttcccat aatatgggaa atatttttaag tctatcattc cattatgagg ataaactgct | 300 |

```
acatttggta tatcttcatt ctttgaaaca caatctatcc ttggcactcc ttcag      355

<210> SEQ ID NO 148
<211> LENGTH: 369
<212> TYPE: DNA
<213> ORGANISM: Homo sapien

<400> SEQUENCE: 148
aggtctctct cccctctcc ctctcctgcc agccaagtga agacatgctt acttcccctt    60
caccttcctt catgatgtgg gaagagtgct gcaacccagc cctagccaac accgcatgag   120
agggagtgtg ccgagggctt ctgagaaggt ttctctcaca tctagaaaga agcgcttaag   180
atgtggcagc ccctcttctt caagtggctc ttgtcctgtt gccctgggag ttctcaaatt   240
gctgcagcag cctccatcca gcctgaggat gacatcaata cacagaggaa gaagagtcag   300
gaaaagatga gagaagttac agactctcct gggcgacccc gagagcttac cattcctcag   360
acttcttca                                                          369

<210> SEQ ID NO 149
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 149
actagtcaaa aatgctaaaa taatttggga gaaaatattt tttaagtagt gttatagttt    60
catgtttatc ttttattatg ttttgtgaag ttgtgtcttt tcactaatta cctatactat   120
gccaatattt ccttatatct atccataaca tttatactac atttgtaana naatatgcac   180
gtgaaactta acactttata aggtaaaaat gaggtttcca anatttaata atctgatcaa   240
gttcttgtta tttccaaata gaatggactt ggtctgttaa gggctaagga gaagaggaag   300
ataaggttaa aagttgttaa tgaccaaaca ttctaaaaga aatgcaaaaa aaagttttat   360
tttcaagcct tcgaactatt taaggaaagc aaaatcattt cctaaatgca tatcatttgt   420
gagaatttct cattaatatc ctgaatcatt catttcacta aggctcatgt tnactccgat   480
atgtctctaa gaaagtacta tttcatggtc caaacctggt tgccatantt gggtaaaggc   540
tttcccttaa gtgtgaaant atttaaaatg aaattttcct cttttaaaa attctttana   600 agggttaagg gtgttgggga                                              620

<210> SEQ ID NO 150
<211> LENGTH: 371
<212> TYPE: DNA
<213> ORGANISM: Homo sapien

<400> SEQUENCE: 150
ggtccgatca aaacctgcta cctccccaag actttactag tgccgataaa ctttctcaaa    60
gagcaaccag tatcacttcc ctgtttataa aacctctaac catctctttg ttctttgaac   120
atgctgaaaa ccacctggtc tgcatgtatg cccgaatttg yaattctttt ctctcaaatg   180
aaaatttaat tttagggatt catttctata ttttcacata tgtagtatta ttatttcctt   240
atatgtgtaa ggtgaaattt atggtatttg agtgtgcaag aaaatatatt tttaaagctt   300 tcattttttcc cccagtgaat gatttagaat ttttatgta aatatacaga atgtttttc    360 ttacttttat a                                                       371
```

<210> SEQ ID NO 151
<211> LENGTH: 4655
<212> TYPE: DNA
<213> ORGANISM: Homo sapien

<400> SEQUENCE: 151

```
gggacttgag ttctgttatc ttcttaagta gattcatatt gtaagggtct cggggtgggg     60
gggttggcaa atcctggag ccagaagaaa ggacagcagc attgatcaat cttacagcta    120
acatgttgta cctggaaaac aatgcccaga ctcaatttag tgagccacag tacacgaacc    180
tgggctcct gaacagcatg gaccagcaga ttcagaacgg ctcctcgtcc accagtccct    240
ataacacaga ccacgcgcag aacagcgtca cggcgccctc gccctacgca cagcccagct    300
ccaccttcga tgctctctct ccatcacccg ccatcccctc caacaccgac tacccaggcc    360
cgcacagttt cgacgtgtcc ttccagcagt cgagcaccgc caagtcggcc acctggacgt    420
attccactga actgaagaaa ctctactgcc aaattgcaaa gacatgcccc atccagatca    480
aggtgatgac cccacctcct cagggagctg ttatccgcgc catgcctgtc tacaaaaaag    540
ctgagcacgt cacggaggtg gtgaagcggt gccccaacca tgagctgagc cgtgaattca    600
acgagggaca gattgcccct yctagtcatt tgattcgagt agaggggaac agccatgccc    660
agtatgtaga agatcccatc acaggaagac agagtgtgct ggtaccttat gagccacccc    720
aggttggcac tgaattcacg acagtcttgt acaatttcat gtgtaacagc agttgtgttg    780
gagggatgaa ccgccgtcca attttaatca ttgttactct ggaaaccaga gatgggcaag    840
tcctgggccg acgctgcttt gaggcccgga tctgtgcttg cccaggaaga gacaggaagg    900
cggatgaaga tagcatcaga aagcagcaag tttcggacag tacaaagaac ggtgatggta    960
cgaagcgccc gtttcgtcag aacacacatg gtatccagat gacatccatc aagaaacgaa   1020
gatccccaga tgatgaactg gtatacttac cagtgagggg ccgtgagact tatgaaatgc   1080
tggtgaagat caaagagtcc ctggaactca tgcagtacct tcttcagcac acaattgaaa   1140
cgtacaggca acagcaacag cagcagcacc agcacttact tcagaaacag acctcaatac   1200
agtctccatc ttcatatggt aacagctccc cacctctgaa caaatgaac agcatgaaca   1260
agctgccttc tgtgagccag cttatcaacc ctcagcagcg caacgccctc actcctacaa   1320
ccattcctga tggcatggga gccaacattc catgatggg cacccacatg ccaatggctg   1380
gagacatgaa tggactcagc cccacccagg cactccctcc cccactctcc atgccatcca   1440
cctcccactg cacacccca cctccgtatc ccacagattg cagcattgtc agtttcttag   1500
cgaggttggg ctgttcatca tgtctggact atttcacgac ccaggggctg accaccatct   1560
atcagattga gcattactcc atggatgatc tggcaagtct gaaaatccct gagcaatttc   1620
gacatgcgat ctgaagggc atcctggacc accggcagct ccacgaattc tcctcccctt   1680
ctcatctcct gcggaccca agcagtgcct ctacagtcag tgtgggctcc agtgagaccc   1740
ggggtgagcg tgttattgat gctgtgcgat tcaccctccg ccagaccatc tctttcccac   1800
cccgagatga gtggaatgac ttcaactttg acatggatgc tcgccgcaat aagcaacagc   1860
gcatcaaaga ggaggggag tgagcctcac catgtgagct cttcctatcc ctctcctaac   1920
tgccagcccc ctaaaagcac tcctgcttaa tcttcaaagc cttctcccta gctcctcccc   1980
ttcctcttgt ctgatttctt aggggaagga gaagtaagag gcttacttct taccctaacc   2040
atctgacctg gcatctaatt ctgattctgg ctttaagcct tcaaaactat agcttgcaga   2100
```

```
actgtagctt gccatggcta ggtagaagtg agcaaaaaag agttgggtgt ctccttaagc   2160
tgcagagatt tctcattgac ttttataaag catgttcacc cttatagtct aagactatat   2220
atataaatgt ataaatatac agtatagatt tttgggtggg gggcattgag tattgtttaa   2280
aatgtaattt aaatgaaaga aaattgagtt gcacttattg accattttt aatttacttg    2340 ttttggatgg cttgtctata ctccttccct taagggtat catgtatggt gataggtatc    2400
tagagcttaa tgctacatgt gagtgacgat gatgtacaga ttctttcagt tctttggatt   2460
ctaaatacat gccacatcaa acctttgagt agatccattt ccattgctta ttatgtaggt   2520
aagactgtag atatgtattc ttttctcagt gttggtatat tttatattac tgacatttct   2580
tctagtgatg atggttcacg ttggggtgat ttaatccagt tataagaaga agttcatgtc   2640
caaacgtcct ctttagtttt tggttgggaa tgaggaaaat tcttaaaagg cccatagcag   2700
ccagttcaaa acacccgac gtcatgtatt tgagcatatc agtaaccccc ttaaatttaa     2760
taccagatac cttatcttac aatattgatt gggaaaacat ttgctgccat tacagaggta   2820
ttaaaactaa atttcactac tagattgact aactcaaata cacatttgct actgttgtaa   2880
gaattctgat tgatttgatt gggatgaatg ccatctatct agttctaaca gtgaagtttt    2940
actgtctatt aatattcagg gtaaatagga atcattcaga aatgttgagt ctgtactaaa   3000
cagtaagata tctcaatgaa ccataaattc aactttgtaa aaatcttttg aagcatagat   3060
aatattgttt ggtaaatgtt tcttttgttt ggtaaatgtt tcyttaaag acctcctat     3120 tctataaaac tctgcatgta gaggcttgtt tacctttctc tctctaaggt ttacaatagg   3180
agtggtgatt tgaaaaatat aaaattatga gattggtttt cctgtggcat aaattgcatc   3240
actgtatcat tttctttttt aaccggtaag agtttcagtt tgttggaaag taactgtgag   3300
aacccagttt cccgtccatc tcccttaggg actacccata gacatgaaag gtccccacag   3360
agcaagagat aagtctttca tggctgctgt tgcttaaacc acttaaacga agagttccct   3420
tgaaactttg ggaaaacatg ttaatgacaa tattccagat ctttcagaaa tataacacat   3480
ttttttgcat gcatgcaaat gagctctgaa atcttcccat gcattctggt caagggctgt   3540
cattgcacat aagcttccat tttaatttta aagtgcaaaa gggccagcgt ggctctaaaa   3600
ggtaatgtgt ggattgcctc tgaaaagtgt gtatatattt tgtgtgaaat tgcatacttt   3660
gtattttgat tattttttt ttcttcttgg gatagtggga tttccagaac cacacttgaa    3720 acctttttt atcgtttttg tattttcatg aaaataccat ttagtaagaa taccacatca    3780
aataagaaat aatgctacaa ttttaagagg ggagggaagg gaaagttttt ttttttatta   3840
tttttttaaa attttgtatg ttaaagaaa tgagtccttg atttcaaagt tttgttgtac    3900
ttaaatggta ataagcactg taaacttctg caacaagcat gcagctttgc aaacccatta   3960
aggggaagaa tgaaagctgt tccttggtcc tagtaagaag acaaactgct tcccttactt    4020
tgctgagggt ttgaataaac ctaggacttc cgagctatgt cagtactatt caggtaacac   4080
tagggccttg gaaatccctg tactgtgtct catggatttg gcactagcca aagcgaggca   4140
ccccttactg gcttacctcc tcatggcagc ctactctcct tgagtgtatg agtagccagg   4200 gtaagggta aaaggatagt aagcatagaa accactagaa agtgggctta atggagttct    4260
tgtggcctca gctcaatgca gttagctgaa gaattgaaaa gttttttgttt ggagacgttt   4320 ataaacagaa atgaaagca gagttttcat taaatccttt tacctttttt ttttcttggt    4380
aatcccctaa aataacagta tgtgggatat tgaatgttaa agggatattt ttttctatta    4440
tttttataat tgtacaaaat taagcaaatg ttaaaagttt tatatgcttt attaatgttt    4500
```

```
tcaaaaggta ttatacatgt gatacatttt ttaagcttca gttgcttgtc ttctggtact    4560
ttctgttatg ggcttttggg gagccagaag ccaatctaca atctctttt gtttgccagg    4620 acatgcaata aaatttaaaa aataaataaa aacta                               4655
```

<210> SEQ ID NO 152
<211> LENGTH: 586
<212> TYPE: PRT
<213> ORGANISM: Homo sapien

<400> SEQUENCE: 152

```
Met Leu Tyr Leu Glu Asn Asn Ala Gln Thr Gln Phe Ser Glu Pro Gln
 1               5                  10                  15

Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Ser Thr Phe Asp Ala
    50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Gln Gly
        115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Ser Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Phe Arg Gln Asn Thr
        275                 280                 285

His Gly Ile Gln Met Thr Ser Ile Lys Lys Arg Arg Ser Pro Asp Asp
    290                 295                 300

Glu Leu Val Tyr Leu Pro Val Arg Gly Arg Glu Thr Tyr Glu Met Leu
305                 310                 315                 320

Val Lys Ile Lys Glu Ser Leu Glu Leu Met Gln Tyr Leu Leu Gln His
                325                 330                 335

Thr Ile Glu Thr Tyr Arg Gln Gln Gln Gln Gln His Gln His Leu
```

-continued

```
                    340                 345                 350
Leu Gln Lys Gln Thr Ser Ile Gln Ser Pro Ser Ser Tyr Gly Asn Ser
                355                 360                 365

Ser Pro Pro Leu Asn Lys Met Asn Ser Met Asn Lys Leu Pro Ser Val
    370                 375                 380

Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
                405                 410                 415

Pro Met Ala Gly Asp Met Asn Gly Leu Ser Pro Thr Gln Ala Leu Pro
                420                 425                 430

Pro Pro Leu Ser Met Pro Ser Thr Ser His Cys Thr Pro Pro Pro Pro
            435                 440                 445

Tyr Pro Thr Asp Cys Ser Ile Val Ser Phe Leu Ala Arg Leu Gly Cys
            450                 455                 460

Ser Ser Cys Leu Asp Tyr Phe Thr Thr Gln Gly Leu Thr Thr Ile Tyr
465                 470                 475                 480

Gln Ile Glu His Tyr Ser Met Asp Asp Leu Ala Ser Leu Lys Ile Pro
                485                 490                 495

Glu Gln Phe Arg His Ala Ile Trp Lys Gly Ile Leu Asp His Arg Gln
            500                 505                 510

Leu His Glu Phe Ser Ser Pro Ser His Leu Leu Arg Thr Pro Ser Ser
        515                 520                 525

Ala Ser Thr Val Ser Val Gly Ser Ser Glu Thr Arg Gly Glu Arg Val
        530                 535                 540

Ile Asp Ala Val Arg Phe Thr Leu Arg Gln Thr Ile Ser Phe Pro Pro
545                 550                 555                 560

Arg Asp Glu Trp Asn Asp Phe Asn Phe Asp Met Asp Ala Arg Arg Asn
                565                 570                 575

Lys Gln Gln Arg Ile Lys Glu Glu Gly Glu
                580                 585
```

<210> SEQ ID NO 153
<211> LENGTH: 2007
<212> TYPE: DNA
<213> ORGANISM: Homo sapien

<400> SEQUENCE: 153

| | | | | | | |
|---|---|---|---|---|---|---|
| gaattcgtcg | ctgctccagg | gaaagttctg | ttactccact | gactctctct | tttcctgata | 60 |
| acatggccag | caagaaagta | attacagtgt | ttggagcaac | aggagctcaa | ggtggctctg | 120 |
| tggccagggc | aattttggag | agcaaaaaat | ttgcagtgag | agcagtgacc | agggatgtga | 180 |
| cttgaccaaa | tgccctggag | ctccagcgcc | ttggagctga | ggtggtcaaa | ggtgacctga | 240 |
| atgataaagc | atcggtggac | agtgccttaa | aaggtgtcta | tggggccttc | ttggtgacca | 300 |
| acttctggga | ccctctcaac | caagataagg | aagtgtgtcg | ggggaagctg | gtggcagact | 360 |
| ccgccaagca | cctgggtctg | aagcacgtgg | tgtacagcgg | cctggagaac | gtcaagcgac | 420 |
| tgacggatgg | caagctggag | gtgccgcact | tgacagcaa | gggcgaggtg | gaggagtact | 480 |
| tctggtccat | tggcatcccc | atgaccagtg | tccgcgtggc | ggcctacttt | gaaaactttc | 540 |
| tcgcggcgtg | gcggcccgtg | aaagcctctg | atggagatta | ctacaccttg | gctgtaccga | 600 |
| tgggagatgt | accaatggat | ggtatctctg | ttgctgatat | tggagcagcc | gtctctagca | 660 |
| tttttaattc | tccagaggaa | tttttaggca | aggccgtggg | gctcagtgca | gaagcactaa | 720 |

```
caatacagca atatgctgat gttttgtcca aggctttggg gaaagaagtc cgagatgcaa    780
agattacccc ggaagctttc gagaagctgg gattccctgc agcaaaggaa atagccaata    840
tgtgtcgttt ctatgaaatg aagccagacc gagatgtcaa tctcacccac caactaaatc    900
ccaaagtcaa aagcttcagc cagtttatct cagagaacca gggagccttc aagggcatgt    960
agaaaatcag ctgttcagat aggcctctgc accacacagc ctctttcctc tctgatcctt   1020 ttcctctttta cggcacaaca ttcatgttga cagaacatgc tggaatgcaa ttgtttgcaa   1080
caccgaagga tttcctgcgg tcgcctcttc agtaggaagc actgcattgg tgataggaca   1140
cggtaatttg attcacattt aacttgctag ttagtgataa gggtggtaca actgtttggt   1200
aaaatgagaa gcctcggaac ttggagcttc tctcctacca ctaatgggag ggcagattat   1260
actgggattt ctcctgggtg agtaatttca agccctaatg ctgaaattcc cctaggcagc   1320
tccagttttc tcaactgcat tgcaaaattc ccagtgaact tttaagtact tttaacttaa   1380
aaaaatgaac atctttgtag agaattttct ggggaacatg gtgttcaatg aacaagcaca   1440
agcattggaa atgctaaaat tcagttttgc ctcaagattg gaagtttatt ttctgactca   1500
ttcatgaagt catctattga gccaccattc aattattcat ctattaattc cttgatcctt   1560
catttatcca ttctgcaaac tttttcttgag caccagcacg ggtggccatt tgtggacttc   1620
tcttcattcc tatgtgtttt cttatcaaag tgatccactc tcgaaaggct cctttccagt   1680
ctgtggttgg gttcaagtca tgccagggcc aggggcccca tctcctcgtt tagctctagg   1740
caaaatccag gggatctgca gtggggagcg ggggcaggaa gctggaggga aggcctgtga   1800
agggtaggga tgtggaaaga caaggtgaca gaaggaccca ataggacctt tctatatctc   1860
tggcttagca ttttctacat catattgtaa tcgtcttatt tgctagtttt cttccttact   1920
gtgagtgact aacagtcatc tttatcccag tgcctggtac ataataagtg atcaataaat   1980
gttgattgac taaaaaaaaa aaaaaaa                                       2007
```

<210> SEQ ID NO 154
<211> LENGTH: 2148
<212> TYPE: DNA
<213> ORGANISM: Homo sapien

<400> SEQUENCE: 154

```
gaattcgtcg ctgctccagg gaaagttctg ttactccact gactctctct tttcctgata     60
acatggccag caagaaagta attacagtgt ttggagcaac aggagctcaa ggtggctctg    120
tggccagggc aattttggag agcaaaaaat ttgcagtgag agcagtgacc agggatgtga    180
cttgaccaaa tgccctggag ctccagcgcc ttggagctga ggtggtcaaa ggtgacctga    240
atgataaagc atcggtggac agtgccttaa aaggggaagc tggtggcaga ctccgccaag    300
cacctgggtc tgaagcacgt ggtgtacagc ggcctggaga acgtcaagcg actgacggat    360
ggcaagctgg aggtgccgca ctttgacagc aagggcgagg tggaggagta cttctggtcc    420
attggcatcc ccatgaccag tgtccgcgtg gcggcctact ttgaaaactt tctcgcggcg    480
tggcggcccg tgaaagcctc tgatggagat tactacacct tggctgtacc gatgggagat    540
gtaccaatgg atggtatctc tgttgctgat attggagcag ccgtctctag cattttttaat    600 tctccagagg aattttttagg caaggccgtg gggctcagtg cagaagcact aacaatacag    660
caatatgctg atgttttgtc caaggctttg gggaaagaag tccgagatgc aaagactatc    720
tgtgctatag atgaccagaa aacagtggaa gaaggtttca tggaagacgt gggcttgagt    780
tggtccttga gggaacatga ccatgtatag acagaggagg catcaagaag gctggcctgg    840
```

```
ctaattctgg aataaacacg acaaaccaga ggcagtacgg gaaggaggca aattctggct    900
ctgcctctat ccttgattac cccggaagct ttcgagaagc tgggattccc tgcagcaaag    960
gaaatagcca atatgtgtcg tttctatgaa atgaagccag accgagatgt caatctcacc   1020
caccaactaa atcccaaagt caaaagcttc agccatttta tctcagagaa ccagggagcc   1080
ttcaagggca tgtagaaaat cagctgttca gataggcctc tgcaccacac agcctctttc   1140
ctctctgatc cttttcctct ttacggcaca acattcatgt tgacagaaca tgctggaatg   1200
caattgtttg caacaccgaa ggatttcctg cggtcgcctc ttcagtagga agcactgcat   1260
tggtgatagg acacggtaat ttgattcaca tttaacttgc tagttagtga aagggtggt    1320
acaactgttt ggtaaaatga gaagcctcgg aacttggagc ttctctccta ccactaatgg   1380
gagggcagat tatactggga tttctcctgg gtgagtaatt tcaagcccta atgctgaaat   1440
tcccctaggc agctccagtt ttctcaactg cattgcaaaa ttcccagtga acttttaagt   1500
acttttaact aaaaaaatg aacatctttg tagagaattt tctggggaac atggtgttca   1560
atgaacaagc acaagcattg gaaatgctaa aattcagttt tgcctcaaga ttggaagttt   1620
atttttctgac tcattcatga agtcatctat tgagccacca ttcaattatt catctattaa   1680
ttccttgatc cttcatttat ccattctgca aacttttctt gagcaccagc acgggtggcc   1740
atttgtggac ttctcttcat tcctatgtgt tttcttatca aagtgatcca ctctcgaaag   1800
gctcctttcc agtctgtggt tgggttcaag tcatgccagg gccaggggggc ccatctcctc   1860
gtttagctct aggcaaaatc caggggatct gcagtgggga gcggggcag gaagctggag   1920
ggaaggcctg tgaagggtag ggatgtggaa agacaaggtg acagaaggac ccaataggac   1980
cttttctatat ctctggctta gcattttcta catcatattg taatcgtctt atttgctagt   2040
tttcttcctt actgtgagtg actaacagtc atctttatcc cagtgcctgg tacataataa   2100
gtgatcaata aatgttgatt gactaaatga aaaaaaaaa aaaaaaaa                  2148
```

<210> SEQ ID NO 155
<211> LENGTH: 153
<212> TYPE: PRT
<213> ORGANISM: Homo sapien

<400> SEQUENCE: 155

| Met | Thr | Ser | Val | Arg | Val | Ala | Ala | Tyr | Phe | Glu | Asn | Phe | Leu | Ala | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Trp | Arg | Pro | Val | Lys | Ala | Ser | Asp | Gly | Asp | Tyr | Tyr | Thr | Leu | Ala | Val |
|     |     |     | 20  |     |     |     |     | 25  |     |     |     |     | 30  |     |     |

| Pro | Met | Gly | Asp | Val | Pro | Met | Asp | Gly | Ile | Ser | Val | Ala | Asp | Ile | Gly |
|     |     | 35  |     |     |     |     | 40  |     |     |     |     | 45  |     |     |     |

| Ala | Ala | Val | Ser | Ser | Ile | Phe | Asn | Ser | Pro | Glu | Glu | Phe | Leu | Gly | Lys |
|     | 50  |     |     |     |     | 55  |     |     |     |     | 60  |     |     |     |     |

| Ala | Val | Gly | Leu | Ser | Ala | Glu | Ala | Leu | Thr | Ile | Gln | Gln | Tyr | Ala | Asp |
| 65  |     |     |     |     | 70  |     |     |     |     | 75  |     |     |     |     | 80  |

| Val | Leu | Ser | Lys | Ala | Leu | Gly | Lys | Glu | Val | Arg | Asp | Ala | Lys | Ile | Thr |
|     |     |     |     | 85  |     |     |     |     | 90  |     |     |     |     | 95  |     |

| Pro | Glu | Ala | Phe | Glu | Lys | Leu | Gly | Phe | Pro | Ala | Ala | Lys | Glu | Ile | Ala |
|     |     |     | 100 |     |     |     |     | 105 |     |     |     |     | 110 |     |     |

| Asn | Met | Cys | Arg | Phe | Tyr | Glu | Met | Lys | Pro | Asp | Arg | Asp | Val | Asn | Leu |
|     |     | 115 |     |     |     |     | 120 |     |     |     |     | 125 |     |     |     |

| Thr | His | Gln | Leu | Asn | Pro | Lys | Val | Lys | Ser | Phe | Ser | Gln | Phe | Ile | Ser |
|     | 130 |     |     |     |     | 135 |     |     |     |     | 140 |     |     |     |     |

```
Glu Asn Gln Gly Ala Phe Lys Gly Met
145                 150
```

<210> SEQ ID NO 156
<211> LENGTH: 128
<212> TYPE: PRT
<213> ORGANISM: Homo sapien

<400> SEQUENCE: 156

```
Met Thr Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
                20                  25                  30

Pro Met Gly Asp Val Pro Met Asp Gly Ile Ser Val Ala Asp Ile Gly
            35                  40                  45

Ala Ala Val Ser Ser Ile Phe Asn Ser Pro Glu Glu Phe Leu Gly Lys
 50                  55                  60

Ala Val Gly Leu Ser Ala Glu Ala Leu Thr Ile Gln Gln Tyr Ala Asp
 65                  70                  75                  80

Val Leu Ser Lys Ala Leu Gly Lys Glu Val Arg Asp Ala Lys Thr Ile
                85                  90                  95

Cys Ala Ile Asp Asp Gln Lys Thr Val Glu Glu Gly Phe Met Glu Asp
            100                 105                 110

Val Gly Leu Ser Trp Ser Leu Arg Glu His Asp His Val Ala Gly Ala
            115                 120                 125
```

<210> SEQ ID NO 157
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 157

```
ctgcagcccg gggatccac tagtccagtg tggtggaatt cattggtctt tacaagactt      60
ggatacatta cagcagacat ggaaatataa ttttaaaaaa tttctctcca acctccttca    120
aattcagtca ccactgttat attaccttct ccaggaaccc tccagtgggg aaggctgcga    180
tattagattt ccttgtatgc aaagtttttg ttgaaagctg tgctcagagg aggtgagagg    240
agaggaagga gaaaactgca tcataacttt acagaattga atctagagtc ttccccgaaa    300
agcccagaaa cttctctgcn gnatctggct tgtccatctg gtctaaggtg gctgcttctt    360
ccccagccat cgagtcagtt tgtgcccatg aataatacac gacctgctat ttcccatgac    420
tgct                                                                 424
```

<210> SEQ ID NO 158
<211> LENGTH: 2099
<212> TYPE: DNA
<213> ORGANISM: Homo sapien

<400> SEQUENCE: 158

```
ccgcggttaa aaggcgcagc aggtgggagc cggggccttc acccgaaacc cgacgagagc     60
ccgacagccg gcggccccg agcccgacct gcctgcccag ccggagcgaa gggcgccgcc    120
ccgcgcagag cccgcgccag ggccgccggc cgcagagcag ttaaaacgtg caggcaccag    180
aaggcacttc ctgtcggtga agaagacctg tctccggtgt cacgggcatc ctgtgttttg    240
```

-continued

```
caaacggggc tgacctccct tcctggggag caggaagggt cagggaagga aagaagtac      300
agaagatctg gctaaacaat ttctgtatgg cgaaagaaaa attctaactt gtacgccctc     360
ttcatgcatc tttaattcaa tttgaatatt ccaggcgaca tcctcactga ccgagcaaag     420
attgacattc gtatcatcac tgtgcaccat tggcttctag cactccagt ggggtaggag      480
aaggaggtct gaaaccctcg cagagggatc ttgccctcat tctttgggtc tgaaacactg     540
gcagtcgttg gaaacaggac tcagggataa accagcgcaa tggattgggg gacgctgcac     600
actttcatcg ggggtgtcaa caaacactcc accagcatcg ggaaggtgtg gatcacagtc     660
atctttattt tccgagtcat gatcctcgtg gtggctgccc aggaagtgtg gggtgacgag     720
caagaggact tcgtctgcaa cacactgcaa ccgggatgca aaaatgtgtg ctatgaccac     780
ttttttcccgg tgtcccacat ccggctgtgg gccctccagc tgatcttcgt ctccacccca    840
gcgctgctgg tggccatgca tgtggcctac tacaggcacg aaaccactcg caagttcagg     900
cgaggagaga agaggaatga tttcaaagac atagaggaca ttaaaaagca gaaggttcgg     960
atagagtggg cgctgtggtg gacgtacacc agcagcatct ttttccgaat catctttgaa    1020
gcagccttta tgtatgtgtt ttacttcctt tacaatgggt accacctgcc ctgggtgttg    1080
aaatgtggga ttgaccctg ccccaacctt gttgactgct ttatttctag gccaacagag     1140
aagaccgtgt ttaccatttt tatgattct gcgtctgtga tttgcatgct gcttaacgtg     1200
gcagagttgt gctacctgct gctgaaagtg tgttttagga gatcaaagag agcacagacg    1260
caaaaaaatc accccaatca tgccctaaag gagagtaagc agaatgaaat gaatgagctg    1320
atttcagata gtggtcaaaa tgcaatcaca ggttcccaag ctaaacattt caaggtaaaa    1380
tgtagctgcg tcataaggag acttctgtct tctccagaag gcaataccaa cctgaaagtt    1440
ccttctgtag cctgaagagt ttgtaaatga ctttcataat aaatagacac ttgagttaac    1500
tttttgtagg atacttgctc cattcataca caacgtaatc aaatatgtgg tccatctctg    1560
aaaacaagag actgcttgac aaggagcat tgcagtcact ttgacaggtt ccttttaagt     1620
ggactctctg acaaagtggg tactttctga aaatttatat aactgttgtt gataaggaac    1680
atttatccag gaattgatac gtttattagg aaaagatatt tttataggct tggatgttttt   1740
tagttctgac tttgaatta tataaagtat tttttataatg actggtcttc cttacctgga    1800
aaaacatgcg atgttagttt tagaattaca ccacaagtat ctaaatttgg aacttacaaa    1860
gggtctatct tgtaaatatt gttttgcatt gtctgttggc aaatttgtga actgtcatga    1920
tacgcttaag gtggaaagtg ttcattgcac aatatattt tactgctttc tgaatgtaga    1980
cggaacagtg tggaagcaga aggctttttt aactcatccg tttgccaatc attgcaaaca    2040
actgaaatgt ggatgtgatt gcctcaataa agctcgtccc cattgcttaa aaaaaaaa    2099
```

<210> SEQ ID NO 159
<211> LENGTH: 291
<212> TYPE: PRT
<213> ORGANISM: Homo sapien

<400> SEQUENCE: 159

```
Met Asp Trp Gly Thr Leu His Thr Phe Ile Gly Gly Val Asn Lys His
 1               5                  10                  15

Ser Thr Ser Ile Gly Lys Val Trp Ile Thr Val Ile Phe Ile Phe Arg
            20                  25                  30

Val Met Ile Leu Val Val Ala Ala Gln Glu Val Trp Gly Asp Glu Gln
        35                  40                  45
```

```
Glu Asp Phe Val Cys Asn Thr Leu Gln Pro Gly Cys Lys Asn Val Cys
 50                  55                  60
Tyr Asp His Phe Phe Pro Val Ser His Ile Arg Leu Trp Ala Leu Gln
 65                  70                  75                  80
Leu Ile Phe Val Ser Thr Pro Ala Leu Leu Val Ala Met His Val Ala
                 85                  90                  95
Tyr Tyr Arg His Glu Thr Thr Arg Lys Phe Arg Arg Gly Glu Lys Arg
                100                 105                 110
Asn Asp Phe Lys Asp Ile Glu Asp Ile Lys Lys Gln Lys Val Arg Ile
            115                 120                 125
Glu Gly Ser Leu Trp Trp Thr Tyr Thr Ser Ser Ile Phe Phe Arg Ile
130                 135                 140
Ile Phe Glu Ala Ala Phe Met Tyr Val Phe Tyr Phe Leu Tyr Asn Gly
145                 150                 155                 160
Tyr His Leu Pro Trp Val Leu Lys Cys Gly Ile Asp Pro Cys Pro Asn
                165                 170                 175
Leu Val Asp Cys Phe Ile Ser Arg Pro Thr Glu Lys Thr Val Phe Thr
            180                 185                 190
Ile Phe Met Ile Ser Ala Ser Val Ile Cys Met Leu Leu Asn Val Ala
        195                 200                 205
Glu Leu Cys Tyr Leu Leu Leu Lys Val Cys Phe Arg Arg Ser Lys Arg
210                 215                 220
Ala Gln Thr Gln Lys Asn His Pro Asn His Ala Leu Lys Glu Ser Lys
225                 230                 235                 240
Gln Asn Glu Met Asn Glu Leu Ile Ser Asp Ser Gly Gln Asn Ala Ile
                245                 250                 255
Thr Gly Ser Gln Ala Lys His Phe Lys Val Lys Cys Ser Cys Val Ile
            260                 265                 270
Arg Arg Leu Leu Ser Ser Pro Glu Gly Asn Thr Asn Leu Lys Val Pro
        275                 280                 285
Ser Val Ala
    290

<210> SEQ ID NO 160
<211> LENGTH: 3951
<212> TYPE: DNA
<213> ORGANISM: Homo sapien

<400> SEQUENCE: 160
tctgcatcca tattgaaaac ctgacacaat gtatgcagca ggctcagtgt gagtgaactg      60
gaggcttctc tacaacatga cccaaaggag cattgcaggt cctatttgca acctgaagtt     120
tgtgactctc ctggttgcct taagttcaga actcccattc ctgggagctg gagtacagct     180
tcaagacaat gggtataatg gattgctcat gcaattaat cctcaggtac ctgagaatca     240
gaacctcatc tcaaacatta aggaaatgat aactgaagct tcattttacc tatttaatgc     300
taccaagaga agagtatttt tcagaaatat aaagatttta atacctgcca catggaaagc     360
taataataac agcaaaataa aacaagaatc atatgaaaag gcaaatgtca tagtgactga     420
ctggtatggg gcacatggag atgatccata caccctacaa tacagagggt gtggaaaaga     480
gggaaaatac attcatttca cacctaattt cctactgaat gataacttaa cagctggcta     540
cggatcacga ggccgagtgt ttgtccatga atgggccac ctccgttggg gtgtgttcga     600
tgagtataac aatgacaaac ctttctacat aaatgggcaa atcaaatta aagtgacaag     660
```

```
gtgttcatct gacatcacag gcattttgt gtgtgaaaaa ggtccttgcc cccaagaaaa    720
ctgtattatt agtaagcttt ttaaagaagg atgcacctt atctacaata gcacccaaaa    780
tgcaactgca tcaataatgt tcatgcaaag tttatcttct gtggttgaat tttgtaatgc    840
aagtacccac aaccaagaag caccaaacct acagaaccag atgtgcagcc tcagaagtgc    900
atgggatgta atcacagact ctgctgactt tcaccacagc tttcccatga acgggactga    960
gcttccacct cctcccacat tctcgcttgt agaggctggt gacaaagtgg tctgtttagt   1020
gctggatgtg tccagcaaga tggcagaggc tgacagactc cttcaactac aacaagccgc   1080
agaattttat ttgatgcaga ttgttgaaat tcataccttc gtgggcattg ccagtttcga   1140
cagcaaagga gagatcagag cccagctaca ccaaattaac agcaatgatg atcgaaagtt   1200
gctggtttca tatctgccca ccactgtatc agctaaaaca gacatcagca tttgttcagg   1260
gcttaagaaa ggatttgagg tggttgaaaa actgaatgga aaagcttatg ctctgtgat    1320 gatattagtg accagcggag atgataagct tcttggcaat tgcttaccca ctgtgctcag   1380
cagtggttca acaattcact ccattgccct gggttcatct gcagcccaa atctggagga    1440 attatcacgt cttacaggag gtttaaagtt ctttgttcca gatatatcaa actccaatag   1500
catgattgat gctttcagta gaatttcctc tggaactgga gacatttcc agcaacatat    1560 tcagcttgaa agtacaggtg aaaatgtcaa acctcaccat caattgaaaa acacagtgac   1620
tgtggataat actgtgggca acgacactat gtttctagtt acgtggcagg ccagtggtcc   1680
tcctgagatt atattatttg atcctgatgg acgaaaatac tacacaaata attttatcac   1740
caatctaact tttcggacag ctagtctttg gattccagga acagctaagc ctgggcactg   1800
gacttacacc ctgaacaata cccatcattc tctgcaagcc ctgaaagtga cagtgacctc   1860
tcgcgcctcc aactcagctg tgcccccagc cactgtggaa gcctttgtgg aaagagacag   1920
cctccatttt cctcatcctg tgatgattta tgccaatgtg aaacagggat tatcccat     1980 tcttaatgcc actgtcactg ccacagttga gccagagact ggagatcctg ttacgctgag   2040
actccttgat gatggagcag gtgctgatgt tataaaaaat gatggaattt actcgaggta   2100 tttttttctcc tttgctgcaa atggtagata tagcttgaaa gtgcatgtca atcactctcc   2160
cagcataagc accccagcc actctattcc agggagtcat gctatgtatg taccaggtta    2220
cacagcaaac ggtaatattc agatgaatgc tccaaggaaa tcagtaggca gaaatgagga   2280
ggagcgaaag tggggcttta gccgagtcag ctcaggaggc tccttttcag tgctgggagt   2340
tccagctggc ccccacccctg atgtgtttcc accatgcaaa attattgacc tggaagctgt   2400
aaaagtagaa gaggaattga ccctatcttg gacagcacct ggagaagact ttgatcaggg   2460
ccaggctaca agctatgaaa taagaatgag taaaagtcta cagaatatcc aagatgactt   2520
taacaatgct atttttagtaa atacatcaaa gcgaaatcct cagcaagctg gcatcaggga   2580
gatatttacg ttctcacccc aaatttccac gaatggacct gaacatcagc caaatggaga   2640
aacacatgaa agccacagaa tttatgttgc aatacgagca atggatagga actccttaca   2700
gtctgctgta tctaacattg cccaggcgcc tctgtttatt ccccccaatt ctgatcctgt   2760
acctgccaga gattatctta tattgaaagg agttttaaca gcaatgggt tgataggaat    2820 catttgcctt attatagttg tgacacatca tactttaagc aggaaaaaga gagcagacaa   2880
gaaagagaat ggaacaaaat tattataaat aaatatccaa agtgtcttcc ttcttagata   2940
taagacccat ggccttcgac tacaaaaaca tactaacaaa gtcaaattaa catcaaaact   3000
gtattaaaat gcattgagtt tttgtacaat acagataaga ttttacatg gtagatcaac    3060
```

```
aaattctttt tggggtaga ttagaaaacc cttacacttt ggctatgaac aaataataaa    3120
aattattctt taaagtaatg tcttaaagg caaagggaag ggtaaagtcg gaccagtgtc    3180
aaggaaagtt tgttttattg aggtggaaaa atagccccaa gcagagaaaa ggagggtagg    3240
tctgcattat aactgtctgt gtgaagcaat catttagtta ctttgattaa ttttctttt    3300 ctccttatct gtgcagaaca ggttgcttgt ttacaactga agatcatgct atatttcata    3360
tatgaagccc ctaatgcaaa gctctttacc tcttgctatt ttgttatata tattacagat    3420
gaaatctcac tgctaatgct cagagatctt ttttcactgt aagaggtaac ctttaacaat    3480
atgggtatta cctttgtctc ttcataccgg ttttatgaca aaggtctatt gaatttattt    3540
gtttgtaagt ttctactccc atcaaagcag ctttttaagt tattgccttg gttattatgg    3600
atgatagtta tagcccttat aatgccttaa ctaaggaaga aaagatgtta ttctgagttt    3660
gttttaatac atatatgaac atagttttt attcaattaa accaagaag aggtcagcag    3720 ggagatacta acctttggaa atgattagct ggctctgttt tttggttaaa taagagtctt    3780
taatcctttc tccatcaaga gttacttacc aagggcaggg gaaggggat atagaggtcc    3840 caaggaaata aaaatcatct ttcatcttta attttactcc ttcctcttat tttttttaaaa    3900 gattatcgaa caataaaatc atttgccttt ttaattaaaa acataaaaaa a             3951
```

<210> SEQ ID NO 161
<211> LENGTH: 943
<212> TYPE: PRT
<213> ORGANISM: Homo sapien

<400> SEQUENCE: 161

```
Met Thr Gln Arg Ser Ile Ala Gly Pro Ile Cys Asn Leu Lys Phe Val
  1               5                  10                  15

Thr Leu Val Ala Leu Ser Ser Glu Leu Pro Phe Leu Gly Ala Gly
             20                  25                  30

Val Gln Leu Gln Asp Asn Gly Tyr Asn Gly Leu Leu Ile Ala Ile Asn
         35                  40                  45

Pro Gln Val Pro Glu Asn Gln Asn Leu Ile Ser Asn Ile Lys Glu Met
     50                  55                  60

Ile Thr Glu Ala Ser Phe Tyr Leu Phe Asn Ala Thr Lys Arg Arg Val
 65                  70                  75                  80

Phe Phe Arg Asn Ile Lys Ile Leu Ile Pro Ala Thr Trp Lys Ala Asn
                 85                  90                  95

Asn Ser Lys Ile Lys Gln Glu Ser Tyr Glu Lys Ala Asn Val Ile
             100                 105                 110

Val Thr Asp Trp Tyr Gly Ala His Gly Asp Asp Pro Tyr Thr Leu Gln
         115                 120                 125

Tyr Arg Gly Cys Gly Lys Glu Gly Lys Tyr Ile His Phe Thr Pro Asn
     130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                 165                 170                 175

Tyr Asn Asn Asp Lys Pro Phe Tyr Ile Asn Gly Gln Asn Gln Ile Lys
             180                 185                 190

Val Thr Arg Cys Ser Ser Asp Ile Thr Gly Ile Phe Val Cys Glu Lys
         195                 200                 205

Gly Pro Cys Pro Gln Glu Asn Cys Ile Ile Ser Lys Leu Phe Lys Glu
```

```
              210                 215                 220
Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                    245                 250                 255

Thr His Asn Gln Glu Ala Pro Asn Leu Gln Asn Gln Met Cys Ser Leu
                260                 265                 270

Arg Ser Ala Trp Asp Val Ile Thr Asp Ser Ala Asp Phe His His Ser
            275                 280                 285

Phe Pro Met Asn Gly Thr Glu Leu Pro Pro Pro Thr Phe Ser Leu
290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Ala Ala Glu
                325                 330                 335

Phe Tyr Leu Met Gln Ile Val Glu Ile His Thr Phe Val Gly Ile Ala
                340                 345                 350

Ser Phe Asp Ser Lys Gly Glu Ile Arg Ala Gln Leu His Gln Ile Asn
                355                 360                 365

Ser Asn Asp Asp Arg Lys Leu Leu Val Ser Tyr Leu Pro Thr Thr Val
370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
                420                 425                 430

Val Leu Ser Ser Gly Ser Thr Ile His Ser Ile Ala Leu Gly Ser Ser
                435                 440                 445

Ala Ala Pro Asn Leu Glu Glu Leu Ser Arg Leu Thr Gly Gly Leu Lys
                450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
                500                 505                 510

Thr Val Thr Val Asp Asn Thr Val Gly Asn Asp Thr Met Phe Leu Val
                515                 520                 525

Thr Trp Gln Ala Ser Gly Pro Pro Glu Ile Ile Leu Phe Asp Pro Asp
530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Asn Asn Thr His His Ser Leu Gln Ala Leu Lys Val Thr
                580                 585                 590

Val Thr Ser Arg Ala Ser Asn Ser Ala Val Pro Pro Ala Thr Val Glu
                595                 600                 605

Ala Phe Val Glu Arg Asp Ser Leu His Phe Pro His Pro Val Met Ile
                610                 615                 620

Tyr Ala Asn Val Lys Gln Gly Phe Tyr Pro Ile Leu Asn Ala Thr Val
625                 630                 635                 640
```

```
                Thr Ala Thr Val Glu Pro Glu Thr Gly Asp Pro Val Thr Leu Arg Leu
                                645                 650                 655

Leu Asp Asp Gly Ala Gly Ala Asp Val Ile Lys Asn Asp Gly Ile Tyr
                            660                 665                 670

Ser Arg Tyr Phe Phe Ser Phe Ala Ala Asn Gly Arg Tyr Ser Leu Lys
                            675                 680                 685

Val His Val Asn His Ser Pro Ser Ile Ser Thr Pro Ala His Ser Ile
                            690                 695                 700

Pro Gly Ser His Ala Met Tyr Val Pro Gly Tyr Thr Ala Asn Gly Asn
                705                 710                 715                 720

Ile Gln Met Asn Ala Pro Arg Lys Ser Val Gly Arg Asn Glu Glu Glu
                                725                 730                 735

Arg Lys Trp Gly Phe Ser Arg Val Ser Ser Gly Gly Ser Phe Ser Val
                            740                 745                 750

Leu Gly Val Pro Ala Gly Pro His Pro Asp Val Phe Pro Pro Cys Lys
                            755                 760                 765

Ile Ile Asp Leu Glu Ala Val Lys Val Glu Glu Leu Thr Leu Ser
                            770                 775                 780

Trp Thr Ala Pro Gly Glu Asp Phe Asp Gln Gly Gln Ala Thr Ser Tyr
                785                 790                 795                 800

Glu Ile Arg Met Ser Lys Ser Leu Gln Asn Ile Gln Asp Asp Phe Asn
                                805                 810                 815

Asn Ala Ile Leu Val Asn Thr Ser Lys Arg Asn Pro Gln Gln Ala Gly
                            820                 825                 830

Ile Arg Glu Ile Phe Thr Phe Ser Pro Gln Ile Ser Thr Asn Gly Pro
                            835                 840                 845

Glu His Gln Pro Asn Gly Glu Thr His Glu Ser His Arg Ile Tyr Val
                850                 855                 860

Ala Ile Arg Ala Met Asp Arg Asn Ser Leu Gln Ser Ala Val Ser Asn
                865                 870                 875                 880

Ile Ala Gln Ala Pro Leu Phe Ile Pro Pro Asn Ser Asp Pro Val Pro
                            885                 890                 895

Ala Arg Asp Tyr Leu Ile Leu Lys Gly Val Leu Thr Ala Met Gly Leu
                            900                 905                 910

Ile Gly Ile Ile Cys Leu Ile Ile Val Val Thr His His Thr Leu Ser
                            915                 920                 925

Arg Lys Lys Arg Ala Asp Lys Leu Glu Asn Gly Thr Lys Leu Leu
                            930                 935                 940

<210> SEQ ID NO 162
<211> LENGTH: 498
<212> TYPE: DNA
<213> ORGANISM: Homo sapien

<400> SEQUENCE: 162
tggagaacca cgtggacagc accatgaaca tgttgggcgg gggaggcagt gctggccgga      60
agcccctcaa gtcgggtatg aaggagctgg ccgtgttccg ggagaaggtc actgagcagc     120
accggcagat gggcaagggt ggcaagcatc accttggcct ggaggagccc aagaagctgc     180
gaccaccccc tgccaggact ccctgccaac aggaactgga ccaggtcctg gagcggatct     240
ccaccatgcg ccttccggat gagcggggcc ctctggagca cctctactcc ctgcacatcc     300
ccaactgtga caagcatggc ctgtacaacc tcaaacagtg gcaagatgtc tctgaacggg     360
cagcgtgggg agtgctggtg tgtgaacccc aacaccggga agctgatcca gggagccccc     420
```

```
accatccggg gggaccccga gtgtcatctc ttctacaatg agcagcagga ggctcgcggg    480
gtgcacaccc cagcggat                                                  498

<210> SEQ ID NO 163
<211> LENGTH: 1128
<212> TYPE: DNA
<213> ORGANISM: Homo sapien

<400> SEQUENCE: 163
gccacctggc cctcctgatc gacgacacac gcacttgaaa cttgttctca ggtgtgtgg     60 aatcaacttt ccggaagcaa ccagcccacc agaggaggtc ccgagcgcga gcggagacga   120
tgcagcggag actggttcag cagtggagcg tcgcggtgtt cctgctgagc tacgcggtgc   180
cctcctgcgg gcgctcggtg gagggtctca gccgccgcct caaaagagct gtgtctgaac   240
atcagctcct ccatgacaag gggaagtcca tccaagattt acggcgacga ttcttccttc   300
accatctgat cgcagaaatc cacacagctg aaatcagagc tacctcggag gtgtccccta   360
actccaagcc ctctcccaac acaaagaacc accccgtccg atttgggtct gatgatgagg   420
gcagatacct aactcaggaa actaacaagg tggagacgta caagagcag ccgctcaaga    480 cacctgggaa gaaaagaaa ggcaagcccg ggaaacgcaa ggagcaggaa agaaaaaac     540 ggcgaactcg ctctgcctgg ttagactctg gagtgactgg gagtgggcta aaggggacc    600 acctgtctga cacctccaca acgtcgctgg agctcgattc acggaggcat tgaaattttc   660
agcagagacc ttccaaggac atattgcagg attctgtaat agtgaacata tggaaagtat   720
tagaaatatt tattgtctgt aaatactgta aatgcattgg aataaaactg tctcccccat   780
tgctctatga aactgcacat tggtcattgt gaatatttt ttttttgcca aggctaatcc     840
aattattatt atcacatttta ccataattta ttttgtccat tgatgtattt attttgtaaa   900
tgtatcttgg tgctgctgaa tttctatatt ttttgtaaca taatgcactt tagatataca    960
tatcaagtat gttgataaat gacacaatga agtgtctcta ttttgtggtt gatttttaatg  1020 aatgcctaaa tataattatc caaattgatt ttcctttgtg catgtaaaaa taacagtatt   1080
ttaaatttgt aaagaatgtc taataaaata taatctaatt acatcatg                1128

<210> SEQ ID NO 164
<211> LENGTH: 1310
<212> TYPE: DNA
<213> ORGANISM: Homo sapien

<400> SEQUENCE: 164
gggcctggtt cgcaaagaag ctgacttcag aggggaaac tttcttcttt taggaggcgg     60
ttagccctgt tccacgaacc caggagaact gctggccaga ttaattagac attgctatgg   120
gagacgtgta aacacactac ttatcattga tgcatatata aaaccatttt attttcgcta   180
ttatttcaga ggaagcgcct ctgatttgtt tcttttttcc cttttttgctc tttctggctg   240 tgtggtttgg agaaagcaca gttggagtag ccggttgcta aataagtccc gagcgcgagc   300
ggagacgatg cagcggagac tggttcagca gtggagcgtc gcggtgttcc tgctgagcta   360
cgcggtgccc tcctgcgggc gctcggtgga gggtctcagc cgccgcctca aaagagctgt   420
gtctgaacat cagctcctcc atgacaaggg gaagtccatc caagatttac ggcgacgatt   480
cttccttcac catctgatcg cagaaatcca cacagctgaa atcagagcta cctcggaggt    540
gtcccctaac tccaagccct ctcccaacac aaagaaccac cccgtccgat ttgggtctga   600
```

```
tgatgagggc agatacctaa ctcaggaaac taacaaggtg agagacgtaca aagagcagcc    660 gctcaagaca cctgggaaga aaagaaagg caagcccggg aaacgcaagg agcaggaaaa     720
gaaaaaacgg cgaactcgct ctgcctggtt agactctgga gtgactggga gtgggctaga    780
aggggaccac ctgtctgaca cctccacaac gtcgctggag ctcgattcac ggaggcattg    840
aaattttcag cagagacctt ccaaggacat attgcaggat tctgtaatag tgaacatatg    900
gaaagtatta gaaatattta ttgtctgtaa atactgtaaa tgcattggaa taaaactgtc    960
tcccccattg ctctatgaaa ctgcacattg gtcattgtga atatttttt ttttgccaag    1020 gctaatccaa ttattattat cacatttacc ataatttatt ttgtccattg atgtatttat   1080
tttgtaaatg tatcttggtg ctgctgaatt tctatatttt ttgtaacata atgcacttta   1140
gatatacata tcaagtatgt tgataaatga cacaatgaag tgtctctatt ttgtggttga   1200
ttttaatgaa tgcctaaata taattatcca aattgatttt cctttgtgcc cgtaaaaata   1260 acagtattt aaatttgtaa agaatgtcta ataaatata atctaattac                1310
```

<210> SEQ ID NO 165
<211> LENGTH: 177
<212> TYPE: PRT
<213> ORGANISM: Homo sapien

<400> SEQUENCE: 165

```
Met Gln Arg Arg Leu Val Gln Gln Trp Ser Val Ala Val Phe Leu Leu
 1               5                  10                  15

Ser Tyr Ala Val Pro Ser Cys Gly Arg Ser Val Glu Gly Leu Ser Arg
                20                  25                  30

Arg Leu Lys Arg Ala Val Ser Glu His Gln Leu Leu His Asp Lys Gly
            35                  40                  45

Lys Ser Ile Gln Asp Leu Arg Arg Arg Phe Phe Leu His His Leu Ile
        50                  55                  60

Ala Glu Ile His Thr Ala Glu Ile Arg Ala Thr Ser Glu Val Ser Pro
    65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
               100                 105                 110

Thr Tyr Lys Glu Gln Pro Leu Lys Thr Pro Gly Lys Lys Lys Lys Gly
           115                 120                 125

Lys Pro Gly Lys Arg Lys Glu Gln Glu Lys Lys Arg Arg Thr Arg
       130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
               165                 170                 175

His
```

<210> SEQ ID NO 166
<211> LENGTH: 177
<212> TYPE: PRT
<213> ORGANISM: Homo sapien

<400> SEQUENCE: 166

```
Met Gln Arg Arg Leu Val Gln Gln Trp Ser Val Ala Val Phe Leu Leu
 1               5                  10                  15

Ser Tyr Ala Val Pro Ser Cys Gly Arg Ser Val Glu Gly Leu Ser Arg
```

```
                   20                  25                  30
Arg Leu Lys Arg Ala Val Ser Glu His Gln Leu Leu His Asp Lys Gly
            35                  40                  45
Lys Ser Ile Gln Asp Leu Arg Arg Phe Phe Leu His His Leu Ile
50                      55                  60
Ala Glu Ile His Thr Ala Glu Ile Arg Ala Thr Ser Glu Val Ser Pro
65                  70                  75                  80
Asn Ser Lys Pro Ser Pro Asn Thr Lys Asn His Pro Val Arg Phe Gly
                85                  90                  95
Ser Asp Asp Glu Gly Arg Tyr Leu Thr Gln Glu Thr Asn Lys Val Glu
                100                 105                 110
Thr Tyr Lys Glu Gln Pro Leu Lys Thr Pro Gly Lys Lys Lys Gly
            115                 120                 125
Lys Pro Gly Lys Arg Lys Glu Gln Glu Lys Lys Lys Arg Arg Thr Arg
        130                 135                 140
Ser Ala Trp Leu Asp Ser Gly Val Thr Gly Ser Gly Leu Glu Gly Asp
145                 150                 155                 160
His Leu Ser Asp Thr Ser Thr Thr Ser Leu Glu Leu Asp Ser Arg Arg
                165                 170                 175
His

<210> SEQ ID NO 167
<211> LENGTH: 3362
<212> TYPE: DNA
<213> ORGANISM: Homo sapien

<400> SEQUENCE: 167
cacaatgtat gcagcaggct cagtgtgagt gaactggagg cttctctaca acatgaccca       60
aaggagcatt gcaggtccta tttgcaacct gaagtttgtg actctcctgg ttgccttaag      120
ttcagaactc ccattcctgg gagctggagt acagcttcaa gacaatgggt ataatggatt      180
gctcattgca attaatcctc aggtacctga gaatcagaac ctcatctcaa acattaagga      240
aatgataact gaagcttcat tttacctatt taatgctacc aagagaagag tatttttcag      300
aaatataaag attttaatac ctgccacatg gaaagctaat aataacagca aaataaaaca      360
agaatcatat gaaaaggcaa atgtcatagt gactgactgg tatggggcac atggagatga      420
tccatacacc ctacaataca gagggtgtgg aaaagaggga aaatacattc atttcacacc      480
taatttccta ctgaatgata acttaacagc tggctacgga tcacgaggcc gagtgtttgt      540
ccatgaatgg gcccacctcc gttggggtgt gttcgatgag tataacaatg acaaaccttt      600
ctacataaat gggcaaaatc aaattaaagt gacaaggtgt tcatctgaca tcacaggcat      660
ttttgtgtgt gaaaaggtc cttgcccca agaaaactgt attattagta agctttttaa       720
agaaggatgc acctttatct acaatagcac ccaaaatgca actgcatcaa taatgttcat      780
gcaaagttta tcttctgtgg ttgaattttg taatgcaagt acccacaacc aagaagcacc      840
aaacctacag aaccagatgt gcagcctcag aagtgcatgg gatgtaatca gagactctgc      900
tgactttcac cacagctttc ccatgaacgg gactgagctt ccacctcctc ccacattctc      960
gcttgtagag gctggtgaca agtggtctg tttagtgctg gatgtgtcca gcaagatggc     1020
agaggctgac agactccttc aactacaaca agccgcagaa ttttatttga tgcagattgt     1080
tgaaattcat accttcgtgg gcattgccag tttgacagc aaaggagaga tcagagccca     1140
gctacaccaa attaacagca atgatgatcg aaagttgctg gtttcatatc tgcccaccac     1200
```

-continued

```
tgtatcagct aaaacagaca tcagcatttg ttcagggctt aagaaaggat ttgaggtggt    1260
tgaaaaactg aatggaaaag cttatggctc tgtgatgata ttagtgacca gcggagatga    1320
taagcttctt ggcaattgct tacccactgt gctcagcagt ggttcaacaa ttcactccat    1380
tgccctgggt tcatctgcag ccccaaatct ggaggaatta tcacgtctta caggaggttt    1440
aaagttcttt gttccagata tatcaaactc aatagcatg attgatgctt tcagtagaat     1500
ttcctctgga actggagaca ttttccagca acatattcag cttgaaagta caggtgaaaa    1560
tgtcaaacct caccatcaat tgaaaaacac agtgactgtg gataatactg tgggcaacga    1620
cactatgttt ctagttacgt ggcaggccag tggtcctcct gagattatat tatttgatcc    1680
tgatggacga aaatactaca caaataattt tatcaccaat ctaactttc ggacagctag     1740 tctttggatt ccaggaacag ctaagcctgg gcactggact tacaccctga tgtgtttcca    1800
ccatgcaaaa ttattgacct ggaagctgta aagtagaag aggaattgac cctatcttgg     1860
acagcacctg agaagactt tgatcagggc caggctacaa gctatgaaat aagaatgagt    1920
aaaagtctac agaatatcca agatgacttt aacaatgcta ttttagtaaa tacatcaaag    1980
cgaaatcctc agcaagctgg catcagggag atatttacgt tctcaccca aatttccacg     2040 aatggacctg aacatcagcc aaatggagaa acacatgaaa gccacagaat ttatgttgca    2100
atacgagcaa tggataggaa ctccttacag tctgctgtat ctaacattgc ccaggcgcct    2160
ctgtttattc ccccaattc tgatcctgta cctgccagag attatcttat attgaaagga     2220
gttttaacag caatgggttt gataggaatc atttgcctta ttatagttgt gacacatcat    2280
actttaagca ggaaaaagag agcagacaag aaagagaatg gaacaaaatt attataaata    2340
aatatccaaa gtgtcttcct tcttagatat aagacccatg gccttcgact acaaaaacat    2400
actaacaaag tcaaattaac atcaaaactg tattaaaatg cattgagttt ttgtacaata    2460
cagataagat ttttacatgg tagatcaaca aattcttttt gggggtagat tagaaaaccc    2520
ttacactttg gctatgaaca ataataaaa attattcttt aaagtaatgt ctttaaaggc     2580
aaagggaagg gtaaagtcgg accagtgtca aggaaagttt gttttattga ggtggaaaaa    2640
tagccccaag cagagaaaag gagggtaggt ctgcattata actgtctgtg tgaagcaatc    2700
atttagttac tttgattaat ttttcttttc tccttatctg tgcagaacag gttgcttgtt    2760
tacaactgaa gatcatgcta tatttcatat atgaagcccc taatgcaaag ctctttacct    2820
cttgctattt tgttatatat attacagatg aaatctcact gctaatgctc agagatcttt    2880
tttcactgta agaggtaacc tttaacaata tgggtattac cttgtctct tcataccggt      2940 tttatgacaa aggtctattg aatttatttg tttgtaagtt tctactccca tcaaagcagc    3000
tttctaagtt attgccttgg ttattatgga tgatagttat agcccttata atgccttaac    3060
taaggaagaa aagatgttat tctgagtttg ttttaataca tatatgaaca tatagtttta    3120
ttcaattaaa ccaaagaaga ggtcagcagg gagatactaa cctttggaaa tgattagctg    3180
gctctgtttt ttggttaaat aagagtcttt aatcctttct ccatcaagag ttacttacca    3240
agggcagggg aaggggata tagaggtcac aaggaaataa aaatcatctt tcatctttaa     3300
ttttactcct tcctcttatt tttttaaaag attatcgaac aataaaatca tttgcctttt    3360
tt                                                                   3362
```

<210> SEQ ID NO 168
<211> LENGTH: 2784
<212> TYPE: DNA
<213> ORGANISM: Homo sapien

<400> SEQUENCE: 168

```
tctgcatcca tattgaaaac ctgacacaat gtatgcagca ggctcagtgt gagtgaactg        60
gaggcttctc tacaacatga cccaaaggag cattgcaggt cctatttgca acctgaagtt       120
tgtgactctc ctggttgcct taagttcaga actcccattc ctgggagctg gagtacagct       180
tcaagacaat gggtataatg gattgctcat tgcaattaat cctcaggtac ctgagaatca       240
gaacctcatc tcaaacatta aggaaatgat aactgaagct tcattttacc tatttaatgc       300
taccaagaga agagtatttt tcagaaatat aaagatttta atacctgcca catggaaagc       360
taataataac agcaaaataa aacaagaatc atatgaaaag gcaaatgtca tagtgactga       420
ctggtatggg gcacatggag atgatccata caccctacaa tacagagggt gtggaaaaga       480
gggaaaatac attcatttca cacctaattt cctactgaat gataacttaa cagctggcta       540
cggatcacga ggccgagtgt ttgtccatga atgggcccac ctccgttggg gtgtgttcga       600
tgagtataac aatgacaaac ctttctacat aaatgggcaa aatcaaatta aagtgacaag       660
gtgttcatct gacatcacag gcattttttgt gtgtgaaaaa ggtccttgcc cccaagaaaa       720
ctgtattatt agtaagcttt ttaaagaagg atgcaccttt atctacaata gcacccaaaa       780
tgcaactgca tcaataatgt tcatgcaaag tttatcttct gtggttgaat tttgtaatgc       840
aagtacccac aaccaagaag caccaaacct acagaaccag atgtgcagcc tcagaagtgc       900
atgggatgta atcacagact ctgctgactt tcaccacagc tttcccatga acgggactga       960
gcttccacct cctcccacat tctcgcttgt agaggctggt gacaaagtgg tctgtttagt      1020
gctggatgtg tccagcaaga tggcagaggc tgacagactc cttcaactac aacaagccgc      1080
agaattttat ttgatgcaga ttgttgaaat tcataccttc gtgggcattg ccagtttcga      1140
cagcaaagga gagatcagag cccagctaca ccaaattaac agcaatgatg atcgaaagtt      1200
gctggtttca tatctgccca ccactgtatc agctaaaaca gacatcagca tttgttcagg      1260
gcttaagaaa ggatttgagg tggttgaaaa actgaatgga aaagcttatg ctctgtgtat      1320
gatattagtg accagcggag atgataagct tcttggcaat tgcttaccca ctgtgctcag      1380
cagtggttca acaattcact ccattgccct gggttcatct gcagcccaa atctggagga      1440
attatcacgt cttacaggag gtttaaagtt cttttgttcca gatatatcaa actccaatag      1500
catgattgat gctttcagta gaatttcctc tggaactgga gacatttttcc agcaacatat      1560
tcagcttgaa agtacaggtg aaaatgtcaa acctcaccat caattgaaaa acacagtgac      1620
tgtggataat actgtgggca acgacactat gtttctagtt acgtggcagg ccagtggtcc      1680
tcctgagatt atattatttg atcctgatgg acgaaaatac tacacaaata atttttatcac      1740
caatctaact tttcggacag ctagtctttg gattccagga acagctaagc ctgggcactg      1800
gacttacacc ctgaacaata cccatcattc tctgcaagcc ctgaaagtga cagtgacctc      1860
tcgcgcctcc aactcagctg tgccccagc cactgtggaa gcctttgtgg aaagagacag      1920
cctccatttt cctcatcctg tgatgattta tgccaatgtg aaacagggat tttatcccat      1980
tcttaatgcc actgtcactg ccacagttga gccagagact ggagatcctg ttacgctgag      2040
actccttgat gatggagcag gtgctgatgt tataaaaaat gatggaattt actcgaggta      2100
tttttttctcc tttgctgcaa atggtagata tagcttgaaa gtgcatgtca atcactctcc      2160
cagcataagc accccagccc actctattcc agggagtcat gctatgtatg taccaggtta      2220
cacagcaaac ggtaatattc agatgaatgc tccaaggaaa tcagtaggca gaaatgagga      2280
```

```
ggagcgaaag tggggctttta gccgagtcag ctcaggaggc tccttttcag tgctgggagt    2340
tccagctggc ccccaccctg atgtgtttcc accatgcaaa attattgacc tggaagctgt    2400
aaatagaaga ggaattgacc ctatcttgga cagcacctgg agaagacttt gatcagggcc    2460
aggctacaag ctatgaaata agaatgagta aaagtctaca gaatatccaa gatgacttta    2520
acaatgctat tttagtaaat acatcaaagc gaaatcctca gcaagctggc atcagggaga    2580
tatttacgtt ctcaccccaa atttccacga atggacctga acatcagcca atggagaaa     2640 cacatgaaag ccacagaatt tatgttgcaa tacgagcaat ggataggaac tccttacagt    2700
ctgctgtatc taacattgcc caggcgcctc tgtttattcc ccccaattct gatcctgtac    2760
ctgccagaga ttatcttata ttga                                            2784
```

<210> SEQ ID NO 169
<211> LENGTH: 592
<212> TYPE: PRT
<213> ORGANISM: Homo sapien

<400> SEQUENCE: 169

```
Met Thr Gln Arg Ser Ile Ala Gly Pro Ile Cys Asn Leu Lys Phe Val
 1               5                  10                  15

Thr Leu Val Ala Leu Ser Ser Glu Leu Pro Phe Leu Gly Ala Gly
            20                  25                  30

Val Gln Leu Gln Asp Asn Gly Tyr Asn Gly Leu Leu Ile Ala Ile Asn
        35                  40                  45

Pro Gln Val Pro Glu Asn Gln Asn Leu Ile Ser Asn Ile Lys Glu Met
    50                  55                  60

Ile Thr Glu Ala Ser Phe Tyr Leu Phe Asn Ala Thr Lys Arg Arg Val
65                  70                  75                  80

Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Asp Pro Tyr Thr Leu Gln
        115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
        195                 200                 205

Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
        275                 280                 285
```

-continued

```
Phe Pro Met Asn Gly Thr Glu Leu Pro Pro Pro Thr Phe Ser Leu
    290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
            340                 345                 350

Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
        435                 440                 445

Ala Ala Pro Asn Leu Glu Glu Leu Ser Arg Leu Thr Gly Gly Leu Lys
    450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
    530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Met Cys Phe His Ala Lys Leu Leu Thr Trp Lys Leu
            580                 585                 590

<210> SEQ ID NO 170
<211> LENGTH: 791
<212> TYPE: PRT
<213> ORGANISM: Homo sapien

<400> SEQUENCE: 170

Met Thr Gln Arg Ser Ile Ala Gly Pro Ile Cys Asn Leu Lys Phe Val
1               5                   10                  15

Thr Leu Leu Val Ala Leu Ser Ser Glu Leu Pro Phe Leu Gly Ala Gly
            20                  25                  30

Val Gln Leu Gln Asp Asn Gly Tyr Asn Gly Leu Leu Ile Ala Ile Asn
        35                  40                  45

Pro Gln Val Pro Glu Asn Gln Asn Leu Ile Ser Asn Ile Lys Glu Met
    50                  55                  60

Ile Thr Glu Ala Ser Phe Tyr Leu Phe Asn Ala Thr Lys Arg Arg Val
```

```
            65                  70                  75                  80
Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Pro Tyr Thr Leu Gln
            115                 120                 125

Tyr Arg Gly Cys Gly Lys Glu Gly Lys Tyr Ile His Phe Thr Pro Asn
        130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
            195                 200                 205

Gly Pro Cys Pro Gln Glu Asn Cys Ile Ile Ser Lys Leu Phe Lys Glu
        210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
            275                 280                 285

Phe Pro Met Asn Gly Thr Glu Leu Pro Pro Pro Thr Phe Ser Leu
290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Ala Ala Glu
                325                 330                 335

Phe Tyr Leu Met Gln Ile Val Glu Ile His Thr Phe Val Gly Ile Ala
            340                 345                 350

Ser Phe Asp Ser Lys Gly Glu Ile Arg Ala Gln Leu His Gln Ile Asn
            355                 360                 365

Ser Asn Asp Asp Arg Lys Leu Leu Val Ser Tyr Leu Pro Thr Thr Val
            370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
            435                 440                 445

Ala Ala Pro Asn Leu Glu Glu Leu Ser Arg Leu Thr Gly Gly Leu Lys
        450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495
```

```
Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
    530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Asn Asn Thr His His Ser Leu Gln Ala Leu Lys Val Thr
                580                 585                 590

Val Thr Ser Arg Ala Ser Asn Ser Ala Val Pro Pro Ala Thr Val Glu
            595                 600                 605

Ala Phe Val Glu Arg Asp Ser Leu His Phe Pro His Pro Val Met Ile
        610                 615                 620

Tyr Ala Asn Val Lys Gln Gly Phe Tyr Pro Ile Leu Asn Ala Thr Val
625                 630                 635                 640

Thr Ala Thr Val Glu Pro Glu Thr Gly Asp Pro Val Thr Leu Arg Leu
                645                 650                 655

Leu Asp Asp Gly Ala Gly Ala Asp Val Ile Lys Asn Asp Gly Ile Tyr
                660                 665                 670

Ser Arg Tyr Phe Phe Ser Phe Ala Ala Asn Gly Arg Tyr Ser Leu Lys
            675                 680                 685

Val His Val Asn His Ser Pro Ser Ile Ser Thr Pro Ala His Ser Ile
        690                 695                 700

Pro Gly Ser His Ala Met Tyr Val Pro Gly Tyr Thr Ala Asn Gly Asn
705                 710                 715                 720

Ile Gln Met Asn Ala Pro Arg Lys Ser Val Gly Arg Asn Glu Glu Glu
                725                 730                 735

Arg Lys Trp Gly Phe Ser Arg Val Ser Ser Gly Ser Phe Ser Val
                740                 745                 750

Leu Gly Val Pro Ala Gly Pro His Pro Asp Val Phe Pro Pro Cys Lys
            755                 760                 765

Ile Ile Asp Leu Glu Ala Val Asn Arg Arg Gly Ile Asp Pro Ile Leu
        770                 775                 780

Asp Ser Thr Trp Arg Arg Leu
785                 790

<210> SEQ ID NO 171
<211> LENGTH: 1491
<212> TYPE: DNA
<213> ORGANISM: Homo sapien

<400> SEQUENCE: 171
cctcctgcca gccaagtgaa gacatgctta cttcccctcc accttccttc atgatgtggg      60
aagagtgctg caacccagcc ctagccaacg ccgcatgaga gggagtgtgc cgagggcttc     120
tgagaaggtt tctctcacat ctagaaagaa gcgcttaaga tgtggcagcc cctcttcttc     180
aagtggctct tgtcctgttg ccctgggagt tctcaaattg ctgcagcagc ctccacccag     240
cctgaggatg acatcaatac acagaggaag aagagtcagg aaaagatgag agaagttaca     300
gactctcctg ggcgaccccg agagcttacc attcctcaga cttcttcaca tggtgctaac     360
agatttgttc ctaaaagtaa agctctagag gccgtcaaat tggcaataga agccgggttc     420
```

-continued

```
caccatattg attctgcaca tgtttacaat aatgaggagc aggttggact ggccatccga      480
agcaagattg cagatggcag tgtgaagaga aagacatat tctacacttc aaagctttgg       540
agcaattccc atcgaccaga gttggtccga ccagccttgg aaaggtcact gaaaaatctt      600
caattggact atgttgacct ctatcttatt cattttccag tgtctgtaaa gccaggtgag      660
gaagtgatcc caaaagatga aaatggaaaa atactatttg acacagtgga tctctgtgcc      720
acatgggagg ccatggagaa gtgtaaagat gcaggattgg ccaagtccat cggggtgtcc      780
aacttcaacc acaggctgct ggagatgatc ctcaacaagc agggctcaa gtacaagcct       840 gtctgcaacc aggtggaatg tcatccttac ttcaaccaga gaaaactgct ggatttctgc      900
aagtcaaaag acattgttct ggttgcctat agtgctctgg gatcccatcg agaagaacca      960
tgggtggacc cgaactcccc ggtgctcttg gaggacccag tcctttgtgc cttggcaaaa     1020
aagcacaagc gaaccccagc cctgattgcc ctgcgctacc agctgcagcg tggggttgtg     1080
gtcctggcca agagctacaa tgagcagcgc atcagacaga acgtgcaggt gtttgaattc     1140
cagttgactt cagaggagat gaaagccata gatggcctaa acagaaatgt gcgatatttg     1200
acccttgata ttttgctgg cccccctaat tatccatttt ctgatgaata ttaacatgga      1260
gggcattgca tgaggtctgc cagaaggccc tgcgtgtgga tggtgacaca gaggatggct     1320
ctatgctggt gactggacac atcgcctctg gttaaatctc tcctgcttgg cgacttcagt     1380
aagctacagc taagcccatc ggccggaaaa gaaagacaat aattttgttt ttcattttga     1440
aaaaattaaa tgctctctcc taaagattct tcacctaaaa aaaaaaaaa a               1491
```

<210> SEQ ID NO 172
<211> LENGTH: 364
<212> TYPE: PRT
<213> ORGANISM: Homo sapien

<400> SEQUENCE: 172

```
Met Trp Gln Pro Leu Phe Phe Lys Trp Leu Leu Ser Cys Cys Pro Gly
 1               5                  10                  15

Ser Ser Gln Ile Ala Ala Ala Ser Thr Gln Pro Glu Asp Asp Ile
            20                  25                  30

Asn Thr Gln Arg Lys Lys Ser Gln Glu Lys Met Arg Glu Val Thr Asp
        35                  40                  45

Ser Pro Gly Arg Pro Arg Glu Leu Thr Ile Pro Gln Thr Ser Ser His
    50                  55                  60

Gly Ala Asn Arg Phe Val Pro Lys Ser Lys Ala Leu Glu Ala Val Lys
65                  70                  75                  80

Leu Ala Ile Glu Ala Gly Phe His Ile Asp Ser Ala His Val Tyr
                85                  90                  95

Asn Asn Glu Glu Gln Val Gly Leu Ala Ile Arg Ser Lys Ile Ala Asp
            100                 105                 110

Gly Ser Val Lys Arg Glu Asp Ile Phe Tyr Thr Ser Lys Leu Trp Ser
        115                 120                 125

Asn Ser His Arg Pro Glu Leu Val Arg Pro Ala Leu Glu Arg Ser Leu
    130                 135                 140

Lys Asn Leu Gln Leu Asp Tyr Val Asp Leu Tyr Leu Ile His Phe Pro
145                 150                 155                 160

Val Ser Val Lys Pro Gly Glu Glu Val Ile Pro Lys Asp Glu Asn Gly
                165                 170                 175

Lys Ile Leu Phe Asp Thr Val Asp Leu Cys Ala Thr Trp Glu Ala Met
```

```
                    180                  185                  190
Glu Lys Cys Lys Asp Ala Gly Leu Ala Lys Ser Ile Gly Val Ser Asn
                195                  200                  205

Phe Asn His Arg Leu Leu Glu Met Ile Leu Asn Lys Pro Gly Leu Lys
        210                  215                  220

Tyr Lys Pro Val Cys Asn Gln Val Glu Cys His Pro Tyr Phe Asn Gln
225                  230                  235                  240

Arg Lys Leu Leu Asp Phe Cys Lys Ser Lys Asp Ile Val Leu Val Ala
                245                  250                  255

Tyr Ser Ala Leu Gly Ser His Arg Glu Glu Pro Trp Val Asp Pro Asn
                260                  265                  270

Ser Pro Val Leu Glu Asp Pro Val Leu Cys Ala Leu Ala Lys Lys
        275                  280                  285

His Lys Arg Thr Pro Ala Leu Ile Ala Leu Arg Tyr Gln Leu Gln Arg
        290                  295                  300

Gly Val Val Val Leu Ala Lys Ser Tyr Asn Glu Gln Arg Ile Arg Gln
305                  310                  315                  320

Asn Val Gln Val Phe Glu Phe Gln Leu Thr Ser Glu Glu Met Lys Ala
                325                  330                  335

Ile Asp Gly Leu Asn Arg Asn Val Arg Tyr Leu Thr Leu Asp Ile Phe
                340                  345                  350

Ala Gly Pro Pro Asn Tyr Pro Phe Ser Asp Glu Tyr
            355                  360

<210> SEQ ID NO 173
<211> LENGTH: 1988
<212> TYPE: DNA
<213> ORGANISM: Homo sapiens

<400> SEQUENCE: 173
cgggagccgc ctccccgcgg cctcttcgct tttgtggcgg cgcccgcgct cgcaggccac    60
tctctgctgt cgcccgtccc gcgcgctcct ccgacccgct ccgctccgct ccgctcggcc   120
ccgcgccgcc cgtcaacatg atccgctgcg gcctggcctg cgagcgctgc cgctggatcc   180 tgccctgct cctactcagc gccatcgcct tcgacatcat cgcgctggcc ggccgcggct   240
ggttgcagtc tagcgaccac ggccagacgt cctcgctgtg gtggaaatgc tcccaagagg   300
gcggcggcag cgggtcctac gaggagggct gtcagagcct catggagtac gcgtggggta   360
gagcagcggc tgccatgctc ttctgtggct tcatcatcct ggtgatctgt ttcatcctct   420
ccttcttcgc cctctgtgga ccccagatgc ttgtcttcct gagagtgatt ggaggtctcc   480
ttgccttggc tgctgtgttc cagatcatct ccctggtaat ttaccccgtg aagtacaccc   540
agaccttcac ccttcatgcc aaccctgctg tcacttacat ctataactgg gcctacggct   600
ttgggtgggg agccacgatt atcctgatcg gctgtgcctt cttcttctgc tgcctcccca   660
actacgaaga tgaccttctg ggcaatgcca agcccaggta cttctacaca tctgcctaac   720
ttgggaatga atgtgggaga aaatcgctgc tgctgagatg gactccagaa gaagaaactg   780
tttctccagg cgactttgaa cccatttttt ggcagtgttc atattattaa actagtcaaa   840
aatgctaaaa taatttggga gaaatatttt tttaagtagt gttatagttt catgtttatc   900
ttttattatg ttttgtgaag ttgtgtcttt tcactaatta cctatactat gccaatattt   960
ccttatatct atccataaca tttatactac atttgtaaga gaatatgcac gtgaaactta  1020
acactttata aggtaaaaat gaggtttcca agatttaata atctgatcaa gttccttgtta 1080
```

-continued

```
tttccaaata gaatggactt ggtctgttaa gggctaagga gaagaggaag ataaggttaa    1140
aagttgttaa tgaccaaaca ttctaaaaga aatgcaaaaa aaaagtttat tttcaagcct    1200
tcgaactatt taaggaaagc aaaatcattt cctaaatgca tatcatttgt gagaatttct    1260
cattaatatc ctgaatcatt catttcagct aaggcttcat gttgactcga tatgtcatct    1320
aggaaagtac tatttcatgg tccaaacctg ttgccatagt tggtaaggct ttcctttaag    1380
tgtgaaatat ttagatgaaa ttttctcttt taaagttctt tatagggtta gggtgtggga    1440
aaatgctata ttaataaatc tgtagtgttt tgtgtttata tgttcagaac cagagtagac    1500
tggattgaaa gatggactgg gtctaattta tcatgactga tagatctggt taagttgtgt    1560
agtaaagcat taggagggtc attcytgtca caaaagtgcc actaaaacag cctcaggaga    1620
ataaatgact tgcttttcta aatctcaggt ttatctgggc tctatcatat agacaggctt    1680
ctgatagttt gcarctgtaa gcagaaacct acatatagtt aaaatcctgg tctttcttgg    1740
taaacagatt ttaaatgtct gatataaaac atgccacagg agaattcggg gatttgagtt    1800
tctctgaata gcatatatat gatgcatcgg ataggtcatt atgatttttt accatttcga    1860
cttacataat gaaaaccaat tcattttaaa tatcagatta ttattttgta agttgtggaa    1920
aaagctaatt gtagttttca ttatgaagtt ttcccaataa accaggtatt ctaaaaaaaa    1980
aaaaaaaa                                                              1988
```

<210> SEQ ID NO 174
<211> LENGTH: 238
<212> TYPE: PRT
<213> ORGANISM: Homo sapiens

<400> SEQUENCE: 174

```
Gly Ala Ala Ser Pro Arg Pro Leu Arg Phe Cys Gly Gly Ala Arg Ala
                 5                  10                  15
Arg Arg Pro Leu Ser Ala Val Ala Arg Pro Ala Arg Ser Ser Asp Pro
             20                  25                  30
Leu Arg Ser Ala Pro Leu Gly Pro Ala Pro Val Asn Met Ile Arg
         35                  40                  45
Cys Gly Leu Ala Cys Glu Arg Cys Arg Trp Ile Leu Pro Leu Leu Leu
     50                  55                  60
Leu Ser Ala Ile Ala Phe Asp Ile Ile Ala Leu Ala Gly Arg Gly Trp
 65                  70                  75                  80
Leu Gln Ser Ser Asp His Gly Gln Thr Ser Ser Leu Trp Trp Lys Cys
                 85                  90                  95
Ser Gln Glu Gly Gly Gly Ser Gly Ser Tyr Glu Glu Gly Cys Gln Ser
            100                 105                 110
Leu Met Glu Tyr Ala Trp Gly Arg Ala Ala Ala Met Leu Phe Cys
        115                 120                 125
Gly Phe Ile Ile Leu Val Ile Cys Phe Ile Leu Ser Phe Phe Ala Leu
    130                 135                 140
Cys Gly Pro Gln Met Leu Val Phe Leu Arg Val Ile Gly Gly Leu Leu
145                 150                 155                 160
Ala Leu Ala Ala Val Phe Gln Ile Ile Ser Leu Val Ile Tyr Pro Val
                165                 170                 175
Lys Tyr Thr Gln Thr Phe Thr Leu His Ala Asn Pro Ala Val Thr Tyr
            180                 185                 190
Ile Tyr Asn Trp Ala Tyr Gly Phe Gly Trp Ala Ala Thr Ile Ile Leu
        195                 200                 205
```

```
Ile Gly Cys Ala Phe Phe Phe Cys Cys Leu Pro Asn Tyr Glu Asp Asp
    210                 215                 220

Leu Leu Gly Asn Ala Lys Pro Arg Tyr Phe Tyr Thr Ser Ala
225                 230                 235

<210> SEQ ID NO 175
<211> LENGTH: 4181
<212> TYPE: DNA
<213> ORGANISM: Homo sapiens
<220> FEATURE:
<221> NAME/KEY: unsure
<222> LOCATION: (3347)
<223> OTHER INFORMATION: n=A,T,C or G
<220> FEATURE:
<221> NAME/KEY: unsure
<222> LOCATION: (3502)
<223> OTHER INFORMATION: n=A,T,C or G
<220> FEATURE:
<221> NAME/KEY: unsure
<222> LOCATION: (3506)
<223> OTHER INFORMATION: n=A,T,C or G
<220> FEATURE:
<221> NAME/KEY: unsure
<222> LOCATION: (3520)
<223> OTHER INFORMATION: n=A,T,C or G
<220> FEATURE:
<221> NAME/KEY: unsure
<222> LOCATION: (3538)
<223> OTHER INFORMATION: n=A,T,C or G
<220> FEATURE:
<221> NAME/KEY: unsure
<222> LOCATION: (3549)
<223> OTHER INFORMATION: n=A,T,C or G
<220> FEATURE:
<221> NAME/KEY: unsure
<222> LOCATION: (3646)
<223> OTHER INFORMATION: n=A,T,C or G
<220> FEATURE:
<221> NAME/KEY: unsure
<222> LOCATION: (3940)
<223> OTHER INFORMATION: n=A,T,C or G
<220> FEATURE:
<221> NAME/KEY: unsure
<222> LOCATION: (3968)
<223> OTHER INFORMATION: n=A,T,C or G
<220> FEATURE:
<221> NAME/KEY: unsure
<222> LOCATION: (3974)
<223> OTHER INFORMATION: n=A,T,C or G
<220> FEATURE:
<221> NAME/KEY: unsure
<222> LOCATION: (4036)
<223> OTHER INFORMATION: n=A,T,C or G
<220> FEATURE:
<221> NAME/KEY: unsure
<222> LOCATION: (4056)
<223> OTHER INFORMATION: n=A,T,C or G
<220> FEATURE:
<221> NAME/KEY: unsure
<222> LOCATION: (4062)
<223> OTHER INFORMATION: n=A,T,C or G
<220> FEATURE:
<221> NAME/KEY: unsure
<222> LOCATION: (4080)
<223> OTHER INFORMATION: n=A,T,C or G
<220> FEATURE:
<221> NAME/KEY: unsure
<222> LOCATION: (4088)
<223> OTHER INFORMATION: n=A,T,C or G
<220> FEATURE:
<221> NAME/KEY: unsure
<222> LOCATION: (4115)
<223> OTHER INFORMATION: n=A,T,C or G

<400> SEQUENCE: 175
ggtggatgcg tttgggttgt agctaggctt tttcttttct ttctctttta aaacacatct    60
```

```
agacaaggaa aaaacaagcc tcggatctga tttttcactc ctcgttcttg tgcttggttc      120
ttactgtgtt tgtgtatttt aaaggcgaga gacgagggg aacaaaacca gctggatcca      180
tccatcaccg tgggtggttt taattttttcg ttttttctcg ttattttttt ttaaacaacc    240
actcttcaca atgaacaaac tgtatatcgg aaacctcagc gagaacgccg ccccctcgga    300
cctagaaagt atcttcaagg acgccaagat cccggtgtcg ggaccttcc tggtgaagac     360 tggctacgcg ttcgtggact gcccggacga gagctgggcc ctcaaggcca tcgaggcgct    420
ttcaggtaaa atagaactgc acgggaaacc catagaagtt gagcactcgg tcccaaaaag    480
gcaaaggatt cggaaacttc agatacgaaa tatcccgcct catttacagt gggaggtgct    540
ggatagttta ctagtccagt atggagtggt ggagagctgt gagcaagtga acactgactc    600
ggaaactgca gttgtaaatg taacctattc cagtaaggac caagctagac aagcactaga    660
caaactgaat ggatttcagt tagagaattt caccttgaaa gtagcctata tccctgatga    720
aatggccgcc cagcaaaacc ccttgcagca gccccgaggt cgccgggggc ttgggcagag    780
gggctcctca aggcagggt ctccaggatc cgtatccaag cagaaaccat gtgatttgcc     840
tctgcgcctg ctggttccca cccaatttgt tggagccatc ataggaaaag aaggtgccac    900
cattcggaac atcaccaaac agacccagtc taaaatcgat gtccaccgta aagaaaatgc    960
gggggctgct gagaagtcga ttactatcct ctctactcct gaaggcacct ctgcggcttg   1020
taagtctatt ctggagatta tgcataagga agctcaagat ataaaattca cagaagagat   1080 cccccttgaag attttagctc ataataactt tgttggacgt cttattggta agaaggaag    1140 aaatcttaaa aaaattgagc aagacacaga cactaaaatc acgatatctc cattgcagga   1200
attgacgctg tataatccag aacgcactat tacagttaaa ggcaatgttg agacatgtgc   1260
caaagctgag gaggagatca tgaagaaaat cagggagtct tatgaaaatg atattgcttc   1320
tatgaatctt caagcacatt taattcctgg attaaatctg aacgccttgg gtctgttccc   1380
acccacttca gggatgccac ctcccacctc agggcccct tcagccatga ctcctccctat   1440 cccgcagttt gagcaatcag aaacggagac tgttcatcag tttatcccag ctctatcagt   1500
cggtgccatc atcggcaagc agggccagca catcaagcag ctttctcgct ttgctggagc   1560
ttcaattaag attgctccag cggaagcacc agatgctaaa gtgaggatgg tgattatcac   1620
tggaccacca gaggctcagt tcaaggctca gggaagaatt tatggaaaaa ttaaagaaga   1680
aaactttgtt agtcctaaag aagaggtgaa acttgaagct catatcagag tgccatcctt   1740
tgctgctggc agagttattg aaaaggagg caaaacggtg aatgaacttc agaatttgtc    1800
aagtgcagaa gttgttgtcc ctcgtgacca gacacctgat gagaatgacc aagtggttgt   1860
caaaataact ggtcacttct atgcttgcca ggttgcccag agaaaaattc aggaaattct   1920
gactcaggta aagcagcacc aacaacagaa ggctctgcaa agtggaccac ctcagtcaag   1980
acggaagtaa aggctcagga aacagcccac cacagaggca gatgccaaac caaagacaga   2040
ttgcttaacc aacagatggg cgctgacccc ctatccagaa tcacatgcac aagttttac    2100 ctagccagtt gtttctgagg accaggcaac ttttgaactc ctgtctctgt gagaatgtat   2160
actttatgct ctctgaaatg tatgacaccc agctttaaaa caaacaaaca acaaacaaa    2220 aaaagggtgg gggagggagg gaaagagaag agctctgcac ttcccttgt tgtagtctca    2280 cagtataaca gatattctaa ttcttcttaa tattccccca taatgccaga aattggctta   2340
atgatgcttt cactaaattc atcaaataga ttgctcctaa atccaattgt taaaattgga   2400
```

```
tcagaataat tatcacagga acttaaatgt taagccatta gcatagaaaa actgttctca    2460
gttttatttt tacctaacac taacatgagt aacctaaggg aagtgctgaa tggtgttggc    2520 agggtatta aacgtgcatt tttactcaac tacctcaggt attcagtaat acaatgaaaa     2580
gcaaaattgt tccttttttt tgaaaatttt atatacttta taatgataga agtccaaccg    2640
ttttttaaaa aataaattta aaatttaaca gcaatcagct aacaggcaaa ttaagatttt    2700
tacttctggc tggtgacagt aaagctggaa aattaatttc agggtttttt gaggcttttg    2760
acacagttat tagttaaatc aaatgttcaa aaatacggag cagtgcctag tatctggaga    2820
gcagcactac catttattct ttcatttata gttgggaaag ttttttgacgg tactaacaaa    2880 gtggtcgcag gagattttgg aacggctggt ttaaatggct tcaggagact tcagtttttt    2940
gtttagctac atgattgaat gcataataaa tgctttgtgc ttctgactat caatacctaa    3000
agaaagtgca tcagtgaaga gatgcaagac tttcaactga ctggcaaaaa gcaagcttta    3060
gcttgtctta taggatgctt agtttgccac tacacttcag accaatggga cagtcataga    3120
tggtgtgaca gtgttaaac gcaacaaaag gctacatttc catggggcca gcactgtcat    3180
gagcctcact aagctatttt gaagattttt aagcactgat aaattaaaaa aaaaaaaaa     3240 aaattagact ccaccttaag tagtaaagta taacaggatt tctgtatact gtgcaatcag    3300
ttctttgaaa aaaaagtcaa aagatagaga atacaagaaa agttttnggg atataatttg    3360
aatgactgtg aaaacatatg acctttgata acgaactcat ttgctcactc cttgacagca    3420
aagcccagta cgtacaattg tgttgggtgt gggtggtctc caaggccacg ctgctctctg    3480
aattgatttt ttgagttttg gnttgnaaga tgatcacagn catgttacac tgatcttnaa    3540
ggacatatnt tataacccctt taaaaaaaaa atcccctgcc tcattcttat ttcgagatga    3600
atttcgatac agactagatg tctttctgaa gatcaattag acattntgaa aatgatttaa    3660
agtgttttcc ttaatgttct ctgaaaacaa gtttcttttg tagttttaac caaaaaagtg    3720 cccttttgt cactggtttc tcctagcatt catgattttt ttttcacaca atgaattaaa      3780
attgctaaaa tcatggactg gctttctggt tggatttcag gtaagatgtg tttaaggcca    3840
gagcttttct cagtatttga ttttttttccc caatatttga ttttttaaaa atatacacat    3900
aggagctgca tttaaaacct gctggtttaa attctgtcan atttcacttc tagccttta     3960 gtatggcnaa tcanaattta cttttactta agcatttgta atttggagta tctggtacta    4020
gctaagaaat aattcnataa ttgagttttg tactcnccaa anatgggtca ttcctcatgn    4080
ataatgtncc cccaatgcag cttcattttc cagaaaccctt gacgcaggat aaattttttc    4140
atcatttagg tccccaaaaa aaaaaaaaaa aaaaaaaaa a                          4181
```

<210> SEQ ID NO 176  
<211> LENGTH: 579  
<212> TYPE: PRT  
<213> ORGANISM: Homo sapiens

<400> SEQUENCE: 176

Met Asn Lys Leu Tyr Ile Gly Asn Leu Ser Glu Asn Ala Ala Pro Ser
                5                   10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

-continued

```
Gly Lys Pro Ile Glu Val Glu His Ser Val Pro Lys Arg Gln Arg Ile
 65                  70                  75                  80

Arg Lys Leu Gln Ile Arg Asn Ile Pro Pro His Leu Gln Trp Glu Val
                 85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
130                 135                 140

Glu Asn Phe Thr Leu Lys Val Ala Tyr Ile Pro Asp Glu Met Ala Ala
145                 150                 155                 160

Gln Gln Asn Pro Leu Gln Gln Pro Arg Gly Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205

Ala Ile Ile Gly Lys Glu Gly Ala Thr Ile Arg Asn Ile Thr Lys Gln
210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
            260                 265                 270

Phe Thr Glu Glu Ile Pro Leu Lys Ile Leu Ala His Asn Asn Phe Val
        275                 280                 285

Gly Arg Leu Ile Gly Lys Glu Gly Arg Asn Leu Lys Lys Ile Glu Gln
290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Ile Met Lys Lys Ile Arg Glu Ser Tyr Glu
            340                 345                 350

Asn Asp Ile Ala Ser Met Asn Leu Gln Ala His Leu Ile Pro Gly Leu
        355                 360                 365

Asn Leu Asn Ala Leu Gly Leu Phe Pro Pro Thr Ser Gly Met Pro Pro
370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Gln Phe Ile Pro Ala Leu Ser
                405                 410                 415

Val Gly Ala Ile Ile Gly Lys Gln Gly Gln His Ile Lys Gln Leu Ser
            420                 425                 430

Arg Phe Ala Gly Ala Ser Ile Lys Ile Ala Pro Ala Glu Ala Pro Asp
        435                 440                 445

Ala Lys Val Arg Met Val Ile Ile Thr Gly Pro Pro Glu Ala Gln Phe
450                 455                 460

Lys Ala Gln Gly Arg Ile Tyr Gly Lys Ile Lys Glu Glu Asn Phe Val
465                 470                 475                 480
```

Ser Pro Lys Glu Glu Val Lys Leu Glu Ala His Ile Arg Val Pro Ser
            485                 490                 495

Phe Ala Ala Gly Arg Val Ile Gly Lys Gly Gly Lys Thr Val Asn Glu
            500                 505                 510

Leu Gln Asn Leu Ser Ser Ala Glu Val Val Pro Arg Asp Gln Thr
            515                 520                 525

Pro Asp Glu Asn Asp Gln Val Val Lys Ile Thr Gly His Phe Tyr
        530                 535                 540

Ala Cys Gln Val Ala Gly Arg Lys Ile Gln Glu Ile Leu Thr Gln Val
545                 550                 555                 560

Lys Gln His Gln Gln Gln Lys Ala Leu Gln Ser Gly Pro Pro Gln Ser
            565                 570                 575

Arg Arg Lys

<210> SEQ ID NO 177
<211> LENGTH: 401
<212> TYPE: DNA
<213> ORGANISM: Homo sapiens

<400> SEQUENCE: 177

| | | | | | | |
|---|---|---|---|---|---|---|
| atgccccgta | aatgtcttca | gtgttcttca | gggtagttgg | gatctcaaaa | gatttggttc | 60 |
| agatccaaac | aaatacacat | tctgtgtttt | agctcagtgt | tttctaaaaa | aagaaactgc | 120 |
| cacacagcaa | aaattgtttt | actttgttgg | acaaaccaaa | tcagttctca | aaaaatgacc | 180 |
| ggtgcttata | aaaagttata | aatatcgagt | agctctaaaa | caaaccacct | gaccaagagg | 240 |
| gaagtgagct | tgtgcttagt | atttacattg | gatgccagtt | ttgtaatcac | tgacttatgt | 300 |
| gcaaactggt | gcagaaattc | tataaactct | ttgctgtttt | tgatacctgc | tttttgtttc | 360 |
| attttgtttt | gttttgtaaa | aatgataaaa | cttcagaaaa | t | | 401 |

<210> SEQ ID NO 178
<211> LENGTH: 561
<212> TYPE: DNA
<213> ORGANISM: Homo sapiens

<400> SEQUENCE: 178

| | | | | | | |
|---|---|---|---|---|---|---|
| acgcctttca | agggtgtacg | caaagcactc | attgataccc | ttttggatgg | ctatgaaaca | 60 |
| gcccgctatg | ggacagggt | ctttggccag | aatgagtacc | tacgctatca | ggaggccctg | 120 |
| agtgagctgg | ccactgcggt | taagcacga | attgggagct | ctcagcgaca | tcaccagtca | 180 |
| gcagccaaag | acctaactca | gtcccctgag | gtctccccaa | caaccatcca | ggtgacatac | 240 |
| ctcccctcca | gtcagaagag | taaacgtgcc | aagcacttcc | ttgaattgaa | gagctttaag | 300 |
| gataactata | acacattgga | gagtactctg | tgacggagct | gaaggactct | tgccgtagat | 360 |
| taagccagtc | agttgcaatg | tgcaagacag | gctgcttgcc | gggccgccct | cggaacatct | 420 |
| ggcccagcag | gcccagactg | tatccatcca | agttcccgtt | gtatccagag | ttcttagagc | 480 |
| ttgtgtctaa | agggtaattc | cccaaccctt | ccttatgagc | attttagaa | cattggctaa | 540 |
| gactattttc | ccccagtagc | g | | | | 561 |

<210> SEQ ID NO 179
<211> LENGTH: 521
<212> TYPE: DNA
<213> ORGANISM: Homo sapiens

<400> SEQUENCE: 179

| | | | | | | |
|---|---|---|---|---|---|---|
| cccaacgcgt | ttgcaaatat | tcccctggta | gcctacttcc | ttaccccga | atattggtaa | 60 |

```
gatcgagcaa tggcttcagg acatgggttc tcttctcctg tgatcattca agtgctcact      120
gcatgaagac tggcttgtct cagtgtttca acctcaccag ggctgtctct tggtccacac      180
ctcgctccct gttagtgccg tatgacagcc cccatcaaat gaccttggcc aagtcacggt      240
ttctctgtgg tcaaggttgg ttggctgatt ggtggaaagt agggtggacc aaaggaggcc      300
acgtgagcag tcagcaccag ttctgcacca gcagcgcctc cgtcctagtg ggtgttcctg      360
tttctcctgg ccctgggtgg gctagggcct gattcgggaa gatgcctttg cagggagggg      420
aggataagtg ggatctacca attgattctg gcaaaacaat ttctaagatt tttttgcttt      480
atgtgggaaa cagatctaaa tctcattttg tgctgtattt t                         521
```

<210> SEQ ID NO 180
<211> LENGTH: 417
<212> TYPE: DNA
<213> ORGANISM: Homo sapiens

<400> SEQUENCE: 180

```
ggtggaattc gccgaagatg gcggaggtgc aggtcctggt gcttgatggt cgaggccatc       60
tcctgggccg cctggcggcc atcgtggcta acaggtact gctgggccgg aaggtggtgg      120
tcgtacgctg tgaaggcatc aacatttctg gcaatttcta cagaaacaag ttgaagtacc      180
tggctttcct ccgcaagcgg atgaacacca acccttcccg aggcccctac cacttccggg      240
cccccagccc catcttctgg cggaccgtgc gaggtatgct gccccacaaa accaagcgag      300
gccaggccgc tctggaccgt ctcaaggtgt ttgacggcat cccaccgccc tacgacaaga      360
aaaagcggat ggtggttcct gctgccctca aggtcgtgcg tctgaagcct acaagaa         417
```

<210> SEQ ID NO 181
<211> LENGTH: 283
<212> TYPE: DNA
<213> ORGANISM: Homo sapiens
<220> FEATURE:
<221> NAME/KEY: unsure
<222> LOCATION: (35)
<223> OTHER INFORMATION: n=A,T,C or G

<400> SEQUENCE: 181

```
gatttcttct aaataggatg taaaacttct ttcanattac tcttcctcag tcctgcctgc       60
caagaactca agtgtaactg tgataaaata acctttccca ggtatattgg caggtatgtg      120
tgtaatctca gaatacacag gtgacataga tatgatatga caactggtaa tggtggattc      180
atttacattg tttacacttc tatgaccagg ccttaaggga aggtcagttt tttaaaaaac      240
caagtagtgt cttcctacct atctccagat acatgtcaaa aaa                       283
```

<210> SEQ ID NO 182
<211> LENGTH: 401
<212> TYPE: DNA
<213> ORGANISM: Homo sapiens

<400> SEQUENCE: 182

```
atattcttgc tgcttatgca gctgacattg ttgccctccc taaagcaacc aagtagcctt       60
tatttcccac agtgaaagaa aacgctggcc tatcagttac attacaaaag gcagatttca      120
agaggattga gtaagtagtt ggatggcttt cataaaaaca agaattcaag aagaggattc      180
atgctttaag aaacatttgt tatacattcc tcacaaatta tacctgggat aaaaactatg      240
tagcaggcag tgtgttttcc ttccatgtct ctctgcacta cctgcagtgt gtcctctgag      300
```

| | |
|---|---|
| gctgcaagtc tgtcctatct gaattcccag cagaagcact aagaagctcc accctatcac | 360 |
| ctagcagata aaactatggg gaaaacttaa atctgtgcat a | 401 |

<210> SEQ ID NO 183
<211> LENGTH: 366
<212> TYPE: DNA
<213> ORGANISM: Homo sapiens
<220> FEATURE:
<221> NAME/KEY: unsure
<222> LOCATION: (325)
<223> OTHER INFORMATION: n=A,T,C or G

<400> SEQUENCE: 183

| | |
|---|---|
| accgtgtcca agttttaga acccttgtta gccagaccga ggtgtcctgg tcaccgtttc | 60 |
| accatcatgc tttgatgttc ccctgtcttt ctctcttctg ctctcaagag caaaggttaa | 120 |
| tttaaggaca aagatgaagt cactgtaaac taatctgtca ttgttttttac cttccttttc | 180 |
| tttttcagtg cagaaattaa agtaagtat aaagcaccgt gattgggagt gttttttgcgt | 240 |
| gtgtcggaat cactggtaaa tgttggctga gaacaatccc tccccttgca cttgtgaaaa | 300 |
| cactttgagc gctttaagag attanccgta gaaataatta aatatctttt ctcttcaaaa | 360 |
| aaaaaa | 366 |

<210> SEQ ID NO 184
<211> LENGTH: 370
<212> TYPE: DNA
<213> ORGANISM: Homo sapiens

<400> SEQUENCE: 184

| | |
|---|---|
| tcttacttca aaagaaaaat aaacataaaa aataagttgc tggttcctaa caggaaaaat | 60 |
| tttaataatt gtactgagag aaactgctta cgtacacatt gcagatcaaa tatttggagt | 120 |
| taaaatgtta gtctacatag atgggtgatt gtaacttat tgccattaaa agatttcaaa | 180 |
| ttgcattcat gcttctgtgt acacataatg aaaaatgggc aaataatgaa gatctctcct | 240 |
| tcagtctgct ctgtttaatt ctgctgtctg ctcttctcta atgctgcgtc cctaattgta | 300 |
| cacagtttag tgatatctag gagtataaag ttgtcgccca tcaataaaaa tcacaaagtt | 360 |
| ggtttaaaaa | 370 |

<210> SEQ ID NO 185
<211> LENGTH: 107
<212> TYPE: DNA
<213> ORGANISM: Homo sapiens

<400> SEQUENCE: 185

| | |
|---|---|
| ctcatattat tttcctttg agaaattgga aactctttct gttgctatta tattaataaa | 60 |
| gttggtgttt attttctggt agtcaccttc cccatttaaa aaaaaaa | 107 |

<210> SEQ ID NO 186
<211> LENGTH: 309
<212> TYPE: DNA
<213> ORGANISM: Homo sapiens

<400> SEQUENCE: 186

| | |
|---|---|
| gaaaggatgg ctctggttgc cacagagctg ggacttcatg ttcttctaga gagggccaca | 60 |
| agagggccac aggggtggcc gggagttgtc agctgatgcc tgctgagagg caggaattgt | 120 |
| gccagtgagt gacagtcatg agggagtgtc tcttcttggg gaggaaagaa ggtagagcct | 180 |
| ttctgtctga atgaaaggcc aaggctacag tacagggccc cgccccagcc agggtgttaa | 240 |

```
tgcccacgta gtggaggcct ctggcagatc ctgcattcca aggtcactgg actgtacgtt    300
tttatggtt                                                            309

<210> SEQ ID NO 187
<211> LENGTH: 477
<212> TYPE: DNA
<213> ORGANISM: Homo sapiens

<400> SEQUENCE: 187
ttcagtccta gcaagaagcg agaattctga gatcctccag aaagtcgagc agcacccacc     60
tccaacctcg ggccagtgtc ttcaggcttt actggggacc tgcgagctgg cctaatgtgg    120
tggcctgcaa gccaggccat ccctgggcgc cacagacgag ctccgagcca ggtcaggctt    180
cggaggccac aagctcagcc tcaggcccag gcactgattg tggcagaggg gccactaccc    240 aagtctagc taggcccaag acctagttac ccagacagtg agaagcccct ggaaggcaga     300
aaagttggga gcatggcaga cagggaaggg aaacattttc agggaaaaga catgtatcac    360
atgtcttcag aagcaagtca ggtttcatgt aaccgagtgt cctcttgcgt gtccaaaagt    420 agcccaggc tgtagcacag gcttcacagt gattttgtgt tcagccgtga gtcacac        477

<210> SEQ ID NO 188
<211> LENGTH: 220
<212> TYPE: DNA
<213> ORGANISM: Homo sapiens

<400> SEQUENCE: 188
taaatatggt agatattaat attcctctta gatgaccagt gattccaatt gtcccaagtt     60
ttaaataagt accctgtgag tatgagataa attagtgaca atcagaacaa gtttcagtat    120
cagatgttca agaggaagtt gctattgcat tgatttttaat atttgtacat aaacactgat   180 tttttttgagc attattttgt atttgttgta ctttaatacc                         220

<210> SEQ ID NO 189
<211> LENGTH: 417
<212> TYPE: DNA
<213> ORGANISM: Homo sapiens
<220> FEATURE:
<221> NAME/KEY: unsure
<222> LOCATION: (76)
<223> OTHER INFORMATION: n=A,T,C or G
<220> FEATURE:
<221> NAME/KEY: unsure
<222> LOCATION: (77)
<223> OTHER INFORMATION: n=A,T,C or G

<400> SEQUENCE: 189
accatcttga cagaggatac atgctcccaa aacgtttgtt accacactta aaaatcactg     60
ccatcattaa gcatcnnttt caaaattata gccattcatg atttactttt tccagatgac    120
tatcattatt ctagtccttt gaatttgtaa ggggaaaaaa aacaaaaaca aaaacttacg    180
atgcactttt ctccagcaca tcagatttca aattgaaaat taaagacatg ctatggtaat    240
gcacttgcta gtactacaca ctttgtacaa caaaaaacag aggcaagaaa caacggaaag    300
agaaaagcct tcctttgttg gcccttaaac tgagtcaaga tctgaaatgt agagatgatc    360
tctgacgata cctgtatgtt cttattgtgt aaataaaatt gctggtatga aatgaca       417

<210> SEQ ID NO 190
<211> LENGTH: 497
<212> TYPE: DNA
```

<213> ORGANISM: Homo sapiens

<400> SEQUENCE: 190

| gcactgcggc | gctctcccgt | cccgcggtgg | ttgctgctgc | tgccgctgct | gctgggcctg | 60 |
| aacgcaggag | ctgtcattga | ctggcccaca | gaggagggca | aggaagtatg | ggattatgtg | 120 |
| acggtccgca | aggatgccta | catgttctgg | tggctctatt | atgccaccaa | ctcctgcaag | 180 |
| aacttctcag | aactgcccct | ggtcatgtgg | cttcagggcg | gtccaggcgg | ttctagcact | 240 |
| ggatttggaa | actttgagga | aattgggccc | cttgacagtg | atctcaaacc | acggaaaacc | 300 |
| acctggctcc | aggctgccag | tctcctattt | gtggataatc | ccgtgggcac | tgggttcagt | 360 |
| tatgtgaatg | gtagtggtgc | ctatgccaag | gacctggcta | tggtggcttc | agacatgatg | 420 |
| gttctcctga | agaccttctt | cagttgccac | aaagaattcc | agacagttcc | attctacatt | 480 |
| ttctcagagt | cctatgg | | | | | 497 |

<210> SEQ ID NO 191
<211> LENGTH: 175
<212> TYPE: DNA
<213> ORGANISM: Homo sapiens

<400> SEQUENCE: 191

| atgttgaata | ttttgcttat | taactttgtt | tattgtcttc | tccctcgatt | agaatattag | 60 |
| ctacttgagt | acaaggattt | gagcctgtta | cattcactgc | tgaattttag | gctcctggaa | 120 |
| gatacccagc | attcaataga | gaccacacaa | taaatatatg | tcaaataaaa | aaaaa | 175 |

<210> SEQ ID NO 192
<211> LENGTH: 526
<212> TYPE: DNA
<213> ORGANISM: Homo sapiens

<400> SEQUENCE: 192

| agtaaacatt | attatttttt | ttatatttgc | aaaggaaaca | tatctaatcc | ttcctataga | 60 |
| aagaacagta | ttgctgtaat | tccttttctt | ttcttcctca | tttcctctgc | cccttaaaag | 120 |
| attgaagaaa | gagaaacttg | tcaactcata | tccacgttat | ctagcaaagt | acataagaat | 180 |
| ctatcactaa | gtaatgtatc | cttcagaatg | tgttggttta | ccagtgacac | cccatattca | 240 |
| tcacaaaatt | aaagcaagaa | gtccatagta | atttatttgc | taatagtgga | ttttttaatgc | 300 |
| tcagagtttc | tgaggtcaaa | ttttatcttt | tcacttacaa | gctctatgat | cttaaataat | 360 |
| ttacttaatg | tattttggtg | tattttcctc | aaattaatat | tggtgttcaa | gactatatct | 420 |
| aattcctctg | atcactttga | gaaacaaact | tttattaaat | gtaaggcact | tttctatgaa | 480 |
| ttttaaatat | aaaaataaat | attgttctga | ttattactga | aaaaaa | | 526 |

<210> SEQ ID NO 193
<211> LENGTH: 553
<212> TYPE: DNA
<213> ORGANISM: Homo sapiens
<220> FEATURE:
<221> NAME/KEY: unsure
<222> LOCATION: (290)
<223> OTHER INFORMATION: n=A,T,C or G
<220> FEATURE:
<221> NAME/KEY: unsure
<222> LOCATION: (300)
<223> OTHER INFORMATION: n=A,T,C or G
<220> FEATURE:
<221> NAME/KEY: unsure
<222> LOCATION: (411)
<223> OTHER INFORMATION: n=A,T,C or G

```
<220> FEATURE:
<221> NAME/KEY: unsure
<222> LOCATION: (441)
<223> OTHER INFORMATION: n=A,T,C or G

<400> SEQUENCE: 193
tccattgtgg tggaattcgc tctctggtaa aggcgtgcag gtgttggccg cggcctctga      60
gctgggatga gccgtgctcc cggtggaagc aagggagccc agccggagcc atggccagta     120
cagtggtagc agttggactg accattgctg ctgcaggatt tgcaggccgt tacgttttgc     180
aagccatgaa gcatatggag cctcaagtaa acaagtttt tcaaagccta ccaaaatctg      240
ccttcagtgg tggctattat agaggtgggt ttgaacccaa aatgacaaan cgggaagcan    300
cattaatact agtgtaagc cctactgcca ataaaggaa aataagagat gctcatcgac       360
gaattatgct tttaaatcat cctgacaaag gaggatctcc ttatatagca nccaaaatca   420
atgaagctaa agatttacta naaggtcaag ctaaaaaatg aagtaaatgt atgatgaatt   480
ttaagttcgt attagtttat gtatatgagt actaagtttt tataataaaa tgcctcagag   540
ctacaatttt aaa                                                        553

<210> SEQ ID NO 194
<211> LENGTH: 320
<212> TYPE: DNA
<213> ORGANISM: Homo sapiens

<400> SEQUENCE: 194
cccttcccaa tccatcagta aagaccccat ctgccttgtc catgccgttt cccaacaggg     60
atgtcacttg atatgagaat ctcaaatctc aatgccttat aagcattcct tcctgtgtcc   120
attaagactc tgataattgt ctcccctcca taggaatttc tcccaggaaa gaaatatatc   180
cccatctccg tttcatatca gaactaccgt ccccgatatt cccttcagag agattaaaga  240
ccagaaaaaa gtgagcctct tcatctgcac ctgtaatagt ttcagttcct attttcttcc   300
attgacccat atttataccct                                                320

<210> SEQ ID NO 195
<211> LENGTH: 320
<212> TYPE: DNA
<213> ORGANISM: Homo sapiens
<220> FEATURE:
<221> NAME/KEY: unsure
<222> LOCATION: (203)
<223> OTHER INFORMATION: n=A,T,C or G
<220> FEATURE:
<221> NAME/KEY: unsure
<222> LOCATION: (218)
<223> OTHER INFORMATION: n=A,T,C or G

<400> SEQUENCE: 195
aagcatgacc tggggaaatg gtcagacctt gtattgtgtt tttggccttg aaagtagcaa     60
gtgaccagaa tctgccatgg caacaggctt taaaaagac ccttaaaaag acactgtctc   120
aactgtggtg ttagcaccag ccagctctct gtacatttgc tagcttgtag ttttctaaga   180
ctgagtaaac ttcttatttt tanaagggg aggctggntt gtaactttcc ttgtacttaa   240
ttgggtaaaa gtcttttcca caaaccacca tctattttgt gaactttgtt agtcatcttt   300
tatttggtaa attatgaact                                                 320

<210> SEQ ID NO 196
<211> LENGTH: 357
<212> TYPE: DNA
```

<213> ORGANISM: Homo sapiens
<220> FEATURE:
<221> NAME/KEY: unsure
<222> LOCATION: (36)
<223> OTHER INFORMATION: n=A,T,C or G

<400> SEQUENCE: 196

| | | | | | |
|---|---|---|---|---|---|
| atataaaata | atacgaaact | ttaaaaagca | ttggantgtc | agtatgttga | atcagtagtt | 60 |
| tcactttaac | tgtaaacaat | ttcttaggac | accatttggg | ctagtttctg | tgtaagtgta | 120 |
| aatactacaa | aaacttattt | atactgttct | tatgtcattt | gttatattca | tagatttata | 180 |
| tgatgatatg | acatctggct | aaaaagaaat | tattgcaaaa | ctaaccacta | tgtacttttt | 240 |
| tataaatact | gtatggacaa | aaaatggcat | tttttatatt | aaattgttta | gctctggcaa | 300 |
| aaaaaaaaaa | ttttaagagc | tggtactaat | aaaggattat | tatgactgtt | aaaaaa | 357 |

<210> SEQ ID NO 197
<211> LENGTH: 565
<212> TYPE: DNA
<213> ORGANISM: Homo sapiens
<220> FEATURE:
<221> NAME/KEY: unsure
<222> LOCATION: (27)
<223> OTHER INFORMATION: n=A,T,C or G

<400> SEQUENCE: 197

| | | | | | |
|---|---|---|---|---|---|
| tcagctgagt | accatcagga | tatttanccc | tttaagtgct | gttttgggag | tagaaaacta | 60 |
| aagcaacaat | acttcctctt | gacagctttg | attggaatgg | ggttattaga | tcattcacct | 120 |
| tggtcctaca | cttttagga | tgcttggtga | acataacacc | acttataatg | aacatccctg | 180 |
| gttcctatat | tttgggctat | gtgggtagga | attgttactt | gttactgcag | cagcagccct | 240 |
| agaaagtaag | cccagggctt | cagatctaag | ttagtccaaa | agctaaatga | tttaaagtca | 300 |
| agttgtaatg | ctaggcataa | gcactctata | atacattaaa | ttataggccg | agcaattagg | 360 |
| gaatgtttct | gaaacattaa | acttgtattt | atgtcactaa | aattctaaca | caaacttaaa | 420 |
| aaatgtgtct | catacatatg | ctgtactagg | cttcatcatg | catttctaaa | tttgtgtatg | 480 |
| atttgaatat | atgaaagaat | ttatacaaga | gtgttattta | aaattattaa | aaataaatgt | 540 |
| atataatttg | tacctattgt | aaaaa | | | | 565 |

<210> SEQ ID NO 198
<211> LENGTH: 484
<212> TYPE: DNA
<213> ORGANISM: Homo sapiens

<400> SEQUENCE: 198

| | | | | | |
|---|---|---|---|---|---|
| tatgtaagta | ttggtgtctg | ctttaaaaaa | ggagacccag | acttcacctg | tccttttaa | 60 |
| acatttgaga | acagtgttac | tctgagcagt | tgggccacct | tcaccttatc | cgacagctga | 120 |
| ctgttggatg | tgtccattgt | cgccagtttg | gctgttgccc | ggacaggaca | ggacctccat | 180 |
| tgggcgcagc | agcaggtggc | agggtgtgg | cttgaggtgg | gtggcagcgt | ctggtcctcc | 240 |
| tctctggtgc | tttctgagag | ggtctctaaa | gcagagtgtg | gttggcctgg | gggaaggcag | 300 |
| agcacgtatt | tctcccctct | agtacctctg | catttgtgag | tgttccctct | ggctttctga | 360 |
| agggcagcag | actcttgagt | atactgcaga | ggacatgctt | tatcagtagg | tcctgagggc | 420 |
| tccaggggct | caactgacca | agtaacacag | aagttggggt | atgtggccta | tttgggtcgg | 480 |
| aaac | | | | | | 484 |

<210> SEQ ID NO 199
<211> LENGTH: 429
<212> TYPE: DNA
<213> ORGANISM: Homo sapiens
<220> FEATURE:
<221> NAME/KEY: unsure
<222> LOCATION: (77)
<223> OTHER INFORMATION: n=A,T,C or G
<220> FEATURE:
<221> NAME/KEY: unsure
<222> LOCATION: (88)
<223> OTHER INFORMATION: n=A,T,C or G
<220> FEATURE:
<221> NAME/KEY: unsure
<222> LOCATION: (134)
<223> OTHER INFORMATION: n=A,T,C or G
<220> FEATURE:
<221> NAME/KEY: unsure
<222> LOCATION: (151)
<223> OTHER INFORMATION: n=A,T,C or G
<220> FEATURE:
<221> NAME/KEY: unsure
<222> LOCATION: (189)
<223> OTHER INFORMATION: n=A,T,C or G
<220> FEATURE:
<221> NAME/KEY: unsure
<222> LOCATION: (227)
<223> OTHER INFORMATION: n=A,T,C or G
<220> FEATURE:
<221> NAME/KEY: unsure
<222> LOCATION: (274)
<223> OTHER INFORMATION: n=A,T,C or G
<220> FEATURE:
<221> NAME/KEY: unsure
<222> LOCATION: (319)
<223> OTHER INFORMATION: n=A,T,C or G

<400> SEQUENCE: 199

```
gcttatgttt tttgttttaa cttttgtttt ttaacattta gaatattaca ttttgtatta      60
tacagtacct ttctcanaca ttttgtanaa ttcatttcgg cagctcacta ggattttgct     120
gaacattaaa aagngtgata gcgatattag ngccaatcaa atggaaaaaa ggtagtctta     180
ataaacaana cacaacgttt ttatacaaca tactttaaaa tattaanaaa actccttaat     240
attgtttcct attaagtatt attctttggg caanattttc tgatgctttt gatttctct      300
caatttagca tttgctttng gttttttttct ctatttagca ttctgttaag gcacaaaaac    360
tatgtactgt atgggaaatg ttgtaaatat taccttttcc acatttaaa cagacaactt     420
tgaatccaa                                                              429
```

<210> SEQ ID NO 200
<211> LENGTH: 279
<212> TYPE: DNA
<213> ORGANISM: Homo sapiens

<400> SEQUENCE: 200

```
gcttttttga ggaattacag ggaagctcct ggaattgtac atggatatct ttatccctag      60
ggggaaatca aggagctggg caccctaat tctttatgga agtgtttaaa actatttaa      120
ttttattaca agtattacta gagtagtggt tctactctaa gatttcaaaa gtgcatttaa     180
aatcatacat gttcccgcct gcaaatatat tgttattttg gtggagaaaa aaatagtata    240
ttctacataa aaaattaaag atattaacta agaaaaaaa                             279
```

<210> SEQ ID NO 201
<211> LENGTH: 569
<212> TYPE: DNA
<213> ORGANISM: Homo sapiens

<400> SEQUENCE: 201

```
taggtcagta tttttagaaa ctcttaatag ctcatactct tgataccaaa agcagccctg      60
attgttaaag cacacacctg cacaagaagc agtgatggtt gcatttacat ttcctgggtg     120
cacaaaaaaa aattctcaaa aagcaaggac ttacgctttt tgcaaagcct tgagaagtt     180
actggatcat aggaagctta taacaagaat ggaagattct taaataactc actttctttg    240
gtatccagta acagtagatg ttcaaaatat gtagctgatt aataccagca ttgtgaacgc    300
tgtacaacct tgtggttatt actaagcaag ttactactag cttctgaaaa gtagcttcat    360
aattaatgtt atttatacac tgccttccat gactttact ttgccctaag ctaatctcca     420
aaatctgaaa tgctactcca atatcagaaa aaaggggga ggtggaatta tatttcctgt     480
gattttaaga gtacagagaa tcatgcacat ctctgattag ttcatatatg tctagtgtgt    540
aataaaagtc aaagatgaac tctcaaaaa                                       569
```

<210> SEQ ID NO 202
<211> LENGTH: 501
<212> TYPE: DNA
<213> ORGANISM: Homo sapiens

<400> SEQUENCE: 202

```
attaataggc ttaataattg ttggcaagga tccttttgct ttctttggca tgcaagctcc      60
tagcatctgg cagtggggcc aagaaaataa ggtttatgca tgtatgatgg ttttcttctt    120
gagcaacatg attgagaacc agtgtatgtc aacaggtgca tttgagataa ctttaaatga    180
tgtacctgtg tggtctaagc tggaatctgg tcaccttcca tccatgcaac aacttgttca    240
aattcttgac aatgaaatga agctcaatgt gcatatggat tcaatcccac accatcgatc    300
atagcaccac ctatcagcac tgaaaactct tttgcattaa gggatcattg caagagcagc    360
gtgactgaca ttatgaaggc ctgtactgaa gacagcaagc tgttagtaca gaccagatgc    420
tttcttggca ggctcgttgt acctcttgga aaacctcaat gcaagatagt gtttcagtgc    480
tggcatattt tggaattctg c                                              501
```

<210> SEQ ID NO 203
<211> LENGTH: 261
<212> TYPE: DNA
<213> ORGANISM: Homo sapiens
<220> FEATURE:
<221> NAME/KEY: unsure
<222> LOCATION: (36)
<223> OTHER INFORMATION: n=A,T,C or G
<220> FEATURE:
<221> NAME/KEY: unsure
<222> LOCATION: (96)
<223> OTHER INFORMATION: n=A,T,C or G

<400> SEQUENCE: 203

```
gacaagctcc tggtcttgag atgtcttctc gttaangaga tgggccttt ggaggtaaag       60
gataaaatga atgagttctg tcatgattca ctattntata acttgcatga cctttactgt    120
gttagctctt tgaatgttct tgaaatttta gactttcttt gtaaacaaat gatatgtcct    180
tatcattgta taaagctgt tatgtgcaac agtgtggaga ttccttgtct gatttaataa     240
aatacttaaa cactgaaaaa a                                              261
```

<210> SEQ ID NO 204
<211> LENGTH: 421
<212> TYPE: DNA
<213> ORGANISM: Homo sapiens

<400> SEQUENCE: 204

```
agcatctttt ctacaacgtt aaaattgcag aagtagctta tcattaaaaa acaacaacaa        60
caacaataac aataaatcct aagtgtaaat cagttattct acccctacc aaggatatca        120
gcctgttttt tcccttttt ctcctgggaa taattgtggg cttcttccca aatttctaca        180
gcctctttcc tcttctcatg cttgagcttc cctgtttgca cgcatgcgtg tgcaggactg        240
gcttgtgtgc ttggactcgg ctccaggtgg aagcatgctt tcccttgtta ctgttggaga        300
aactcaaacc ttcaagccct agtgtagcc attttgtcaa gtcatcaact gtattttgt          360
actggcatta acaaaaaaag aagataaaat attgtaccat taaactttaa taaaacttta        420
a                                                                         421
```

<210> SEQ ID NO 205
<211> LENGTH: 460
<212> TYPE: DNA
<213> ORGANISM: Homo sapiens

<400> SEQUENCE: 205

```
tactctcaca atgaaggacc tggaatgaaa atctgtgtc taaacaagtc ctctttagat         60
tttagtgcaa atccagagcc agcgtcggtt gcctcgagta attctttcat gggtaccttt        120
ggaaaagctc tcaggagacc tcacctagat gcctattcaa gctttggaca gccatcagat        180
tgtcagccaa gagccttta tttgaaagct cattcttccc cagacttgga ctctgggtca         240
gaggaagatg ggaaagaaag gacagatttt caggaagaaa atcacatttg tacctttaaa        300
cagactttag aaaactacag gactccaaat tttcagtctt atgacttgga cacatagact        360
gaatgagacc aaaggaaaag cttaacatac tacctcaagg tgaacttta tttaaaagag         420
agagaatctt atgtttttta aatggagtta tgaattttaa                              460
```

<210> SEQ ID NO 206
<211> LENGTH: 481
<212> TYPE: DNA
<213> ORGANISM: Homo sapiens

<400> SEQUENCE: 206

```
tgtggtggaa ttcgggacgc ccccagaccc tgacttttc ctgcgtgggc cgtctcctcc          60
tgcggaagca gtgacctctg accctggtg accttcgctt tgagtgcctt ttgaacgctg         120
gtcccgcggg acttggtttt ctcaagctct gtctgtccaa agacgctccg gtcgaggtcc        180
cgcctgccct gggtggatac ttgaacccca gacgccctc tgtgctgctg tgtccggagg         240
cggccttccc atctgcctgc ccacccggag ctctttccgc cggcgcaggg tcccaagccc        300
acctcccgcc ctcagtcctg cggtgtgcgt ctgggcacgt cctgcacaca caatgcaagt        360
cctggcctcc gcgcccgccc gcccacgcga gccgtacccg ccgccaactc tgttatttat        420
ggtgtgaccc cctggaggtg ccctcggccc accggggcta tttattgttt aatttatttg       480
t                                                                         481
```

<210> SEQ ID NO 207
<211> LENGTH: 605
<212> TYPE: DNA
<213> ORGANISM: Homo sapiens

<400> SEQUENCE: 207

```
acccttttg gattcagggc tcctcacaat taaaatgagt gtaatgaaac aaggtgaaaa         60
```

| | |
|---|---|
| tatagaagca tcccttttgta tactgttttg ctacttacag tgtacttggc attgctttat | 120 |
| ctcactggat tctcacggta ggatttctga gatcttaatc taagctccaa agttgtctac | 180 |
| ttttttgatc ctagggtgct ccttttgttt tacagagcag ggtcacttga tttgctagct | 240 |
| ggtggcagaa ttggcaccat tacccaggtc tgactgacca ccagtcagag cactttatt | 300 |
| tgtatcatga aatgatttga aatcattgta aagcagcgaa gtctgataat gaatgccagc | 360 |
| tttccttgtg ctttgataac aaagactcca aatattctgg agaacctgga taaaagtttg | 420 |
| aagggctaga ttgggatttg aagacaaaat tgtaggaaat cttacatttt tgcaataaca | 480 |
| aacattaatg aaagcaaaac attataaaag taattttaat tcaccacata cttatcaatt | 540 |
| tcttgatgct tccaaatgac atctaccaga tatggttttg tggacatctt tttctgttta | 600 |
| cataa | 605 |

<210> SEQ ID NO 208
<211> LENGTH: 655
<212> TYPE: DNA
<213> ORGANISM: Homo sapiens

<400> SEQUENCE: 208

| | |
|---|---|
| ggcgttgttc tggattcccg tcgtaactta aagggaaact ttcacaatgt ccggagccct | 60 |
| tgatgtcctg caaatgaagg aggaggatgt ccttaagttc cttgcagcag gaacccactt | 120 |
| aggtggcacc aatcttgact tccagatgga acagtacatc tataaaagga aaagtgatgg | 180 |
| catctatatc ataaatctca agaggacctg ggagaagctt ctgctggcag ctcgtgcaat | 240 |
| tgttgccatt gaaaaccctg ctgatgtcag tgttatatcc tccaggaata ctggccagag | 300 |
| ggctgtgctg aagtttgctg ctgccactgg agccactcca attgctggcc gcttcactcc | 360 |
| tggaaccttc actaaccaga tccaggcagc cttccgggag ccacggcttc ttgtggttac | 420 |
| tgaccccagg gctgaccacc agcctctcac ggaggcatct tatgttaacc tacctaccat | 480 |
| tgcgctgtgt aacacagatt ctcctctgcg ctatgtggac attgccatcc catgcaacaa | 540 |
| caagggagct cactcagtgg gtttgatgtg gtggatgctg gctcgggaag ttctgcgcat | 600 |
| gcgtggcacc atttcccgtg aacacccatg ggaggtcatg cctgatctgt acttc | 655 |

<210> SEQ ID NO 209
<211> LENGTH: 621
<212> TYPE: DNA
<213> ORGANISM: Homo sapiens

<400> SEQUENCE: 209

| | |
|---|---|
| catttagaac atggttatca tccaagacta ctctaccctg caacattgaa ctcccaagag | 60 |
| caaatccaca ttcctcttga gttctgcagc ttctgtgtaa atagggcagc tgtcgtctat | 120 |
| gccgtagaat cacatgatct gaggaccatt catggaagct gctaaatagc ctagtctggg | 180 |
| gagtcttcca taaagttttg catggagcaa acaaacagga ttaaactagg tttggttcct | 240 |
| tcagccctct aaaagcatag ggcttagcct gcaggcttcc ttgggctttc tctgtgtgtg | 300 |
| tagttttgta aacactatag catctgttaa gatccagtgt ccatggaaac cttcccacat | 360 |
| gccgtgactc tggactatat cagttttttgg aaagcagggt tcctctgcct gctaacaagc | 420 |
| ccacgtggac cagtctgaat gtctttcctt tacacctatg ttttttaaata gtcaaacttc | 480 |
| aagaaacaat ctaaacaagt ttctgttgca tatgtgtttg tgaacttgta tttgtattta | 540 |
| gtaggcttct atattgcatt taacttgttt ttgtaactcc tgattcttcc ttttcggata | 600 |
| ctattgatga ataaagaaat t | 621 |

<210> SEQ ID NO 210
<211> LENGTH: 533
<212> TYPE: DNA
<213> ORGANISM: Homo sapiens
<220> FEATURE:
<221> NAME/KEY: unsure
<222> LOCATION: (20)
<223> OTHER INFORMATION: n=A,T,C or G
<220> FEATURE:
<221> NAME/KEY: unsure
<222> LOCATION: (21)
<223> OTHER INFORMATION: n=A,T,C or G
<220> FEATURE:
<221> NAME/KEY: unsure
<222> LOCATION: (61)
<223> OTHER INFORMATION: n=A,T,C or G

<400> SEQUENCE: 210

| | | | | | |
|---|---|---|---|---|---|
| cgccttgggg | agccggcggn | ngagtccggg | acgtggagac | ccggggtccc | ggcagccggg | 60
| nggcccgcgg | gcccagggtg | gggatgcacc | gccgcgggt | gggagctggc | gccatcgcca | 120
| agaagaaact | tgcagaggcc | aagtataagg | agcgagggac | ggtcttggct | gaggaccagc | 180
| tagcccagat | gtcaaagcag | ttggacatgt | tcaagaccaa | cctggaggaa | tttgccagca | 240
| aacacaagca | ggagatccgg | aagaatcctg | agttccgtgt | gcagttccag | gacatgtgtg | 300
| caaccattgg | cgtggatccg | ctggcctctg | gaaaaggatt | ttggtctgag | atgctgggcg | 360
| tgggggactt | ctattacgaa | ctaggtgtcc | aaattatcga | agtgtgcctg | gcgctgaagc | 420
| atcggaatgg | aggtctgata | actttggagg | aactacatca | acaggtgttg | aagggaaggg | 480
| gcaagttcgc | ccaggatgtc | agtcaagatg | acctgatcag | agccatcaag | aaa | 533

<210> SEQ ID NO 211
<211> LENGTH: 451
<212> TYPE: DNA
<213> ORGANISM: Homo sapiens

<400> SEQUENCE: 211

| | | | | | |
|---|---|---|---|---|---|
| ttagcttgag | ccgagaacga | ggcgagaaag | ctggagaccg | aggagaccgc | ctagagcgga | 60
| gtgaacgggg | aggggaccgt | ggggaccggc | ttgatcgtgc | gcggacacct | gctaccaagc | 120
| ggagcttcag | caaggaagtg | gaggagcgga | gtagagaacg | gccctcccag | cctgaggggc | 180
| tgcgcaaggc | agctagcctc | acggaggatc | gggaccgtgg | gcgggatgcc | gtgaagcgag | 240
| aagctgccct | accccagtg | agcccctga | aggcggctct | ctctgaggag | gagttagaga | 300
| agaaatccaa | ggctatcatt | gaggaatatc | tccatctcaa | tgacatgaaa | gaggcagtcc | 360
| agtgcgtgca | ggagctggcc | tcaccctcct | tgctcttcat | ctttgtacgg | catggtgtcg | 420
| agtctacgct | ggagcgcagt | gccattgctc | g | | | 451

<210> SEQ ID NO 212
<211> LENGTH: 471
<212> TYPE: DNA
<213> ORGANISM: Homo sapiens
<220> FEATURE:
<221> NAME/KEY: unsure
<222> LOCATION: (54)
<223> OTHER INFORMATION: n=A,T,C or G

<400> SEQUENCE: 212

| | | | | | |
|---|---|---|---|---|---|
| gtgattattc | ttgatcaggg | agaagatcat | ttagatttgt | tttgcattcc | ttanaatgga | 60
| gggcaacatt | ccacagctgc | cctggctgtg | atgagtgtcc | ttgcaggggc | cggagtagga | 120

| | |
|---|---|
| gcactgggt ggggggcggaa ttggggttac tcgatgtaag ggattccttg ttgttgtgtt | 180 |
| gagatccagt gcagttgtga tttctgtgga tcccagcttg gttccaggaa ttttgtgtga | 240 |
| ttggcttaaa tccagttttc aatcttcgac agctgggctg gaacgtgaac tcagtagctg | 300 |
| aacctgtctg acccggtcac gttcttggat cctcagaact ctttgctctt gtcggggtgg | 360 |
| gggtgggaac tcacgtgggg agcggtggct gagaaaatgt aaggattctg gaatacatat | 420 |
| tccatgggac tttccttccc tctcctgctt cctcttttcc tgctccctaa c | 471 |

<210> SEQ ID NO 213
<211> LENGTH: 511
<212> TYPE: DNA
<213> ORGANISM: Homo sapiens
<220> FEATURE:
<221> NAME/KEY: unsure
<222> LOCATION: (27)
<223> OTHER INFORMATION: n=A,T,C or G
<220> FEATURE:
<221> NAME/KEY: unsure
<222> LOCATION: (63)
<223> OTHER INFORMATION: n=A,T,C or G
<220> FEATURE:
<221> NAME/KEY: unsure
<222> LOCATION: (337)
<223> OTHER INFORMATION: n=A,T,C or G
<220> FEATURE:
<221> NAME/KEY: unsure
<222> LOCATION: (442)
<223> OTHER INFORMATION: n=A,T,C or G

<400> SEQUENCE: 213

| | |
|---|---|
| ctaattagaa acttgctgta cttttttnttt tcttttaggg gtcaaggacc ctctttatag | 60 |
| ctnccatttg cctacaataa attattgcag cagtttgcaa tactaaaata ttttttatag | 120 |
| actttatatt tttccttttg ataaagggat gctgcatagt agagttggtg taattaaact | 180 |
| atctcagccg tttccctgct ttcccttctg ctccatatgc ctcattgtcc ttccagggag | 240 |
| ctcttttaat cttaaagttc tacatttcat gctcttagtc aaattctgtt accttttttaa | 300 |
| taactcttcc cactgcatat ttccatcttg aattggnggt tctaaattct gaaactgtag | 360 |
| ttgagataca gctatttaat atttctggga gatgtgcatc cctcttcttt gtggttgccc | 420 |
| aaggttgttt tgcgtaactg anactccttg atatgcttca gagaatttag gcaaacactg | 480 |
| gccatggccg tgggagtact gggagtaaaa t | 511 |

<210> SEQ ID NO 214
<211> LENGTH: 521
<212> TYPE: DNA
<213> ORGANISM: Homo sapiens

<400> SEQUENCE: 214

| | |
|---|---|
| agcattgcca aataatccct aattttccac taaaaatata atgaaatgat gttaagcttt | 60 |
| ttgaaaagtt taggttaaac ctactgttgt tagattaatg tatttgttgc ttccctttat | 120 |
| ctggaatgtg gcattagctt ttttatttta accctcttta attcttattc aattccatga | 180 |
| cttaaggttg gagagctaaa cactgggatt tttggataac agactgacag ttttgcataa | 240 |
| ttataatcgg cattgtacat agaaaggata tggctaccTt ttgttaaatc tgcactttct | 300 |
| aaatatcaaa aaagggaaat gaagtataaa tcaatttttg tataatctgt ttgaaacatg | 360 |
| agtttttattt gcttaatatt agggctttgc ccctttctg taagtctctt gggatcctgt | 420 |
| gtagaagctg ttctcattaa acaccaaaca gttaagtcca ttctctggta ctagctacaa | 480 |
| attcggtttc atattctact taacaattta aataaactga a | 521 |

<210> SEQ ID NO 215
<211> LENGTH: 381
<212> TYPE: DNA
<213> ORGANISM: Homo sapiens
<220> FEATURE:
<221> NAME/KEY: unsure
<222> LOCATION: (17)
<223> OTHER INFORMATION: n=A,T,C or G
<220> FEATURE:
<221> NAME/KEY: unsure
<222> LOCATION: (20)
<223> OTHER INFORMATION: n=A,T,C or G
<220> FEATURE:
<221> NAME/KEY: unsure
<222> LOCATION: (60)
<223> OTHER INFORMATION: n=A,T,C or G
<220> FEATURE:
<221> NAME/KEY: unsure
<222> LOCATION: (61)
<223> OTHER INFORMATION: n=A,T,C or G
<220> FEATURE:
<221> NAME/KEY: unsure
<222> LOCATION: (365)
<223> OTHER INFORMATION: n=A,T,C or G

<400> SEQUENCE: 215

```
gagcggagag cggaccngtn agagccctga gcagccccac cgccgccgcc ggcctagttn      60
ncatcacacc ccgggaggag ccgcagctgc cgcagccggc cccagtcacc atcaccgcaa     120
ccatgagcag cgaggccgag acccagcagc cgccgccgcc ccccccgccc gccccgcccc    180
tcagcgccgc cgacaccaag cccggcacta cgggcagcgg cgcagggagc ggtggcccgg     240
gcggcctcac atcggcggcg cctgccggcg gggacaagaa ggtcatcgca acgaaggttt     300
tgggaacagt aaaatggttc aatgtaagga acggatatgg tttcatcaac aggaatgaca     360
ccaangaaga tgtatttgta c                                               381
```

<210> SEQ ID NO 216
<211> LENGTH: 425
<212> TYPE: DNA
<213> ORGANISM: Homo sapiens

<400> SEQUENCE: 216

```
ttactaacta ggtcattcaa ggaagtcaag ttaacttaaa catgtcacct aaatgcactt      60
gatggtgttg aaatgtccac cttcttaaat ttttaagatg aacttagttc taaagaagat     120
aacaggccaa tcctgaaggt actccctgtt tgctgcagaa tgtcagatat tttggatgtt     180
gcataagagt cctatttgcc ccagttaatt caacttttgt ctgcctgttt tgtggactgg     240
ctggctctgt tagaactctg tccaaaaagt gcatggaata taacttgtaa agcttcccac     300
aattgacaat atatatgcat gtgtttaaac caaatccaga aagcttaaac aatagagctg     360
cataatagta tttattaaag aatcacaact gtaaacatga gaataactta aggattctag     420
tttag                                                                 425
```

<210> SEQ ID NO 217
<211> LENGTH: 181
<212> TYPE: DNA
<213> ORGANISM: Homo sapiens

<400> SEQUENCE: 217

```
gagaaaccaa atgataggtt gtagagcctg atgactccaa acaaagccat cacccgcatt      60
cttcctcctt cttctggtgc tacagctcca agggcccttc accttcatgt ctgaaatgga     120
```

```
actttggctt tttcagtgga agaatatgtt gaaggtttca ttttgttcta gaaaaaaaaa    180
a                                                                    181
```

```
<210> SEQ ID NO 218
<211> LENGTH: 405
<212> TYPE: DNA
<213> ORGANISM: Homo sapiens

<400> SEQUENCE: 218
caggccttcc agttcactga caaacatggg gaagtgtgcc cagctggctg gaaacctggc     60
agtgatacca tcaagcctga tgtccaaaag agcaaagaat atttctccaa gcagaagtga    120
gcgctgggct gttttagtgc caggctgcgg tgggcagcca tgagaacaaa acctcttctg    180
tatttttttt ttccattagt aaaacacaag acttcagatt cagccgaatt gtggtgtctt    240
acaaggcagg cctttcctac aggggtggga gagaccagcc tttcttcctt tggtaggaat    300
ggcctgagtt ggcgttgtgg gcaggctact ggtttgtatg atgtattagt agagcaaccc    360
attaatcttt gtagtttgt attaaacttg aactgagaaa aaaaa                     405
```

```
<210> SEQ ID NO 219
<211> LENGTH: 216
<212> TYPE: DNA
<213> ORGANISM: Homo sapiens
<220> FEATURE:
<221> NAME/KEY: unsure
<222> LOCATION: (207)
<223> OTHER INFORMATION: n=A,T,C or G
<220> FEATURE:
<221> NAME/KEY: unsure
<222> LOCATION: (210)
<223> OTHER INFORMATION: n=A,T,C or G

<400> SEQUENCE: 219
actccaagag ttagggcagc agagtggagc gatttagaaa gaacatttta aaacaatcag     60
ttaatttacc atgtaaaatt gctgtaaatg ataatgtgta cagattttct gttcaaatat    120
tcaattgtaa acttcttgtt aagactgtta cgttttctatt gcttttgtat gggatattgc   180
aaaaataaaa aggaaagaac cctcttnaan aaaaaa                              216
```

```
<210> SEQ ID NO 220
<211> LENGTH: 380
<212> TYPE: DNA
<213> ORGANISM: Homo sapiens

<400> SEQUENCE: 220
cttacaaatt gccccatgt gtaggggaca cagaacccctt tgagaaaact tagatttttg     60
tctgtacaaa gtctttgcct ttttccttct tcatttttt ccagtacatt aaatttgtca    120
atttcatctt tgagggaaac tgattagatg ggttgtgttt gtgttctgat ggagaaaaca    180
gcaccccaag gactcagaag atgattttaa cagttcagaa cagatgtgtg caatattggt    240
gcatgtaata atgttgagtg gcagtcaaaa gtcatgattt ttatcttagt tcttcattac    300
tgcattgaaa aggaaaacct gtctgagaaa atgcctgaca gtttaattta aaactatggt    360
gtaagtcttt gacaaaaaaa                                                380
```

```
<210> SEQ ID NO 221
<211> LENGTH: 398
<212> TYPE: DNA
<213> ORGANISM: Homo sapiens

<400> SEQUENCE: 221
```

```
ggttagtaag ctgtcgactt tgtaaaaaag ttaaaatga aaaaaaagg aaaaatgaat      60 tgtatattta atgaatgaac atgtacaatt tgccactggg aggaggttcc ttttttgttgg   120 gtgagtctgc aagtgaattt cactgatgtt gatattcatt gtgtgtagtt ttatttcggt   180
cccagccccg tttccttta ttttggagct aatgccagct gcgtgtctag ttttgagtgc    240
agtaaaatag aatcagcaaa tcactcttat ttttcatcct tttccggtat tttttgggtt  300
gtttctgtgg gagcagtgta caccaactct tcctgtatat tgccttttg ctggaaaatg   360 ttgtatgttg aataaaattt tctataaaaa ttaaaaaa                            398
```

```
<210> SEQ ID NO 222
<211> LENGTH: 301
<212> TYPE: DNA
<213> ORGANISM: Homo sapiens
<220> FEATURE:
<221> NAME/KEY: unsure
<222> LOCATION: (49)
<223> OTHER INFORMATION: n=A,T,C or G
<220> FEATURE:
<221> NAME/KEY: unsure
<222> LOCATION: (64)
<223> OTHER INFORMATION: n=A,T,C or G

<400> SEQUENCE: 222
```

```
ttcgataatt gatctcatgg gctttccctg gaggaaaggt ttttttttgnt gtttattttt    60 taanaacttg aaacttgtaa actgagatgt ctgtagcttt tttgcccatc tgtagtgtat   120
gtgaagattt caaaacctga gagcactttt tctttgttta gaattatgag aaaggcacta  180 gatgactta ggatttgcat ttttcccttt attgcctcat ttcttgtgac gccttgttgg    240
ggagggaaat ctgtttattt tttcctacaa ataaaaagct aagattctat atcgcaaaaa 300
a                                                                    301
```

```
<210> SEQ ID NO 223
<211> LENGTH: 200
<212> TYPE: DNA
<213> ORGANISM: Homo sapiens

<400> SEQUENCE: 223
```

```
gtaagtgctt aggaagaaac tttgcaaaca tttaatgagg atacactgtt cattttaaa     60 attccttcac actgtaattt aatgtgtttt atattctttt gtagtaaaac aacataactc   120
agatttctac aggagacagt ggttttattt ggattgtctt ctgtaatagg tttcaataaa  180
gctggatgaa cttaaaaaaa                                                200
```

```
<210> SEQ ID NO 224
<211> LENGTH: 385
<212> TYPE: DNA
<213> ORGANISM: Homo sapiens

<400> SEQUENCE: 224
```

```
gaaaggtttg atccggactc aaagaaagca aaggagtgtg agccgccatc tgctggagca    60
gctgtaactg caagacctgg acaagagatt cgtcagcgaa ctgcagctca agaaaccttt  120
tctccaacac cagcaagccc taaccagggc cctcctccac aagttccagt atctcctgga  180
ccaccaaagg acagttctgc ccctggtgga cccccagaaa ggactgttac tccagcccta  240
tcatcaaatg tgttaccaag acatcttgga tcccctgcta cttcagtgcc tggaatgggt  300
aaacagagca cttaatgtta tttacagttt atattgtttt ctctggttac caataaaacg   360
```

```
ggccattttc aggtggtaaa aaaaa                                                    385
```

<210> SEQ ID NO 225
<211> LENGTH: 560
<212> TYPE: PRT
<213> ORGANISM: Homo sapien

<400> SEQUENCE: 225

```
Met Glu Cys Leu Tyr Tyr Phe Leu Gly Phe Leu Leu Ala Ala Arg
 1               5                  10                  15

Leu Pro Leu Asp Ala Ala Lys Arg Phe His Asp Val Leu Gly Asn Glu
                20                  25                  30

Arg Pro Ser Ala Tyr Met Arg Glu His Asn Gln Leu Asn Gly Trp Ser
                35                  40                  45

Ser Asp Glu Asn Asp Trp Asn Glu Lys Leu Tyr Pro Val Trp Lys Arg
 50                  55                  60

Gly Asp Met Arg Trp Lys Asn Ser Trp Lys Gly Arg Val Gln Ala
 65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
               100                 105                 110

Asn Ile Val Tyr Glu Lys Asn Cys Arg Asn Glu Ala Gly Leu Ser Ala
               115                 120                 125

Asp Pro Tyr Val Tyr Asn Trp Thr Ala Trp Ser Glu Asp Ser Asp Gly
               130                 135                 140

Glu Asn Gly Thr Gly Gln Ser His His Asn Val Phe Pro Asp Gly Lys
145                 150                 155                 160

Pro Phe Pro His His Pro Gly Trp Arg Trp Asn Phe Ile Tyr Val
               165                 170                 175

Phe His Thr Leu Gly Gln Tyr Phe Gln Lys Leu Gly Arg Cys Ser Val
               180                 185                 190

Arg Val Ser Val Asn Thr Ala Asn Val Thr Leu Gly Pro Gln Leu Met
               195                 200                 205

Glu Val Thr Val Tyr Arg Arg His Gly Arg Ala Tyr Val Pro Ile Ala
               210                 215                 220

Gln Val Lys Asp Val Tyr Val Val Thr Asp Gln Ile Pro Val Phe Val
225                 230                 235                 240

Thr Met Phe Gln Lys Asn Asp Arg Asn Ser Ser Asp Glu Thr Phe Leu
               245                 250                 255

Lys Asp Leu Pro Ile Met Phe Asp Val Leu Ile His Asp Pro Ser His
               260                 265                 270

Phe Leu Asn Tyr Ser Thr Ile Asn Tyr Lys Trp Ser Phe Gly Asp Asn
               275                 280                 285

Thr Gly Leu Phe Val Ser Thr Asn His Thr Val Asn His Thr Tyr Val
               290                 295                 300

Leu Asn Gly Thr Phe Ser Leu Asn Leu Thr Val Lys Ala Ala Ala Pro
305                 310                 315                 320

Gly Pro Cys Pro Pro Pro Pro Pro Arg Pro Ser Lys Pro Thr
               325                 330                 335

Pro Ser Leu Gly Pro Ala Gly Asp Asn Pro Leu Glu Leu Ser Arg Ile
               340                 345                 350

Pro Asp Glu Asn Cys Gln Ile Asn Arg Tyr Gly His Phe Gln Ala Thr
               355                 360                 365
```

```
Ile Thr Ile Val Glu Gly Ile Leu Glu Val Asn Ile Ile Gln Met Thr
    370                 375                 380

Asp Val Leu Met Pro Val Pro Trp Pro Glu Ser Ser Leu Ile Asp Phe
385                 390                 395                 400

Val Val Thr Cys Gln Gly Ser Ile Pro Thr Glu Val Cys Thr Ile Ile
                405                 410                 415

Ser Asp Pro Thr Cys Glu Ile Thr Gln Asn Thr Val Cys Ser Pro Val
            420                 425                 430

Asp Val Asp Glu Met Cys Leu Leu Thr Val Arg Arg Thr Phe Asn Gly
                435                 440                 445

Ser Gly Thr Tyr Cys Val Asn Leu Thr Leu Gly Asp Asp Thr Ser Leu
        450                 455                 460

Ala Leu Thr Ser Thr Leu Ile Ser Val Pro Asp Arg Asp Pro Ala Ser
465                 470                 475                 480

Pro Leu Arg Met Ala Asn Ser Ala Leu Ile Ser Val Gly Cys Leu Ala
                485                 490                 495

Ile Phe Val Thr Val Ile Ser Leu Leu Val Tyr Lys Lys His Lys Glu
                500                 505                 510

Tyr Asn Pro Ile Glu Asn Ser Pro Gly Asn Val Val Arg Ser Lys Gly
            515                 520                 525

Leu Ser Val Phe Leu Asn Arg Ala Lys Ala Val Phe Phe Pro Gly Asn
        530                 535                 540

Gln Glu Lys Asp Pro Leu Leu Lys Asn Gln Glu Phe Lys Gly Val Ser
545                 550                 555                 560

<210> SEQ ID NO 226
<211> LENGTH: 9
<212> TYPE: PRT
<213> ORGANISM: Homo sapien

<400> SEQUENCE: 226

Ile Leu Ile Pro Ala Thr Trp Lys Ala
1               5

<210> SEQ ID NO 227
<211> LENGTH: 9
<212> TYPE: PRT
<213> ORGANISM: Homo sapien

<400> SEQUENCE: 227

Phe Leu Leu Asn Asp Asn Leu Thr Ala
1               5

<210> SEQ ID NO 228
<211> LENGTH: 9
<212> TYPE: PRT
<213> ORGANISM: Homo sapien

<400> SEQUENCE: 228

Leu Leu Gly Asn Cys Leu Pro Thr Val
1               5

<210> SEQ ID NO 229
<211> LENGTH: 10
<212> TYPE: PRT
<213> ORGANISM: Homo sapien

<400> SEQUENCE: 229

Lys Leu Leu Gly Asn Cys Leu Pro Thr Val
1               5                   10
```

<210> SEQ ID NO 230
<211> LENGTH: 10
<212> TYPE: PRT
<213> ORGANISM: Homo sapien

<400> SEQUENCE: 230

Arg Leu Thr Gly Gly Leu Lys Phe Phe Val
 1               5                  10

<210> SEQ ID NO 231
<211> LENGTH: 9
<212> TYPE: PRT
<213> ORGANISM: Homo sapien

<400> SEQUENCE: 231

Ser Leu Gln Ala Leu Lys Val Thr Val
 1               5

<210> SEQ ID NO 232
<211> LENGTH: 20
<212> TYPE: PRT
<213> ORGANISM: Homo sapiens

<400> SEQUENCE: 232

Ala Gly Ala Asp Val Ile Lys Asn Asp Gly Ile Tyr Ser Arg Tyr Phe
                 5                  10                  15

Phe Ser Phe Ala
             20

<210> SEQ ID NO 233
<211> LENGTH: 21
<212> TYPE: PRT
<213> ORGANISM: Homo sapiens

<400> SEQUENCE: 233

Phe Phe Ser Phe Ala Ala Asn Gly Arg Tyr Ser Leu Lys Val His Val
                 5                  10                  15

Asn His Ser Pro Ser
             20

<210> SEQ ID NO 234
<211> LENGTH: 20
<212> TYPE: PRT
<213> ORGANISM: Homo sapiens

<400> SEQUENCE: 234

Phe Leu Val Thr Trp Gln Ala Ser Gly Pro Pro Glu Ile Ile Leu Phe
                 5                  10                  15

Asp Pro Asp Gly
             20

<210> SEQ ID NO 235
<211> LENGTH: 20
<212> TYPE: PRT
<213> ORGANISM: Homo sapiens

<400> SEQUENCE: 235

Leu Gln Ser Ala Val Ser Asn Ile Ala Gln Ala Pro Leu Phe Ile Pro
                 5                  10                  15

Pro Asn Ser Asp
             20

-continued

<210> SEQ ID NO 236
<211> LENGTH: 20
<212> TYPE: PRT
<213> ORGANISM: Homo sapiens

<400> SEQUENCE: 236

Ile Gln Asp Asp Phe Asn Asn Ala Ile Leu Val Asn Thr Ser Lys Arg
                 5                  10                  15

Asn Pro Gln Gln
            20

<210> SEQ ID NO 237
<211> LENGTH: 21
<212> TYPE: PRT
<213> ORGANISM: Homo sapiens

<400> SEQUENCE: 237

Arg Asn Ser Leu Gln Ser Ala Val Ser Asn Ile Ala Gln Ala Pro Leu
                 5                  10                  15

Phe Ile Pro Pro Asn
            20

<210> SEQ ID NO 238
<211> LENGTH: 20
<212> TYPE: PRT
<213> ORGANISM: Homo sapiens

<400> SEQUENCE: 238

Thr His Glu Ser His Arg Ile Tyr Val Ala Ile Arg Ala Met Asp Arg
                 5                  10                  15

Asn Ser Leu Gln
            20

<210> SEQ ID NO 239
<211> LENGTH: 20
<212> TYPE: PRT
<213> ORGANISM: Homo sapiens

<400> SEQUENCE: 239

Arg Asn Pro Gln Gln Ala Gly Ile Arg Glu Ile Phe Thr Phe Ser Pro
                 5                  10                  15

Gln Ile Ser Thr
            20

<210> SEQ ID NO 240
<211> LENGTH: 21
<212> TYPE: PRT
<213> ORGANISM: Homo sapiens

<400> SEQUENCE: 240

Gly Gln Ala Thr Ser Tyr Glu Ile Arg Met Ser Lys Ser Leu Gln Asn
                 5                  10                  15

Ile Gln Asp Asp Phe
            20

<210> SEQ ID NO 241
<211> LENGTH: 20
<212> TYPE: PRT
<213> ORGANISM: Homo sapiens

<400> SEQUENCE: 241

Glu Arg Lys Trp Gly Phe Ser Arg Val Ser Ser Gly Gly Ser Phe Ser

```
                         5                  10                  15

Val Leu Gly Val
            20

<210> SEQ ID NO 242
<211> LENGTH: 20
<212> TYPE: PRT
<213> ORGANISM: Homo sapiens

<400> SEQUENCE: 242

Gly Ser His Ala Met Tyr Val Pro Gly Tyr Thr Ala Asn Gly Asn Ile
                  5                  10                  15

Gln Met Asn Ala
            20

<210> SEQ ID NO 243
<211> LENGTH: 20
<212> TYPE: PRT
<213> ORGANISM: Homo sapiens

<400> SEQUENCE: 243

Val Asn His Ser Pro Ser Ile Ser Thr Pro Ala His Ser Ile Pro Gly
                  5                  10                  15

Ser His Ala Met
            20

<210> SEQ ID NO 244
<211> LENGTH: 20
<212> TYPE: PRT
<213> ORGANISM: Homo sapiens

<400> SEQUENCE: 244

Ala Val Pro Pro Ala Thr Val Glu Ala Phe Val Glu Arg Asp Ser Leu
                  5                  10                  15

His Phe Pro His
            20

<210> SEQ ID NO 245
<211> LENGTH: 20
<212> TYPE: PRT
<213> ORGANISM: Homo sapiens

<400> SEQUENCE: 245

Lys Pro Gly His Trp Thr Tyr Thr Leu Asn Asn Thr His His Ser Leu
                  5                  10                  15

Gln Ala Leu Lys
            20

<210> SEQ ID NO 246
<211> LENGTH: 20
<212> TYPE: PRT
<213> ORGANISM: Homo sapiens

<400> SEQUENCE: 246

Asn Leu Thr Phe Arg Thr Ala Ser Leu Trp Ile Pro Gly Thr Ala Lys
                  5                  10                  15

Pro Gly His Trp
            20

<210> SEQ ID NO 247
<211> LENGTH: 20
<212> TYPE: PRT
```

```
<213> ORGANISM: Homo sapiens

<400> SEQUENCE: 247

Leu His Phe Pro His Pro Val Met Ile Tyr Ala Asn Val Lys Gln Gly
                 5                  10                  15

Phe Tyr Pro Ile
            20

<210> SEQ ID NO 248
<211> LENGTH: 20
<212> TYPE: PRT
<213> ORGANISM: Homo sapiens

<400> SEQUENCE: 248

Pro Glu Thr Gly Asp Pro Val Thr Leu Arg Leu Leu Asp Asp Gly Ala
                 5                  10                  15

Gly Ala Asp Val
            20

<210> SEQ ID NO 249
<211> LENGTH: 20
<212> TYPE: PRT
<213> ORGANISM: Homo sapiens

<400> SEQUENCE: 249

Gly Phe Tyr Pro Ile Leu Asn Ala Thr Val Thr Ala Thr Val Glu Pro
                 5                  10                  15

Glu Thr Gly Asp
            20

<210> SEQ ID NO 250
<211> LENGTH: 20
<212> TYPE: PRT
<213> ORGANISM: Homo sapiens

<400> SEQUENCE: 250

Phe Asp Pro Asp Gly Arg Lys Tyr Tyr Thr Asn Asn Phe Ile Thr Asn
                 5                  10                  15

Leu Thr Phe Arg
            20

<210> SEQ ID NO 251
<211> LENGTH: 20
<212> TYPE: PRT
<213> ORGANISM: Homo sapiens

<400> SEQUENCE: 251

Leu Gln Ala Leu Lys Val Thr Val Thr Ser Arg Ala Ser Asn Ser Ala
                 5                  10                  15

Val Pro Pro Ala
            20

<210> SEQ ID NO 252
<211> LENGTH: 153
<212> TYPE: PRT
<213> ORGANISM: Homo sapien

<400> SEQUENCE: 252

Met Ala Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
                20                  25                  30
```

```
Pro Met Gly Asp Val Pro Met Asp Gly Ile Ser Val Ala Asp Ile Gly
            35                  40                  45

Ala Ala Val Ser Ser Ile Phe Asn Ser Pro Glu Glu Phe Leu Gly Lys
 50                  55                  60

Ala Val Gly Leu Ser Ala Glu Ala Leu Thr Ile Gln Gln Tyr Ala Asp
 65                  70                  75                  80

Val Leu Ser Lys Ala Leu Gly Lys Glu Val Arg Asp Ala Lys Ile Thr
                 85                  90                  95

Pro Glu Ala Phe Glu Lys Leu Gly Phe Pro Ala Ala Lys Glu Ile Ala
                100                 105                 110

Asn Met Cys Arg Phe Tyr Glu Met Lys Pro Asp Arg Asp Val Asn Leu
                115                 120                 125

Thr His Gln Leu Asn Pro Lys Val Lys Ser Phe Ser Gln Phe Ile Ser
130                 135                 140

Glu Asn Gln Gly Ala Phe Lys Gly Met
145                 150

<210> SEQ ID NO 253
<211> LENGTH: 462
<212> TYPE: DNA
<213> ORGANISM: Homo sapien

<400> SEQUENCE: 253
atggccagtg tccgcgtggc ggcctacttt gaaaactttc tcgcggcgtg gcggcccgtg    60
aaagcctctg atggagatta ctacaccttg gctgtaccga tgggagatgt accaatggat   120
ggtatctctg ttgctgatat tggagcagcc gtctctagca ttttttaattc tccagaggaa   180 ttttttaggca aggccgtggg gctcagtgca gaagcactaa caatacagca atatgctgat   240
gttttgtcca aggctttggg gaagaagtc cgagatgcaa agattacccc ggaagctttc   300
gagaagctgg gattccctgc agcaaaggaa atagccaata tgtgtcgttt ctatgaaatg   360
aagccagacc gagatgtcaa tctcacccac caactaaatc ccaaagtcaa agcttcagc   420 cagtttatct cagagaacca gggagccttc aagggcatgt ag                      462

<210> SEQ ID NO 254
<211> LENGTH: 8031
<212> TYPE: DNA
<213> ORGANISM: Homo sapien

<400> SEQUENCE: 254 tgcgaatgg gacgcgccct gtagcggcgc attaagcgcg gcgggtgtgg tggttacgcg     60
cagcgtgacc gctacacttg ccagcgccct agcgcccgct cctttcgctt tcttcccttc   120
ctttctcgcc acgttcgccg gctttccccg tcaagctcta atcgggggc tccctttagg   180 gttccgattt agtgctttac ggcacctcga ccccaaaaaa cttgattagg gtgatggttc   240
acgtagtggg ccatcgccct gatagacggt ttttcgccct tgacgttgg agtccacgtt   300 ctttaatagt ggactcttgt tccaaactgg aacaacactc aaccctatct cggtctattc   360
ttttgattta agggatttt gccgatttc ggcctattgg ttaaaaaatg agctgattta   420
acaaaaattt aacgcgaatt ttaacaaaat attaacgttt acaatttcag gtggcacttt   480
tcggggaaat gtgcgcggaa cccctatttg tttattttttc taaatacatt caaatatgta   540
tccgctcatg aattaattct tagaaaaact catcgagcat caaatgaaac tgcaattttat   600 tcatatcagg attatcaata ccatattttt gaaaaagccg tttctgtaat gaaggagaaa   660
```

-continued

```
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg caacgctac    1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa atcccttaa    1440
cgtgagtttt cgttccactg agcgtcagac cccgtagaaa agatcaaagg atcttcttga   1500
gatcctttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc gaagggaga    1920
aagcggaca ggtatccggt aagcggcagg gtcggaacag gagagcgcac gagggagctt    1980
ccaggggaa acgcctggta tctttatagt cctgtcgggt ttcgccacct ctgacttgag    2040
cgtcgattt tgtgatgctc gtcaggggg cggagcctat ggaaaaacgc cagcaacgcg    2100
gcctttttac ggttcctggc cttttgctgg cctttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
```

-continued

```
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgcggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcagcat caccaccatc accacggagt    5100
acagcttcaa gacaatgggt ataatggatt gctcattgca attaatcctc aggtacctga    5160
gaatcagaac ctcatctcaa acattaagga aatgataact gaagcttcat tttacctatt    5220
taatgctacc aagagaagag tattttttcag aaatataaag attttaatac ctgccacatg    5280
gaaagctaat aataacagca aaataaaaca agaatcatat gaaaaggcaa atgtcatagt    5340
gactgactgg tatgggcac atggagatga tccatacacc ctacaataca gagggtgtgg    5400
```

-continued

| | |
|---|---|
| aaaagaggga aaatacattc atttcacacc taatttccta ctgaatgata acttaacagc | 5460 |
| tggctacgga tcacgaggcc gagtgtttgt ccatgaatgg gcccacctcc gttggggtgt | 5520 |
| gttcgatgag tataacaatg acaaacctttt ctacataaat gggcaaaatc aaattaaagt | 5580 |
| gacaaggtgt tcatctgaca tcacaggcat ttttgtgtgt gaaaaaggtc cttgccccca | 5640 |
| agaaaactgt attattagta agcttttttaa agaaggatgc acctttatct acaatagcac | 5700 |
| ccaaaatgca actgcatcaa taatgttcat gcaaagttta tcttctgtgg ttgaattttg | 5760 |
| taatgcaagt acccacaacc aagaagcacc aaacctacag aaccagatgt gcagcctcag | 5820 |
| aagtgcatgg gatgtaatca cagactctgc tgactttcac cacagctttc ccatgaacgg | 5880 |
| gactgagctt ccacctcctc ccacattctc gcttgtagag gctggtgaca aagtggtctg | 5940 |
| tttagtgctg gatgtgtcca gcaagatggc agaggctgac agactccttc aactacaaca | 6000 |
| agccgcagaa ttttatttga tgcagattgt tgaaattcat accttcgtgg gcattgccag | 6060 |
| tttcgacagc aaaggagaga tcagagccca gctacaccaa attaacagca atgatgatcg | 6120 |
| aaagttgctg gtttcatatc tgcccaccac tgtatcagct aaaacagaca tcagcatttg | 6180 |
| ttcagggctt aagaaaggat ttgaggtggt tgaaaaactg aatggaaaag cttatggctc | 6240 |
| tgtgatgata ttagtgacca gcggagatga taagcttctt ggcaattgct tacccactgt | 6300 |
| gctcagcagt ggttcaacaa ttcactccat tgccctgggt tcatctgcag ccccaaatct | 6360 |
| ggaggaatta tcacgtctta caggaggttt aaagttctttt gttccagata tatcaaactc | 6420 |
| caatagcatg attgatgctt tcagtagaat ttcctctgga actggagaca ttttccagca | 6480 |
| acatattcag cttgaaagta caggtgaaaa tgtcaaacct caccatcaat tgaaaaacac | 6540 |
| agtgactgtg gataatactg tgggcaacga cactatgttt ctagttacgt ggcaggccag | 6600 |
| tggtcctcct gagattatat tatttgatcc tgatggacga aaatactaca caaataattt | 6660 |
| tatcaccaat ctaactttttc ggacagctag tctttggatt ccaggaacag ctaagcctgg | 6720 |
| gcactggact tacaccctga acaataccca tcattctctg caagccctga agtgacagt | 6780 |
| gacctctcgc gcctccaact cagctgtgcc cccagccact gtggaagcct tgtggaaag | 6840 |
| agacagcctc cattttcctc atcctgtgat gatttatgcc aatgtgaaac agggattttta | 6900 |
| tcccattctt aatgccactg tcactgccac agttgagcca gagactggag atcctgttac | 6960 |
| gctgagactc cttgatgatg gagcaggtgc tgatgttata aaaaatgatg gaatttactc | 7020 |
| gaggtatttt ttctcctttg ctgcaaatgg tagatatagc ttgaaagtgc atgtcaatca | 7080 |
| ctctcccagc ataagcaccc cagcccactc tattccaggg agtcatgcta tgtatgtacc | 7140 |
| aggttacaca gcaaacggta atattcagat gaatgctcca aggaaatcag taggcagaaa | 7200 |
| tgaggaggag cgaaagtggg gctttagccg agtcagctca ggaggctcct tttcagtgct | 7260 |
| gggagttcca gctggccccc accctgatgt gtttccacca tgcaaaatta ttgacctgga | 7320 |
| agctgtaaaa gtagaagagg aattgaccct atcttggaca gcacctggag aagactttga | 7380 |
| tcagggccag gctacaagct atgaaataag aatgagtaaa agtctacaga atatccaaga | 7440 |
| tgactttaac aatgctattt tagtaaatac atcaaagcga aatcctcagc aagctggcat | 7500 |
| cagggagata tttacgttct caccccaaat ttccacgaat ggacctgaac atcagccaaa | 7560 |
| tggagaaaca catgaaagcc acagaattta tgttgcaata cgagcaatgg ataggaactc | 7620 |
| cttacagtct gctgtatcta acattgccca ggcgcctctg tttattcccc ccaattctga | 7680 |
| tcctgtacct gccagagatt atcttatatt gaaaggagtt ttaacagcaa tgggtttgat | 7740 |
| aggaatcatt tgccttatta tagttgtgac acatcatact ttaagcagga aaaagagagc | 7800 |

| | |
|---|---:|
| agacaagaaa gagaatggaa caaaattatt ataatgaatt ctgcagatat ccatcacact | 7860 |
| ggcggccgct cgagcaccac caccaccacc actgagatcc ggctgctaac aaagcccgaa | 7920 |
| aggaagctga gttggctgct gccaccgctg agcaataact agcataaccc cttggggcct | 7980 |
| ctaaacgggt cttgagggt tttttgctga aggaggaac tatatccgga t | 8031 |

<210> SEQ ID NO 255
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 255

| | |
|---|---:|
| gtggccagng actagaaggc gaggcgccgc gggaccatgg cggcggcggc ggacgagcgg | 60 |
| agtccanagg acggagaaga cgaggaagag gaggagcagt tggttctggt ggaattatca | 120 |
| ggaattattg attcagactt cctctcaaaa tgtgaaaata aatgcaaggt tttgggcatt | 180 |
| gacactgaga ggcccattct gcaagtggac agctgtgtct ttgctgggga gtatgaagac | 240 |
| actctangga cctgtgttat atttgaagaa atgntnaac atgctgatac agaaggcaat | 300 |
| aataaaacag tgctaaaata taaatgccat acaatgaaga agctcagcat gacaagaact | 360 |
| ctcctgacag agaagaagga aggagaagaa aacatangtg g | 401 |

<210> SEQ ID NO 256
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 256

| | |
|---|---:|
| tggtggncct gggatgggga accgcggtgg cttccgngga ggtttcggca ntggcatccg | 60 |
| gggccggggt cgcggccgng acgggggccg gggccnangc cgnnganctc gcggangcaa | 120 |
| ggccgaggat aaggagtgga tgcccgtcac caacttgggc cgcttgncca aggacatgaa | 180 |
| nancaagccc ctgnaggaga tctatntctt cttccctgcc ccattaagga atcaagagat | 240 |
| catttgattt cttcctgggg gcctctctca aggatnaggt ttttgaagat tatgccagtg | 300 |
| canaaannan accccgttgc ccngtccatc tncacccaac ncttccaagg gcnatttttg | 360 |
| tttaggcctc attncngggg ggaaccttaa cccaatttgg g | 401 |

<210> SEQ ID NO 257
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 257

| | |
|---|---:|
| atgtatgtaa aacacttcat aaaatgtaaa gggctataac aaatatgtta taaagtgatt | 60 |
| ctctcagccc tgaggtatac agaatcattt gcctcagact gctgttggat tttaaaattt | 120 |
| ttaaaatatc tgctaagtaa tttgctatgt cttctcccac actatcaata tgcctgcttc | 180 |

| | |
|---|---:|
| taacaggctc cccactttct tttaatgtgc tgttatgagc tttggacatg agataaccgt | 240 |
| gcctgttcag agtgtctaca gtaagagctg acaaactct ggagggacac agtctttgag | 300 |
| acagctcttt tggttgcttt ccacttttct gaaaggttca cagtaacctt ctagataata | 360 |
| gaaactccca gttaaagcct angctancaa ttttttttag t | 401 |

<210> SEQ ID NO 258
<211> LENGTH: 401
<212> TYPE: DNA
<213> ORGANISM: Homo sapien

<400> SEQUENCE: 258

| | |
|---|---:|
| ggagcgctag gtcggtgtac gaccgagatt agggtgcgtg ccagctccgg gaggccgcgg | 60 |
| tgagggccg ggcccaagct gccgacccga gccgatcgtc agggtcgcca gcgcctcagc | 120 |
| tctgtggagg agcagcagta gtcggagggt gcaggatatt agaaatggct actcccagt | 180 |
| caattttcat ctttgcaatc tgcattttaa tgataacaga attaattctg gcctcaaaaa | 240 |
| gctactatga tatcttaggt gtgccaaaat cggcatcaga gcgccaaatc aagaaggcct | 300 |
| ttcacaagtt ggccatgaag taccaccctg acaaaaataa gacccagatg ctgaagcaaa | 360 |
| attcagagag attgcagaag catatgaaac actctcagat g | 401 |

<210> SEQ ID NO 259
<211> LENGTH: 401
<212> TYPE: DNA
<213> ORGANISM: Homo sapien

<400> SEQUENCE: 259

| | |
|---|---:|
| attgggtttg gagggaggat gatgacagag gaatgcccct tggccatcac ggttttgatt | 60 |
| ctccagaata ttgtgggttt gatcatcaat gcagtcatgt taggctgcat tttcatgaaa | 120 |
| acagctcagg ctcacagaag ggcagaaact ttgattttca gccgccatgc tgtgattgcc | 180 |
| gtccgaaatg gcaagctgtg cttcatgttc cgagtgggtg acctgaggaa aagcatgatc | 240 |
| attagtgcct ctgtgcgcat ccaggtggtc aagaaaacaa ctacacctga ggggaggtg | 300 |
| gttcctattc accaactgga cattcctgtt gataacccaa tcgagagcaa taacattttt | 360 |
| ctggtggccc ctttgatcat ctgccacgtg attgacaagc g | 401 |

<210> SEQ ID NO 260
<211> LENGTH: 363
<212> TYPE: DNA
<213> ORGANISM: Homo sapien
<220> FEATURE:
<221> NAME/KEY: misc_feature
<222> LOCATION: (1)...(363)
<223> OTHER INFORMATION: n = A,T,C or G

<400> SEQUENCE: 260

| | |
|---|---:|
| aggaganang gaggggana tgaataggga tggagaggga natagtggat gagcagggca | 60 |
| canggagagg aancagaaag gagaggcaag acagggagac acacancaca nangangana | 120 |
| caggtggggg ctgggtggg gcatggagag cctttnangt cnccaggcc accctgctct | 180 |
| cgctggnctg ttgaaaccca ctccatggct tcctgccact gcagttgggc ccagggctgg | 240 |
| cttattnctg gaatgcaagt ggctgtggct tggagcctcc cctctggnnn anggaaannn | 300 |
| attgctccct tatctgcttg gaatatctga gttttccan cccggaaata aaacacacac | 360 |
| aca | 363 |

<210> SEQ ID NO 261
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 261

| | | | | | |
|---|---|---|---|---|---|
| cggctctccg | ccgctctccc | ggggtttcgg | ggcacttggg | tcccacagtc | tggtcctgct | 60 |
| tcaccttccc | ctgacctgag | tagtcgccat | ggcacaggtt | ctcagaggca | ctgngactga | 120 |
| cttccctgga | tttgatgagc | gggctgatgc | anaaactctt | cggaaggcta | tgaaaggctt | 180 |
| gggcacagat | gaggagagca | tcctgactct | gttgacatcc | cgaagtaatg | ctcagcgcca | 240 |
| ggaaatctct | gcagctttta | agactctgtt | tggcagggat | cttctggatg | acctgaaatc | 300 |
| agaactaact | ggaaaatttg | aaaaattaat | tgtggctctg | atgaaaccct | ctcggcttta | 360 |
| tgatgcttat | gaactgaaac | atgccttgaa | gggagctgga | a | | 401 |

<210> SEQ ID NO 262
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 262

| | | | | | |
|---|---|---|---|---|---|
| agtctanaac | atttctaata | ttttgngctt | tcatatatca | aaggagatta | tgtgaaacta | 60 |
| tttttaaata | ctgtaaagtg | acatatagtt | ataagatata | tttctgtaca | gtagagaaag | 120 |
| agtttataac | atgaagaata | ttgtaccatt | atacattttc | attctcgatc | tcataagaaa | 180 |
| ttcaaaagaa | taatgataga | ggtgaaaata | tgtttacttt | ctctaaatca | agcctagttg | 240 |
| tcaactcaaa | aattatgntg | catagtttta | ttttgaattt | aggttttggg | actacttttt | 300 |
| tccancttca | atgagaaaat | aaaatctaca | actcaggagt | tactacagaa | gttctaanta | 360 |
| tttttttgct | aannagcnaa | aaatataaac | atatgaaaat | g | | 401 |

<210> SEQ ID NO 263
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 263

| | | | | | |
|---|---|---|---|---|---|
| ctgtccgacc | aagagaggcc | ggccgagccc | gaggcttggg | cttttgcttt | ctggcggagg | 60 |
| gatctgcggc | ggtttaggag | gcggcgctga | tcctgggagg | aagaggcagc | tacggcggcg | 120 |
| gcggcggtgg | cggctagggc | ggcggcgaat | aaaggggccg | ccgccgggtg | atgcggtgac | 180 |
| cactgcggca | ggcccaggag | ctgagtgggc | cccggccctc | agcccgtccc | gncggacccg | 240 |
| ctttcctcaa | ctctccatct | tctcctgccg | accgagatcg | ccgaggcggn | ctcaggctcc | 300 |
| ctancccctt | ccccgtccct | tccccncccc | cgtcccgcc | ccggggccg | ccgccacccg | 360 |
| cctcccacca | tggctctgaa | ganaatccac | aaggaattga | a | | 401 |

<210> SEQ ID NO 264

<211> LENGTH: 401
<212> TYPE: DNA
<213> ORGANISM: Homo sapien

<400> SEQUENCE: 264

```
aacaccagcc actccaggac ccctgaaggc ctctaccagg tcaccagtgt tctgcgccta      60
aagccacccc ctggcagaaa cttcagctgt gtgttctgga atactcacgt gagggaactt     120
actttggcca gcattgacct tcaaagtcag atggaaccca ggacccatcc aacttggctg     180
cttcacattt tcatcccctc ctgcatcatt gctttcattt tcatagccac agtgatagcc     240
ctaagaaaac aactctgtca aaagctgtat tcttcaaaag acacaacaaa agacctgtc      300
accacaacaa agagggaagt gaacagtgct gtgaatctga acctgtggtc ttgggagcca     360
gggtgacctg atatgacatc taaagaagct tctggactct g                          401
```

<210> SEQ ID NO 265
<211> LENGTH: 271
<212> TYPE: DNA
<213> ORGANISM: Homo sapien
<220> FEATURE:
<221> NAME/KEY: misc_feature
<222> LOCATION: (1)...(271)
<223> OTHER INFORMATION: n = A,T,C or G

<400> SEQUENCE: 265

```
gccacttcct gtggacatgg gcagagcgct gctgccagtt cctggtagcc ttgaccacna      60
cgctgggggg tctttgtgat ggtcatgggt ctcatttgca cttgggggtg tgggattcaa     120
gttagaagtt tctagatctg gccgggcgca gtggctcaca cctgtaatcc cagcacttta    180
ggaggctgag gcaggcggat catgaggtca ggagatcgag accgtcctgg ctaacacagt     240
gaaacccccgt ctctactaaa aatacaaaaa a                                    271
```

<210> SEQ ID NO 266
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 266

```
attcataaat ttagctgaaa gatactgatt caatttgtat acagngaata taaatgagac      60
gacagcaaaa ttttcatgaa atgtaaaata tttttatagt ttgttcatac tatatgaggt     120
tctatttttaa atgactttct ggattttaaa aaatttcttt aaatacaatc attttttgtaa    180
tatttatttt atgcttatga tctagataat tgcagaatat cattttatct gactctgtct     240
tcataagaga gctgtggccg aatttttgaac atctgttata gggagtgatc aaattagaag    300
gcaatgtgga aaaacaattc tgggaaagat ttctttatat gaagtccctg ccactagcca    360
gccatcctaa ttgatgaaag ttatctgttc acaggcctgc a                          401
```

<210> SEQ ID NO 267
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 267

```
gaagaggcat cacctgatcc cggagacctt tggagttaag aggcggcgga agcgagggcc     60
tgtggagtcg gatcctcttc ggggtgagcc agggtcggcg cgcgcggctg tctcanaact    120
catgcagctg ttcccgcgag gcctgtttga ggacgcgctg ccgcccatcg tgctgaggag    180
ccaggtgtac agccttgtgc ctgacaggac cgtggccgac cggcagctga aggagcttca    240
agagcanggg gagacaaaat cgtccagctg ggcttcnact tggatgccca tggaanttat    300
tctttcnctt ganggactta cnnggaccc aagaancct tncaaggggc ccttngtgga      360
tgggncccga aaccccnnta tttgcccttg gggggncca a                         401
```

<210> SEQ ID NO 268
<211> LENGTH: 223
<212> TYPE: DNA
<213> ORGANISM: Homo sapien

<400> SEQUENCE: 268

```
tcgccatgtt ggccaggctg gtcttgaact cctgacttta agtgatccac ccgcctcaac     60
ctcccaaagt gctgggatta caggtgtgag ccaccgcgcc tggcctgata catacttttta   120 gaatcaagta gtcacgcact ttttctgttc atttttctaa aaagtaaata tacaaatgtt    180 ttgtttttg tttttttgt ttgtttgttt ctgttttttt ttt                        223
```

<210> SEQ ID NO 269
<211> LENGTH: 401
<212> TYPE: DNA
<213> ORGANISM: Homo sapien

<400> SEQUENCE: 269

```
actatgtaaa ccacattgta cttttttta ctttggcaac aaatatttat acatacaaga     60
tgctagttca tttgaatatt tctcccaact tatccaagga tctccagctc taacaaaatg    120 gtttatttt atttaaatgt caatagttgt tttttaaaat ccaaatcaga ggtgcaggcc    180
accagttaaa tgccgtctat caggttttgt gccttaagag actacagagt caaagctcat    240
ttttaaagga gtaggacaaa gttgtcacag gtttttgttg ttgtttttat tgcccccaaa   300
attacatgtt aatttccatt tatatcaggg attctatta cttgaagact gtgaagttgc     360
cattttgtct cattgttttc tttgacataa ctaggatcca t                        401
```

<210> SEQ ID NO 270
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 270

```
tggctgttga ttcacctcag cactgcttgg tatctgcacc ctacctctct ttagaggctg     60
ccttgtcaac tgaaaaatgc acctgacttc gagcaagact ctttccttag gttctggatc    120
tgtttgagcc ccatggcact gagctggaat ctgagggtct tgttccaagg atgtgatgat    180
gtgggagaat gttcttttgaa agagcagaaa tccagtctgc atggaaacag cctgtagagn   240
agaagtttcc agtgataagt gttcactgtt ctaaggaggt acaccacagc tacctgaatt    300
ttcccaaaat gagtgcttct gtgcgttaca actggccttt gtacttgact gtgatgactt    360 tgtttttct tttcaattct anatgaacat gggaaaaaat g                         401
```

<210> SEQ ID NO 271
<211> LENGTH: 329
<212> TYPE: DNA
<213> ORGANISM: Homo sapien

<400> SEQUENCE: 271

| | | | | | |
|---|---|---|---|---|---|
| ccacagcctc | caagtcaggt | ggggtggagt | cccagagctg | cacagggttt | ggcccaagtt | 60 |
| tctaagggag | gcacttcctc | ccctcgccca | tcagtgccag | ccctgctgg | ctggtgcctg | 120 |
| agccctcag | acagcccct | gccccgcagg | cctgccttct | cagggacttc | tgcggggcct | 180 |
| gaggcaagcc | atggagtgag | acccaggagc | cggacacttc | tcaggaaatg | gcttttccca | 240 |
| acccccagcc | cccacccggt | ggttcttcct | gttctgtgac | tgtgtatagt | gccaccacag | 300 |
| cttatggcat | ctcattgagg | acaaaaaaa | | | | 329 |

<210> SEQ ID NO 272
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 272

| | | | | | |
|---|---|---|---|---|---|
| nggctgntaa | cntcggaggt | nacttcctgg | actatcctgg | agacccctc | cgcttccacg | 60 |
| nncatnatat | cnctcatngc | tgggcccntn | angacacnat | cccactccaa | cacctgngng | 120 |
| atgctggncn | cctnggaacc | ancntcagaa | ngaccctgnt | cntntgtnnt | ccgcaanctg | 180 |
| aagnnaangc | gggntacacc | tncntgcant | ggnccacnct | gcngggaact | ntacacacct | 240 |
| acgggatgtg | gctgcgccan | gagccaagag | cntttctgga | tgattcccca | gcctcttgnn | 300 |
| agggantcta | caacattgct | nnntaccttt | ntccnncngc | nnntnnttgga | ntacaggngn | 360 |
| tnntaacact | acatctttt | tactgcnccn | tncttggtgg | g | | 401 |

<210> SEQ ID NO 273
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 273

| | | | | | |
|---|---|---|---|---|---|
| cagcaccatg | aagatcaaga | tcatcgcacc | cccagagcgc | aagtactcgg | tgtggatcgg | 60 |
| tggctccatc | ctggcctcac | tgtccacctt | ccagcagatg | tggattagca | agcaggagta | 120 |
| cgacgagtcg | ggcccctcca | tcgtccaccg | caaatgcttc | taaacggact | cagcagatgc | 180 |
| gtagcatttg | ctgcatgggt | taattgagaa | tagaaatttg | ccctggcaa | atgcacacac | 240 |
| ctcatgctag | cctcacgaaa | ctggaataag | ccttcgaaaa | gaaattgtcc | ttgaagcttg | 300 |
| tatctgatat | cagcactgga | ttgtagaact | tgttgctgat | tttgaccttg | tattgaagtt | 360 |
| aactgttccc | cttggtatta | acgtgtcagg | gctgagtgnt | c | | 401 |

<210> SEQ ID NO 274
<211> LENGTH: 401
<212> TYPE: DNA
<213> ORGANISM: Homo sapien

<400> SEQUENCE: 274

```
ccacccacac ccaccgcgcc ctcgttcgcc tcttctccgg gagccagtcc gcgccaccgc      60
cgccgcccag gccatcgcca ccctccgcag ccatgtccac caggtccgtg tcctcgtcct     120
cctaccgcag gatgttcggc ggcccgggca ccgcgagccg gccgagctcc agccggagct     180
acgtgactac gtccacccgc acctacagcc tgggcagcgc gctgcgcccc agcaccagcc     240
gcagcctcta cgcctcgtcc ccgggcggcg tgtatgccac gcgctcctct gccgtgcgcc     300
tgcggagcag cgtgcccggg gtgcggctcc tgcaggactc ggtggacttc tcgctggccg     360
acgccatcaa caccgagttc aagaacaccc gcaccaacga g                        401

<210> SEQ ID NO 275
<211> LENGTH: 401
<212> TYPE: DNA
<213> ORGANISM: Homo sapien

<400> SEQUENCE: 275
ccacttccac cactttgtgg agcagtgcct tcagcgcaac ccggatgcca ggtatccctg      60
ctggcctggg cctgggcttc gggagagcag agggtgctca ggagggtaag gccagggtgt     120
gaagggactt acctcccaaa ggttctgcag gggaatctgg agctacacac aggagggatc     180
agctcctggg tgtgtcagag gccagcctgg ggagctctgg ccactgcttc ccatgagctg     240
agggagaggg agagggggacc cgaggctgag gcataagtgg caggatttcg ggaagctggg     300
gacacggcag tgatgctgcg gtctctcctc ccctttccct ccaggcccag tgccagcacc     360
ctcctgaacc actctttctt caagcagatc aagcgacgtg c                        401

<210> SEQ ID NO 276
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 276
tctgatattg ntaccettga gccacctaag ttagaagaaa ttggaaatca agaagttgtc      60
attgttgaag aagcacagag ttcagaagac tttaacatgg gctcttcctc tagcagccag     120
tatactttct gtcagccaga aactgtattt tcatctcagc ctagtgatga tgaatcaagt     180
agtgatgaaa ccagtaatca gcccagtcct gcctttagac gacgccgtgc taggaagaag     240
accgtttctg cttcagaatc tgaagaccgg ctagttggtg aacaagaaac tgaaccttct     300
aaggagttga gtaaacgtca gttcagtagt ggtctcaata agtgtgttat acttgctttg     360
gtgattgcaa tcagcatggg atttggccat ttctatggca c                        401

<210> SEQ ID NO 277
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 277
aactttggca acatatctca gcaaaaacta cagctatgtt attcatgcca aaataaaagc      60
tgtgcagagg agtggctgca atgaggtcac aacggtggtg gatgtaaaag agatcttcaa     120
```

| | |
|---|---|
| gtcctcatca cccatccctc gaactcaagt cccgctcatt acaaattctt cttgccagtg | 180 |
| tccacacatc ctgccccatc aagatgttct catcatgtgt tacgagnggc gctcaaggat | 240 |
| gatgcttctt gaaaattgct tagttgaaaa atggagagat cagcttagta aaagatccat | 300 |
| acagtgggaa gagaggctgc aggaacagcg ganaacagtt caggacaaga agaaaacagc | 360 |
| cgggcgcacc agtcgtagta atcccccaa accaaaggga a | 401 |

<210> SEQ ID NO 278
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 278

| | |
|---|---|
| aatgagtgtg agaccacaaa tgaatgccgg gaggatgaaa tgtgttggaa ttatcatggc | 60 |
| ggcttccgtt gttatccacg aaatccttgt caagatccct acattctaac accagagaac | 120 |
| cgatgtgttt gcccagtctc aaatgccatg tgccgagaac tgccccagtc aatagtctac | 180 |
| aaatacatga gcatccgatc tgataggtct gtgccatcag acatcttcca gatacaggcc | 240 |
| acaactattt atgccaacac catcaatact tttcggatta aatctggaaa tgaaaatgga | 300 |
| gagtctacct acgacaacaa anccctgtaa gtgcaatgct tgtgctcgtg aagncattat | 360 |
| caggaccaag agaacatatc gtggacctgg agatgctgac a | 401 |

<210> SEQ ID NO 279
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 279

| | |
|---|---|
| aaattattgc ctctgataca tacctaagtn aacanaacat taatacctaa gtaaacataa | 60 |
| cattacttgg agggttgcag nttctaantg aaactgtatt tgaaactttt aagtatactt | 120 |
| taggaaacaa gcatgaacgg cagtctagaa taccagaaac atctacttgg gtagcttggn | 180 |
| gccattatcc tgtggaatct gatatgtctg gnagcatgtc attgatggga catgaagaca | 240 |
| tctttggaaa tgatgagatt atttcctgtg ttaaaaaaaa aaaaaatctt aaattcctac | 300 |
| aatgtgaaac tgaaactaat aattttgatc ctgatgtatg ggacagcgta tctgtaccag | 360 |
| gctctaaata acaaaagnta gggngacaag nacatgttcc t | 401 |

<210> SEQ ID NO 280
<211> LENGTH: 326
<212> TYPE: DNA
<213> ORGANISM: Homo sapien

<400> SEQUENCE: 280

| | |
|---|---|
| gaagtggaat tgtataattc aattcgataa ttgatctcat gggctttccc tggaggaaag | 60 |
| gttttttttg ttgttttttt tttaagaact tgaaacttgt aaactgagat gtctgtagct | 120 |
| tttttgccca tctgtagtgt atgtgaagat ttcaaaacct gagagcactt tttcttttgtt | 180 |
| tagaattatg agaaaggcac tagatgactt taggatttgc attttttccct ttattgcctc | 240 |
| atttcttgtg acgccttgtt ggggagggaa atctgtttat ttttttcctac aaataaaaag | 300 | ctaagattct atatcgcaaa aaaaaa 326

<210> SEQ ID NO 281
<211> LENGTH: 374
<212> TYPE: DNA
<213> ORGANISM: Homo sapien

<400> SEQUENCE: 281

```
caacgcgttt gcaaatattc ccctggtagc ctacttcctt accccgaat attggtaaga      60
tcgagcaatg gcttcaggac atgggttctc ttctcctgtg atcattcaag tgctcactgc    120
atgaagactg gcttgtctca gtgtttcaac ctcaccaggg ctgtctcttg gtccacacct   180
cgctccctgt tagtgccgta tgacagcccc catcaaatga ccttggccaa gtcacggttt   240
ctctgtggtc aaggttggtt ggctgattgg tggaaagtag ggtggaccaa aggaggccac   300
gtgagcagtc agcaccagtt ctgcaccagc agcgcctccg tcctagtggg tgttcctgtt   360
tctcctggcc ctgg                                                    374
```

<210> SEQ ID NO 282
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 282

```
agtgtggtgg aattcccgca tcctanncgc cgactcacac aaggcagagt ngccatggag     60
aaaattccag tgtcagcatt cttgctcctt gtggccctct cctacactct ggccagagat   120
accacagtca aacctgnagc caaaaaggac acaaaggact ctcgacccaa actgccccan   180
accctctcca gaggttgggg tgaccaactc atctggactc anacatatga agaagctcta   240
tataaatcca agacaagcaa caaacccttg atgattattc atcacttgga tgagtgccca   300
cacagtcaag ctttaaagaa agtgtttgct gaaaataaag aaatccagaa attggcagag   360
cagtttgtcc tcctcaatct ggtttatgaa acaactgaca aaca                   404
```

<210> SEQ ID NO 283
<211> LENGTH: 184
<212> TYPE: DNA
<213> ORGANISM: Homo sapien
<220> FEATURE:
<221> NAME/KEY: misc_feature
<222> LOCATION: (1)...(184)
<223> OTHER INFORMATION: n = A,T,C or G

<400> SEQUENCE: 283

```
agtgtggtgg aattcacttg cttaanttgt gggcaaaaga gaaaagaag gattgatcag      60
agcattgtgc aatacagttt cattaactcc ttccctcgct cccccaaaaa tttgaatttt   120
tttttcaaca ctcttacacc tgttatggaa aatgtcaacc tttgtaagaa aaccaaaata   180
aaaa                                                                184
```

<210> SEQ ID NO 284
<211> LENGTH: 421
<212> TYPE: DNA
<213> ORGANISM: Homo sapien
<220> FEATURE:
<221> NAME/KEY: misc_feature
<222> LOCATION: (1)...(421)

<223> OTHER INFORMATION: n = A,T,C or G

<400> SEQUENCE: 284

```
ctattaatcc tgccacaata tttttaatta cgtacaaaga tctgacatgt cacccaggga    60
cccatttcac ccactgctct gtttggccgc cagtcttttg tctctctctt cagcaatggt   120
gaggcggata ccctttcctc ggggaanana aatccatgtt ttgttgccct tgccaataac   180
aaaaatgttg gaaagtcgag tggcaaagct gttgccattg gcatctttca cgtgaaccac   240
gtcaaaagat ccagggtgcc tctctctgtt ggtgatcaca ccaattcttc ctaggttagc   300
acctccagtc accatacaca ggttaccagt gtcgaacttg atgaaatcag taatcttgcc   360
agtctctaaa tcaatctgaa tggtatcatt caccttgatg aggggatcgg ggtagcggat   420
g                                                                    421
```

<210> SEQ ID NO 285
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 285

```
ctgggtggta actctttatt tcattgtccg gaanaaagat gggagtggga acaggtgga    60
cactgtgcag gcttcagctt ccactccggg caggattcag gctatctggg accgcaggga   120
ctgccaggtg cacagccctg gctcccgagg caggcaggca aggtgacggg actggaagcc   180
cttttcanag ccttggagga gctggtccgt ccacaagcaa tgagtgccac tctgcagttt   240
gcagggatg gataaacagg gaaacactgt gcattcctca cagccaacag tgtaggtctt   300
ggtgaagccc cggcgctgag ctaagctcag gctgttccag ggagccacga aactgcaggt   360
a                                                                    361
```

<210> SEQ ID NO 286
<211> LENGTH: 336
<212> TYPE: DNA
<213> ORGANISM: Homo sapien
<220> FEATURE:
<221> NAME/KEY: misc_feature
<222> LOCATION: (1)...(336)
<223> OTHER INFORMATION: n = A,T,C or G

<400> SEQUENCE: 286

```
tttgagtggc agcgccttta tttgtggggg ccttcaaggn agggtcgtgg ggggcagcgg    60
ggaggaanag ccganaaact gtgtgaccgg ggcctcaggt ggtgggcatt ggggctcct   120
cttgcanatg cccattggca tcaccggtgc agccattggt ggcagcgggt accggtcctt   180
tcttgttcaa catagggtag gtggcagcca cgggtccaac tcgcttgagg ctgggccctg   240
ggcgctccat tttgtgttcc angagcatgt ggttctgtgg cgggagcccc acgcaggccc   300
tgaggatgtt ctcgatgcag ctgcgctggc ggaaaa                              336
```

<210> SEQ ID NO 287
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 287

```
tgggtaccaa atttntttat ttgaaggaat ggnacaaatc aaanaactta agnggatgtt      60
ttggtacaac ttatanaaaa ggnaaaggaa accccaacat gcatgcnctg ccttggngac     120
cagggaagtc accccacggc tatggggaaa ttancccgag gcttancttt cattatcact     180
gtctcccagg gngngcttgt caaaaanata ttccnccaag ccaaattcgg gcgctcccat     240
nttgcncaag ttggtcacgt ggtcacccaa ttctttgatg gctttcacct gctcattcag     300
g                                                                    301
```

<210> SEQ ID NO 288
<211> LENGTH: 358
<212> TYPE: DNA
<213> ORGANISM: Homo sapien
<220> FEATURE:
<221> NAME/KEY: misc_feature
<222> LOCATION: (1)...(358)
<223> OTHER INFORMATION: n = A,T,C or G

<400> SEQUENCE: 288

```
aagtttttaa acttttatt tgcatattaa aaaaattgng cattccaata attaaaatca      60
tttgaacaaa aaaaaaaatg gcactctgat taaactgcat tacagcctgc aggacacctt    120
gggccagctt ggttttactc tanatttcac tgtcgtccca ccccacttct tccacccac     180
ttcttccttc accaacatgc aagttctttc cttccctgcc agccanatag atagacagat    240
gggaaaggca ggcgcggcct tcgttgtcag tagttctttg atgtgaaagg ggcagcacag    300
tcatttaaac ttgatccaac ctctttgcat cttacaaagt taaacagcta aagaagt       358
```

<210> SEQ ID NO 289
<211> LENGTH: 462
<212> TYPE: DNA
<213> ORGANISM: Homo sapien
<220> FEATURE:
<221> NAME/KEY: misc_feature
<222> LOCATION: (1)...(462)
<223> OTHER INFORMATION: n = A,T,C or G

<400> SEQUENCE: 289

```
ggcatcagaa atgctgttta tttctctgct gctcccaagc tggctggcct ttgcagagga     60
gcagacaaca gatgcatagt tggggananaaa gggaggacag gttccaggat agagggtgca  120
ggctgaggga ggaagggtaa naggaaggaa ggccatcctg gatccccaca tttcagtctc    180
anatgaggac aaagggactc ccaagccccc aaatcatcan aaaacaccaa ggagcaggag    240
gagcttgagc aggcccagg gagcctcana gccataccag ccactgtcta cttcccatcc     300
tcctctccca ttccctgtct gcttcanacc acctcccagc taagccccag ctccattccc    360
ccaatcctgg cccttgccag cttgacagtc acagtgcctg gaattccacc actgaggctt    420
ctcccagttg gattaggacg tcgccctgtt agcatgctgc cc                       462
```

<210> SEQ ID NO 290
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 290

```
tactttccta aactttatta aagaaaaaag caataagcaa tggnggtaaa tctctanaac      60
atacccaatt ttctgggctt cctccccga gaatgtgaca ttttgatttc caaacatgcc     120
anaagtgtat ggttcccaac tgtactaaag taggtganaa gctgaagtcc tcaagtgttc    180
atcttccaac ttttcccagt ctgtggtctg tctttggatc agcaataatt gcctgaacag    240
ctactatggc ttcgttgatt tttgtctgta gctctctgag ctcctctatg tgcagcaatc    300
gcanaatttg agcagcttca ttaanaactg catctcctgt gtcaaaacca anaatatgtt    360
tgtctaaagc aacaggtaag ccctcttttg tttgatttgc cttancaact gcatcctgtg    420
tcaggcgctc ctgaaccaaa atccgaattg ccttaagcat taccaggtaa tcatcatgac    480
g                                                                    481
```

<210> SEQ ID NO 291
<211> LENGTH: 381
<212> TYPE: DNA
<213> ORGANISM: Homo sapien
<220> FEATURE:
<221> NAME/KEY: misc_feature
<222> LOCATION: (1)...(381)
<223> OTHER INFORMATION: n = A,T,C or G

<400> SEQUENCE: 291

```
tcatagtaat gtaaaaccat ttgtttaatt ctaaatcaaa tcactttcac aacagtgaaa     60
attagtgact ggttaaggng tgccactgta catatcatca ttttctgact ggggtcagga    120
cctggtccta gtccacaagg gtggcaggag gagggtggag gctaanaaca cagaaaacac    180
acaaaanaaa ggaaagctgc cttggcanaa ggatgaggng gtgagcttgc cgaaggatgg    240
tgggaagggg gctccctgtt ggggccgagc caggagtccc aagtcagctc tcctgcctta    300
cttagctcct ggcanagggt gagtggggac ctacgaggtt caaaatcaaa tggcatttgg    360
ccagcctggc tttactaaca g                                              381
```

<210> SEQ ID NO 292
<211> LENGTH: 371
<212> TYPE: DNA
<213> ORGANISM: Homo sapien
<220> FEATURE:
<221> NAME/KEY: misc_feature
<222> LOCATION: (1)...(371)
<223> OTHER INFORMATION: n = A,T,C or G

<400> SEQUENCE: 292

```
gaaaaaataa tccgtttaat tgaaaaacct gnaggatact attccactcc cccanatgag     60
gaggctgagg anaccaaacc cctacatcac ctcgtagcca cttctgatac tcttcacgag    120
gcagcaggca aagacaattc ccaaaacctc nacaaaagca attccaaggg ctgctgcagc    180
taccaccanc catttttcc tcagccagcc cccaatcttc tccacacagc cctccttatg     240
gatcgccttc tcgttgaaat taatcccaca gcccacagta acattaatgc ancaggagtc    300
ggggactcgg ttcttcgaca tggaagggat tttctcccaa tctgtgtagt tagcagcccc    360
acagcactta a                                                         371
```

<210> SEQ ID NO 293
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 293

| gatttaaaag aaaacacttt attgttcagc aattaaaagt tagccaaata tgtattttc | 60 |
| tccataattt attgngatgt tatcaacatc aagtaaaatg ctcattttca tcatttgctt | 120 |
| ctgttcatgt tttcttgaac acgtcttcaa ttttccttcc aaaatgctgc atgccacact | 180 |
| tgaggtaacg aagcanaagt attttaaac atgacagcta anaacattca tctacagcaa | 240 |
| cctatatgct caatacatgc cgcgtgatcc tagtagtttt ttcacaacct tctacaagtt | 300 |
| tttggaaaac atctgttatg atgactttca tacaccttca cctcaaaggc tttcttgcac | 360 |
| c | 361 |

<210> SEQ ID NO 294
<211> LENGTH: 391
<212> TYPE: DNA
<213> ORGANISM: Homo sapien
<220> FEATURE:
<221> NAME/KEY: misc_feature
<222> LOCATION: (1)...(391)
<223> OTHER INFORMATION: n = A,T,C or G

<400> SEQUENCE: 294

| tattttaaag tttaattatg attcanaaaa aatcgagcga ataactttct ctgaaaaaat | 60 |
| atattgactc tgtatanacc acagttattg ggganaagg gctggtaggt taaattatcc | 120 |
| tatttttat tctgaaaatg atattaatan aaagtcccgt ttccagtctg attataaaga | 180 |
| tacatatgcc caaatggct ganaataaat acaacaggaa atgcaaaagc tgtaaagcta | 240 |
| agggcatgca ananaaaatc tcanaatacc caaagnggca acaaggaacg tttggctgga | 300 |
| atttgaagtt atttcagtca tctttgtctt tggctccatg tttcaggatg cgtgtgaact | 360 |
| cgatgtaatt gaaattcccc tttttatcaa t | 391 |

<210> SEQ ID NO 295
<211> LENGTH: 343
<212> TYPE: DNA
<213> ORGANISM: Homo sapien
<220> FEATURE:
<221> NAME/KEY: misc_feature
<222> LOCATION: (1)...(343)
<223> OTHER INFORMATION: n = A,T,C or G

<400> SEQUENCE: 295

| ttcttttgtt ttattgataa cagaaactgt gcataattac agatttgatg aggaatctgc | 60 |
| aaataataaa gaatgtgtct actgccagca aaatacaatt attccatgcc ctctcaacat | 120 |
| acaaatatag agttcttcac accanatggc tctggtgtaa caaagccatt ttanatgttt | 180 |
| aattgtgctt ctacaaaacc ttcanagcat gaggtagttt cttttaccta cnatattttc | 240 |
| cacatttcca ttattacact tttagtgagc taaaatcctt ttaacatagc ctgcggatga | 300 |
| tctttcacaa agccaagcc tcatttacaa agggtttatt tct | 343 |

<210> SEQ ID NO 296
<211> LENGTH: 241
<212> TYPE: DNA
<213> ORGANISM: Homo sapien
<220> FEATURE:
<221> NAME/KEY: misc_feature
<222> LOCATION: (1)...(241)
<223> OTHER INFORMATION: n = A,T,C or G

<400> SEQUENCE: 296

```
ttcttggata ttggttgttt ttgtgaaaaa gttttgtttt ttcttctcag tcaactgaat    60
tatttctcta ctttgccctc ctgatgccca catgananaa cttaanataa ttctaacag     120 cttccacttt ggaaaaaaaa aaaacctgtt ttcctcatgg aacccagga gttgaaagtg    180 gatanatcgc tctcaaaatc taaggctctg ttcagcttta cattatgtta cctgacgttt    240
t                                                                    241
```

<210> SEQ ID NO 297
<211> LENGTH: 391
<212> TYPE: DNA
<213> ORGANISM: Homo sapien
<220> FEATURE:
<221> NAME/KEY: misc_feature
<222> LOCATION: (1)...(391)
<223> OTHER INFORMATION: n = A,T,C or G

<400> SEQUENCE: 297

```
gttgtggctg anaatgctgg agatgctcag ttctctccct cacaaggtag gccacaaatt    60
cttggtggtg ccctcacatc tgggtcttc aggcaccagc catgcctgcc gaggagtgct    120
gtcaggacan accatgtccg tgctaggccc aggcacagcc caaccactcc tcatccaagt    180
ctctcccagg tttctggtcc cgatgggcaa ggatgacccc tccagtggct ggtaccccac    240
catcccacta cccctcacat gctctcactc tccatcaggt ccccaatcct ggcttccctc    300
ttcacgaact ctcaaagaaa aggaaggata aaacctaaat aaaccagaca gaagcagctc    360
tggaaaagta caaaaagaca gccagaggtg t                                   391
```

<210> SEQ ID NO 298
<211> LENGTH: 321
<212> TYPE: DNA
<213> ORGANISM: Homo sapien
<220> FEATURE:
<221> NAME/KEY: misc_feature
<222> LOCATION: (1)...(321)
<223> OTHER INFORMATION: n = A,T,C or G

<400> SEQUENCE: 298

```
caagccaaac tgtntccagc tttattaaan atactttcca taaacaatca tggtatttca    60
ggcaggacat gggcanacaa tcgttaacag tatacaacaa ctttcaaact cccttnttca    120
atggactacc aaaaatcaaa aagccactat aaaacccaat gaagtcttca tctgatgctc    180
tgaacaggga agtttaaag ngagggttga catttcacat ttagcatgtt gtttaacaac     240
ttttcacaag ccgaccctga ctttcaggaa gtgaaatgaa aatggcanaa tttatctgaa    300
natccacaat ctaaaaatgg a                                              321
```

<210> SEQ ID NO 299
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 299

```
tatcataaag agtgttgaag tttatttatt atagcaccat tgagacattt tgaaattgga    60
attggtaaaa aaataaaaca aaaagcattt gaattgtatt tggnggaaca gcaaaaaaag    120
agaagtatca tttttctttg tcaaattata ctgtttccaa acattttgga aataaataac    180
tggaattttg tcggtcactt gcactggttg acaagattag aacaagagga acacatatgg    240
```

```
agttaaattt tttttgttgg gatttcanat agagtttggt ttataaaaag caaacagggc    300
caacgtccac accaaattct tgatcaggac caccaatgtc atagggngca atatctacaa    360
taggtagtct cacagccttg cgtgttcgat attcaaagac t                        401
```

<210> SEQ ID NO 300
<211> LENGTH: 188
<212> TYPE: DNA
<213> ORGANISM: Homo sapien
<220> FEATURE:
<221> NAME/KEY: misc_feature
<222> LOCATION: (1)...(188)
<223> OTHER INFORMATION: n = A,T,C or G

<400> SEQUENCE: 300

```
tgaatgcttt gtcatattaa gaaagttaaa gtgcaataat gtttgaanac aataagtggt     60
ggtgtatctt gtttctaata agataaactt ttttgtcttt gctttatctt attagggagt    120
tgtatgtcag tgtataaaac atactgtgtg gtataacagg cttaataaat tctttaaaag    180
gaaaaaaa                                                            188
```

<210> SEQ ID NO 301
<211> LENGTH: 291
<212> TYPE: DNA
<213> ORGANISM: Homo sapien

<400> SEQUENCE: 301

```
aagattttgt tttattttat tatggctaga aagacactgt tatagccaaa atcggcaatg     60
acactaaaga aatcctctgt gcttttcaat atgcaaatat atttcttcca agagttgccc    120
tggtgtgact tcaagagttc atgttaactt cttttctgga aacttccttt tcttagttgt    180
tgtattcttg aagagcctgg gccatgaaga gcttgcctaa gttttgggca gtgaactcct    240
tgatgttctg gcagtaagtg tttatctggc ctgcaatgag cagcgagtcc a             291
```

<210> SEQ ID NO 302
<211> LENGTH: 341
<212> TYPE: DNA
<213> ORGANISM: Homo sapien
<220> FEATURE:
<221> NAME/KEY: misc_feature
<222> LOCATION: (1)...(341)
<223> OTHER INFORMATION: n = A,T,C or G

<400> SEQUENCE: 302

```
tgatttttca taattttatt aaatnatcac tgggaaaact aatggttcgc gtatcacaca     60
attacactac aatctgatag gagtggtaaa accagccaat ggaatccagg taaagtacaa    120
aaacgccacc ttttattgtc ctgtcttatt tctcgggaag gagggttcta ctttacacat    180
ttcatgagcc agcagtggac ttgagttaca atgtgtaggt tccttgtggt tatagctgca    240
gaagaagcca tcaaattctt gaggacttga catctctcgg aaagaagcaa actagtggat    300
cccccgggct gcaggaattc gatatcaagc ttatcgatac c                        341
```

<210> SEQ ID NO 303
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

```
<400> SEQUENCE: 303
tgcagacagt aaatnaattt tatttgngtt cacagaacat actaggcgat ctcgacagtc      60
gctccgtgac agcccaccaa cccccaaccc tntacctcgc agccaccta aaggcgactt     120 caanaanatg gaaggatctc acggatctca ttcctaatgg tccgccgaag tctcacacag    180
tanacagacg gagttganat gctggaggat gcagtcacct cctaaactta cgacccacca   240
ccanacttca tcccagccgg gacgtcctcc cccacccgag tcctccccat ttcttctcct   300
actttgccgc agttccaggn gtcctgcttc caccagtccc acaaagctca ataaatacca  360
a                                                                   361

<210> SEQ ID NO 304
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 304
ctctttacaa cagcctttat ttncggccct tgatcctgct cggatgctgg tggaggccct     60
tagctccgcc cgccaggctc tgtgccgcct ccccgcaggc gcanattcat gaacacggtg   120
ctcaggggct tgaggccgta ctcccccagc gggagctggt cctccagggg cttcccctcg   180
aaggtcagcc anaacaggtc gtcctgcaca ccctccagcc cgctcacttg ctgcttcagg   240
tgggccacgg tctgcgtcag ccgcacctcg taggtgctgc tgcggccctt gttattcctc  300
a                                                                   301

<210> SEQ ID NO 305
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 305
ganaggctag taacatcagt tttattgggt tggggnggca accatagcct ggctgggggn     60
ggggctggcc ctcacaggtt gttgagttcc agcagggtct ggtccaaggt ctggtgaatc   120
tcgacgttct cctccttggc actggccaag gtctcttcta ggtcatcgat ggttttctcc   180
aactttgcca canacctctc ggcaaactct gctcgggtct cancctcctt cagcttctcc   240
tccaacagtt tgatctcctc ttcatattta tcttctttgg gggaatactc ctcctctgag  300
gccatcaggg acttgagggc ctggtccatg g                                 331

<210> SEQ ID NO 306
<211> LENGTH: 457
<212> TYPE: DNA
<213> ORGANISM: Homo sapien

<400> SEQUENCE: 306
aatatgtaaa ggtaataact tttattatat taaagacaat gcaaacgaaa aacagaattg     60
agcagtgcaa aatttaaagg actgttttgt tctcaaagtt gcaagtttca agccaaaag   120 aattatatgt atcaaatata taagtaaaaa aaagttagac tttcaagcct gtaatcccag  180
cactttggga ggctgaggca ggtggatcac taacattaaa aagacaacat tagattttgt  240
```

| | |
|---|---|
| cgatttatag caattttata aatatataac tttgtcactt ggatcctgaa gcaaaataat | 300 |
| aaagtgaatt tgggattttt gtacttggta aaaagtttaa caccctaaat tcacaactag | 360 |
| tggatccccc gggctgcagg aattcgatat caagcttatc gataccgtcg acctcgaggg | 420 |
| ggggcccggt acccaattcg ccctatagtg agtcgta | 457 |

<210> SEQ ID NO 307
<211> LENGTH: 491
<212> TYPE: DNA
<213> ORGANISM: Homo sapien

<400> SEQUENCE: 307

| | |
|---|---|
| gtgcttggac ggaacccggc gctcgttccc caccccggcc ggccgcccat agccagccct | 60 |
| ccgtcacctc ttcaccgcac cctcggactg ccccaaggcc cccgccgccg ctccagcgcc | 120 |
| gcgcagccac cgccgccgcc gccgcctctc cttagtcgcc gccatgacga ccgcgtccac | 180 |
| ctcgcaggtg cgccagaact accaccagga ctcagaggcc gccatcaacc gccagatcaa | 240 |
| cctggagctc tacgcctcct acgtttacct gtccatgtct tactactttg accgcgatga | 300 |
| tgtggctttg aagaactttg ccaaatactt tcttcaccaa tctcatgagg agagggaaca | 360 |
| tgctgagaaa ctgatgaagc tgcagaacca acgaggtggc cgaatcttcc ttcaggatat | 420 |
| caagaaacca gactgtgatg actgggagag cgggctgaat gcaatggagt gtgcattaca | 480 |
| tttggaaaaa a | 491 |

<210> SEQ ID NO 308
<211> LENGTH: 421
<212> TYPE: DNA
<213> ORGANISM: Homo sapien

<400> SEQUENCE: 308

| | |
|---|---|
| ctcagcgctt cttctttctt ggtttgatcc tgactgctgt catggcgtgc cctctggaga | 60 |
| aggccctgga tgtgatggtg tccaccttcc acaagtactc gggcaaagag ggtgacaagt | 120 |
| tcaagctcaa caagtcagaa ctaaaggagc tgctgacccg ggagctgccc agcttcttgg | 180 |
| ggaaaaggac agatgaagct gctttccaga agctgatgag caacttggac agcaacaggg | 240 |
| acaacgaggt ggacttccaa gagtactgtg tcttcctgtc ctgcatcgcc atgatgtgta | 300 |
| acgaattctt tgaaggcttc ccagataagc agcccaggaa gaaatgaaaa ctcctctgat | 360 |
| gtggttgggg ggtctgccag ctggggccct ccctgtcgcc agtgggcact ttttttttc | 420 |
| c | 421 |

<210> SEQ ID NO 309
<211> LENGTH: 321
<212> TYPE: DNA
<213> ORGANISM: Homo sapien

<400> SEQUENCE: 309

| | |
|---|---|
| accaaatggc ggatgacgcc ggtgcagcgg gggggcccgg gggccctggt ggccctggga | 60 |
| tggggaaccg cggtggcttc cgcggaggtt tcggcagtgg catccggggc cggggtcgcg | 120 |
| gccgtggacg gggccgggc cgaggccgcg gagctcgcgg aggcaaggcc gaggataagg | 180 |
| agtggatgcc cgtcaccaag ttgggccgct tggtcaagga catgaagatc aagtccctgg | 240 |
| aggagatcta tctcttctcc ctgcccatta aggaatcaga gatcattgat ttcttcctgg | 300 |
| gggcctctct caaggatgag g | 321 |

<210> SEQ ID NO 310
<211> LENGTH: 381
<212> TYPE: DNA
<213> ORGANISM: Homo sapien

<400> SEQUENCE: 310

```
ttaaccagcc atattggctc aataaatagc ttcggtaagg agttaatttc cttctagaaa    60
tcagtgccta ttttcctgg aaactcaatt ttaaatagtc caattccatc tgaagccaag    120
ctgttgtcat tttcattcgg tgacattctc tcccatgaca cccagaaggg gcagaagaac    180
cacatttttc atttatagat gtttgcatcc tttgtattaa aattattttg aagggttgc    240
ctcattggat ggcttttttt ttttcctcc agggagaagg ggagaaatgt acttggaaat    300
taatgtatgt ttacatctct ttgcaaattc ctgtacatag agatatattt tttaagtgtg    360
aatgtaacaa catactgtga a                                              381
```

<210> SEQ ID NO 311
<211> LENGTH: 538
<212> TYPE: DNA
<213> ORGANISM: Homo sapien

<400> SEQUENCE: 311

```
tttgaattta caccaagaac ttctcaataa aagaaaatca tgaatgctcc acaatttcaa    60
cataccacaa gagaagttaa tttcttaaca ttgtgttcta tgattatttg taagaccttc    120
accaagttct gatatctttt aaagacatag ttcaaaattg cttttgaaaa tctgtattct    180
tgaaaatatc cttgttgtgt attaggtttt taaataccag ctaaaggatt acctcactga    240
gtcatcagta ccctcctatt cagctcccca agatgatgtg ttttgctta ccctaagaga    300
ggttttcttc ttatttttag ataattcaag tgcttagata aattatgttt tctttaagtg    360
tttatggtaa actcttttaa agaaaattta atatgttata gctgaatctt tttggtaact    420
ttaaatcttt atcatagact ctgtacatat gttcaaatta gctgcttgcc tgatgtgtgt    480
atcatcggtg ggatgacaga acaaacatat ttatgatcat gaataatgtg ctttgtaa     538
```

<210> SEQ ID NO 312
<211> LENGTH: 176
<212> TYPE: DNA
<213> ORGANISM: Homo sapien

<400> SEQUENCE: 312

```
ggaggagcag ctgagagata gggtcagtga atgcggttca gcctgctacc tctcctgtct    60
tcatagaacc attgccttag aattattgta tgacacgttt tttgttggtt aagctgtaag    120
gttttgttct ttgtgaacat gggtattttg aggggagggt ggagggagta gggaag        176
```

<210> SEQ ID NO 313
<211> LENGTH: 396
<212> TYPE: DNA
<213> ORGANISM: Homo sapien

<400> SEQUENCE: 313

```
ccagcacccc caggccctgg gggacctggg ttctcagact gccaaagaag ccttgccatc    60
tggcgctccc atggctcttg caacatctcc ccttcgtttt tgagggggtc atgccggggg    120
agccaccagc ccctcactgg gttcggagga gagtcaggaa gggccaagca cgacaaagca    180
gaaacatcgg atttggggaa cgcgtgtcaa tcccttgtgc cgcagggctg ggcgggagag    240
actgttctgt tccttgtgta actgtgttgc tgaaagacta cctcgttctt gtcttgatgt    300
```

```
gtcaccgggg caactgcctg ggggcgggga tgggggcagg gtggaagcgg ctccccattt      360
tataccaaag gtgctacatc tatgtgatgg gtgggg                                396
```

<210> SEQ ID NO 314
<211> LENGTH: 311
<212> TYPE: DNA
<213> ORGANISM: Homo sapien

<400> SEQUENCE: 314

```
cctcaacatc ctcagagagg actggaagcc agtccttacg ataaactcca taatttatgg       60
cctgcagtat ctcttcttgg agcccaaccc cgaggaccca ctgaacaagg aggccgcaga      120
ggtcctgcag aacaaccggc ggctgtttga gcagaacgtg cagcgctcca tgcggggtgg      180
ctacatcggc tccacctact ttgagcgctg cctgaaatag ggttggcgca tacccacccc      240
cgccacggcc acaagccctg gcatcccctg caaatattta ttggggggcca tgggtagggg      300 tttgggggc g                                                           311
```

<210> SEQ ID NO 315
<211> LENGTH: 336
<212> TYPE: DNA
<213> ORGANISM: Homo sapien

<400> SEQUENCE: 315

```
tttagaacat ggttatcatc caagactact ctaccctgca acattgaact cccaagagca       60
aatccacatt cctcttgagt tctgcagctt ctgtgtaaat agggcagctg tcgtctatgc      120
cgtagaatca catgatctga ggaccattca tggaagctgc taaatagcct agtctgggga      180
gtcttccata aagttttgca tggagcaaac aaacaggatt aaactaggtt tggttccttc      240
agccctctaa aagcataggg cttagcctgc aggcttcctt gggctttctc tgtgtgtgta      300
gttttgtaaa cactatagca tctgttaaga tccagt                                336
```

<210> SEQ ID NO 316
<211> LENGTH: 436
<212> TYPE: DNA
<213> ORGANISM: Homo sapien

<400> SEQUENCE: 316

```
aacatggtct gcgtgcctta agagagacgc ttcctgcaga acaggacctg actacaaaga       60
atgtttccat tggaattgtt ggtaaagact tggagtttac aatctatgat gatgatgatg      120
tgtctccatt cctggaaggt cttgaagaaa gaccacagag aaaggcacag cctgctcaac      180
ctgctgatga acctgcagaa aaggctgatg aaccaatgga acattaagtg ataagccagt      240
ctatatatgt attatcaaat atgtaagaat acaggcacca catactgatg acaataatct      300
atactttgaa ccaaaagttg cagagtggtg gaatgctatg ttttaggaat cagtccagat      360
gtgagttttt tccaagcaac ctcactgaaa cctatataat ggaatacatt tttctttgaa      420
agggtctgta taatca                                                     436
```

<210> SEQ ID NO 317
<211> LENGTH: 196
<212> TYPE: DNA
<213> ORGANISM: Homo sapien

<400> SEQUENCE: 317

```
tattccttgt gaagatgata tactattttt gttaagcgtg tctgtattta tgtgtgagga       60
```

```
gctgctggct tgcagtgcgc gtgcacgtgg agagctggtg cccggagatt ggacggcctg    120
atgctccctc ccctgccctg gtccagggaa gctggccgag ggtcctggct cctgagggc    180 atctgcccct ccccca                                                    196
```

<210> SEQ ID NO 318
<211> LENGTH: 381
<212> TYPE: DNA
<213> ORGANISM: Homo sapien
<220> FEATURE:
<221> NAME/KEY: misc_feature
<222> LOCATION: (1)...(381)
<223> OTHER INFORMATION: n = A,T,C or G

<400> SEQUENCE: 318

```
gacgcttnng ccgtaacgat gatcggagac atcctgctgt tcgggacgtt gctgatgaat    60
gccggggcgg tgctgaactt taagctgaaa aagaaggaca cncagggctt tggggaggag   120
tncagggagc ccaacacagg tgacaacatc cgggaattct tgctgancct cagatacttt   180
cnaatcttca tcnccctgtg gaacatcttc atgatgttct gcatgattgt gctgntcggc   240
tcttgaatcc cancgatgaa accannaact cactttcccg ggatgccgan tctccattcc   300
tccattcctg atgacttcaa naatgttttt gaccaaaaaa ccgacaacct tcccagaaag   360
tccaagctcg tggtgggngg a                                              381
```

<210> SEQ ID NO 319
<211> LENGTH: 506
<212> TYPE: DNA
<213> ORGANISM: Homo sapien

<400> SEQUENCE: 319

```
ctaagcttta cgaatggggt gacaacttat gataaaaact agagctagtg aattagccta    60
tttgtaaata cctttgttat aattgatagg atacatcttg acatggaat tgttaagcca   120 cctctgagca gtgtatgtca ggacttgttc attaggttgg cagcagaggg gcagaaggaa   180
ttatacaggt agagatgtat gcagatgtgt ccatatatgt ccatatttac attttgatag   240
ccattgatgt atgcatctct tggctgtact ataagaacac attaattcaa tggaaataca   300
ctttgctaat attttaatgg tatagatctg ctaatgaatt ctcttaaaaa catactgtat   360
tctgttgctg tgtgtttcat tttaaattga gcattaaggg aatgcagcat ttaaatcaga   420
actctgccaa tgcttttatc tagaggcgtg ttgccatttt tgtcttatat gaaatttctg   480
tcccaagaaa ggcaggatta catctt                                         506
```

<210> SEQ ID NO 320
<211> LENGTH: 351
<212> TYPE: DNA
<213> ORGANISM: Homo sapien

<400> SEQUENCE: 320

```
ctgacctgca ggacgaaacc atgaagagcc tgatccttct tgccatcctg gccgccttag    60
cggtagtaac tttgtgttat gaatcacatg aaagcatgga atcttatgaa cttaatccct   120
tcattaacag gagaaatgca aataccttca tatcccctca gcagagatgg agagctaaag   180
tccaagagag gatccgagaa cgctctaagc ctgtccacga gctcaatagg gaagcctgtg   240
atgactacag actttgcgaa cgctacgcca tggtttatgg atacaatgct gcctataatc   300
gctacttcag gaagcgccga gggaccaaat gagactgagg gaagaaaaaa a            351
```

<210> SEQ ID NO 321
<211> LENGTH: 421
<212> TYPE: DNA
<213> ORGANISM: Homo sapien

<400> SEQUENCE: 321

| | | | | | |
|---|---|---|---|---|---|
| ctcggaggcg | ttcagctgct | tcaagatgaa | gctgaacatc | tccttcccag | ccactggctg | 60 |
| ccagaaactc | attgaagtgg | acgatgaacg | caaacttcgt | actttctatg | agaagcgtat | 120 |
| ggccacagaa | gttgctgctg | acgctctggg | tgaagaatgg | aagggttatg | tggtccgaat | 180 |
| cagtggtggg | aacgacaaac | aaggtttccc | catgaagcag | ggtgtcttga | cccatggccg | 240 |
| tgtccgcctg | ctactgagta | agggcattc | ctgttacaga | ccaaggagaa | ctggagaaag | 300 |
| aaagagaaaa | tcagttcgtg | gttgcattgt | ggatgcaaat | ctgagcgttc | tcaacttggt | 360 |
| tattgtaaaa | aaaggagaga | aggatattcc | tggactgact | gatactacag | tgcctcgccg | 420 |
| c | | | | | | 421 |

<210> SEQ ID NO 322
<211> LENGTH: 521
<212> TYPE: DNA
<213> ORGANISM: Homo sapien

<400> SEQUENCE: 322

| | | | | | |
|---|---|---|---|---|---|
| agcagctctc | ctgccacagc | tcctcacccc | ctgaaaatgt | tcgcctgctc | caagtttgtc | 60 |
| tccactccct | ccttggtcaa | gagcacctca | cagctgctga | gccgtccgct | atctgcagtg | 120 |
| gtgctgaaac | gaccggagat | actgacagat | gagagcctca | gcagcttggc | agtctcatgt | 180 |
| ccccttacct | cacttgtctc | tagccgcagc | ttccaaacca | gcgccatttc | aagggacatc | 240 |
| gacacagcag | ccaagttcat | tggagctggg | gctgccacag | ttggggtggc | tggttctggg | 300 |
| gctgggattg | gaactgtgtt | tgggagcctc | atcattggtt | atgccaggaa | cccttctctg | 360 |
| aagcaacagc | tcttctccta | cgccattctg | ggctttgccc | tctcggaggc | catggggctc | 420 |
| ttttgtctga | tggtagcctt | tctcatcctc | tttgccatgt | gaaggagccg | tctccacctc | 480 |
| ccatagttct | cccgcgtctg | gttggccccg | tgtgttcctt | t | | 521 |

<210> SEQ ID NO 323
<211> LENGTH: 435
<212> TYPE: DNA
<213> ORGANISM: Homo sapien

<400> SEQUENCE: 323

| | | | | | |
|---|---|---|---|---|---|
| ccgaggtcgc | acgcgtgaga | cttctccgcc | gcagacgccg | ccgcgatgcg | ctacgtcgcc | 60 |
| tcctacctgc | tggctgccct | aggggggcaac | tcctcccca | gcgccaagga | catcaagaag | 120 |
| atcttggaca | gcgtgggtat | cgaggcggac | gacgaccggc | tcaacaaggt | tatcagtgag | 180 |
| ctgaatggaa | aaacattga | agacgtcatt | gcccagggta | ttggcaagct | tgccagtgta | 240 |
| cctgctggtg | gggctgtagc | cgtctctgct | gccccaggct | ctgcagcccc | tgctgctggt | 300 |
| tctgcccctg | ctgcagcaga | ggagaagaaa | gatgagaaga | aggaggagtc | tgaagagtca | 360 |
| gatgatgaca | tgggatttgg | ccttttttgat | taaattcctg | ctccctgca | aataaagcct | 420 |
| ttttacacat | ctcaa | | | | | 435 |

<210> SEQ ID NO 324
<211> LENGTH: 521
<212> TYPE: DNA
<213> ORGANISM: Homo sapien

```
<400> SEQUENCE: 324
aggagatcga ctttcggtgc ccgcaagacc agggctggaa cgccgagatc acgctgcaga      60
tggtgcagta caagaatcgt caggccatcc tggcggtcaa atccacgcgg cagaagcagc     120
agcacctggt ccagcagcag ccccctcgc agccgcagcc gcagccgcag ctccagcccc      180
aaccccagcc tcagcctcag ccgcaacccc agccccaatc acaacccag cctcagcccc      240
aacccaagcc tcagccccag cagctccacc cgtatccgca tccacatcca catccacact     300
ctcatcctca ctcgcaccca caccctcacc cgcaccccgca tccgcaccaa ataccgcacc     360
cacacccaca gccgcactcg cagccgcacg gcaccggct tctccgcagc acctccaact      420
ctgcctgaaa ggggcagctc ccgggcaaga caaggttttg aggacttgag gaagtgggac     480
gagcacattt ctattgtctt cacttggatc aaaagcaaaa c                         521

<210> SEQ ID NO 325
<211> LENGTH: 451
<212> TYPE: DNA
<213> ORGANISM: Homo sapien

<400> SEQUENCE: 325
attttcattt ccattaacct ggaagctttc atgaatattc tcttcttta aaacattta       60
acattattta aacagaaaaa gatgggctct ttctggttag ttgttacatg atagcagaga    120
tattttact tagattactt tgggaatgag agattgttgt cttgaactct ggcactgtac     180
agtgaatgtg tctgtagttg tgttagtttg cattaagcat gtataacatt caagtatgtc    240
atccaaataa gaggcatata cattgaattg tttttaatcc tctgacaagt tgactcttcg    300
accccaccc ccacccaaga cattttaata gtaaatagag agagagagaa gagttaatga    360
acatgaggta gtgttccact ggcaggatga cttttcaata gctcaaatca atttcagtgc    420
ctttatcact tgaattatta acttaatttg a                                    451

<210> SEQ ID NO 326
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 326
cgcggtcgta agggctgagg attttttggtc cgcacgctcc tgctcctgac tcaccgctgt     60
tcgctctcgc cgaggaacaa gtcggtcagg aagcccgcgc gcaacagcca tggcttttaa    120
ggataccgga aaaacacccg tggagccgga ggtggcaatt caccgaattc gaatcaccct    180
aacaagccgc aacgtaaaat ccttggaaaa ggtgtgtgct gacttgataa gaggcgcaaa    240
agaaaagaat ctcaaagtga aaggaccagt tcgaatgcct accaagactt tgagantcac    300
tacaagaaaa actccttgtg gtgaaggttc taagacgtgg gatcgtttcc agatgagaat    360
tcacaagcga ctcattgact tgcacagtcc ttctgagatt gttaagcaga ttacttccat    420
c                                                                     421

<210> SEQ ID NO 327
<211> LENGTH: 456
<212> TYPE: DNA
<213> ORGANISM: Homo sapien

<400> SEQUENCE: 327
```

```
atcttgacga ggctgcggtg tctgctgcta ttctccgagc ttcgcaatgc cgcctaagga      60
cgacaagaag aagaaggacg ctggaaagtc ggccaagaaa gacaaagacc cagtgaacaa     120
atccgggggc aaggccaaaa agaagaagtg gtccaaaggc aaagttcggg acaagctcaa     180
taacttagtc ttgtttgaca agctaccta tgataaactc tgtaaggaag ttcccaacta      240
taaacttata accccagctg tggtctctga gagactgaag attcgaggct ccctggccag     300 ggcagcccttt caggagctcc ttagtaaagg acttatcaaa ctggtttcaa agcacagagc    360
tcaagtaatt tacaccagaa ataccaaggg tgggagatgct ccagctgctg gtgaagatgc    420
atgaataggt ccaaccagct gtacatttgg aaaaat                               456
```

<210> SEQ ID NO 328
<211> LENGTH: 471
<212> TYPE: DNA
<213> ORGANISM: Homo sapien

<400> SEQUENCE: 328

```
gtggaagtga catcgtcttt aaaccctgcg tggcaatccc tgacgcaccg ccgtgatgcc      60
cagggaagac agggcgacct ggaagtccaa ctacttcctt aagatcatcc aactattgga     120
tgattatccg aaatgtttca ttgtgggagc agacaatgtg ggctccaagc agatgcagca     180
gatccgcatg tcccttcgcg ggaaggctgt ggtgctgatg ggcaagaaca ccatgatgcg     240
caaggccatc cgagggcacc tggaaaacaa cccagctctg gagaaactgc tgcctcatat     300
ccgggggaat gtgggctttg tgttcaccaa ggaggacctc actgagatca gggacatgtt     360
gctggccaat aaggtgccag ctgctgcccg tgctggtgcc attgccccat gtgaagtcac     420
tgtgccagcc cagaacactg gtctcgggcc cgagaagacc tcctttttcc a             471
```

<210> SEQ ID NO 329
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 329

```
gtttaaactt aagcttggta ccgagctcgg atccactagt ccagtgtggt ggaattctag      60
aaattgagat gccccccag gccagcaaat gttccttttt gttcaaagtc tatttttatt     120
ccttgatatt tttctttttt tttttttttt ttgnggatgg ggacttgtga attttctaa     180 aggtgctatt taacatggga gganagcgtg tgcggctcca gcccagcccg ctgctcactt     240
tccaccctct ctccacctgc ctctggcttc tcaggcct                             278
```

<210> SEQ ID NO 330
<211> LENGTH: 338
<212> TYPE: DNA
<213> ORGANISM: Homo sapien

<400> SEQUENCE: 330

```
ctcaggcttc aacatcgaat acgccgcagg ccccttcgcc ctattcttca tagccgaata      60
cacaaacatt attataataa acaccctcac cactacaatc ttcctaggaa caacatatga     120
cgcactctcc cctgaactct acacaacata ttttgtcacc aagaccctac ttctaacctc     180
cctgttctta tgaattcgaa cagcataccc ccgattccgc tacgaccaac tcatacacct     240
```

-continued

| | |
|---|---|
| cctatgaaaa aacttcctac cactcaccct agcattactt atatgatatg tctccatacc | 300 |
| cattacaatc tccagcattc cccctcaaac ctaaaaaa | 338 |

<210> SEQ ID NO 331
<211> LENGTH: 2820
<212> TYPE: DNA
<213> ORGANISM: Homo sapiens

<400> SEQUENCE: 331

| | |
|---|---|
| tggcaaaatc tggagccag aagaaaggac agcagcattg atcaatctta cagctaacat | 60 |
| gttgtacctg gaaaacaatg cccagactca atttagtgag ccacagtaca cgaacctggg | 120 |
| gctcctgaac agcatggacc agcagattcg gaacggctcc tcgtccacca gtccctataa | 180 |
| cacagaccac gcgcagaaca gcgtcacggc gccctcgccc tacgcacagc ccagccccac | 240 |
| cttcgatgct ctctctccat cacccgccat cccctccaac accgactacc caggcccgca | 300 |
| cagttccgac gtgtccttcc agcagtcgag caccgccaag tcggccacct ggacgtattc | 360 |
| cactgaactg aagaaactct actgccaaat tgcaaagaca tgccccatcc agatcaaggt | 420 |
| gatgaccca cctcctcagg gagctgttat ccgcgccatg cctgtctaca aaaagctga | 480 |
| gcacgtcacg gaggtggtga agcggtgccc caaccatgag ctgagccgtg agttcaacga | 540 |
| gggacagatt gccctccta gtcatttgat tcgagtagag gggaacagcc atgcccagta | 600 |
| tgtagaagat cccatcacag gaagacagag tgtgctggta ccttatgagc caccccaggt | 660 |
| tggcactgaa ttcacgacag tcttgtacaa tttcatgtgt aacagcagtt gtgttggagg | 720 |
| gatgaaccgc cgtccaattt taatcattgt tactctggaa accagagatg ggcaagtcct | 780 |
| gggccgacgc tgctttgagg cccggatctg tgcttgccca ggaagagaca ggaaggcgga | 840 |
| tgaagatagc atcagaaagc agcaagtttc ggacagtaca agaacggtg atggtacgaa | 900 |
| gcgcccgttt cgtcagaaca cacatggtat ccagatgaca tccatcaaga aacgaagatc | 960 |
| cccagatgat gaactgttat acttaccagt gaggggccgt gagacttatg aaatgctgtt | 1020 |
| gaagatcaaa gagtccctgg aactcatgca gtaccttcct cagcacacaa ttgaaacgta | 1080 |
| caggcaacag caacagcagc agcaccagca cttacttcag aaacagacct caatacagtc | 1140 |
| tccatcttca tatggtaaca gctcccccacc tctgaacaaa atgaacagca tgaacaagct | 1200 |
| gccttctgtg agccagctta tcaaccctca gcagcgcaac gccctcactc ctacaaccat | 1260 |
| tcctgatggc atgggagcca acattccat gatgggcacc cacatgccaa tggctggaga | 1320 |
| catgaatgga ctcagcccca ccaggcact ccctcccca ctctccatgc catccacctc | 1380 |
| ccactgcaca cccccaccctc cgtatcccac agattgcagc attgtcagtt tcttagcgag | 1440 |
| gttgggctgt tcatcatgtc tggactattt cacgacccag gggctgacca ccatctatca | 1500 |
| gattgagcat tactccatgg atgatctggc aagtctgaaa atccctgagc aatttcgaca | 1560 |
| tgcgatctgg aagggcatcc tggaccaccg gcagctccac gaattctcct cccttctca | 1620 |
| tctcctgcgg accccaagca gtgcctctac agtcagtgtg ggctccagtg agacccgggg | 1680 |
| tgagcgtgtt attgatgctg tgcgattcac cctccgccca accatctctt tcccaccccg | 1740 |
| agatgagtgg aatgacttca actttgacat ggatgctcgc cgcaataagc aacagcgcat | 1800 |
| caaagaggag ggggagtgag cctcaccatg tgagctcttc ctatccctct cctaactgcc | 1860 |
| agccccctaa aagcactcct gcttaatctt caaagccttc tccctagctc ctccccttcc | 1920 |
| tcttgtctga tttcttaggg gaaggagaag taagaggcta cctcttacct aacatctgac | 1980 |
| ctggcatcta attctgattc tggctttaag ccttcaaaac tatagcttgc agaactgtag | 2040 |

```
ctgccatggc taggtagaag tgagcaaaaa agagttgggt gtctccttaa gctgcagaga    2100
tttctcattg acttttataa agcatgttca cccttatagt ctaagactat atatataaat    2160
gtataaatat acagtataga ttttggggtg ggggcattg agtattgttt aaaatgtaat     2220
ttaaatgaaa gaaaattgag ttgcacttat tgaccatttt ttaatttact tgttttggat    2280
ggcttgtcta tactccttcc cttaagggt atcatgtatg gtgataggta tctagagctt     2340
aatgctacat gtgagtgcga tgatgtacag attctttcag ttctttggat tctaaataca    2400
tgccacatca aacctttgag tagatccatt tccattgctt attatgtagg taagactgta    2460
gatatgtatt cttttctcag tgttggtata ttttatatta ctgacatttc ttctagtgat    2520
gatggttcac gttggggtga tttaatccag ttataagaag aagttcatgt ccaaacggtc    2580
ctctttagtt tttggttggg aatgaggaaa attcttaaaa ggcccatagc agccagttca    2640
aaaacacccg acgtcatgta tttgagcata tcagtaaccc ccttaaattt aatacccaga    2700
taccttatct tacaatgttg attgggaaaa catttgctgc ccattacaga ggtattaaaa    2760
ctaaatttca ctactagatt gactaactca aatacacatt tgctactgtt gtaagaattc    2820

<210> SEQ ID NO 332
<211> LENGTH: 2270
<212> TYPE: DNA
<213> ORGANISM: Homo sapiens

<400> SEQUENCE: 332
tcgttgatat caaagacagt tgaaggaaat gaattttgaa acttcacggt gtgccaccct      60
acagtactgc cctgacccct acatccagcg tttcgtagaa acccagctca tttctcttgg    120
aaagaaagtt attaccgatc caccatgtcc cagagcacac agacaaatga attcctcagt    180
ccagaggttt tccagcatat ctgggatttt ctggaacagc ctatatgttc agttcagccc    240
attgacttga actttgtgga tgaaccatca gaagatggtg cgacaaacaa gattgagatt    300
agcatggact gtatccgcat gcaggactcg gacctgagtg accccatgtg gccacagtac    360
acgaacctgg ggctcctgaa cagcatggac cagcagattc agaacggctc ctcgtccacc    420
agtccctata acacagacca cgcgcagaac agcgtcacgg cgccctcgcc ctacgcacag    480
cccagctcca ccttcgatgc tctctctcca tcacccgcca tcccctccaa caccgactac    540
ccaggcccgc acagtttcga cgtgtccttc cagcagtcga gcaccgccaa gtcggccacc    600
tggacgtatt ccactgaact gaagaaactc tactgccaaa ttgcaaagac atgccccatc    660
cagatcaagg tgatgacccc acctcctcag ggagctgtta ccgcgccat gcctgtctac    720 aaaaaagctg agcacgtcac ggaggtggtg aagcggtgcc ccaaccatga gctgagccgt    780
gaattcaacg agggacagat tgcccctcct agtcatttga ttcgagtaga ggggaacagc    840
catgcccagt atgtagaaga tcccatcaca ggaagacaga gtgtgctggt accttatgag    900
ccaccccagg ttggcactga attcacgaca gtcttgtaca atttcatgtg taacagcagt    960
tgtgttggag ggatgaaccg ccgtccaatt ttaatcattg ttactctgga aaccagagat   1020
gggcaagtcc tgggccgacg ctgctttgag gcccggatct gtgcttgccc aggaagagac   1080 aggaaggcg atgaagatag catcagaaag cagcaagttt cggacagtac aaagaacggt   1140
gatggtacga agcgcccgtt tcgtcagaac acacatggta tccagatgac atccatcaag   1200 aaaacgaagat cccagatga tgaactgtta tacttaccag tgaggggccg tgagacttat   1260
gaaatgctgt tgaagatcaa agagtccctg gaactcatgc agtaccttcc tcagcacaca   1320
```

```
attgaaacgt acaggcaaca gcaacagcag cagcaccagc acttacttca gaaacagacc    1380
tcaatacagt ctccatcttc atatggtaac agctccccac ctctgaacaa aatgaacagc    1440
atgaacaagc tgccttctgt gagccagctt atcaaccctc agcagcgcaa cgccctcact    1500
cctacaacca ttcctgatgg catgggagcc aacattccca tgatgggcac ccacatgcca    1560
atggctggag acatgaatgg actcagcccc acccaggcac tccctcccc actctccatg    1620 ccatccacct cccactgcac acccccacct ccgtatccaa cagattgcag cattgtcggt    1680
ttcttagcga ggttgggctg ttcatcatgt ctggactatt tcacgaccca ggggctgacc    1740
accatctatc agattgagca ttactccatg gatgatctgg caagtctgaa atccctgag    1800 caatttcgac atgcgatctg aagggcatc ctggaccacc ggcagctcca cgaattctcc    1860
tccccttctc atctcctgcg acccccaagc agtgcctcta cagtcagtgt gggctccagt    1920
gagacccggg gtgagcgtgt tattgatgct gtgcgattca ccctccgcca gaccatctct    1980
ttcccacccc gagatgagtg gaatgacttc aactttgaca tggatgctcg ccgcaataag    2040
caacagcgca tcaaagagga gggggagtga gcctcaccat gtgagctctt cctatccctc    2100
tcctaactgc cagcccccta aaagcactcc tgcttaatct tcaaagcctt ctccctagct    2160 cctcccttc ctcttgtctg atttcttagg ggaaggagaa gtaagaggct acctcttacc    2220
taacatctga cctggcatct aattctgatt ctggctttaa gccttcaaaa                2270
```

<210> SEQ ID NO 333
<211> LENGTH: 2816
<212> TYPE: DNA
<213> ORGANISM: Homo sapiens

<400> SEQUENCE: 333

```
tcgttgatat caaagacagt tgaaggaaat gaattttgaa acttcacggt gtgccaccct      60
acagtactgc cctgacccct acatccagcg tttcgtagaa acccagctca tttctcttgg     120
aaagaaagtt attaccgatc caccatgtcc cagagcacac agacaaatga attcctcagt     180
ccagaggttt tccagcatat ctgggatttt ctggaacagc ctatatgttc agttcagccc     240
attgacttga actttgtgga tgaaccatca agagatggtg cgacaaacaa gattgagatt     300
agcatggact gtatccgcat gcaggactcg gacctgagtg accccatgtg ccacagtac     360 acgaacctgg ggctcctgaa cagcatggac cagcagattc agaacggctc ctcgtccacc     420
agtccctata acacagacca cgcgcagaac agcgtcacgg cgccctcgcc ctacgcacag     480
cccagctcca ccttcgatgc tctctctcca tcacccgcca tcccctccaa caccgactac     540
ccaggcccgc acagtttcga cgtgtccttc cagcagtcga gcaccgccaa gtcggccacc     600
tggacgtatt ccactgaact gaagaaactc tactgccaaa ttgcaaagac atgccccatc     660
cagatcaagg tgatgacccc acctcctcag ggagctgtta ccgcgccat gcctgtctac     720 aaaaaagctg agcacgtcac ggaggtggtg aagcggtgcc ccaaccatga gctgagccgt    780
gaattcaacg agggacagat tgcccctcct agtcatttga ttcgagtaga ggggaacagc    840
catgcccagt atgtagaaga tcccatcaca ggaagacaga gtgtgctggt accttatgag    900
ccaccccagg ttggcactga attcacgaca gtccttgtaca atttcatgtg taacagcagt    960
tgtgttggag ggatgaaccg ccgtccaatt ttaatcattg ttactctgga aaccagagat    1020
gggcaagtcc tggccgacg ctgctttgag gcccggatct gtgcttgccc aggaagagac   1080
aggaaggcgg atgaagatag catcagaaag cagcaagttt cggacagtac aaagaacggt    1140
gatggtacga agcgcccgtt tcgtcagaac acacatggta tccagatgac atccatcaag    1200
```

-continued

```
aaacgaagat ccccagatga tgaactgtta tacttaccag tgaggggccg tgagacttat    1260
gaaatgctgt tgaagatcaa agagtccctg gaactcatgc agtaccttcc tcagcacaca    1320
attgaaacgt acaggcaaca gcaacagcag cagcaccagc acttacttca gaaacatctc    1380
ctttcagcct gcttcaggaa tgagcttgtg gagccccgga gagaaactcc aaaacaatct    1440
gacgtcttct ttagacattc caagccccca aaccgatcag tgtacccata gagccctatc    1500
tctatatttt aagtgtgtgt gttgtatttc catgtgtata tgtgagtgtg tgtgtgtgta    1560
tgtgtgtgcg tgtgtatcta gccctcataa acaggacttg aagacacttt ggctcagaga    1620
cccaactgct caaaggcaca aagccactag tgagagaatc ttttgaaggg actcaaacct    1680
ttacaagaaa ggatgttttc tgcagatttt gtatccttag accggccatt ggtgggtgag    1740
gaaccactgt gtttgtctgt gagctttctg ttgtttcctg ggagggaggg gtcaggtggg    1800 gaaagggca ttaagatgtt tattggaacc cttttctgtc ttcttctgtt gttttctaa     1860 aattcacagg gaagcttttg agcaggtctc aaacttaaga tgtcttttta agaaaggag    1920 aaaaagttg ttattgtctg tgcataagta agttgtaggt gactgagaga ctcagtcaga    1980 ccctttaat gctggtcatg taataatatt gcaagtagta agaaacgaag gtgtcaagtg    2040
tactgctggg cagcgaggtg atcattacca aaagtaatca actttgtggg tggagagttc    2100
tttgtgagaa cttgcattat ttgtgtcctc ccctcatgtg taggtagaac atttcttaat    2160
gctgtgtacc tgcctctgcc actgtatgtt ggcatctgtt atgctaaagt ttttcttgta    2220
catgaaaccc tggaagacct actacaaaaa aactgttgtt tggcccccat agcaggtgaa    2280
ctcattttgt gcttttaata gaaagacaaa tccaccccag taatattgcc cttacgtagt    2340
tgtttaccat tattcaaagc tcaaaataga atttgaagcc ctctcacaaa atctgtgatt    2400
aatttgctta attagagctt ctatccctca agcctaccta ccataaaacc agccatatta    2460
ctgatactgt tcagtgcatt tagccaggag acttacgttt tgagtaagtg agatccaagc    2520
agacgtgtta aaatcagcac tcctggactg gaaattaaag attgaaaggg tagactactt    2580 ttctttttttt tactcaaaag tttagagaat ctctgtttct ttccatttta aaacatatt    2640 ttaagataat agcataaaga ctttaaaaat gttcctcccc tccatcttcc cacacccagt    2700
caccagcact gtattttctg tcaccaagac aatgattcct tgttattgag gctgttgctt    2760
ttgtggatgt gtgattttaa ttttcaataa acttttgcat cttggtttaa aagaaa       2816
```

<210> SEQ ID NO 334
<211> LENGTH: 2082
<212> TYPE: DNA
<213> ORGANISM: Homo sapiens

<400> SEQUENCE: 334

```
agatgctaca gcgactgcac acccaggctg tatgatacag cctattgctc ccgggctgca      60
aacctgtcca gcatgtgatg tggtgggata ctgaattgaa taccgaatac tgtaggcaat     120
tgtaacacag tggtaagtct ttgtgtatct aaacatagct aaacaccaaa aggtatagta     180
agaatatggt attataatct tatggaacta tcattgtata tgtggtttgt caaccagaat     240
gtagttatac agcacaggac tgtgcttatg atgtgccaag cacagctctc agtactaact     300
cctttaatct tcatatcaac cctaggaggt aacttcttaa gtagattcat attgtaaggg     360 tctcgggggtg gggggttgg caaaatcctg gagccagaag aaaggacagc agcattgatc     420
aatcttacag ctaacatgtt gtacctggaa aacaatgccc agactcaatt tagtgagcca     480
```

-continued

```
cagtacacga acctgggget cctgaacagc atggaccagc agattcagaa cggctcctcg    540
tccaccagtc cctataacac agaccacgcg cagaacagcg tcacggcgcc ctcgccctac    600
gcacagccca gctccacctt cgatgctctc tctccatcac ccgccatccc ctccaacacc    660
gactacccag gcccgcacag tttcgacgtg tccttccagc agtcgagcac cgccaagtcg    720
gccacctgga cgtattccac tgaactgaag aaactctact gccaaattgc aaagacatgc    780
cccatccaga tcaaggtgat gaccccacct cctcagggag ctgttatccg cgccatgcct    840
gtctacaaaa aagctgagca cgtcacggag gtggtgaagg ggtgccccaa ccatgagctg    900
agccgtgaat caacgaggg acagattgcc cctcctagtc atttgattcg agtagagggg    960
aacagccatg cccagtatgt agaagatccc atcacaggaa gacagagtgt gctggtacct   1020
tatgagccac cccaggttgg cactgaattc acgacagtct tgtacaattt catgtgtaac   1080
agcagttgtg ttggagggat gaaccgccgt ccaattttaa tcattgttac ctgaaaacc    1140 agagatgggc aagtcctggg ccgacgctgc tttgaggccc ggatctgtgc ttgcccagga   1200
agagacagga aggcggatga agatagcatc agaaagcagc aagtttcgga cagtacaaag   1260
aacggtgatg gtacgaagcg cccgtctcgt cagaacacac atggtatcca gatgacatcc   1320
atcaagaaac gaagatcccc agatgatgaa ctgttatact taccagtgag gggccgtgag   1380
acttatgaaa tgctgttgaa gatcaaagag tccctggaac tcatgcagta ccttcctcag   1440
cacacaattg aaacgtacag gcaacagcaa cagcagcagc accagcactt acttcagaaa   1500
cagtgagtgt atcaacgtgt cattttagga ggcatgagtg acggtgactt tatttggatc   1560
agcaataggg tgattgatga gcaatgtgga acataatggg agatagcaga ttgtcataga   1620
ttcagatgac ctggtatggc aaccctcttt cagttgcaac cttttttacg tgtcttatta   1680
taaccttccc ttcagaattc cacttatgtt ctgaaattaa atacaaacca tttctggtga   1740
attacaaaga aactcacact aacagttctc ttctctatat gcctggtcca tacacactaa   1800
cagtaagtac acactctatt tggtagtgat gtgtatattt gaaaacatga aatcttttct   1860
catcccaatg gattgtctta taatctcct gggatgcaca ctatccactt ttgggaataa   1920
cactgtagac cagggatagc aaataggctt tactataata taaagtgact tgtttgaatg   1980
ctgtaatgag aagaattctg agacctagtg catgataatt ggggaaatat ctgggtgcag   2040
aaggataagg tagcatcatg ttgccgtatt ttagcatctc tg                      2082
```

<210> SEQ ID NO 335
<211> LENGTH: 4849
<212> TYPE: DNA
<213> ORGANISM: Homo sapiens

<400> SEQUENCE: 335

```
cgttgatatc aaagacagtt gaaggaaatg aattttgaaa cttcacggtg tgccacccta     60
cagtactgcc ctgaccctta catccagcgt ttcgtagaaa ccccagctca tttctcttgg    120
aaagaaagtt attaccgatc caccatgtcc cagagcacac agacaaatga attcctcagt    180
ccagaggttt tccagcatat ctgggatttt ctggaacagc ctatatgttc agttcagccc    240
attgacttga actttgtgga tgaaccatca gaagatggtg cgacaaacaa gattgagatt    300
agcatggact gtatccgcat gcaggactcg gacctgagtg accccatgtg ccacagtac    360 acgaacctgg ggctcctgaa cagcatggac cagcagattc agaacggctc ctcgtccacc    420 agtcccatата acacagacca cgcgcagaac agcgtcacgg cgcccctcgcc ctacgcacag    480 cccagctcca ccttcgatgc tctctctcca tcacccgcca tcccctccaa caccgactac    540
```

-continued

```
ccaggcccgc acagtttcga cgtgtccttc cagcagtcga gcaccgccaa gtcggccacc    600
tggacgtatt ccactgaact gaagaaactc tactgccaaa ttgcaaagac atgcccatc    660
cagatcaagg tgatgacccc acctcctcag ggagctgtta ccgcgccat gcctgtctac    720
aaaaaagctg agcacgtcac ggaggtggtg aagcggtgcc ccaaccatga gctgagccgt    780
gaattcaacg agggacagat tgcccctcct agtcatttga ttcgagtaga ggggaacagc    840
catgcccagt atgtagaaga tcccatcaca ggaagacaga gtgtgctggt accttatgag    900
ccaccccagg ttggcactga attcacgaca gtcttgtaca atttcatgtg taacagcagt    960
tgtgttggag ggatgaaccg ccgtccaatt ttaatcattg ttactctgga accagagat    1020
gggcaagtcc tgggccgacg ctgctttgag gcccggatct gtgcttgccc aggaagagac   1080
aggaaggcgg atgaagatag catcagaaag cagcaagttt cggacagtac aaagaacggt   1140
gatggtacga agcgcccgtt tcgtcagaac acacatggta tccagatgac atccatcaag   1200
aaacgaagat ccccagatga tgaactgtta tacttaccag tgagggggccg tgagacttat  1260
gaaatgctgt tgaagatcaa agagtccctg gaactcatgc agtaccttcc tcagcacaca   1320
attgaaacgt acaggcaaca gcaacagcag cagcaccagc acttacttca gaaacagacc   1380
tcaatacagt ctccatcttc atatggtaac agctccccac ctctgaacaa atgaacagc    1440
atgaacaagc tgccttctgt gagccagctt atcaaccctc agcagcgcaa cgccctcact   1500
cctacaacca ttcctgatgg catgggagcc aacattccca tgatgggcac ccacatgcca   1560
atggctggag acatgaatgg actcagcccc acccaggcac tccctccccc actctccatg   1620
ccatccacct cccagtgcac accccacct ccgtatccca cagattgcag cattgtcagt    1680
ttcttagcga ggttgggctg ttcatcatgt ctggactatt tcacgaccca ggggctgacc   1740
accatctatc agattgagca ttactccatg gatgatctgg caagtctgaa atccctgag    1800
caatttcgac atgcgatctg gaagggcatc ctggaccacc ggcagctcca cgaattctcc   1860
tccccttctc atctcctgcg gaccccaagc agtgcctcta cagtcagtgt gggctccagt   1920
gagacccggg gtgagcgtgt tattgatgct gtgcgattca ccctccgcca gaccatctct   1980
ttcccacccc gagatgagtg gaatgacttc aactttgaca tggatgctcg ccgcaataag   2040
caacagcgca tcaaagagga gggggagtga gcctcaccat gtgagctctt cctatccctc   2100
tcctaactgc cagcycccta aaagcactcc tgcttaatct tcaaagcctt ctccctagct   2160
cctcccctttc ctcttgtctg atttcttagg ggaaggagaa gtaagaggct acctcttacc   2220
taacatctga cctggcatct aattctgatt ctggctttaa gccttcaaaa ctatagcttg   2280
cagaactgta gctgccatgg ctaggtagaa gtgagcaaaa aagagttggg tgtctcctta   2340
agctgcagag atttctcatt gactttata aagcatgttc acccttatag tctaagacta    2400
tatatataaa tgtataaata tacagtatag attttttggt gggggcatt gagtattgtt    2460
taaaatgtaa tttaaatgaa agaaaattga gttgcactta ttgaccattt tttaatttac   2520
ttgttttgga tggcttgtct atactccttc ccttaagggg tatcatgtat ggtgataggt   2580
atctagagct taatgctaca tgtgagtgac gatgatgtac agattctttc agttctttgg   2640
attctaaata catgccacat caaacctttg agtagatcca tttccattgc ttattatgta   2700
ggtaagactg tagatatgta ttcttttctc agtgttggta tattttatat tactgacatt   2760
tcttctagtg atgatggttc acgttgggt gatttaatcc agttataaga agaagttcat    2820
gtccaaacgt cctctttagt ttttggttgg gaatgaggaa aattcttaaa aggcccatag   2880
```

| | |
|---|---|
| cagccagttc aaaaacaccc gacgtcatgt atttgagcat atcagtaacc cccttaaatt | 2940 |
| taataccaga taccttatct tacaatattg attgggaaaa catttgctgc cattacagag | 3000 |
| gtattaaaac taaatttcac tactagattg actaactcaa atacacattt gctactgttg | 3060 |
| taagaattct gattgatttg attgggatga atgccatcta tctagttcta acagtgaagt | 3120 |
| tttactgtct attaatattc agggtaaata ggaatcattc agaaatgttg agtctgtact | 3180 |
| aaacagtaag atatctcaat gaaccataaa ttcaactttg taaaaatctt ttgaagcata | 3240 |
| gataatattg tttggtaaat gttctttttg tttggtaaat gtttctttta aagaccctcc | 3300 |
| tattctataa aactctgcat gtagaggctt gtttaccttt ctctctctaa ggtttacaat | 3360 |
| aggagtggtg atttgaaaaa tataaaatta tgagattggt tttcctgtgg cataaattgc | 3420 |
| atcactgtat catttctttt tttaaccggt aagagtttca gtttgttgga agtaactgt | 3480 |
| gagaacccag tttcccgtcc atctccctta ggactaccc atagacatga aaggtcccca | 3540 |
| cagagcaaga gataagtctt tcatggctgc tgttgcttaa accacttaaa cgaagagttc | 3600 |
| ccttgaaact ttgggaaaac atgttaatga caatattcca gatctttcag aaatataaca | 3660 |
| cattttttg catgcatgca aatgagctct gaaatcttcc catgcattct ggtcaagggc | 3720 |
| tgtcattgca cataagcttc catttaatt ttaaagtgca aaagggccag cgtggctcta | 3780 |
| aaaggtaatg tgtggattgc ctctgaaaag tgtgtatata ttttgtgtga aattgcatac | 3840 |
| tttgtattt gattattttt ttttcttct tgggatagtg ggatttccag aaccacactt | 3900 |
| gaaaccttt tttatcgttt ttgtattttc atgaaaatac catttagtaa gaataccaca | 3960 |
| tcaaataaga aataatgcta caattttaag aggggaggga agggaaagtt ttttttatt | 4020 |
| atttttttaa aattttgtat gttaaagaga atgagtcctt gatttcaaag ttttgttgta | 4080 |
| cttaaatggt aataagcact gtaaacttct gcaacaagca tgcagctttg caaacccatt | 4140 |
| aaggggaaga atgaaagctg ttccttggtc ctagtaagaa gacaaactgc ttcccttact | 4200 |
| ttgctgaggg tttgaataaa cctaggactt ccgagctatg tcagtactat tcaggtaaca | 4260 |
| ctagggcctt ggaaattcct gtactgtgtc tcatggattt ggcactagcc aaagcgaggc | 4320 |
| acccttactg gcttacctcc tcatggcagc ctactctcct tgagtgtatg agtagccagg | 4380 |
| gtaagggta aaaggatagt aagcatagaa accactagaa agtgggctta atggagttct | 4440 |
| tgtggcctca gctcaatgca gttagctgaa gaattgaaaa gttttgttt ggagacgttt | 4500 |
| ataaacagaa atggaaagca gagttttcat taaatccttt tacctttttt ttttcttggt | 4560 |
| aatcccctaa aataacagta tgtgggatat tgaatgttaa agggatattt tttttctatt | 4620 |
| attttttataa ttgtacaaaa ttaagcaaat gttaaaagtt ttatatgctt tattaatgtt | 4680 |
| ttcaaaaggt attatacatg tgatacattt tttaagcttc agttgcttgt cttctggtac | 4740 |
| tttctgttat gggcttttgg ggagccagaa gccaatctac aatctctttt tgtttgccag | 4800 |
| gacatgcaat aaaatttaaa aaataaataa aaactaatta agaaataaa | 4849 |

<210> SEQ ID NO 336
<211> LENGTH: 1386
<212> TYPE: DNA
<213> ORGANISM: Homo sapiens

<400> SEQUENCE: 336

| | |
|---|---|
| atgttgtacc tggaaaacaa tgcccagact caatttagtg agccacagta cacgaacctg | 60 |
| gggctcctga acagcatgga ccagcagatt cagaacggct cctcgtccac cagtccctat | 120 |
| aacacagacc acgcgcagaa cagcgtcacg gcgccctcgc cctacgcaca gccagctcc | 180 |

```
accttcgatg ctctctctcc atcacccgcc atcccctcca acaccgacta cccaggcccg      240
cacagtttcg acgtgtcctt ccagcagtcg agcaccgcca agtcggccac ctggacgtat      300
tccactgaac tgaagaaact ctactgccaa attgcaaaga catgcccat ccagatcaag       360 gtgatgaccc cacctcctca gggagctgtt atccgcgcca tgcctgtcta caaaaaagct      420
gagcacgtca cggaggtggt gaagcggtgc cccaaccatg agctgagccg tgaattcaac      480
gagggacaga ttgcccctcc tagtcatttg attcgagtag aggggaacag ccatgcccag      540
tatgtagaag atcccatcac aggaagacag agtgtgctgg taccttatga gccaccccag      600
gttggcactg aattcacgac agtcttgtac aatttcatgt gtaacagcag ttgtgttgga      660
gggatgaacc gccgtccaat tttaatcatt gttactctgg aaaccagaga tgggcaagtc      720
ctgggccgac gctgctttga ggcccggatc tgtgcttgcc caggaagaga caggaaggcg      780
gatgaagata gcatcagaaa gcagcaagtt cggacagta caaagaacgg tgatggtacg       840
aagcgcccgt ttcgtcagaa cacacatggt atccagatga catccatcaa gaaacgaaga      900
tccccagatg atgaactgtt atacttacca gtgaggggcc gtgagactta tgaaatgctg      960
ttgaagatca aagagtccct ggaactcatg cagtaccttc ctcagcacac aattgaaacg     1020
tacaggcaac agcaacagca gcagcaccag cacttacttc agaaacagac ctcaatacag     1080
tctccatctt catatggtaa cagctcccca cctctgaaca aaatgaacag catgaacaag     1140
ctgccttctg tgagccagct tatcaaccct cagcagcgca acgccctcac tcctacaacc     1200
attcctgatg gcatgggagc caacattccc atgatgggca cccacatgcc aatggctgga     1260
gacatgaatg gactcagccc cacccaggca ctccctcccc cactctccat gccatccacc     1320
tcccactgca cacccccacc tccgtatccc acagattgca gcattgtcag gatctggcaa     1380
gtctga                                                                1386

<210> SEQ ID NO 337
<211> LENGTH: 1551
<212> TYPE: DNA
<213> ORGANISM: Homo sapiens

<400> SEQUENCE: 337
atgtcccaga gcacacagac aaatgaattc ctcagtccag aggttttcca gcatatctgg       60
gattttctgg aacagcctat atgttcagtt cagcccattg acttgaactt tgtggatgaa      120
ccatcagaag atggtgcgac aaacaagatt gagattagca tggactgtat ccgcatgcag      180
gactcggacc tgagtgaccc catgtggcca cagtacacga acctggggct cctgaacagc      240
atggaccagc agattcagaa cggctcctcg tccaccagtc cctataacac agaccacgcg      300
cagaacagcg tcacggcgcc ctcgccctac gcacagccca gctccacctt cgatgctctc      360
tctccatcac ccgccatccc ctccaacacc gactacccag gccgcacag tttcgacgtg      420 tccttccagc agtcgagcac cgccaagtcg gccacctgga cgtattccac tgaactgaag     480
aaactctact gccaaattgc aaagacatgc ccatcagaa tcaaggtgat gaccccacct      540
cctcagggag ctgttatccg cgccatgcct gtctacaaaa aagctgagca cgtcacggag      600
gtggtgaagc ggtgccccaa ccatgagctg agccgtgaat tcaacgaggg acagattgcc      660
cctcctagtc atttgattcg agtagagggg aacagccatg cccagtatgt agaagatccc      720
atcacaggaa gacagagtgt gctggtacct tatgagccac cccaggttgg cactgaattc      780
acgacagtct tgtacaattt catgtgtaac agcagttgtg ttggagggat gaaccgccgt      840
```

-continued

```
ccaattttaa tcattgttac tctggaaacc agagatgggc aagtcctggg ccgacgctgc      900
tttgaggccc ggatctgtgc ttgcccagga agagacagga aggcggatga agatagcatc      960
agaaagcagc aagtttcgga cagtacaaag aacggtgatg gtacgaagcg cccgtttcgt     1020
cagaacacac atggtatcca gatgacatcc atcaagaaac gaagatcccc agatgatgaa     1080
ctgttatact taccagtgag gggccgtgag acttatgaaa tgctgttgaa gatcaaagag     1140
tccctggaac tcatgcagta ccttcctcag cacacaattg aaacgtacag gcaacagcaa     1200
cagcagcagc accagcactt acttcagaaa cagacctcaa tacagtctcc atcttcatat     1260
ggtaacagct ccccacctct gaacaaaatg aacagcatga acaagctgcc ttctgtgagc     1320
cagcttatca accctcagca gcgcaacgcc ctcactccta caaccattcc tgatggcatg     1380
ggagccaaca ttcccatgat gggcacccac atgccaatgg ctggagacat gaatggactc     1440
agccccaccc aggcactccc tccccactc tccatgccat ccacctccca ctgcacaccc     1500
ccacctccgt atcccacaga ttgcagcatt gtcaggatct ggcaagtctg a              1551
```

<210> SEQ ID NO 338
<211> LENGTH: 586
<212> TYPE: PRT
<213> ORGANISM: Homo sapiens

<400> SEQUENCE: 338

```
Met Leu Tyr Leu Glu Asn Asn Ala Gln Thr Gln Phe Ser Glu Pro Gln
                 5                  10                  15

Tyr Thr Asn Leu Gly Leu Leu Asn Ser Met Asp Gln Gln Ile Arg Asn
             20                  25                  30

Gly Ser Ser Ser Thr Ser Pro Tyr Asn Thr Asp His Ala Gln Asn Ser
         35                  40                  45

Val Thr Ala Pro Ser Pro Tyr Ala Gln Pro Ser Pro Thr Phe Asp Ala
     50                  55                  60

Leu Ser Pro Ser Pro Ala Ile Pro Ser Asn Thr Asp Tyr Pro Gly Pro
 65                  70                  75                  80

His Ser Ser Asp Val Ser Phe Gln Gln Ser Ser Thr Ala Lys Ser Ala
                 85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Gln Gly
        115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255
```

```
Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Phe Arg Gln Asn Thr
            275                 280                 285

His Gly Ile Gln Met Thr Ser Ile Lys Lys Arg Arg Ser Pro Asp Asp
            290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln His Gln His Leu
            340                 345                 350

Leu Gln Lys Gln Thr Ser Ile Gln Ser Pro Ser Ser Tyr Gly Asn Ser
            355                 360                 365

Ser Pro Pro Leu Asn Lys Met Asn Ser Met Asn Lys Leu Pro Ser Val
370                 375                 380

Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
            405                 410                 415

Pro Met Ala Gly Asp Met Asn Gly Leu Ser Pro Thr Gln Ala Leu Pro
            420                 425                 430

Pro Pro Leu Ser Met Pro Ser Thr Ser His Cys Thr Pro Pro Pro Pro
            435                 440                 445

Tyr Pro Thr Asp Cys Ser Ile Val Ser Phe Leu Ala Arg Leu Gly Cys
            450                 455                 460

Ser Ser Cys Leu Asp Tyr Phe Thr Thr Gln Gly Leu Thr Thr Ile Tyr
465                 470                 475                 480

Gln Ile Glu His Tyr Ser Met Asp Asp Leu Ala Ser Leu Lys Ile Pro
                485                 490                 495

Glu Gln Phe Arg His Ala Ile Trp Lys Gly Ile Leu Asp His Arg Gln
            500                 505                 510

Leu His Glu Phe Ser Ser Pro Ser His Leu Leu Arg Thr Pro Ser Ser
            515                 520                 525

Ala Ser Thr Val Ser Val Gly Ser Ser Glu Thr Arg Gly Glu Arg Val
            530                 535                 540

Ile Asp Ala Val Arg Phe Thr Leu Arg Gln Thr Ile Ser Phe Pro Pro
545                 550                 555                 560

Arg Asp Glu Trp Asn Asp Phe Asn Phe Asp Met Asp Ala Arg Arg Asn
                565                 570                 575

Lys Gln Gln Arg Ile Lys Glu Glu Gly Glu
            580                 585

<210> SEQ ID NO 339
<211> LENGTH: 641
<212> TYPE: PRT
<213> ORGANISM: Homo sapiens

<400> SEQUENCE: 339

Met Ser Gln Ser Thr Gln Thr Asn Glu Phe Leu Ser Pro Glu Val Phe
                5                   10                  15

Gln His Ile Trp Asp Phe Leu Glu Gln Pro Ile Cys Ser Val Gln Pro
            20                  25                  30

Ile Asp Leu Asn Phe Val Asp Glu Pro Ser Glu Asp Gly Ala Thr Asn
```

-continued

```
                35                  40                  45
Lys Ile Glu Ile Ser Met Asp Cys Ile Arg Met Gln Asp Ser Asp Leu
         50                  55                  60
Ser Asp Pro Met Trp Pro Gln Tyr Thr Asn Leu Gly Leu Leu Asn Ser
 65                  70                  75                  80
Met Asp Gln Gln Ile Gln Asn Gly Ser Ser Thr Ser Pro Tyr Asn
                 85                  90                  95
Thr Asp His Ala Gln Asn Ser Val Thr Ala Pro Ser Pro Tyr Ala Gln
                100                 105                 110
Pro Ser Ser Thr Phe Asp Ala Leu Ser Pro Ser Pro Ala Ile Pro Ser
                115                 120                 125
Asn Thr Asp Tyr Pro Gly Pro His Ser Phe Asp Val Ser Phe Gln Gln
            130                 135                 140
Ser Ser Thr Ala Lys Ser Ala Thr Trp Thr Tyr Ser Thr Glu Leu Lys
145                 150                 155                 160
Lys Leu Tyr Cys Gln Ile Ala Lys Thr Cys Pro Ile Gln Ile Lys Val
                165                 170                 175
Met Thr Pro Pro Pro Gln Gly Ala Val Ile Arg Ala Met Pro Val Tyr
                180                 185                 190
Lys Lys Ala Glu His Val Thr Glu Val Val Lys Arg Cys Pro Asn His
            195                 200                 205
Glu Leu Ser Arg Glu Phe Asn Glu Gly Gln Ile Ala Pro Pro Ser His
            210                 215                 220
Leu Ile Arg Val Glu Gly Asn Ser His Ala Gln Tyr Val Glu Asp Pro
225                 230                 235                 240
Ile Thr Gly Arg Gln Ser Val Leu Val Pro Tyr Glu Pro Pro Gln Val
                245                 250                 255
Gly Thr Glu Phe Thr Thr Val Leu Tyr Asn Phe Met Cys Asn Ser Ser
                260                 265                 270
Cys Val Gly Gly Met Asn Arg Arg Pro Ile Leu Ile Ile Val Thr Leu
            275                 280                 285
Glu Thr Arg Asp Gly Gln Val Leu Gly Arg Arg Cys Phe Glu Ala Arg
            290                 295                 300
Ile Cys Ala Cys Pro Gly Arg Asp Arg Lys Ala Asp Glu Asp Ser Ile
305                 310                 315                 320
Arg Lys Gln Gln Val Ser Asp Ser Thr Lys Asn Gly Asp Gly Thr Lys
                325                 330                 335
Arg Pro Phe Arg Gln Asn Thr His Gly Ile Gln Met Thr Ser Ile Lys
            340                 345                 350
Lys Arg Arg Ser Pro Asp Asp Glu Leu Leu Tyr Leu Pro Val Arg Gly
            355                 360                 365
Arg Glu Thr Tyr Glu Met Leu Leu Lys Ile Lys Glu Ser Leu Glu Leu
            370                 375                 380
Met Gln Tyr Leu Pro Gln His Thr Ile Glu Thr Tyr Arg Gln Gln Gln
385                 390                 395                 400
Gln Gln Gln His Gln His Leu Leu Gln Lys Gln Thr Ser Ile Gln Ser
                405                 410                 415
Pro Ser Ser Tyr Gly Asn Ser Ser Pro Pro Leu Asn Lys Met Asn Ser
                420                 425                 430
Met Asn Lys Leu Pro Ser Val Ser Gln Leu Ile Asn Pro Gln Gln Arg
            435                 440                 445
Asn Ala Leu Thr Pro Thr Thr Ile Pro Asp Gly Met Gly Ala Asn Ile
450                 455                 460
```

```
Pro Met Met Gly Thr His Met Pro Met Ala Gly Asp Met Asn Gly Leu
465                 470                 475                 480

Ser Pro Thr Gln Ala Leu Pro Pro Leu Ser Met Pro Ser Thr Ser
            485                 490                 495

His Cys Thr Pro Pro Pro Tyr Pro Thr Asp Cys Ser Ile Val Gly
            500                 505                 510

Phe Leu Ala Arg Leu Gly Cys Ser Ser Cys Leu Asp Tyr Phe Thr Thr
            515                 520                 525

Gln Gly Leu Thr Thr Ile Tyr Gln Ile Glu His Tyr Ser Met Asp Asp
530                 535                 540

Leu Ala Ser Leu Lys Ile Pro Glu Gln Phe Arg His Ala Ile Trp Lys
545                 550                 555                 560

Gly Ile Leu Asp His Arg Gln Leu His Glu Phe Ser Ser Pro Ser His
            565                 570                 575

Leu Leu Arg Thr Pro Ser Ser Ala Ser Thr Val Ser Val Gly Ser Ser
            580                 585                 590

Glu Thr Arg Gly Glu Arg Val Ile Asp Ala Val Arg Phe Thr Leu Arg
            595                 600                 605

Gln Thr Ile Ser Phe Pro Pro Arg Asp Glu Trp Asn Asp Phe Asn Phe
            610                 615                 620

Asp Met Asp Ala Arg Arg Asn Lys Gln Gln Arg Ile Lys Glu Glu Gly
625                 630                 635                 640

Glu

<210> SEQ ID NO 340
<211> LENGTH: 448
<212> TYPE: PRT
<213> ORGANISM: Homo sapiens

<400> SEQUENCE: 340

Met Ser Gln Ser Thr Gln Thr Asn Glu Phe Leu Ser Pro Glu Val Phe
                5                   10                  15

Gln His Ile Trp Asp Phe Leu Glu Gln Pro Ile Cys Ser Val Gln Pro
            20                  25                  30

Ile Asp Leu Asn Phe Val Asp Glu Pro Ser Glu Asp Gly Ala Thr Asn
        35                  40                  45

Lys Ile Glu Ile Ser Met Asp Cys Ile Arg Met Gln Asp Ser Asp Leu
50                  55                  60

Ser Asp Pro Met Trp Pro Gln Tyr Thr Asn Leu Gly Leu Leu Asn Ser
65                  70                  75                  80

Met Asp Gln Gln Ile Gln Asn Gly Ser Ser Ser Thr Ser Pro Tyr Asn
                85                  90                  95

Thr Asp His Ala Gln Asn Ser Val Thr Ala Pro Ser Pro Tyr Ala Gln
            100                 105                 110

Pro Ser Ser Thr Phe Asp Ala Leu Ser Pro Ser Pro Ala Ile Pro Ser
            115                 120                 125

Asn Thr Asp Tyr Pro Gly Pro His Ser Phe Asp Val Ser Phe Gln Gln
        130                 135                 140

Ser Ser Thr Ala Lys Ser Ala Thr Trp Thr Tyr Ser Thr Glu Leu Lys
145                 150                 155                 160

Lys Leu Tyr Cys Gln Ile Ala Lys Thr Cys Pro Ile Gln Ile Lys Val
                165                 170                 175

Met Thr Pro Pro Pro Gln Gly Ala Val Ile Arg Ala Met Pro Val Tyr
            180                 185                 190
```

-continued

```
Lys Lys Ala Glu His Val Thr Glu Val Val Lys Arg Cys Pro Asn His
            195                 200                 205
Glu Leu Ser Arg Glu Phe Asn Glu Gly Gln Ile Ala Pro Pro Ser His
    210                 215                 220
Leu Ile Arg Val Glu Gly Asn Ser His Ala Gln Tyr Val Glu Asp Pro
225                 230                 235                 240
Ile Thr Gly Arg Gln Ser Val Leu Val Pro Tyr Glu Pro Pro Gln Val
                245                 250                 255
Gly Thr Glu Phe Thr Thr Val Leu Tyr Asn Phe Met Cys Asn Ser Ser
            260                 265                 270
Cys Val Gly Gly Met Asn Arg Arg Pro Ile Leu Ile Ile Val Thr Leu
        275                 280                 285
Glu Thr Arg Asp Gly Gln Val Leu Gly Arg Arg Cys Phe Glu Ala Arg
    290                 295                 300
Ile Cys Ala Cys Pro Gly Arg Asp Arg Lys Ala Asp Glu Asp Ser Ile
305                 310                 315                 320
Arg Lys Gln Gln Val Ser Asp Ser Thr Lys Asn Gly Asp Gly Thr Lys
                325                 330                 335
Arg Pro Phe Arg Gln Asn Thr His Gly Ile Gln Met Thr Ser Ile Lys
            340                 345                 350
Lys Arg Arg Ser Pro Asp Asp Glu Leu Leu Tyr Leu Pro Val Arg Gly
        355                 360                 365
Arg Glu Thr Tyr Glu Met Leu Leu Lys Ile Lys Glu Ser Leu Glu Leu
    370                 375                 380
Met Gln Tyr Leu Pro Gln His Thr Ile Glu Thr Tyr Arg Gln Gln Gln
385                 390                 395                 400
Gln Gln Gln His Gln His Leu Leu Gln Lys His Leu Leu Ser Ala Cys
                405                 410                 415
Phe Arg Asn Glu Leu Val Glu Pro Arg Arg Glu Thr Pro Lys Gln Ser
            420                 425                 430
Asp Val Phe Phe Arg His Ser Lys Pro Pro Asn Arg Ser Val Tyr Pro
        435                 440                 445

<210> SEQ ID NO 341
<211> LENGTH: 356
<212> TYPE: PRT
<213> ORGANISM: Homo sapiens

<400> SEQUENCE: 341

Met Leu Tyr Leu Glu Asn Asn Ala Gln Thr Gln Phe Ser Glu Pro Gln
                5                   10                  15
Tyr Thr Asn Leu Gly Leu Leu Asn Ser Met Asp Gln Gln Ile Gln Asn
            20                  25                  30
Gly Ser Ser Ser Thr Ser Pro Tyr Asn Thr Asp His Ala Gln Asn Ser
        35                  40                  45
Val Thr Ala Pro Ser Pro Tyr Ala Gln Pro Ser Ser Thr Phe Asp Ala
    50                  55                  60
Leu Ser Pro Ser Pro Ala Ile Pro Ser Asn Thr Asp Tyr Pro Gly Pro
65                  70                  75                  80
His Ser Phe Asp Val Ser Phe Gln Gln Ser Ser Thr Ala Lys Ser Ala
                85                  90                  95
Thr Trp Thr Tyr Ser Thr Glu Leu Lys Lys Leu Tyr Cys Gln Ile Ala
            100                 105                 110
Lys Thr Cys Pro Ile Gln Ile Lys Val Met Thr Pro Pro Gln Gly
```

```
            115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Val Ser Asp
            260                 265                 270

Ser Thr Lys Asn Gly Asp Gly Thr Lys Arg Pro Ser Arg Gln Asn Thr
        275                 280                 285

His Gly Ile Gln Met Thr Ser Ile Lys Lys Arg Arg Ser Pro Asp Asp
    290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln His Gln His Leu
            340                 345                 350

Leu Gln Lys Gln
        355

<210> SEQ ID NO 342
<211> LENGTH: 680
<212> TYPE: PRT
<213> ORGANISM: Homo sapiens

<400> SEQUENCE: 342

Met Asn Phe Glu Thr Ser Arg Cys Ala Thr Leu Gln Tyr Cys Pro Asp
                5                   10                  15

Pro Tyr Ile Gln Arg Phe Val Glu Thr Pro Ala His Phe Ser Trp Lys
            20                  25                  30

Glu Ser Tyr Tyr Arg Ser Thr Met Ser Gln Ser Thr Gln Thr Asn Glu
        35                  40                  45

Phe Leu Ser Pro Glu Val Phe Gln His Ile Trp Asp Phe Leu Glu Gln
    50                  55                  60

Pro Ile Cys Ser Val Gln Pro Ile Asp Leu Asn Phe Val Asp Glu Pro
65                  70                  75                  80

Ser Glu Asp Gly Ala Thr Asn Lys Ile Glu Ile Ser Met Asp Cys Ile
                85                  90                  95

Arg Met Gln Asp Ser Asp Leu Ser Asp Pro Met Trp Pro Gln Tyr Thr
            100                 105                 110

Asn Leu Gly Leu Leu Asn Ser Met Asp Gln Gln Ile Gln Asn Gly Ser
        115                 120                 125
```

```
Ser Ser Thr Ser Pro Tyr Asn Thr Asp His Ala Gln Asn Ser Val Thr
130                 135                 140

Ala Pro Ser Pro Tyr Ala Gln Pro Ser Ser Thr Phe Asp Ala Leu Ser
145                 150                 155                 160

Pro Ser Pro Ala Ile Pro Ser Asn Thr Asp Tyr Pro Gly Pro His Ser
                165                 170                 175

Phe Asp Val Ser Phe Gln Gln Ser Ser Thr Ala Lys Ser Ala Thr Trp
            180                 185                 190

Thr Tyr Ser Thr Glu Leu Lys Lys Leu Tyr Cys Gln Ile Ala Lys Thr
        195                 200                 205

Cys Pro Ile Gln Ile Lys Val Met Thr Pro Pro Gln Gly Ala Val
    210                 215                 220

Ile Arg Ala Met Pro Val Tyr Lys Lys Ala Glu His Val Thr Glu Val
225                 230                 235                 240

Val Lys Arg Cys Pro Asn His Glu Leu Ser Arg Glu Phe Asn Glu Gly
                245                 250                 255

Gln Ile Ala Pro Pro Ser His Leu Ile Arg Val Glu Gly Asn Ser His
            260                 265                 270

Ala Gln Tyr Val Glu Asp Pro Ile Thr Gly Arg Gln Ser Val Leu Val
        275                 280                 285

Pro Tyr Glu Pro Pro Gln Val Gly Thr Glu Phe Thr Thr Val Leu Tyr
    290                 295                 300

Asn Phe Met Cys Asn Ser Ser Cys Val Gly Gly Met Asn Arg Arg Pro
305                 310                 315                 320

Ile Leu Ile Ile Val Thr Leu Glu Thr Arg Asp Gly Gln Val Leu Gly
                325                 330                 335

Arg Arg Cys Phe Glu Ala Arg Ile Cys Ala Cys Pro Gly Arg Asp Arg
            340                 345                 350

Lys Ala Asp Glu Asp Ser Ile Arg Lys Gln Gln Val Ser Asp Ser Thr
        355                 360                 365

Lys Asn Gly Asp Gly Thr Lys Arg Pro Phe Arg Gln Asn Thr His Gly
    370                 375                 380

Ile Gln Met Thr Ser Ile Lys Lys Arg Arg Ser Pro Asp Asp Glu Leu
385                 390                 395                 400

Leu Tyr Leu Pro Val Arg Gly Arg Glu Thr Tyr Glu Met Leu Leu Lys
                405                 410                 415

Ile Lys Glu Ser Leu Glu Leu Met Gln Tyr Leu Pro Gln His Thr Ile
            420                 425                 430

Glu Thr Tyr Arg Gln Gln Gln Gln Gln His Gln His Leu Leu Gln
        435                 440                 445

Lys Gln Thr Ser Ile Gln Ser Pro Ser Ser Tyr Gly Asn Ser Ser Pro
    450                 455                 460

Pro Leu Asn Lys Met Asn Ser Met Asn Lys Leu Pro Ser Val Ser Gln
465                 470                 475                 480

Leu Ile Asn Pro Gln Gln Arg Asn Ala Leu Thr Pro Thr Thr Ile Pro
            485                 490                 495

Asp Gly Met Gly Ala Asn Ile Pro Met Met Gly Thr His Met Pro Met
        500                 505                 510

Ala Gly Asp Met Asn Gly Leu Ser Pro Thr Gln Ala Leu Pro Pro Pro
    515                 520                 525

Leu Ser Met Pro Ser Thr Ser Gln Cys Thr Pro Pro Pro Tyr Pro
530                 535                 540

Thr Asp Cys Ser Ile Val Ser Phe Leu Ala Arg Leu Gly Cys Ser Ser
```

```
545                 550                 555                 560

Cys Leu Asp Tyr Phe Thr Thr Gln Gly Leu Thr Thr Ile Tyr Gln Ile
                565                 570                 575

Glu His Tyr Ser Met Asp Asp Leu Ala Ser Leu Lys Ile Pro Glu Gln
                580                 585                 590

Phe Arg His Ala Ile Trp Lys Gly Ile Leu Asp His Arg Gln Leu His
                595                 600                 605

Glu Phe Ser Ser Pro Ser His Leu Leu Arg Thr Pro Ser Ser Ala Ser
                610                 615                 620

Thr Val Ser Val Gly Ser Ser Glu Thr Arg Gly Glu Arg Val Ile Asp
625                 630                 635                 640

Ala Val Arg Phe Thr Leu Arg Gln Thr Ile Ser Phe Pro Pro Arg Asp
                645                 650                 655

Glu Trp Asn Asp Phe Asn Phe Asp Met Asp Ala Arg Arg Asn Lys Gln
                660                 665                 670

Gln Arg Ile Lys Glu Glu Gly Glu
                675                 680

<210> SEQ ID NO 343
<211> LENGTH: 461
<212> TYPE: PRT
<213> ORGANISM: Homo sapiens

<400> SEQUENCE: 343

Met Leu Tyr Leu Glu Asn Asn Ala Gln Thr Gln Phe Ser Glu Pro Gln
                5                   10                  15

Tyr Thr Asn Leu Gly Leu Leu Asn Ser Met Asp Gln Gln Ile Gln Asn
                20                  25                  30

Gly Ser Ser Ser Thr Ser Pro Tyr Asn Thr Asp His Ala Gln Asn Ser
                35                  40                  45

Val Thr Ala Pro Ser Pro Tyr Ala Gln Pro Ser Ser Thr Phe Asp Ala
            50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
                100                 105                 110

Lys Thr Cys Pro Ile Gln Ile Lys Val Met Thr Pro Pro Pro Gln Gly
            115                 120                 125

Ala Val Ile Arg Ala Met Pro Val Tyr Lys Lys Ala Glu His Val Thr
130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
                195                 200                 205

Leu Tyr Asn Phe Met Cys Asn Ser Ser Cys Val Gly Gly Met Asn Arg
            210                 215                 220

Arg Pro Ile Leu Ile Ile Val Thr Leu Glu Thr Arg Asp Gly Gln Val
225                 230                 235                 240
```

```
Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
                260                 265                 270

Ser Thr Lys Asn Gly Asp Gly Thr Lys Arg Pro Phe Arg Gln Asn Thr
                275                 280                 285

His Gly Ile Gln Met Thr Ser Ile Lys Lys Arg Arg Ser Pro Asp Asp
290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln His Gln His Leu
                340                 345                 350

Leu Gln Lys Gln Thr Ser Ile Gln Ser Pro Ser Ser Tyr Gly Asn Ser
                355                 360                 365

Ser Pro Pro Leu Asn Lys Met Asn Ser Met Asn Lys Leu Pro Ser Val
370                 375                 380

Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
                405                 410                 415

Pro Met Ala Gly Asp Met Asn Gly Leu Ser Pro Thr Gln Ala Leu Pro
                420                 425                 430

Pro Pro Leu Ser Met Pro Ser Thr Ser His Cys Thr Pro Pro Pro Pro
                435                 440                 445

Tyr Pro Thr Asp Cys Ser Ile Val Arg Ile Trp Gln Val
                450                 455                 460

<210> SEQ ID NO 344
<211> LENGTH: 516
<212> TYPE: PRT
<213> ORGANISM: Homo sapiens

<400> SEQUENCE: 344

Met Ser Gln Ser Thr Gln Thr Asn Glu Phe Leu Ser Pro Glu Val Phe
                5                   10                  15

Gln His Ile Trp Asp Phe Leu Glu Gln Pro Ile Cys Ser Val Gln Pro
                20                  25                  30

Ile Asp Leu Asn Phe Val Asp Glu Pro Ser Glu Asp Gly Ala Thr Asn
                35                  40                  45

Lys Ile Glu Ile Ser Met Asp Cys Ile Arg Met Gln Asp Ser Asp Leu
50                  55                  60

Ser Asp Pro Met Trp Pro Gln Tyr Thr Asn Leu Gly Leu Leu Asn Ser
65                  70                  75                  80

Met Asp Gln Gln Ile Gln Asn Gly Ser Ser Thr Ser Pro Tyr Asn
                85                  90                  95

Thr Asp His Ala Gln Asn Ser Val Thr Ala Pro Ser Pro Tyr Ala Gln
                100                 105                 110

Pro Ser Ser Thr Phe Asp Ala Leu Ser Pro Ser Pro Ala Ile Pro Ser
                115                 120                 125

Asn Thr Asp Tyr Pro Gly Pro His Ser Phe Asp Val Ser Phe Gln Gln
                130                 135                 140

Ser Ser Thr Ala Lys Ser Ala Thr Trp Thr Tyr Ser Thr Glu Leu Lys
145                 150                 155                 160
```

-continued

```
Lys Leu Tyr Cys Gln Ile Ala Lys Thr Cys Pro Ile Gln Ile Lys Val
                165                 170                 175
Met Thr Pro Pro Pro Gln Gly Ala Val Ile Arg Ala Met Pro Val Tyr
                180                 185                 190
Lys Lys Ala Glu His Val Thr Glu Val Val Lys Arg Cys Pro Asn His
                195                 200                 205
Glu Leu Ser Arg Glu Phe Asn Glu Gly Gln Ile Ala Pro Pro Ser His
                210                 215                 220
Leu Ile Arg Val Glu Gly Asn Ser His Ala Gln Tyr Val Glu Asp Pro
225                 230                 235                 240
Ile Thr Gly Arg Gln Ser Val Leu Val Pro Tyr Glu Pro Pro Gln Val
                245                 250                 255
Gly Thr Glu Phe Thr Thr Val Leu Tyr Asn Phe Met Cys Asn Ser Ser
                260                 265                 270
Cys Val Gly Gly Met Asn Arg Arg Pro Ile Leu Ile Ile Val Thr Leu
                275                 280                 285
Glu Thr Arg Asp Gly Gln Val Leu Gly Arg Arg Cys Phe Glu Ala Arg
                290                 295                 300
Ile Cys Ala Cys Pro Gly Arg Asp Arg Lys Ala Asp Glu Asp Ser Ile
305                 310                 315                 320
Arg Lys Gln Gln Val Ser Asp Ser Thr Lys Asn Gly Asp Gly Thr Lys
                325                 330                 335
Arg Pro Phe Arg Gln Asn Thr His Gly Ile Gln Met Thr Ser Ile Lys
                340                 345                 350
Lys Arg Arg Ser Pro Asp Asp Glu Leu Leu Tyr Leu Pro Val Arg Gly
                355                 360                 365
Arg Glu Thr Tyr Glu Met Leu Leu Lys Ile Lys Glu Ser Leu Glu Leu
                370                 375                 380
Met Gln Tyr Leu Pro Gln His Thr Ile Glu Thr Tyr Arg Gln Gln Gln
385                 390                 395                 400
Gln Gln Gln His Gln His Leu Leu Gln Lys Gln Thr Ser Ile Gln Ser
                405                 410                 415
Pro Ser Ser Tyr Gly Asn Ser Ser Pro Pro Leu Asn Lys Met Asn Ser
                420                 425                 430
Met Asn Lys Leu Pro Ser Val Ser Gln Leu Ile Asn Pro Gln Gln Arg
                435                 440                 445
Asn Ala Leu Thr Pro Thr Thr Ile Pro Asp Gly Met Gly Ala Asn Ile
                450                 455                 460
Pro Met Met Gly Thr His Met Pro Met Ala Gly Asp Met Asn Gly Leu
465                 470                 475                 480
Ser Pro Thr Gln Ala Leu Pro Pro Leu Ser Met Pro Ser Thr Ser
                485                 490                 495
His Cys Thr Pro Pro Pro Tyr Pro Thr Asp Cys Ser Ile Val Arg
                500                 505                 510
Ile Trp Gln Val
        515

<210> SEQ ID NO 345
<211> LENGTH: 1800
<212> TYPE: DNA
<213> ORGANISM: Homo sapiens

<400> SEQUENCE: 345
gcgcctcatt gccactgcag tgactaaagc tgggaagacg ctggtcagtt cacctgcccc      60
```

-continued

```
actggttgtt ttttaaacaa attctgatac aggcgacatc ctcactgacc gagcaaagat    120
tgacattcgt atcatcactg tgcaccattg gcttctaggc actccagtgg ggtaggagaa    180
ggaggtctga aaccctcgca gagggatctt gccctcattc tttgggtctg aaacactggc    240
agtcgttgga aacaggactc agggataaac cagcgcaatg gattggggga cgctgcacac    300
tttcatcggg ggtgtcaaca aacactccac cagcatcggg aaggtgtgga tcacagtcat    360
ctttattttc cgagtcatga tcctagtggt ggctgcccag gaagtgtggg gtgacgagca    420
agaggacttc gtctgcaaca cactgcaacc gggatgcaaa aatgtgtgct atgaccactt    480
tttcccggtg tcccacatcc ggctgtgggc cctccagctg atcttcgtct ccaccccagc    540
gctgctggtg gccatgcatg tggcctacta caggcacgaa accactcgca agttcaggcg    600
aggagagaag aggaatgatt tcaaagacat agaggacatt aaaaagcaca aggttcggat    660
agaggggtcg ctgtggtgga cgtacaccag cagcatcttt ttccgaatca tctttgaagc    720
agcctttatg tatgtgtttt acttcccttta caatgggtac cacctgccct gggtgttgaa    780
atgtgggatt gaccccctgcc ccaaccttgt tgactgcttt atttctaggc caacagagaa    840
gaccgtgttt accatttttta tgatttctgc gtctgtgatt tgcatgctgc ttaacgtggc    900
agagttgtgc tacctgctgc tgaaagtgtg ttttaggaga tcaaagagag cacagacgca    960
aaaaaatcac cccaatcatg ccctaaagga gagtaagcag aatgaaatga atgagctgat   1020
ttcagatagt ggtcaaaatg caatcacagg tttcccaagc taaacatttc aaggtaaaat   1080
gtagctgcgt cataaggaga cttctgtctt ctccagaagg caataccaac ctgaaagttc   1140
cttctgtagc ctgaagagtt tgtaaatgac tttcataata aatagacact tgagttaact   1200
ttttgtagga tacttgctcc attcatacac aacgtaatca aatatgtggt ccatctctga   1260
aaacaagaga ctgcttgaca aaggagcatt gcagtcactt tgacaggttc cttttaagtg   1320
gactctctga caaagtgggt actttctgaa aatttatata actgttgttg ataaggaaca   1380
tttatccagg aattgatacg tttattagga aaagatattt ttataggctt ggatgttttt   1440
agttccgact ttgaatttat ataaagtatt tttataatga ctggtcttcc ttacctggaa   1500
aaacatgcga tgttagtttt agaattacac cacaagtatc taaatttcca acttacaaag   1560
ggtcctatct tgtaaatatt gttttgcatt gtctgttggc aaatttgtga actgtcatga   1620
tacgcttaag gtgggaaagt gttcattgca caatatattt ttactgcttt ctgaatgtag   1680
acggaacagt gtggaagcag aaggcttttt taactcatcc gtttggccga tcgttgcaga   1740
ccactgggag atgtggatgt ggttgcctcc ttttgctcgt ccccgtggct taacccttct   1800
```

<210> SEQ ID NO 346
<211> LENGTH: 261
<212> TYPE: PRT
<213> ORGANISM: Homo sapiens

<400> SEQUENCE: 346

```
Met Asp Trp Gly Thr Leu His Thr Phe Ile Gly Val Asn Lys His
              5                  10                  15

Ser Thr Ser Ile Gly Lys Val Trp Ile Thr Val Ile Phe Ile Phe Arg
              20                  25                  30

Val Met Ile Leu Val Val Ala Ala Gln Glu Val Trp Gly Asp Glu Gln
              35                  40                  45

Glu Asp Phe Val Cys Asn Thr Leu Gln Pro Gly Cys Lys Asn Val Cys
              50                  55                  60
```

```
Tyr Asp His Phe Phe Pro Val Ser His Ile Arg Leu Trp Ala Leu Gln
 65                  70                  75                  80

Leu Ile Phe Val Ser Thr Pro Ala Leu Leu Val Ala Met His Val Ala
                 85                  90                  95

Tyr Tyr Arg His Glu Thr Thr Arg Lys Phe Arg Arg Gly Glu Lys Arg
            100                 105                 110

Asn Asp Phe Lys Asp Ile Glu Asp Ile Lys Lys His Lys Val Arg Ile
            115                 120                 125

Glu Gly Ser Leu Trp Trp Thr Tyr Thr Ser Ser Ile Phe Phe Arg Ile
130                 135                 140

Ile Phe Glu Ala Ala Phe Met Tyr Val Phe Tyr Phe Leu Tyr Asn Gly
145                 150                 155                 160

Tyr His Leu Pro Trp Val Leu Lys Cys Gly Ile Asp Pro Cys Pro Asn
                165                 170                 175

Leu Val Asp Cys Phe Ile Ser Arg Pro Thr Glu Lys Thr Val Phe Thr
            180                 185                 190

Ile Phe Met Ile Ser Ala Ser Val Ile Cys Met Leu Leu Asn Val Ala
            195                 200                 205

Glu Leu Cys Tyr Leu Leu Lys Val Cys Phe Arg Arg Ser Lys Arg
210                 215                 220

Ala Gln Thr Gln Lys Asn His Pro Asn His Ala Leu Lys Glu Ser Lys
225                 230                 235                 240

Gln Asn Glu Met Asn Glu Leu Ile Ser Asp Ser Gly Gln Asn Ala Ile
                245                 250                 255

Thr Gly Phe Pro Ser
            260

<210> SEQ ID NO 347
<211> LENGTH: 1740
<212> TYPE: DNA
<213> ORGANISM: Homo sapiens

<400> SEQUENCE: 347
atgaacaaac tgtatatcgg aaacctcagc gagaacgccg cccctcgga cctagaaagt      60 atcttcaagg acgccaagat cccggtgtcg ggacccttcc tggtgaagac tggctacgcg    120
ttcgtggact gcccggacga gagctgggcc ctcaaggcca tcgaggcgct ttcaggtaaa    180
atagaactgc acgggaaacc catagaagtt gagcactcgg tcccaaaaag gcaaaggatt    240
cggaaacttc agatacgaaa tatcccgcct catttacagt gggaggtgct ggatagttta    300
ctagtccagt atggagtggt ggagagctgt gagcaagtga acactgactc ggaaactgca    360
gttgtaaatg taacctattc cagtaaggac caagctagac aagcactaga caaactgaat    420
ggatttcagt tagagaattt caccttgaaa gtagcctata tccctgatga acggccgcc     480 cagcaaaacc ccttgcagca gccccgaggt cgccggggcc ttgggcagag gggctcctca    540 aggcagggggt ctccaggatc cgtatccaag cagaaaccat gtgatttgcc tctgcgcctg    600
ctggttccca cccaatttgt tggagccatc ataggaaaag aaggtgccac cattcggaac    660
atcaccaaac agaccccgagtc taaaatcgat gtccaccgta agaaaatgc ggggggctgct    720 gagaagtcga ttactatcct ctctactcct gaaggcacct ctgcggcttg taagtctatt    780
ctggagatta tgcataagga agctcaagat ataaaattca cagaagagat ccccttgaag    840 atttttagctc ataataactt tgttggacgt cttattggta agaaggaag aaatcttaaa    900 aaaattgagc aagacacaga cactaaaatc acgatatctc cattgcagga attgacgctg    960
```

-continued

```
tataatccag aacgcactat tacagttaaa ggcaatgttg agacatgtgc caaagctgag   1020
gaggagatca tgaagaaaat cagggagtct tatgaaaatg atattgcttc tatgaatctt   1080
caagcacatt taattcctgg attaaatctg aacgccttgg gtctgttccc acccacttca   1140
gggatgccac ctcccacctc agggcccct tcagccatga ctcctcccta cccgcagttt    1200
gagcaatcag aaacggagac tgttcatctg tttatcccag ctctatcagt cggtgccatc   1260
atcggcaagc agggccagca catcaagcag ctttctcgct ttgctggagc ttcaattaag   1320
attgctccag cggaagcacc agatgctaaa gtgaggatgg tgattatcac tggaccacca   1380
gaggctcagt tcaaggctca gggaagaatt tatggaaaaa ttaaagaaga aactttgtt    1440 agtcctaaag aagaggtgaa acttgaagct catatcagag tgccatcctt tgctgctggc   1500
agagttattg gaaaggagg caaaacggtg aatgaacttc agaatttgtc aagtgcagaa    1560
gttgttgtcc ctcgtgacca gacacctgat gagaatgacc aagtggttgt caaaataact   1620
ggtcacttct atgcttgcca ggttgcccag agaaaaattc aggaaattct gactcaggta   1680
aagcagcacc aacaacagaa ggctctgcaa agtggaccac ctcagtcaag acggaagtaa   1740
```

<210> SEQ ID NO 348
<211> LENGTH: 579
<212> TYPE: PRT
<213> ORGANISM: Homo sapiens

<400> SEQUENCE: 348

```
Met Asn Lys Leu Tyr Ile Gly Asn Leu Ser Glu Asn Ala Ala Pro Ser
                5                   10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Thr Ala Ala
145                 150                 155                 160

Gln Gln Asn Pro Leu Gln Pro Arg Gly Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240
```

```
Glu Lys Ser Ile Thr Ile Leu Ser Thr Pro Glu Gly Thr Ser Ala Ala
            245                 250                 255
Cys Lys Ser Ile Leu Glu Ile Met His Lys Glu Ala Gln Asp Ile Lys
            260                 265                 270
Phe Thr Glu Glu Ile Pro Leu Lys Ile Leu Ala His Asn Asn Phe Val
            275                 280                 285
Gly Arg Leu Ile Gly Lys Glu Gly Arg Asn Leu Lys Lys Ile Glu Gln
            290                 295                 300
Asp Thr Asp Thr Lys Ile Thr Ile Ser Pro Leu Gln Glu Leu Thr Leu
305                 310                 315                 320
Tyr Asn Pro Glu Arg Thr Ile Thr Val Lys Gly Asn Val Glu Thr Cys
                325                 330                 335
Ala Lys Ala Glu Glu Ile Met Lys Lys Ile Arg Glu Ser Tyr Glu
            340                 345                 350
Asn Asp Ile Ala Ser Met Asn Leu Gln Ala His Leu Ile Pro Gly Leu
            355                 360                 365
Asn Leu Asn Ala Leu Gly Leu Phe Pro Pro Thr Ser Gly Met Pro Pro
            370                 375                 380
Pro Thr Ser Gly Pro Pro Ser Ala Met Thr Pro Pro Tyr Pro Gln Phe
385                 390                 395                 400
Glu Gln Ser Glu Thr Glu Thr Val His Leu Phe Ile Pro Ala Leu Ser
                405                 410                 415
Val Gly Ala Ile Ile Gly Lys Gln Gly Gln His Ile Lys Gln Leu Ser
            420                 425                 430
Arg Phe Ala Gly Ala Ser Ile Lys Ile Ala Pro Ala Glu Ala Pro Asp
            435                 440                 445
Ala Lys Val Arg Met Val Ile Ile Thr Gly Pro Pro Glu Ala Gln Phe
            450                 455                 460
Lys Ala Gln Gly Arg Ile Tyr Gly Lys Ile Lys Glu Glu Asn Phe Val
465                 470                 475                 480
Ser Pro Lys Glu Glu Val Lys Leu Glu Ala His Ile Arg Val Pro Ser
                485                 490                 495
Phe Ala Ala Gly Arg Val Ile Gly Lys Gly Gly Lys Thr Val Asn Glu
            500                 505                 510
Leu Gln Asn Leu Ser Ser Ala Glu Val Val Pro Arg Asp Gln Thr
            515                 520                 525
Pro Asp Glu Asn Asp Gln Val Val Val Lys Ile Thr Gly His Phe Tyr
530                 535                 540
Ala Cys Gln Val Ala Gln Arg Lys Ile Gln Glu Ile Leu Thr Gln Val
545                 550                 555                 560
Lys Gln His Gln Gln Lys Ala Leu Gln Ser Gly Pro Pro Gln Ser
                565                 570                 575
Arg Arg Lys

<210> SEQ ID NO 349
<211> LENGTH: 207
<212> TYPE: DNA
<213> ORGANISM: Homo sapiens

<400> SEQUENCE: 349
atgtggcagc ccctcttctt caagtggctc ttgtcctgtt gccctgggag ttctcaaatt   60
gctgcagcag cctccaccca gcctgaggat gacatcaata cacagaggaa gaagagtcag  120
gaaaagatga gaagagttac agactctcct gggcgacccc gagagcttac cattcctcag  180
```
acttcttcac atggtgctaa cagattt                                         207

<210> SEQ ID NO 350
<211> LENGTH: 69
<212> TYPE: PRT
<213> ORGANISM: Homo sapiens

<400> SEQUENCE: 350

Met Trp Gln Pro Leu Phe Phe Lys Trp Leu Leu Ser Cys Cys Pro Gly
                 5                  10                  15

Ser Ser Gln Ile Ala Ala Ala Ser Thr Gln Pro Glu Asp Asp Ile
             20                  25                  30

Asn Thr Gln Arg Lys Lys Ser Gln Glu Lys Met Arg Glu Val Thr Asp
         35                  40                  45

Ser Pro Gly Arg Pro Arg Glu Leu Thr Ile Pro Gln Thr Ser Ser His
     50                  55                  60

Gly Ala Asn Arg Phe
 65

<210> SEQ ID NO 351
<211> LENGTH: 1012
<212> TYPE: DNA
<213> ORGANISM: Homo sapiens

<400> SEQUENCE: 351
ccctctagaa ataattttgt ttaactttaa gaaggagata tacatatgca tcaccatcac     60
catcacacgg ccgcgtccga taacttccag ctgtcccagg gtgggcaggg attcgccatt    120
ccgatcgggc aggcgatggc gatcgcgggc cagatcaagc ttcccaccgt tcatatcggg    180
cctaccgcct tcctcggctt gggtgttgtc gacaacaacg gcaacggcgc acgagtccaa    240
cgcgtggtcg ggagcgctcc ggcggcaagt ctcggcatct ccaccggcga cgtgatcacc    300
gcggtcgacg gcgctccgat caactcggcc accgcgatgg cggacgcgct taacgggcat    360
catcccggtg acgtcatctc ggtgacctgg caaaccaagt cgggcggcac gcgtacaggg    420
aacgtgacat tggccgaggg acccccggcc gaattcatgg attggggac gctgcacact    480
ttcatcgggg gtgtcaacaa acactccacc agcatcggga aggtgtggat cacagtcatc    540
tttattttcc gagtcatgat cctcgtggtg gctgcccagg aagtgtgggg tgacgagcaa    600
gaggacttcg tctgcaacac actgcaaccg ggatgcaaaa atgtgtgcta tgaccacttt    660
ttcccggtgt cccacatccg gctgtgggcc ctccagctga tcttcgtctc caccccagcg    720
ctgctggtgg ccatgcatgt ggcctactac aggcacgaaa ccactcgcaa gttcaggcga    780
ggagagaaga ggaatgattt caaagacata gaggacatta aaaagcagaa ggttcggata    840
gagggggtgac tcgagcacca ccaccaccac cactgagatc cggctgctaa caaagcccga    900
aaggaagctg agttggctgc tgccaccgct gagcaataac tagcataacc ccttggggcc    960
tctaaacggg tcttgagggt ttttttgctg aaaggaggaa ctatatccgg at          1012

<210> SEQ ID NO 352
<211> LENGTH: 267
<212> TYPE: PRT
<213> ORGANISM: Homo sapiens

<400> SEQUENCE: 352

Met His His His His His His Thr Ala Ala Ser Asp Asn Phe Gln Leu
                 5                  10                  15

Ser Gln Gly Gly Gln Gly Phe Ala Ile Pro Ile Gly Gln Ala Met Ala

```
                  20                  25                  30
Ile Ala Gly Gln Ile Lys Leu Pro Thr Val His Ile Gly Pro Thr Ala
             35                  40                  45
Phe Leu Gly Leu Gly Val Val Asp Asn Asn Gly Asn Gly Ala Arg Val
         50                  55                  60
Gln Arg Val Val Gly Ser Ala Pro Ala Ser Leu Gly Ile Ser Thr
 65                  70                  75                  80
Gly Asp Val Ile Thr Ala Val Asp Gly Ala Pro Ile Asn Ser Ala Thr
                 85                  90                  95
Ala Met Ala Asp Ala Leu Asn Gly His His Pro Gly Asp Val Ile Ser
            100                 105                 110
Val Thr Trp Gln Thr Lys Ser Gly Gly Thr Arg Thr Gly Asn Val Thr
            115                 120                 125
Leu Ala Glu Gly Pro Pro Ala Glu Phe Met Asp Trp Gly Thr Leu His
        130                 135                 140
Thr Phe Ile Gly Gly Val Asn Lys His Ser Thr Ser Ile Gly Lys Val
145                 150                 155                 160
Trp Ile Thr Val Ile Phe Ile Phe Arg Val Met Ile Leu Val Val Ala
                165                 170                 175
Ala Gln Glu Val Trp Gly Asp Glu Gln Glu Asp Phe Val Cys Asn Thr
            180                 185                 190
Leu Gln Pro Gly Cys Lys Asn Val Cys Tyr Asp His Phe Phe Pro Val
            195                 200                 205
Ser His Ile Arg Leu Trp Ala Leu Gln Leu Ile Phe Val Ser Thr Pro
        210                 215                 220
Ala Leu Leu Val Ala Met His Val Ala Tyr Tyr Arg His Glu Thr Thr
225                 230                 235                 240
Arg Lys Phe Arg Arg Gly Glu Lys Arg Asn Asp Phe Lys Asp Ile Glu
                245                 250                 255
Asp Ile Lys Lys Gln Lys Val Arg Ile Glu Gly
            260                 265

<210> SEQ ID NO 353
<211> LENGTH: 900
<212> TYPE: DNA
<213> ORGANISM: Homo sapiens

<400> SEQUENCE: 353
atgcatcacc atcaccatca cacggccgcg tccgataact tccagctgtc ccagggtggg      60
cagggattcg ccattccgat cgggcaggcg atggcgatcg cgggccagat caagcttccc     120
accgttcata tcgggcctac cgccttcctc ggcttggtg ttgtcgacaa caacggcaac      180
ggcgcacgag tccaacgcgt ggtcgggagc gctccggcgg caagtctcgg catctccacc     240
ggcgacgtga tcaccgcggt cgacggcgct ccgatcaact cggccaccgc gatggcggac     300
gcgcttaacg gcatcatcc cggtgacgtc atctcggtga cctggcaaac caagtcgggc     360
ggcacgcgta cagggaacgt gacattggcc gagggacccc cggccgaatt ccacgaaacc     420
actcgcaagt tcaggcgagg agagaagagg aatgatttca agacataga ggacattaaa      480 aagcagaagg ttcggataga ggggtcgctg tggtggacgt acaccagcag catctttttc     540
cgaatcatct ttgaagcagc ctttatgtat gtgttttact tcctttacaa tgggtaccac     600
ctgccctggg tgttgaaatg tgggattgac ccctgcccca accttgttga ctgctttatt     660
tctaggccaa cagagaagac cgtgtttacc atttttatga tttctgcgtc tgtgatttgc     720
```

```
atgctgctta acgtggcaga gttgtgctac ctgctgctga aagtgtgttt taggagatca    780
aagagagcac agacgcaaaa aaatcacccc aatcatgccc taaaggagag taagcagaat    840
gaaatgaatg agctgatttc agatagtggt caaaatgcaa tcacaggttt cccaagctaa    900
```

<210> SEQ ID NO 354
<211> LENGTH: 299
<212> TYPE: PRT
<213> ORGANISM: Homo sapiens

<400> SEQUENCE: 354

```
Met His His His His His His Thr Ala Ala Ser Asp Asn Phe Gln Leu
                  5                  10                  15

Ser Gln Gly Gly Gln Gly Phe Ala Ile Pro Ile Gly Gln Ala Met Ala
             20                  25                  30

Ile Ala Gly Gln Ile Lys Leu Pro Thr Val His Ile Gly Pro Thr Ala
         35                  40                  45

Phe Leu Gly Leu Gly Val Val Asp Asn Asn Gly Asn Gly Ala Arg Val
     50                  55                  60

Gln Arg Val Val Gly Ser Ala Pro Ala Ala Ser Leu Gly Ile Ser Thr
 65                  70                  75                  80

Gly Asp Val Ile Thr Ala Val Asp Gly Ala Pro Ile Asn Ser Ala Thr
                 85                  90                  95

Ala Met Ala Asp Ala Leu Asn Gly His His Pro Gly Asp Val Ile Ser
            100                 105                 110

Val Thr Trp Gln Thr Lys Ser Gly Gly Thr Arg Thr Gly Asn Val Thr
        115                 120                 125

Leu Ala Glu Gly Pro Pro Ala Glu Phe His Glu Thr Thr Arg Lys Phe
    130                 135                 140

Arg Arg Gly Glu Lys Arg Asn Asp Phe Lys Asp Ile Glu Asp Ile Lys
145                 150                 155                 160

Lys Gln Lys Val Arg Ile Glu Gly Ser Leu Trp Trp Thr Tyr Thr Ser
                165                 170                 175

Ser Ile Phe Phe Arg Ile Ile Phe Glu Ala Ala Phe Met Tyr Val Phe
            180                 185                 190

Tyr Phe Leu Tyr Asn Gly Tyr His Leu Pro Trp Val Leu Lys Cys Gly
        195                 200                 205

Ile Asp Pro Cys Pro Asn Leu Val Asp Cys Phe Ile Ser Arg Pro Thr
    210                 215                 220

Glu Lys Thr Val Phe Thr Ile Phe Met Ile Ser Ala Ser Val Ile Cys
225                 230                 235                 240

Met Leu Leu Asn Val Ala Glu Leu Cys Tyr Leu Leu Lys Val Cys
                245                 250                 255

Phe Arg Arg Ser Lys Arg Ala Gln Thr Gln Lys Asn His Pro Asn His
            260                 265                 270

Ala Leu Lys Glu Ser Lys Gln Asn Glu Met Asn Glu Leu Ile Ser Asp
        275                 280                 285

Ser Gly Gln Asn Ala Ile Thr Gly Phe Pro Ser
    290                 295
```

<210> SEQ ID NO 355
<211> LENGTH: 29
<212> TYPE: DNA
<213> ORGANISM: Artificial Sequence
<220> FEATURE:
<223> OTHER INFORMATION: PCR Primer -continued

```
<400> SEQUENCE: 355
cggcgaattc atggattggg ggacgctgc                                          29

<210> SEQ ID NO 356
<211> LENGTH: 35
<212> TYPE: DNA
<213> ORGANISM: Artificial Sequence
<220> FEATURE:
<223> OTHER INFORMATION: PCR Primer

<400> SEQUENCE: 356
cggcctcgag tcacccctct atccgaacct tctgc                                   35

<210> SEQ ID NO 357
<211> LENGTH: 32
<212> TYPE: DNA
<213> ORGANISM: Artificial Sequence
<220> FEATURE:
<223> OTHER INFORMATION: PCR Primer

<400> SEQUENCE: 357
cggcgaattc cacgaaccac tcgcaagttc ag                                      32

<210> SEQ ID NO 358
<211> LENGTH: 30
<212> TYPE: DNA
<213> ORGANISM: Artificial Sequence
<220> FEATURE:
<223> OTHER INFORMATION: PCR Primer

<400> SEQUENCE: 358
cggctcgagt tagcttgggc ctgtgattgc                                         30
```

COMPOSITIONS AND METHODS FOR THE THERAPY AND DIAGNOSIS OF LUNG CANCER

REFERENCE TO RELATED APPLICATIONS

This application is a continuation-in-part of U.S. patent application Ser. No. 09/542,615 filed Apr. 4, 2000, which is a continuation-in-part of U.S. patent application Ser. No. 09/510,376, filed Feb. 22, 2000, which is a continuation-in-part of U.S. patent application Ser. No. 09/480,884, filed Jan. 10, 2000, which is a continuation-in-part of U.S. patent application Ser. No. 09/476,496, filed Dec. 30, 1999, which is a continuation-in-part of U.S. patent application Ser. No. 09/466,396, filed Dec. 17, 1999, which is a continuation-in-part of U.S. patent application Ser. No. 09/285,479, filed Apr. 2, 1999, which claims priority from and is a continuation of PCT Application No. PCT/US99/05798, filed Mar. 17, 1999, which claims priority from and is a continuation-in-part of U.S. patent application Ser. No. 09/221,107, filed Dec. 22, 1998, which is a continuation-in-part of U.S. patent application Ser. No. 09/123,912, filed Jul. 27, 1998, now U.S. Pat. No. 6,312,695, which is a continuation-in-part of U.S. patent application Ser. No. 09/040,802, filed Mar. 18, 1998, abandoned May 23, 2001.

TECHNICAL FIELD OF THE INVENTION

The present invention relates generally to therapy and diagnosis of cancer, such as lung cancer. The invention is more specifically related to polypeptides comprising at least a portion of a lung tumor protein, and to polynucleotides encoding such polypeptides. Such polypeptides and polynucleotides may be used in vaccines and pharmaceutical compositions for prevention and treatment of lung cancer, and for the diagnosis and monitoring of such cancers.

BACKGROUND OF THE INVENTION

Lung cancer is the primary cause of cancer death among both men and women in the U.S., with an estimated 172,000 new cases being reported in 1994. The five-year survival rate among all lung cancer patients, regardless of the stage of disease at diagnosis, is only 13%. This contrasts with a five-year survival rate of 46% among cases detected while the disease is still localized. However, only 16% of lung cancers are discovered before the disease has spread.

Early detection is difficult since clinical symptoms are often not seen until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for the disease, lung cancer remains difficult to treat.

Accordingly, there remains a need in the art for improved vaccines, treatment methods and diagnostic techniques for lung cancer.

SUMMARY OF THE INVENTION

Briefly stated, the present invention provides compositions and methods for the diagnosis and therapy of cancer, such as lung cancer. In one aspect, the present invention provides polypeptides comprising at least a portion of a lung tumor protein, or a variant thereof. Certain portions and other variants are immunogenic, such that the ability of the variant to react with antigen-specific antisera is not substantially diminished. Within certain embodiments, the polypeptide comprises a sequence that is encoded by a polynucleotide sequence selected from the group consisting of: (a) sequences recited in any one of SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347 and 349; (b) variants of a sequence recited in any one of SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347 and 349; and (c) complements of a sequence of (a) or (b). In specific embodiments, the polypeptides of the present invention comprise at least a portion of a tumor protein that includes an amino acid sequence selected from the group consisting of sequences recited in any one of SEQ ID NO: 152, 155, 156, 165, 166, 169, 170, 172, 174, 176, 226–252, 338–344 and 346, and variants thereof.

The present invention further provides polynucleotides that encode a polypeptide as described above, or a portion thereof (such as a portion encoding at least 15 amino acid residues of a lung tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, vaccines for prophylactic or therapeutic use are provided. Such vaccines comprise a polypeptide or polynucleotide as described above and an immunostimulant.

The present invention further provides pharmaceutical compositions that comprise: (a) an antibody or antigen-binding fragment thereof that specifically binds to a lung tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, vaccines are provided that comprise: (a) an antigen presenting cell that expresses a polypeptide as described above, and (b) an immunostimulant.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Vaccines are further provided, within other aspects, that comprise a fusion protein, or a polynucleotide encoding a fusion protein, in combination with an immunostimulant.

Within further aspects, the present invention provides methods for inhibiting the development of a cancer in a patient, comprising administering to a patient a pharmaceutical composition or vaccine as recited above.

The present invention further provides, within other aspects, methods for removing tumor cells from a biological sample, comprising contacting a biological sample with T cells that specifically react with a lung tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a lung tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Determined T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating CD4$^+$ and/or CD8$^+$ T cells determined from a patient with one or more of: (i) a polypeptide comprising at least an immunogenic portion of a lung tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be lung cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a lung tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a lung tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description. All references disclosed herein are hereby incorporated by reference in their entirety as if each was incorporated individually.

BRIEF DESCRIPTION OF THE SEQUENCE IDENTIFIERS

SEQ ID NO: 1 is the determined cDNA sequence for LST-S1-2.

SEQ ID NO: 2 is the determined cDNA sequence for LST-S1-28.

SEQ ID NO: 3 is the determined cDNA sequence for LST-S1-90.

SEQ ID NO: 4 is the determined cDNA sequence for LST-S1-144.

SEQ ID NO: 5 is the determined cDNA sequence for LST-S1-133.

SEQ ID NO: 6 is the determined cDNA sequence for LST-S1-169.

SEQ ID NO: 7 is the determined cDNA sequence for LST-S2-6.

SEQ ID NO: 8 is the determined cDNA sequence for LST-S2-11.

SEQ ID NO: 9 is the determined cDNA sequence for LST-S2-17.

SEQ ID NO: 10 is the determined cDNA sequence for LST-S2-25.

SEQ ID NO: 11 is the determined cDNA sequence for LST-S2-39.

SEQ ID NO: 12 is a first determined cDNA sequence for LST-S2-43.

SEQ ID NO: 13 is a second determined cDNA sequence for LST-S2-43.

SEQ ID NO: 14 is the determined cDNA sequence for LST-S2-65.
SEQ ID NO: 15 is the determined cDNA sequence for LST-S2-68.
SEQ ID NO: 16 is the determined cDNA sequence for LST-S2-72.
SEQ ID NO: 17 is the determined cDNA sequence for LST-S2-74.
SEQ ID NO: 18 is the determined cDNA sequence for LST-S2-103.
SEQ ID NO: 19 is the determined cDNA sequence for LST-S2-N1-1F.
SEQ ID NO: 20 is the determined cDNA sequence for LST-S2-N1-2A.
SEQ ID NO: 21 is the determined cDNA sequence for LST-S2-N1-4H.
SEQ ID NO: 22 is the determined cDNA sequence for LST-S2-N1-5A.
SEQ ID NO: 23 is the determined cDNA sequence for LST-S2-N1-6B.
SEQ ID NO: 24 is the determined cDNA sequence for LST-S2-N1-7B.
SEQ ID NO: 25 is the determined cDNA sequence for LST-S2-N1-7H.
SEQ ID NO: 26 is the determined cDNA sequence for LST-S2-N1-8A.
SEQ ID NO: 27 is the determined cDNA sequence for LST-S2-N1-8D.
SEQ ID NO: 28 is the determined cDNA sequence for LST-S2-N1-9A.
SEQ ID NO: 29 is the determined cDNA sequence for LST-S2-N1-9E.
SEQ ID NO: 30 is the determined cDNA sequence for LST-S2-N1-10A.
SEQ ID NO: 31 is the determined cDNA sequence for LST-S2-N1-10G.
SEQ ID NO: 32 is the determined cDNA sequence for LST-S2-N1-11A.
SEQ ID NO: 33 is the determined cDNA sequence for LST-S2-N1-12C.
SEQ ID NO: 34 is the determined cDNA sequence for LST-S2-N1-12E.
SEQ ID NO: 35 is the determined cDNA sequence for LST-S2-B1-3D.
SEQ ID NO: 36 is the determined cDNA sequence for LST-S2-B1-6C.
SEQ ID NO: 37 is the determined cDNA sequence for LST-S2-B1-5D.
SEQ ID NO: 38 is the determined cDNA sequence for LST-S2-B1-5F.
SEQ ID NO: 39 is the determined cDNA sequence for LST-S2-B1-6G.
SEQ ID NO: 40 is the determined cDNA sequence for LST-S2-B1-8A.
SEQ ID NO: 41 is the determined cDNA sequence for LST-S2-B1-8D.
SEQ ID NO: 42 is the determined cDNA sequence for LST-S2-B1-10A.
SEQ ID NO: 43 is the determined cDNA sequence for LST-S2-B1-9B.
SEQ ID NO: 44 is the determined cDNA sequence for LST-S2-B1-9F.
SEQ ID NO: 45 is the determined cDNA sequence for LST-S2-B1-12D.
SEQ ID NO: 46 is the determined cDNA sequence for LST-S2-I2-2B.
SEQ ID NO: 47 is the determined cDNA sequence for LST-S2-I2-5F.
SEQ ID NO: 48 is the determined cDNA sequence for LST-S2-I2-6B.
SEQ ID NO: 49 is the determined cDNA sequence for LST-S2-I2-7F.
SEQ ID NO: 50 is the determined cDNA sequence for LST-S2-I2-8G.
SEQ ID NO: 51 is the determined cDNA sequence for LST-S2-I2-9E.
SEQ ID NO: 52 is the determined cDNA sequence for LST-S2-I2-12B.
SEQ ID NO: 53 is the determined cDNA sequence for LST-S2-H2-2C.
SEQ ID NO: 54 is the determined cDNA sequence for LST-S2-H2-1G.
SEQ ID NO: 55 is the determined cDNA sequence for LST-S2-H2-4G.
SEQ ID NO: 56 is the determined cDNA sequence for LST-S2-H2-3H.
SEQ ID NO: 57 is the determined cDNA sequence for LST-S2-H2-5G.
SEQ ID NO: 58 is the determined cDNA sequence for LST-S2-H2-9B.
SEQ ID NO: 59 is the determined cDNA sequence for LST-S2-H2-10H.
SEQ ID NO: 60 is the determined cDNA sequence for LST-S2-H2-12D.
SEQ ID NO: 61 is the determined cDNA sequence for LST-S3-2.
SEQ ID NO: 62 is the determined cDNA sequence for LST-S3-4.
SEQ ID NO: 63 is the determined cDNA sequence for LST-S3-7.
SEQ ID NO: 64 is the determined cDNA sequence for LST-S3-8.
SEQ ID NO: 65 is the determined cDNA sequence for LST-S3-12.
SEQ ID NO: 66 is the determined cDNA sequence for LST-S3-13.
SEQ ID NO: 67 is the determined cDNA sequence for LST-S3-14.
SEQ ID NO: 68 is the determined cDNA sequence for LST-S3-16.
SEQ ID NO: 69 is the determined cDNA sequence for LST-S3-21.
SEQ ID NO: 70 is the determined cDNA sequence for LST-S3-22.
SEQ ID NO: 71 is the determined cDNA sequence for LST-S1-7.
SEQ ID NO: 72 is the determined cDNA sequence for LST-S1-A-1E.
SEQ ID NO: 73 is the determined cDNA sequence for LST-S1-A-1G.
SEQ ID NO: 74 is the determined cDNA sequence for LST-S1-A-3E.
SEQ ID NO: 75 is the determined cDNA sequence for LST-S1-A-4E.
SEQ ID NO: 76 is the determined cDNA sequence for LST-S1-A-6D.
SEQ ID NO: 77 is the determined cDNA sequence for LST-S1-A-8D.
SEQ ID NO: 78 is the determined cDNA sequence for LST-S1-A-10A.
SEQ ID NO: 79 is the determined cDNA sequence for LST-S1-A-10C.
SEQ ID NO: 80 is the determined cDNA sequence for LST-S1-A-9D.
SEQ ID NO: 81 is the determined cDNA sequence for LST-S1-A-10D.

SEQ ID NO: 82 is the determined cDNA sequence for LST-S1-A-9H.
SEQ ID NO: 83 is the determined cDNA sequence for LST-S1-A-11D.
SEQ ID NO: 84 is the determined cDNA sequence for LST-S1-A-12D.
SEQ ID NO: 85 is the determined cDNA sequence for LST-S1-A-11E.
SEQ ID NO: 86 is the determined cDNA sequence for LST-S1-A-12E.
SEQ ID NO: 87 is the determined cDNA sequence for L513S (T3).
SEQ ID NO: 88 is the determined cDNA sequence for L513S contig 1.
SEQ ID NO: 89 is a first determined cDNA sequence for L514S.
SEQ ID NO: 90 is a second determined cDNA sequence for L514S.
SEQ ID NO: 91 is a first determined cDNA sequence for L516S.
SEQ ID NO: 92 is a second determined cDNA sequence for L516S.
SEQ ID NO: 93 is the determined cDNA sequence for L517S.
SEQ ID NO: 94 is the extended cDNA sequence for LST-S1-169 (also known as L519S).
SEQ ID NO: 95 is a first determined cDNA sequence for L520S.
SEQ ID NO: 96 is a second determined cDNA sequence for L520S.
SEQ ID NO: 97 is a first determined cDNA sequence for L521S.
SEQ ID NO: 98 is a second determined cDNA sequence for L521S.
SEQ ID NO: 99 is the determined cDNA sequence for L522S.
SEQ ID NO: 100 is the determined cDNA sequence for L523S.
SEQ ID NO: 101 is the determined cDNA sequence for L524S.
SEQ ID NO: 102 is the determined cDNA sequence for L525S.
SEQ ID NO: 103 is the determined cDNA sequence for L526S.
SEQ ID NO: 104 is the determined cDNA sequence for L527S.
SEQ ID NO: 105 is the determined cDNA sequence for L528S.
SEQ ID NO: 106 is the determined cDNA sequence for L529S.
SEQ ID NO: 107 is a first determined cDNA sequence for L530S.
SEQ ID NO: 108 is a second determined cDNA sequence for L530S.
SEQ ID NO: 109 is the determined full-length cDNA sequence for L531S short form.
SEQ ID NO: 110 is the predicted amino acid sequence encoded by SEQ ID NO: 109.
SEQ ID NO: 111 is the determined full-length cDNA sequence for L531S long form.
SEQ ID NO: 112 is the predicted amino acid sequence encoded by SEQ ID NO: 111.
SEQ ID NO: 113 is the determined full-length cDNA sequence for L520S.
SEQ ID NO: 114 is the predicted amino acid sequence encoded by SEQ ID NO: 113.
SEQ ID NO: 115 is the determined cDNA sequence for contig 1.
SEQ ID NO: 116 is the determined cDNA sequence for contig 3.
SEQ ID NO: 117 is the determined cDNA sequence for contig 4.
SEQ ID NO: 118 is the determined cDNA sequence for contig 5.
SEQ ID NO: 119 is the determined cDNA sequence for contig 7.
SEQ ID NO: 120 is the determined cDNA sequence for contig 8.
SEQ ID NO: 121 is the determined cDNA sequence for contig 9.
SEQ ID NO: 122 is the determined cDNA sequence for contig 10.
SEQ ID NO: 123 is the determined cDNA sequence for contig 12.
SEQ ID NO: 124 is the determined cDNA sequence for contig 11.
SEQ ID NO: 125 is the determined cDNA sequence for contig 13.
SEQ ID NO: 126 is the determined cDNA sequence for contig 15.
SEQ ID NO: 127 is the determined cDNA sequence for contig 16.
SEQ ID NO: 128 is the determined cDNA sequence for contig 17.
SEQ ID NO: 129 is the determined cDNA sequence for contig 19.
SEQ ID NO: 130 is the determined cDNA sequence for contig 20.
SEQ ID NO: 131 is the determined cDNA sequence for contig 22.
SEQ ID NO: 132 is the determined cDNA sequence for contig 24.
SEQ ID NO: 133 is the determined cDNA sequence for contig 29.
SEQ ID NO: 134 is the determined cDNA sequence for contig 31.
SEQ ID NO: 135 is the determined cDNA sequence for contig 33.
SEQ ID NO: 136 is the determined cDNA sequence for contig 38.
SEQ ID NO: 137 is the determined cDNA sequence for contig 39.
SEQ ID NO: 138 is the determined cDNA sequence for contig 41.
SEQ ID NO: 139 is the determined cDNA sequence for contig 43.
SEQ ID NO: 140 is the determined cDNA sequence for contig 44.
SEQ ID NO: 141 is the determined cDNA sequence for contig 45.
SEQ ID NO: 142 is the determined cDNA sequence for contig 47.
SEQ ID NO: 143 is the determined cDNA sequence for contig 48.
SEQ ID NO: 144 is the determined cDNA sequence for contig 49.
SEQ ID NO: 145 is the determined cDNA sequence for contig 50.
SEQ ID NO: 146 is the determined cDNA sequence for contig 53.
SEQ ID NO: 147 is the determined cDNA sequence for contig 54.
SEQ ID NO: 148 is the determined cDNA sequence for contig 56.
SEQ ID NO: 149 is the determined cDNA sequence for contig 57.

SEQ ID NO: 150 is the determined cDNA sequence for contig 58.
SEQ ID NO: 151 is the full-length cDNA sequence for L530S.
SEQ ID NO: 152 is the amino acid sequence encoded by SEQ ID NO: 151.
SEQ ID NO: 153 is the full-length cDNA sequence of a first variant of L514S.
SEQ ID NO: 154 is the full-length cDNA sequence of a second variant of L514S.
SEQ ID NO: 155 is the amino acid sequence encoded by SEQ ID NO: 153.
SEQ ID NO: 156 is the amino acid sequence encoded by SEQ ID NO: 154.
SEQ ID NO: 157 is the determined cDNA sequence for contig 59.
SEQ ID NO: 158 is the full-length cDNA sequence for L763P (also referred to as contig 22).
SEQ ID NO: 159 is the amino acid sequence encoded by SEQ ID NO: 158.
SEQ ID NO: 160 is the full-length cDNA sequence for L762P (also referred to as contig 17).
SEQ ID NO: 161 is the amino acid sequence encoded by SEQ ID NO: 160.
SEQ ID NO: 162 is the determined cDNA sequence for L515S.
SEQ ID NO: 163 is the full-length cDNA sequence of a first variant of L524S.
SEQ ID NO: 164 is the full-length cDNA sequence of a second variant of L524S.
SEQ ID NO: 165 is the amino acid sequence encoded by SEQ ID NO: 163.
SEQ ID NO: 166 is the amino acid sequence encoded by SEQ ID NO: 164.
SEQ ID NO: 167 is the full-length cDNA sequence of a first variant of L762P.
SEQ ID NO: 168 is the full-length cDNA sequence of a second variant of L762P.
SEQ ID NO: 169 is the amino acid sequence encoded by SEQ ID NO: 167.
SEQ ID NO: 170 is the amino acid sequence encoded by SEQ ID NO: 168.
SEQ ID NO: 171 is the full-length cDNA sequence for L773P (also referred to as contig 56).
SEQ ID NO: 172 is the amino acid sequence encoded by SEQ ID NO: 171.
SEQ ID NO: 173 is an extended cDNA sequence for L519S.
SEQ ID NO: 174 is the predicted amino acid sequence encoded by SEQ ID NO: 174.
SEQ ID NO: 175 is the full-length cDNA sequence for L523S.
SEQ ID NO: 176 is the predicted amino acid sequence encoded by SEQ ID NO: 175.
SEQ ID NO: 177 is the determined cDNA sequence for LST-sub5-7A.
SEQ ID NO: 178 is the determined cDNA sequence for LST-sub5-8G.
SEQ ID NO: 179 is the determined cDNA sequence for LST-sub5-8H.
SEQ ID NO: 180 is the determined cDNA sequence for LST-sub5-10B.
SEQ ID NO: 181 is the determined cDNA sequence for LST-sub5-10H.
SEQ ID NO: 182 is the determined cDNA sequence for LST-sub5-12B.
SEQ ID NO: 183 is the determined cDNA sequence for LST-sub5-11C.
SEQ ID NO: 184 is the determined cDNA sequence for LST-sub6-1c.
SEQ ID NO: 185 is the determined cDNA sequence for LST-sub6-2f
SEQ ID NO: 186 is the determined cDNA sequence for LST-sub6-2G.
SEQ ID NO: 187 is the determined cDNA sequence for LST-sub6-4d.
SEQ ID NO: 188 is the determined cDNA sequence for LST-sub6-4e.
SEQ ID NO: 189 is the determined cDNA sequence for LST-sub6-4f.
SEQ ID NO: 190 is the determined cDNA sequence for LST-sub6-3h.
SEQ ID NO: 191 is the determined cDNA sequence for LST-sub6-5d.
SEQ ID NO: 192 is the determined cDNA sequence for LST-sub6-5h.
SEQ ID NO: 193 is the determined cDNA sequence for LST-sub6-6h.
SEQ ID NO: 194 is the determined cDNA sequence for LST-sub6-7a.
SEQ ID NO: 195 is the determined cDNA sequence for LST-sub6-8a.
SEQ ID NO: 196 is the determined cDNA sequence for LST-sub6-7d.
SEQ ID NO: 197 is the determined cDNA sequence for LST-sub6-7e.
SEQ ID NO: 198 is the determined cDNA sequence for LST-sub6-8e.
SEQ ID NO: 199 is the determined cDNA sequence for LST-sub6-7g.
SEQ ID NO: 200 is the determined cDNA sequence for LST-sub6-9f.
SEQ ID NO: 201 is the determined cDNA sequence for LST-sub6-9h.
SEQ ID NO: 202 is the determined cDNA sequence for LST-sub6-11b.
SEQ ID NO: 203 is the determined cDNA sequence for LST-sub6-11c.
SEQ ID NO: 204 is the determined cDNA sequence for LST-sub6-12c.
SEQ ID NO: 205 is the determined cDNA sequence for LST-sub6-12e.
SEQ ID NO: 206 is the determined cDNA sequence for LST-sub6-12f.
SEQ ID NO: 207 is the determined cDNA sequence for LST-sub6-11g.
SEQ ID NO: 208 is the determined cDNA sequence for LST-sub6-12g.
SEQ ID NO: 209 is the determined cDNA sequence for LST-sub6-12h.
SEQ ID NO: 210 is the determined cDNA sequence for LST-sub6-II-1a.
SEQ ID NO: 211 is the determined cDNA sequence for LST-sub6-II-2b.
SEQ ID NO: 212 is the determined cDNA sequence for LST-sub6-II-2g.
SEQ ID NO: 213 is the determined cDNA sequence for LST-sub6-II-1h.
SEQ ID NO: 214 is the determined cDNA sequence for LST-sub6-II-4a.
SEQ ID NO: 215 is the determined cDNA sequence for LST-sub6-II-4b.
SEQ ID NO: 216 is the determined cDNA sequence for LST-sub6-II-3e.
SEQ ID NO: 217 is the determined cDNA sequence for LST-sub6-II-4f.

SEQ ID NO: 218 is the determined cDNA sequence for LST-sub6-II-4g.
SEQ ID NO: 219 is the determined cDNA sequence for LST-sub6-II-4h.
SEQ ID NO: 220 is the determined cDNA sequence for LST-sub6-II-5c.
SEQ ID NO: 221 is the determined cDNA sequence for LST-sub6-II-5e.
SEQ ID NO: 222 is the determined cDNA sequence for LST-sub6-II-6f.
SEQ ID NO: 223 is the determined cDNA sequence for LST-sub6-II-5g.
SEQ ID NO: 224 is the determined cDNA sequence for LST-sub6-II-6g.
SEQ ID NO: 225 is the amino acid sequence for L528S.
SEQ ID NO: 226–251 are synthetic peptides derived from L762P.
SEQ ID NO: 252 is the expressed amino acid sequence of L514S.
SEQ ID NO: 253 is the DNA sequence corresponding to SEQ ID NO: 252.
SEQ ID NO: 254 is the DNA sequence of a L762P expression construct.
SEQ ID NO: 255 is the determined cDNA sequence for clone 23785.
SEQ ID NO: 256 is the determined cDNA sequence for clone 23786.
SEQ ID NO: 257 is the determined cDNA sequence for clone 23788.
SEQ ID NO: 258 is the determined cDNA sequence for clone 23790.
SEQ ID NO: 259 is the determined cDNA sequence for clone 23793.
SEQ ID NO: 260 is the determined cDNA sequence for clone 23794.
SEQ ID NO: 261 is the determined cDNA sequence for clone 23795.
SEQ ID NO: 262 is the determined cDNA sequence for clone 23796.
SEQ ID NO: 263 is the determined cDNA sequence for clone 23797.
SEQ ID NO: 264 is the determined cDNA sequence for clone 23798.
SEQ ID NO: 265 is the determined cDNA sequence for clone 23799.
SEQ ID NO: 266 is the determined cDNA sequence for clone 23800.
SEQ ID NO: 267 is the determined cDNA sequence for clone 23802.
SEQ ID NO: 268 is the determined cDNA sequence for clone 23803.
SEQ ID NO: 269 is the determined cDNA sequence for clone 23804.
SEQ ID NO: 270 is the determined cDNA sequence for clone 23805.
SEQ ID NO: 271 is the determined cDNA sequence for clone 23806.
SEQ ID NO: 272 is the determined cDNA sequence for clone 23807.
SEQ ID NO: 273 is the determined cDNA sequence for clone 23808.
SEQ ID NO: 274 is the determined cDNA sequence for clone 23809.
SEQ ID NO: 275 is the determined cDNA sequence for clone 23810.
SEQ ID NO: 276 is the determined cDNA sequence for clone 23811.
SEQ ID NO: 277 is the determined cDNA sequence for clone 23812.
SEQ ID NO: 278 is the determined cDNA sequence for clone 23813.
SEQ ID NO: 279 is the determined cDNA sequence for clone 23815.
SEQ ID NO: 280 is the determined cDNA sequence for clone 25298.
SEQ ID NO: 281 is the determined cDNA sequence for clone 25299.
SEQ ID NO: 282 is the determined cDNA sequence for clone 25300.
SEQ ID NO: 283 is the determined cDNA sequence for clone 25301.
SEQ ID NO: 284 is the determined cDNA sequence for clone 25304.
SEQ ID NO: 285 is the determined cDNA sequence for clone 25309.
SEQ ID NO: 286 is the determined cDNA sequence for clone 25312.
SEQ ID NO: 287 is the determined cDNA sequence for clone 25317.
SEQ ID NO: 288 is the determined cDNA sequence for clone 25321.
SEQ ID NO: 289 is the determined cDNA sequence for clone 25323.
SEQ ID NO: 290 is the determined cDNA sequence for clone 25327.
SEQ ID NO: 291 is the determined cDNA sequence for clone 25328.
SEQ ID NO: 292 is the determined cDNA sequence for clone 25332.
SEQ ID NO: 293 is the determined cDNA sequence for clone 25333.
SEQ ID NO: 294 is the determined cDNA sequence for clone 25336.
SEQ ID NO: 295 is the determined cDNA sequence for clone 25340.
SEQ ID NO: 296 is the determined cDNA sequence for clone 25342.
SEQ ID NO: 297 is the determined cDNA sequence for clone 25356.
SEQ ID NO: 298 is the determined cDNA sequence for clone 25357.
SEQ ID NO: 299 is the determined cDNA sequence for clone 25361.
SEQ ID NO: 300 is the determined cDNA sequence for clone 25363.
SEQ ID NO: 301 is the determined cDNA sequence for clone 25397.
SEQ ID NO: 302 is the determined cDNA sequence for clone 25402.
SEQ ID NO: 303 is the determined cDNA sequence for clone 25403.
SEQ ID NO: 304 is the determined cDNA sequence for clone 25405.
SEQ ID NO: 305 is the determined cDNA sequence for clone 25407.
SEQ ID NO: 306 is the determined cDNA sequence for clone 25409.
SEQ ID NO: 307 is the determined cDNA sequence for clone 25396.
SEQ ID NO: 308 is the determined cDNA sequence for clone 25414.
SEQ ID NO: 309 is the determined cDNA sequence for clone 25410.
SEQ ID NO: 310 is the determined cDNA sequence for clone 25406.

SEQ ID NO: 311 is the determined cDNA sequence for clone 25306.
SEQ ID NO: 312 is the determined cDNA sequence for clone 25362.
SEQ ID NO: 313 is the determined cDNA sequence for clone 25360.
SEQ ID NO: 314 is the determined cDNA sequence for clone 25398.
SEQ ID NO: 315 is the determined cDNA sequence for clone 25355.
SEQ ID NO: 316 is the determined cDNA sequence for clone 25351.
SEQ ID NO: 317 is the determined cDNA sequence for clone 25331.
SEQ ID NO: 318 is the determined cDNA sequence for clone 25338.
SEQ ID NO: 319 is the determined cDNA sequence for clone 25335.
SEQ ID NO: 320 is the determined cDNA sequence for clone 25329.
SEQ ID NO: 321 is the determined cDNA sequence for clone 25324.
SEQ ID NO: 322 is the determined cDNA sequence for clone 25322.
SEQ ID NO: 323 is the determined cDNA sequence for clone 25319.
SEQ ID NO: 324 is the determined cDNA sequence for clone 25316.
SEQ ID NO: 325 is the determined cDNA sequence for clone 25311.
SEQ ID NO: 326 is the determined cDNA sequence for clone 25310.
SEQ ID NO: 327 is the determined cDNA sequence for clone 25302.
SEQ ID NO: 328 is the determined cDNA sequence for clone 25315.
SEQ ID NO: 329 is the determined cDNA sequence for clone 25308.
SEQ ID NO: 330 is the determined cDNA sequence for clone 25303.
SEQ ID NO: 331–337 are the cDNA sequences of isoforms of the p53 tumor suppressor homologue, p63 (also referred to as L530S).
SEQ ID NO: 338–344 are the amino acid sequences encoded by SEQ ID NO: 331–337, respectively.
SEQ ID NO: 345 is a second cDNA sequence for the antigen L763P.
SEQ ID NO: 346 is the amino acid sequence encoded by the sequence of SEQ ID NO: 345.
SEQ ID NO: 347 is a determined full-length cDNA sequence for L523S.
SEQ ID NO: 348 is the predicted amino acid sequence encoded by SEQ ID NO: 347.
SEQ ID NO: 349 is the cDNA sequence encoding the N-terminal portion of L773P.
SEQ ID NO: 350 is the amino acid sequence of the N-terminal portion of L773P.
SEQ ID NO: 351 is polynucleotide sequence encoding the fusion of Ra12 and the N-terminal portion of L763P.
SEQ ID NO: 352 is the amino acid sequence of the fusion of Ra12 and the N-terminal portion of L763P.
SEQ ID NO: 353 is polynucleotide sequence encoding the fusion of Ra12 and the C-terminal portion of L763P.
SEQ ID NO: 354 is the amino acid sequence of the fusion of Ra12 and the C-terminal portion of L763P.

DETAILED DESCRIPTION OF THE INVENTION

As noted above, the present invention is generally directed to compositions and methods for the therapy and diagnosis of cancer, such as lung cancer. The compositions described herein may include lung tumor polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a lung tumor protein or a variant thereof. A "lung tumor protein" is a protein that is expressed in lung tumor cells at a level that is at least two fold, and preferably at least five fold, greater than the level of expression in a normal tissue, as determined using a representative assay provided herein. Certain lung tumor proteins are tumor proteins that react detectably (within an immunoassay, such as an ELISA or Western blot) with antisera of a patient afflicted with lung cancer. Polynucleotides of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery human lung tumor proteins. Sequences of polynucleotides encoding specific tumor proteins are provided in SEQ ID NO: 1–109, 111, 113, 115–151, 153, 154,157, 158, 160, 162–164, 167, 168, 171, 173, 175, 177–224, 255–337, 345, 347 and 349.

Therefore, in accordance with the above, and as described further below, the present invention provides illustrative polynucleotide compositions having sequences set forth in SEQ ID NO:1–109, 111, 113, 115–151, 153, 154,157, 158, 160, 162–164, 167, 168, 171, 173, 175, 177–224, 255–337, 345, 347 and 349, illustrative polypeptide compositions having amino acid sequences set forth in SEQ ID NO:110, 112, 114, 152, 155, 156, 159, 161, 165, 166, 169, 170, 172, 174, 176, 225, 252, 338–344, 346, 348, and 350, antibody compositions capable of binding such polypeptides, and numerous additional embodiments employing such compositions, for example in the detection, diagnosis and/or therapy of human lung cancer.

Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

"Isolated," as used herein, means that a polynucleotide is substantially away from other coding sequences, and that the DNA segment does not contain large portions of unrelated coding DNA, such as large chromosomal fragments or other functional genes or polypeptide coding regions. Of course, this refers to the DNA segment as originally isolated, and does not exclude genes or coding regions later added to the segment by the hand of man.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a lung tumor protein or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M.O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Heim J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Any polynucleotide that encodes a lung tumor protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a lung tumor protein. More preferably, a polynucleotide encodes an immunogenic portion of a lung tumor protein. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Probes and Primers

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO:1–109, 111, 113, 115–151, 153, 154, 157, 158, 160, 162–164, 167, 168, 171, 173, 175, 177–224, 255–337, 345, 347 and 349, or to any continuous portion of the sequence, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

Polynucleotide Identification and Characterization

Polynucleotides may be identified, prepared and/or manipulated using any of a variety of well established techniques. For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein, such as lung tumor cells. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a full length gene from a suitable library (e.g., a lung tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215–223, Horn, T. et al. (1980) *Nucl. Acids Res. Symp. Ser.* 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, W H Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding polypeptides may be driven by any of a number of promoters. For example, viral promoters such as the 35S and 1 9S promoters of CaMV may be used alone or in combination with the omega leader sequence from TMV (Takamatsu, N. (1987) *EMBO J.* 6:307–311. Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or Trichoplusia larvae in which the polypeptide of interest may be expressed (Engelhard, E. K. et al. (1994) *Proc. Natl. Acad. Sci.* 91:3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Prob. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al (1977) *Cell* 11:223–32) and adenine phosphoribosyltransferase (Lowy, I. et al. (1990) *Cell* 22:817–23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al. (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et a. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263–281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Site-specific Mutagenesis

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the antigenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

Polynucleotide Amplification Techniques

A number of template dependent processes are available to amplify the target sequences of interest present in a sample. One of the best known amplification methods is the polymerase chain reaction (PCRTM) which is described in detail in U.S. Pat. Nos. 4,683,195, 4,683,202 and 4,800,159, each of which is incorporated herein by reference in its entirety. Briefly, in PCRT, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308 (specifically incorporated herein by reference in its entirety). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having a 3' and 5' sequences of non-target DNA and an internal or "middle" sequence of the target protein specific RNA is hybridized to DNA which is present in a sample. Upon hybridization, the reaction is treated with RNaseH, and the products of the probe are identified as distinctive products by generating a signal that is released after digestion. The original template is annealed to another cycling probe and the reaction is repeated. Thus, CPR involves amplifying a signal generated by hybridization of a probe to a target gene specific expressed nucleic acid.

Still other amplification methods described in Great Britain Pat. Appl. No. 2 202 328, and in PCT Intl. Pat. Appl. Publ. No. PCT/US89/01025, each of which is incorporated herein by reference in its entirety, may be used in accordance with the present invention. In the former application, "modified" primers are used in a PCR-like, template and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer that has sequences specific to the target sequence. Following polymerization, DNA/RNA hybrids are digested with RNase H while double stranded DNA molecules are heat-denatured again. In either case the single stranded DNA is made fully double stranded by addition of second target-specific primer, followed by polymerization. The double stranded DNA molecules are then multiply transcribed by a polymerase such as T7 or SP6. In an isothermal cyclic reaction, the RNAs are reverse transcribed into DNA, and transcribed once again with a polymerase such as T7 or SP6. The resulting products, whether truncated or complete, indicate target-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

Biological Functional equivalents

Modification and changes may be made in the structure of the polynucleotides and polypeptides of the present invention and still obtain a functional molecule that encodes a polypeptide with desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |

TABLE 1-continued

| Amino Acids | | | Codons |
|---|---|---|---|
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

2. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

3. Adeno-associated Viruses

AAV (Ridgeway, 1988; Hermonat and Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs (FIG. 2). There are two major genes in the AAV genome: rep and cap. The rep gene codes for proteins responsible for viral replications, whereas cap codes for capsid protein VP1–3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

There are several factors that prompted researchers to study the possibility of using rAAV as an expression vector One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., 1988), lentiviruses, polio viruses and herpes viruses may be employed. They offer several attractive features for various mammalian cells (Friedmann, 1989; Ridgeway, 1988; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

5. Non-viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

Antisense Oligonucleotides

The end result of the flow of genetic information is the synthesis of protein. DNA is transcribed by polymerases into messenger RNA and translated on the ribosome to yield a folded, functional protein. Thus there are several steps along the route where protein synthesis can be inhibited. The native DNA segment coding for a polypeptide described herein, as all such mammalian DNA strands, has two strands: a sense strand and an antisense strand held together by hydrogen bonding. The messenger RNA coding for polypeptide has the same nucleotide sequence as the sense DNA strand except that the DNA thymidine is replaced by uridine. Thus, synthetic antisense nucleotide sequences will bind to a mRNA and inhibit expression of the protein encoded by that mRNA.

The targeting of antisense oligonucleotides to mRNA is thus one mechanism to shut down protein synthesis, and, consequently, represents a powerful and targeted therapeutic approach. For example, the synthesis of polygalactauronase and the muscarine type 2 acetylcholine receptor are inhibited by antisense oligonucleotides directed to their respective MRNA sequences (U.S. Pat. Nos. 5,739,119 and 5,759,829, each specifically incorporated herein by reference in its entirety). Further, examples of antisense inhibition have been demonstrated with the nuclear protein cyclin, the multiple drug resistance gene (MDGI), ICAM-1, E-selectin, STK-1, striatal GABA$_A$ receptor and human EGF (Jaskulski et al., 1988; Vasanthakumar and Ahmed, 1989; Peris et al., 1998; U.S. Pat. Nos. 5,801,154; 5,789,573; 5,718,709 and 5,610,288, each specifically incorporated herein by reference in its entirety). Antisense constructs have also been described that inhibit and can be used to treat a variety of abnormal cellular proliferations, e.g. cancer (U.S. Pat. Nos. 5,747,470; 5,591,317 and 5,783,683, each specifically incorporated herein by reference in its entirety).

Therefore, in exemplary embodiments, the invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein.

Selection of antisense compositions specific for a given gene sequence is based upon analysis of the chosen target sequence (i.e. in these illustrative examples the rat and human sequences) and determination of secondary structure, $T_m$, binding energy, relative stability, and antisense compositions were selected based upon their relative inability to form dimers, hairpins, or other secondary structures that would reduce or prohibit specific binding to the target mRNA in a host cell.

Highly preferred target regions of the mRNA, are those which are at or near the AUG translation initiation codon, and those sequences which were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane (Morris et al., 1997).

Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); Neurospora VS RNA ribozynic motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al., 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes are well known in the art, and include detection of the presence of mRNA associated with an IL-5 related condition. Such RNA is detected by determining the presence of a cleavage product after treatment with a ribozyme using standard methodology.

Peptide Nucleic Acids

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (1997) and is incorporated herein by reference. As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass.). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Ruskowski et al., 1997). U.S. Pat. No. 5,700,922 discusses PNA-DNA-PNA chimeric molecules and their uses in diagnostics, modulating protein in organisms, and treatment of conditions susceptible to therapeutics.

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11–13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al. (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al. (1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

Polypeptide Compositions

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

In the present invention, a polypeptide composition is also understood to comprise one or more polypeptides that are immunologically reactive with antibodies generated against a polypeptide of the invention, particularly a polypeptide having the amino acid sequence disclosed in SEQ ID NO:110, 112, 114, 152, 155, 156, 159, 161, 165, 166, 169, 170, 172, 174, 176, 225, 226–251, 252, 338–344, 346, 348 and 350, or to active fragments, or to variants or biological functional equivalents thereof.

Likewise, a polypeptide composition of the present invention is understood to comprise one or more polypeptides that are capable of eliciting antibodies that are immunologically reactive with one or more polypeptides encoded by one or more contiguous nucleic acid sequences contained in SEQ ID NO:1–109, 111, 113, 115–151, 153, 154, 157, 158, 160, 162–164, 167, 168, 171, 173, 175, 177–224, 255–337, 345, 347 and 349, or to active fragments, or to variants thereof, or to one or more nucleic acid sequences which hybridize to one or more of these sequences under conditions of moderate to high stringency. Particularly illustrative polypeptides include the amino acid sequence disclosed in SEQ ID NO:110, 112, 114, 152, 155, 156, 159, 161, 165, 166, 169, 170, 172, 174, 176, 225, 226–251, 252, 338–344, 346, 348 and 350.

As used herein, an active fragment of a polypeptide includes a whole or a portion of a polypeptide which is modified by conventional techniques, e.g., mutagenesis, or by addition, deletion, or substitution, but which active fragment exhibits substantially the same structure function, antigenicity, etc., as a polypeptide as described herein.

In certain illustrative embodiments, the polypeptides of the invention will comprise at least an immunogenic portion of a lung tumor protein or a variant thereof, as described herein. As noted above, a "lung tumor protein" is a protein that is expressed by lung tumor cells. Proteins that are lung tumor proteins also react detectably within an immunoassay (such as an ELISA) with antisera from a patient with lung cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a lung tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native lung tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native lung tumor protein. A polypeptide "variant," as used herein, is a polypeptide that differs from a native lung tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96%, 97%, 98%, or 99% or more identity (determined as described above) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a lung tumor protein. As used herein, an antibody, or antigen-binding fragment thereof, is said to "specifically bind" to a lung tumor protein if it reacts at a detectable level (within, for example, an ELISA) with a lung tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as lung cancer, using the representative assays provided herein. In other words, antibodies or other binding agents that bind to a lung tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on selective medium that supports the growth of hybrid cells, but not myeloma cells. A referred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a lung tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. Nos. 5,240,856; 5,215,926; WO 89/06280; WO 91/16116 and WO 92/07243). Alternatively, T cells may be derived from related or unrelated humans, non-human mammals, cell lines or cultures.

T cells may be stimulated with a lung tumor polypeptide, polynucleotide encoding a lung tumor polypeptide and/or an antigen presenting cell (APC) that expresses such a polypeptide. Such stimulation is performed under conditions and for a time sufficient to permit the generation of T cells that are specific for the polypeptide. Preferably, a lung tumor polypeptide or polynucleotide is present within a delivery vehicle, such as a microsphere, to facilitate the generation of specific T cells.

T cells are considered to be specific for a lung tumor polypeptide if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a lung tumor polypeptide (100 ng/ml–100 µ/ml, preferably 200 ng/ml–25 µ/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a lung tumor polypeptide, polynucleotide or polypeptide-expressing APC may be $CD4^+$ and/or $CD8^+$. Lung tumor protein-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a lung tumor polypeptide, polynucleotide or APC can be expanded in number either in vitro or in vivo. Proliferation of such T cells in vitro may be accomplished in a variety of ways. For example, the T cells can be re-exposed to a lung tumor polypeptide, or a short peptide corresponding to an immunogenic portion of such a polypeptide, with or without the addition of T cell growth factors, such as interleukin-2, and/or stimulator cells that synthesize a lung tumor polypeptide. Alternatively, one or more T cells that proliferate in the presence of a lung tumor protein can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable solutions for administration to a cell or an animal, either alone, or in combination with one or more other modalities of therapy.

It will also be understood that, if desired, the nucleic acid segment, RNA, DNA or PNA compositions that express a polypeptide as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

1. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In certain circumstances it will be desirable to deliver the pharmaceutical compositions disclosed herein parenterally, intravenously, intramuscularly, or even intraperitoneally as described in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffer carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SLNs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 µm) should be designed using polymers able to be degraded in vivo. Biodegradable polyalkylcyanoacrylate nanoparticles that meet these requirements are contemplated for use in the present invention. Such particles may be are easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety).

Vaccines

In certain preferred embodiments of the present invention, vaccines are provided. The vaccines will generally comprise one or more pharmaceutical compositions, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

Illustrative vaccines may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

It will be apparent that a vaccine may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the vaccine compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. No. 08/853,826, now U.S. Pat. No. 6,113,918, and Ser. No. 09/074,720, now U.S. Pat. No. 6,355,257, the disclosures of which are incorporated herein by reference in their entireties.

Any vaccine provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429–1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a lung tumor protein (or portion or other variant thereof) such that the lung tumor polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the lung tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

Cancer Therapy

In further aspects of the present invention, the compositions described herein may be used for immunotherapy of cancer, such as lung cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs. Administration may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8$^+$ cytotoxic T lymphocytes and CD4$^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a lung tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnosis

In general, a cancer may be detected in a patient based on the presence of one or more lung tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as lung cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a lung tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length lung tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with lung cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as lung cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use lung tumor polypeptides to detect antibodies that bind to such polypeptides in a biological sample. The detection of such lung tumor protein specific antibodies may correlate with the presence of a cancer.

A cancer may also, or alternatively, be detected based on the presence of T cells that specifically react with a lung tumor protein in a biological sample. Within certain methods, a biological sample comprising $CD4^+$ and/or $CD8^+$ T cells isolated from a patient is incubated with a lung tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 µg/ml). It may be desirable to incubate another aliquot of a T cell sample in the absence of lung tumor polypeptide to serve as a control. For CD4+ T cells, activation is preferably detected by evaluating proliferation of the T cells. For CD8+ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a lung tumor protein in a biological sample. For example, at least two oligonucleotide primers may be employed in a polymerase chain reaction (PCR) based assay to amplify a portion of a lung tumor cDNA derived from a biological sample, wherein at least one of the oligonucleotide primers is specific for (i.e., hybridizes to) a polynucleotide encoding the lung tumor protein. The amplified cDNA is then separated and detected using techniques well known in the art, such as gel electrophoresis. Similarly, oligonucleotide probes that specifically hybridize to a polynucleotide encoding a lung tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a lung tumor protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO:1–109, 111, 113, 115–151, 153, 154, 157, 158, 160, 162–164, 167, 168, 171, 173, 175, 177–224, 255–337, 345, 347 and 349. Techniques for both PCR based assays and hybridization assays are well known in the art (see, for example, Mullis et al., *Cold Spring Harbor Symp. Quant. Biol.,* 51:263, 1987; Erlich ed., *PCR Technology,* Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple lung tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a lung tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a lung tumor protein in a biological sample. Such kits generally comprise at least one oligonucleotide probe or primer, as described above, that hybridizes to a polynucleotide encoding a lung tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a lung tumor protein.

The following Examples are offered by way of illustration and not by way of limitation.

EXAMPLE

Example 1

Isolation and Characterization of cDNA Sequences Encoding Lung Tumor Polypeptides This example illustrates the isolation of cDNA molecules encoding lung tumor-specific polypeptides from lung tumor cDNA libraries.

A. Isolation of CDNA Sequences from a Lung Squamous Cell Carcinoma Library

A human lung squamous cell carcinoma cDNA expression library was constructed from poly A$^+$ RNA from a pool of two patient tissues using a Superscript Plasmid System for cDNA Synthesis and Plasmid Cloning kit (BRL Life Technologies, Gaithersburg, Md.) following the manufacturer's protocol. Specifically, lung carcinoma tissues were homogenized with polytron (Kinematica, Switzerland) and total RNA was extracted using Trizol reagent (BRL Life Technologies) as directed by the manufacturer. The poly A$^+$ RNA was then purified using an oligo dT cellulose column as described in Sambrook et al., *Molecular Cloning: A Laboratory Manual*, Cold Spring Harbor Laboratories, Cold Spring Harbor, N.Y., 1989. First-strand cDNA was synthesized using the NotI/Oligo-dT18 primer. Double-stranded cDNA was synthesized, ligated with BstXI/EcoRI adaptors (Invitrogen, San Diego, Calif.) and digested with NotI. Following size fractionation with cDNA size fractionation columns (BRL Life Technologies), the cDNA was ligated into the BstXI/NotI site of pcDNA3.1 (Invitrogen) and transformed into ElectroMax *E. coli* DH10B cells (BRL Life Technologies) by electroporation.

Using the same procedure, a normal human lung cDNA expression library was prepared from a pool of four tissue specimens. The cDNA libraries were characterized by determining the number of independent colonies, the percentage of clones that carried insert, the average insert size and by sequence analysis. The lung squamous cell carcinoma library contained 2.7×10$^6$ independent colonies, with 100% of clones having an insert and the average insert size being 2100 base pairs. The normal lung cDNA library contained 1.4×10$^6$ independent colonies, with 90% of clones having inserts and the average insert size being 1800 base pairs. For both libraries, sequence analysis showed that the majority of clones had a full length cDNA sequence and were synthesized from mRNA.

cDNA library subtraction was performed using the above lung squamous cell carcinoma and normal lung cDNA libraries, as described by Hara et al. (*Blood*, 84:189–199, 1994) with some modifications. Specifically, a lung squamous cell carcinoma-specific subtracted cDNA library was generated as follows. Normal tissue cDNA library (80 µg) was digested with BamHI and XhoI, followed by a filling-in reaction with DNA polymerase Klenow fragment. After phenol-chloroform extraction and ethanol precipitation, the DNA was dissolved in 133 µl of H$_2$O, heat-denatured and mixed with 133 µl (133 µg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (67 µl) was added and the biotinylation reaction was repeated. After extraction with butanol five times, the DNA was ethanol-precipitated and dissolved in 23 µl H$_2$O to form the driver DNA.

To form the tracer DNA, 10 µg lung squamous cell carcinoma cDNA library was digested with NotI and SpeI, phenol chloroform extracted and passed through Chroma spin-400 columns (Clontech, Palo Alto, Calif.). Typically, 5 µg of cDNA was recovered after the sizing column. Following ethanol precipitation, the tracer DNA was dissolved in 5 µl H$_2$O. Tracer DNA was mixed with 15 µl driver DNA and 20 µl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 µl H$_2$O, mixed with 8 µl driver DNA and 20 µl of 2×hybridization buffer, and subjected to a hybridization at 68° C. for 2 hours (short hybridization [SH]). After removal of biotinylated double-stranded DNA, subtracted cDNA was ligated into NotI/SpeI site of chloramphenicol resistant pBCSK$^+$ (Stratagene, La Jolla, Calif.) and transformed into ElectroMax *E. coli* DH10B cells by electroporation to generate a lung squamous cell carcinoma specific subtracted cDNA library (herein after referred to as "lung subtraction I").

A second lung squamous cell carcinoma specific subtracted cDNA library (referred to as "lung subtraction II") was generated in a similar way to the lung subtraction library I, except that eight frequently recovered genes from lung subtraction I were included in the driver DNA, and 24,000 independent clones were recovered.

To analyze the subtracted cDNA libraries, plasmid DNA was prepared from 320 independent clones, randomly picked from the subtracted lung squamous cell carcinoma specific libraries. Representative cDNA clones were further characterized by DNA sequencing with a Perkin Elmer/Applied Biosystems Division Automated Sequencer Model 373A and/or Model 377 (Foster City, Calif.). The cDNA sequences for sixty isolated clones are provided in SEQ ID NO: 1–60. These sequences were compared to known sequences in the gene bank using the EMBL and GenBank databases (release 96). No significant homologies were found to the sequences provided in SEQ ID NO: 2, 3, 19, 38 and 46. The sequences of SEQ ID NO: 1, 6–8, 10–13, 15, 17, 18, 20–27, 29, 30, 32, 34–37, 39–45, 47–49, 51, 52, 54, 55 and 57–59 were found to show some homology to previously identified expressed sequence tags (ESTs). The sequences of SEQ ID NO: 9, 28, 31 and 33 were found to show some homology to previously identified non-human gene sequences and the sequences of SEQ ID NO: 4, 5, 14, 50, 53, 56 and 60 were found to show some homology to gene sequences previously identified in humans.

The subtraction procedure described above was repeated using the above lung squamous cell carcinoma cDNA library as the tracer DNA, and the above normal lung tissue cDNA library and a cDNA library from normal liver and heart (constructed from a pool of one sample of each tissue as described above), plus twenty other cDNA clones that were frequently recovered in lung subtractions I and II, as the driver DNA (lung subtraction III). The normal liver and heart cDNA library contained 1.76×10$^6$ independent colonies, with 100% of clones having inserts and the average insert size being 1600 base pairs. Ten additional clones were isolated (SEQ ID NO: 61–70). Comparison of these cDNA sequences with those in the gene bank as described above, revealed no significant homologies to the sequences provided in SEQ ID NO: 62 and 67. The sequences of SEQ ID NO: 61, 63–66, 68 and 69 were found to show some homology to previously isolated ESTs and the sequence provided in SEQ ID NO: 70 was found to show some homology to a previously identified rat gene.

In further studies, the subtraction procedure described above was repeated using the above lung squamous cell carcinoma cDNA library as the tracer DNA, and a cDNA library from a pool of normal lung, kidney, colon, pancreas, brain, resting PBMC, heart, skin and esophagus as the driver DNA, with esophagus cDNAs making up one third of the driver material. Since esophagus is enriched in normal epithelial cells, including differentiated squamous cells, this procedure is likely to enrich genes that are tumor specific rather than tissues specific. The cDNA sequences of 48 clones determined in this subtraction are provided in SEQ ID NO: 177–224. The sequences of SEQ ID NO: 177, 178, 180, 181, 183, 187, 192, 195–197, 208, 211, 212, 215, 216, 218 and 219 showed some homology to previously identified genes. The sequences of SEQ ID NO: 179, 182, 184–186, 188–191, 193, 194, 198–207, 209 210, 213, 214, 217, 220 and 224 showed some homology to previously determined ESTs. The sequence of SEQ ID NO: 221–223 showed no homology to any previously determined sequence.

B. Isolation of cDNA Sequences from a Lung Adenocarcinoma Library

A human lung adenocarcinoma cDNA expression library was constructed as described above. The library contained $3.2 \times 10^6$ independent colonies, with 100% of clones having an insert and the average insert size being 1500 base pairs. Library subtraction was performed as described above using the normal lung and normal liver and heart cDNA expression libraries described above as the driver DNA. Twenty-six hundred independent clones were recovered.

Initial cDNA sequence analysis from 100 independent clones revealed many ribosomal protein genes. The cDNA sequences for fifteen clones isolated in this subtraction are provided in SEQ ID NO: 71–86. Comparison of these sequences with those in the gene bank as described above revealed no significant homologies to the sequence provided in SEQ ID NO: 84. The sequences of SEQ ID NO: 71, 73, 74, 77, 78 and 80–82 were found to show some homology to previously isolated ESTs, and the sequences of SEQ ID NO: 72, 75, 76, 79, 83 and 85 were found to show some homology to previously identified human genes.

In further studies, a cDNA library (referred to as mets3616A) was constructed from a metastatic lung adenocarcinoma. The determined cDNA sequences of 25 clones sequenced at random from this library are provided in SEQ ID NO: 255–279. The mets3616A cDNA library was subtracted against a cDNA library prepared from a pool of normal lung, liver, pancreas, skin, kidney, brain and resting PBMC. To increase the specificity of the subtraction, the driver was spiked with genes that were determined to be most abundant in the mets3616A cDNA library, such as EF1-alpha, integrin-beta and anticoagulant protein PP4, as well as with cDNAs that were previously found to be differentially expressed in subtracted lung adenocarcinoma cDNA libraries. The determined cDNA sequences of 51 clones isolated from the subtracted library (referred to as mets3616A-S1) are provided in SEQ ID NO: 280–330.

Comparison of the sequences of SEQ ID NO: 255–330 with those in the public databases revealed no significant homologies to the sequences of SEQ ID NO: 255–258, 260, 262–264, 270, 272, 275, 276, 279, 281, 287, 291, 296, 300 and 310. The sequences of SEQ ID NO: 259, 261, 265–269, 271, 273, 274, 277, 278, 282–285, 288–290, 292, 294, 297–299, 301, 303–309, 313, 314, 316, 320–324 and 326–330 showed some homology to previously identified gene sequences, while the sequences of SEQ ID NO: 280, 286, 293, 302, 310, 312, 315, 317–319 and 325 showed some homology to previously isolated expressed sequence tags (ESTs).

Example 2

Determination of Tissue Specificity of Lung Tumor Polypeptides

Using gene specific primers, mRNA expression levels for seven representative lung tumor polypeptides described in Example 1 were examined in a variety of normal and tumor tissues using RT-PCR.

Briefly, total RNA was extracted from a variety of normal and tumor tissues using Trizol reagent as described above. First strand synthesis was carried out using 2 µg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. 1 µl of 1:30 dilution of cDNA was employed to enable the linear range amplification of the β-actin template and was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in five different types of tumor tissue (lung squamous cell carcinoma from 3 patients, lung adenocarcinoma, colon tumor from 2 patients, breast tumor and prostate tumor), and thirteen different normal tissues (lung from 4 donors, prostate, brain, kidney, liver, ovary, skeletal muscle, skin, small intestine, stomach, myocardium, retina and testes). Using a 10-fold amount of cDNA, the antigen LST-S1-90 (SEQ ID NO: 3) was found to be expressed at high levels in lung squamous cell carcinoma and in breast tumor, and at low to undetectable levels in the other tissues examined.

The antigen LST-S2-68 (SEQ ID NO: 15) appears to be specific to lung and breast tumor, however, expression was also detected in normal kidney. Antigens LST-S1-169 (SEQ ID NO: 6) and LST-S1-133 (SEQ ID NO: 5) appear to be very abundant in lung tissues (both normal and tumor), with the expression of these two genes being decreased in most of the normal tissues tested. Both LST-S1-169 and LST-S1-133 were also expressed in breast and colon tumors. Antigens LST-S1-6 (SEQ ID NO: 7) and LST-S2-I2-5F (SEQ ID NO: 47) did not show tumor or tissue specific expression, with the expression of LST-S1-28 being rare and only detectable in a few tissues. The antigen LST-S3-7 (SEQ ID NO: 63) showed lung and breast tumor specific expression, with its message only being detected in normal testes when the PCR was performed for 30 cycles. Lower level expression was detected in some normal tissues when the cycle number was increased to 35. Antigen LST-S3-13 (SEQ ID NO: 66) was found to be expressed in 3 out of 4 lung tumors, one breast tumor and both colon tumor samples. Its expression in normal tissues was lower compared to tumors, and was only detected in 1 out of 4 normal lung tissues and in normal tissues from kidney, ovary and retina. Expression of antigens LST-S3-4 (SEQ ID NO: 62) and LST-S3-14 (SEQ ID NO: 67) was rare and did not show any tissue or tumor specificity. Consistent with Northern blot analyses, the RT-PCT results on antigen LAT-S1-A-10A (SEQ ID NO: 78) suggested that its expression is high in lung, colon, stomach and small intestine tissues, including lung and colon tumors, whereas its expression was low or undetectable in other tissues.

A total of 2002 cDNA fragments isolated in lung subtractions I, II and III, described above, were colony PCR amplified and their mRNA expression levels in lung tumor, normal lung, and various other normal and tumor tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Seventeen non-redundant cDNA clones showed over-expression in lung squamous tumors, with expression in normal tissues tested (lung, skin, lymph node, colon, liver, pancreas, breast, heart, bone marrow, large intestine, kidney, stomach, brain, small intestine, bladder and salivary gland) being either undetectable, or 10-fold less compared to lung squamous tumors. The determined partial cDNA sequences for the clone L513S are provided in SEQ ID NO: 87 and 88; those for L514S are provided in SEQ ID NO: 89 and 90; those for L516S in SEQ ID NO: 91 and 92; that for L517S in SEQ ID NO: 93; that for L519S in SEQ ID NO: 94; those for L520S in SEQ ID NO: 95 and 96; those for L521S in SEQ ID NO: 97 and 98; that for L522S in SEQ ID NO: 99; that for L523S in SEQ ID NO: 100; that for L524S in SEQ ID NO: 101; that for L525S in SEQ ID NO: 102; that for L526S in SEQ ID NO: 103; that for L527S in SEQ ID NO: 104; that for L528S in SEQ ID NO: 105; that for L529S in SEQ ID NO: 106; and those for L530S in SEQ ID NO: 107 and 108. Additionally, the full-length cDNA sequence for L530S is provided in SEQ ID NO: 151, with the corresponding predicted amino acid sequence being provided in SEQ ID NO: 152. L530S shows homology to a splice variant of a p53 tumor suppressor homologue, p63. The cDNA sequences of 7 known isoforms of p63 are provided in SEQ ID NO: 331–337, with the corresponding predicted amino acid sequences being provided in SEQ ID NO: 338–344, respectively.

Due to polymorphisms, the clone L531S appears to have two forms. A first determined full-length cDNA sequence for L531S is provided in SEQ ID NO: 109, with the corresponding predicted amino acid sequence being provided in SEQ ID NO: 110. A second determined full-length cDNA sequence for L531S is provided in SEQ ID NO: 111, with the corresponding predicted amino acid sequence being provided in SEQ ID NO: 112. The sequence of SEQ ID NO: 111 is identical to that of SEQ ID NO: 109, except that it contains a 27 bp insertion. Similarly, L514S also has two alternatively spliced forms; the first variant cDNA is listed as SEQ ID NO: 153, with the corresponding amino acid sequence being provided in SEQ ID NO: 155. The second variant form of L514S full-length cDNA is provided in SEQ ID NO: 154, with its corresponding amino acid sequence being provided in SEQ ID NO: 156.

Full length cloning for L524S (SEQ ID NO: 101) yielded two variants (SEQ ID NO: 163 and 164) with the corresponding predicted amino acid sequences of SEQ ID NO: 165 and 166, respectively. Both variants have been shown to encode parathyroid hormone-related peptide.

Attempts to isolate the full-length cDNA for L519S, resulted in the isolation of the extended cDNA sequence provided in SEQ ID NO: 173, which contains a potential open reading frame. The predicted amino acid sequence encoded by the sequence of SEQ ID NO: 173 is provided in SEQ ID NO: 174. Additionally, the full-length cDNA sequence for the clone of SEQ ID NO: 100 (known as L523S), a known gene, is provided in SEQ ID NO: 175, with the corresponding predicted amino acid sequence provided in SEQ ID NO: 176. In further studies, a full-length cDNA sequence for L523S was isolated from a L523S-positive tumor cDNA library by PCR amplification using gene specific primers designed from the sequence of SEQ ID NO: 175. The determined cDNA sequence is provided in SEQ ID NO: 347. The amino acid sequence encoded by this sequence is provided in SEQ ID NO: 348. This protein sequence differs from the previously published protein sequence at two amino acid positions, namely at positions 158 and 410.

Comparison of the sequences of L514S and L531 S (SEQ ID NO: 87 and 88, 89 and 90, and 109, respectively) with those in the gene bank, as described above, revealed no significant homologies to known sequences. The sequences of L513S, L516S, L517S, L519S, L520S and L530S (SEQ ID NO: 87 and 88, 91 and 92, 93, 94, 95 and 96, 107 and 108, respectively) were found to show some homology to previously identified ESTs. The sequences of L521S, L522S, L523S, L524S, L525S, L526S, L527S, L528S and L529S (SEQ ID NO: 97 and 98, 99, 99, 101, 102, 103, 104, 105, and 106, respectively) were found to represent known genes. The determined full-length cDNA sequences for L520S is provided in SEQ ID NO: 113, with the corresponding predicted amino acid sequence being provided in SEQ ID NO: 114. Subsequent microarray analysis has shown L520S to be overexpressed in breast tumors in addition to lung squamous tumors.

Further analysis has demonstrated that L529S (SEQ ID NO: 106 and 115), L525S (SEQ ID NO: 102 and 120) and L527S (SEQ ID NO: 104) are cytoskeletal components and potentially squamous cell specific proteins. L529S is connexin 26, a gap junction protein. It is highly expressed in lung squamous tumor 9688T, and moderately over-expressed in two others. However, lower level expression of connexin 26 is also detectable in normal skin, colon, liver and stomach. The over-expression of connexin 26 in some breast tumors has been reported and a mutated form of L529S may result in over-expression in lung tumors. L525S is plakophilin 1, a desmosomal protein found in plaque-bearing adhering junctions of the skin. Expression levels for L525S mRNA is highly elevated in three out of four lung squamous tumors tested, and in normal skin. L527S has been identified as keratin 6 isoform, type II 58 Kd keratin, and cytokeratin 13 and shows over-expression in squamous tumors and low expression in normal skin, breast and colon tissues. Notably, keratin and keratin-related genes have been extensively documented as potential markers for lung cancer including CYFRA2.1 (Pastor, A., et al., *Eur. Respir. J.*, 10:603–609, 1997). L513S (SEQ ID NO: 87 and 88) shows moderate over-expression in several tumor tissues tested, and encodes a protein that was first isolated as a pemphigus vulgaris antigen.

L520S (SEQ ID NO: 95 and 96) and L521S (SEQ ID NO: 97 and 98) are highly expressed in lung squamous tumors, and L520S is up-regulated in normal salivary gland and L521S is over-expressed in normal skin. Both belong to a family of small proline rich proteins and represent markers for fully differentiated squamous cells. L521S has been described as a specific marker for lung squamous tumor (Hu, R., et al., *Lung Cancer*, 20:25–30, 1998). L515S (SEQ ID NO: 162) encodes IGF-β2 and L516S is an aldose reductase homologue and both are moderately expressed in lung squamous tumors and in normal colon. Notably, L516S (SEQ ID NO: 91 and 92) is up-regulated in metastatic tumors but not primary lung adenocarcinoma, an indication of its potential role in metastasis and a potential prognostic marker. L522S (SEQ ID NO: 99) is moderately over-expressed in lung squamous tumors with minimum expression in normal tissues. L522S has been shown to belong to a class IV alcohol dehydrogenase, ADH7, and its expression profile suggests it is a squamous cell specific antigen. L523S (SEQ ID NO: 100) is moderately over-expressed in lung squamous tumor, human pancreatic cancer cell lines and pancreatic cancer tissues, suggesting this gene may be a shared antigen between pancreatic and lung squamous cell cancer.

L524S (SEQ ID NO: 101) is over-expressed in the majority of squamous tumors tested and is homologous with parathyroid hormone-related peptide (PTHrP), which is best known to cause humoral hypercalcaemia associated with malignant tumors such as leukemia, prostate and breast cancer. It is also believed that PTHrP is most commonly associated with squamous carcinoma of lung and rarely with lung adenocarcinoma (Davidson, L. A., et al., *J. Pathol.*, 178: 398–401, 1996). L528S (SEQ ID NO: 105) is highly over-expressed in two lung squamous tumors with moderate expression in two other squamous tumors, one lung adenocarcinoma and some normal tissues, including skin, lymph nodes, heart, stomach and lung. It encodes the NMB gene that is similar to the precursor of melanocyte specific gene Pmel17, which is reported to be preferentially expressed in low-metastatic potential melanoma cell lines. This suggests that L528S may be a shared antigen in both melanoma and lung squamous cell carcinoma. L526S (SEQ ID NO: 103) is overexpressed in all lung squamous cell tumor tissues tested and has been shown to share homology with a gene (ATM) in which a mutation causes ataxia telangiectasia, a genetic disorder in humans causing a predisposition to cancer, among other symptoms. ATM encodes a protein that activates p53 mediated cell-cycle checkpoint through direct binding and phosphorylation of the p53 molecule. Approximately 40% of lung cancer is associated with p53 mutations, and it is speculated that over-expression of ATM is a result of compensation for loss of p53 function, but it is unknown whether over-expression is the cause of result of lung squamous cell carcinoma. Additionally, expression of L526S (ATM) is also detected in a metastatic but not lung adenocarcinoma, suggesting a role in metastasis.

Expression of L523S (SEQ ID NO: 175), was also examined by real time RT-PCR as described above. In a first study using a panel of lung squamous tumors, L523S was found to be expressed in 4/7 lung squamous tumors, 2/3 head and neck squamous tumors and 2/2 lung adenocarcinomas, with low level expression being observed in skeletal muscle, soft palate and tonsil. In a second study using a lung adenocarcinoma panel, expression of L523S was observed in 4/9 primary adenocarcinomas, 2/2 lung pleural effusions, 1/1 metastatic lung adenocarcinomas and 2/2 lung squamous tumors, with little expression being observed in normal tissues.

Expression of L523S in lung tumors and various normal tissues was also examined by Northern blot analysis, using standard techniques. In a first study, L523S was found to be expressed in a number of lung adenocarcinomas and squamous cell carcinomas, as well as normal tonsil. No expression was observed in normal lung. In a second study using a normal tissue blot (HB-12) from Clontech, no expression was observed in brain, skeletal muscle, colon, thymus, spleen, kidney, liver, small intestine, lung or PBMC, although there was strong expression in placenta.

Example 3

Isolation and Characterization of Lung Tumor Polypeptides by PCR-based Subtraction Eight hundred and fifty seven clones from a cDNA subtraction library, containing cDNA from a pool of two human lung squamous tumors subtracted against eight normal human tissue cDNAs including lung, PBMC, brain, heart, kidney, liver, pancreas, and skin, (Clontech, Palo Alto, Calif.) were derived and submitted to a first round of PCR amplification. This library was subjected to a second round of PCR amplification, following the manufacturer's protocol. The resulting cDNA fragments were subcloned into the vector P7-Adv vector (Clontech, Palo Alto, Calif.) and transformed into DH5α *E. coli* (Gibco, BRL). DNA was isolated from independent clones and sequenced using a Perkin Elmer/Applied Biosystems Division Automated Sequencer Model 373A.

One hundred and sixty two positive clones were sequenced. Comparison of the DNA sequences of these clones with those in the EMBL and GenBank databases, as described above, revealed no significant homologies to 13 of these clones, hereinafter referred to as Contigs 13, 16, 17, 19, 22, 24, 29, 47, 49, 56–59. The determined cDNA sequences for these clones are provided in SEQ ID NO: 125, 127–129, 131–133, 142, 144, 148–150, and 157, respectively. Contigs 1, 3–5, 7–10, 12, 11, 15, 20, 31, 33, 38, 39, 41, 43, 44, 45, 48, 50, 53, 54 (SEQ ID NO: 115–124, 126, 130, 134–141, 143, 145–147, respectively) were found to show some degree of homology to previously identified DNA sequences. Contig 57 (SEQ ID NO: 149) was found to represent the clone L519S (SEQ ID NO: 94) disclosed in U.S. patent application Ser. No. 09/123,912, filed Jul. 27, 1998, now U.S. Pat. No. 6,312,695. To the best of the inventors' knowledge, none of these sequences have been previously shown to be differentially over-expressed in lung tumors.

mRNA expression levels for representative clones in lung tumor tissues, normal lung tissues (n=4), resting PBMC, salivary gland, heart, stomach, lymph nodes, skeletal muscle, soft palate, small intestine, large intestine, bronchial, bladder, tonsil, kidney, esophagus, bone marrow, colon, adrenal gland, pancreas, and skin, (all derived from human) were determined by RT-PCR as described above. Expression levels using microarray technology, as described above, were examined in one sample of each tissue type unless otherwise indicated.

Contig 3 (SEQ ID NO: 116) was found to be highly expressed in all head and neck squamous cell tumors tested (17/17), and expressed in the majority (8/12) of lung squamous tumors, (high expression in 7/12, moderate in 2/12, and low in 2/12), while showing negative expression for 2/4 normal lung tissues and low expression in the remaining two samples. Contig 3 showed moderate expression in skin and soft palate, and lowered expression levels in resting PBMC, large intestine, salivary gland, tonsil, pancreas, esophagus, and colon. Contig II (SEQ ID NO: 124) was found to be expressed in all head and neck squamous cell tumors tested (17/17): highly expressed in 14/17, and moderately expressed in 3/17. Additionally, expression in lung squamous tumors showed high expression in 3/12 and moderate in 4/12. Contig 11 was negative for 3/4 normal lung samples, with the remaining sample having only low expression. Contig 11 showed low to moderate reactivity to salivary gland, soft palate, bladder, tonsil, skin, esophagus, and large intestine. Contig 13 (SEQ ID NO: 125) was found to be expressed in all head and neck squamous cell tumors tested (17/17): highly expressed in 12/17, and moderately expressed in 5/17. Contig 13 was expressed in 7/12 lung squamous tumors, with high expression in 4/12 and moderate expression in three samples. Analysis of normal lung samples showed negative expression for 2/4 and low to moderate expression in the remaining two samples. Contig 13 did show low to moderate reactivity to resting PBMC, salivary gland, bladder, pancreas, tonsil, skin, esophagus, and large intestine, as well as high expression in soft palate. Contig 16 (SEQ ID NO: 127) was found to be moderately expressed in some head and neck squamous cell tumors (6/17) and one lung squamous tumor; while showing no expression in any normal lung samples tested. Contig 16 did show low reactivity to resting PBMC, large intestine, skin, salivary gland, and soft palate. Contig 17 (SEQ ID NO: 128) was shown to be expressed in all head and neck squamous cell tumors tested (17/17): highly expressed in 5/17, and moderately expressed in 12/17. Expression levels in lung squamous tumors showed one tumor sample with high expression and 3/12 with moderate levels. Contig 17 was negative for 2/4 normal lung samples, with the remaining samples having only low expression. Additionally, low level expression was found in esophagus and soft palate. Contig 19 (SEQ ID NO: 129) was found to be expressed in most head and neck squamous cell tumors tested (11/17); with two samples having high levels, 6/17 showing moderate expression, and low expression being found in 3/17. Testing in lung squamous tumors revealed only moderate expression in 3/12 samples. Expression levels in 2/4 of normal lung samples were negative, the two other samples having only low expression. Contig 19 showed low expression levels in esophagus, resting PBMC, salivary gland, bladder, soft palate and pancreas.

Contig 22 (SEQ ID NO: 131), was shown to be expressed in most head and neck squamous cell tumors tested (13/17) with high expression in four of these samples, moderate expression in 6/17, and low expression in 3/17. Expression levels in lung squamous tumors were found to be moderate to high for 3/12 tissues tested, with negative expression in two normal lung samples and low expression in two other samples (n=4). Contig 22 showed low expression in skin, salivary gland and soft palate. Similarly, Contig 24 (SEQ ID NO: 132) was found to be expressed in most head and neck squamous cell tumors tested (13/17) with high expression in three of these samples, moderate expression in 6/17, and low expression in 4/17. Expression levels in lung squamous tumors were found to be moderate to high for 3/12 tissues tested, with negative expression for three normal lung samples and low expression in one sample (n=4). Contig 24 showed low expression in skin, salivary gland and soft palate. Contig 29 (SEQ ID NO: 133) was expressed in nearly all head and neck squamous cell tumors tested (16/17): highly expressed in 4/17, moderately expressed in 11/17, with low expression in one sample. Also, it was moderately expressed in 3/12 lung squamous tumors, while being negative for 2/4 normal lung samples. Contig 29 showed low to moderate expression in large intestine, skin, salivary gland, pancreas, tonsil, heart and soft palate. Contig 47 (SEQ ID NO: 142) was expressed in most head and neck squamous cell tumors tested (12/17): moderate expression in 10/17, and low expression in two samples. In lung squamous tumors, it was highly expressed in one sample and moderately expressed in two others (n=1 3). Contig 47 was negative for 2/4 normal lung samples, with the remaining two samples having moderate expression. Also, Contig 47 showed moderate expression in large intestine, and pancreas, and low expression in skin, salivary gland, soft palate, stomach, bladder, resting PBMC, and tonsil.

Contig 48 (SEQ ID NO: 143) was expressed in all head and neck squamous cell tumors tested (17/17): highly expressed in 8/17 and moderately expressed in 7/17, with low expression in two samples. Expression levels in lung squamous tumors were high to moderate in three samples (n=1 3). Contig 48 was negative for one out of four normal lung samples, the remaining showing low or moderate expression. Contig 48 showed moderate expression in soft palate, large intestine, pancreas, and bladder, and low expression in esophagus, salivary gland, resting PBMC, and heart. Contig 49 (SEQ ID NO: 144) was expressed at low to moderate levels in 6/17 head and neck squamous cell tumors tested. Expression levels in lung squamous tumors were moderate in three samples (n=13). Contig 49 was negative for 2/4 normal lung samples, the remaining samples showing low expression. Moderate expression levels in skin, salivary gland, large intestine, pancreas, bladder and resting PBMC were shown, as well as low expression in soft palate, lymph nodes, and tonsil. Contig 56 (SEQ ID NO: 148) was expressed in low to moderate levels in 3/17 head and neck squamous cell tumors tested, and in lung squamous tumors, showing low to moderate levels in three out of thirteen samples. Notably, low expression levels were detected in one adenocarcinoma lung tumor sample (n=2). Contig 56 was negative for 3/4 normal lung samples, and showed moderate expression levels in only large intestine, and low expression in salivary gland, soft palate, pancreas, bladder, and resting PBMC. Contig 58, also known as L769P, (SEQ ID NO: 150) was expressed at moderate levels in 11/17 head and neck squamous cell tumors tested and low expression in one additional sample. Expression in lung squamous tumors showed low to moderate levels in three out of thirteen samples. Contig 58 was negative for 3/4 normal lung samples, with one sample having low expression. Moderate expression levels in skin, large intestine, and resting PBMC were demonstrated, as well as low expression in salivary gland, soft palate, pancreas, and bladder. Contig 59 (SEQ ID NO: 157) was expressed in some head, neck, and lung squamous tumors. Low level expression of Contig 59 was also detected in salivary gland and large intestine.

The full-length cDNA sequence for Contig 22, also referred to as L763P, is provided in SEQ ID NO: 158, with the corresponding predicted amino acid sequence being provided in SEQ ID NO: 159. Real-time RT-PCR analysis of L763P revealed that it is highly expressed in 3/4 lung squamous tumors as well as 4/4 head and neck squamous tumors, with low level expression being observed in normal brain, skin, soft pallet and trachea. Subsequent database searches revealed that the sequence of SEQ ID NO: 158 contains a mutation, resulting in a frameshift in the corresponding protein sequence. A second cDNA sequence for L763P is provided in SEQ ID NO: 345, with the corresponding amino acid sequence being provided in SEQ ID NO: 346. The sequences of SEQ ID NO: 159 and 346 are identical with the exception of the C-terminal 33 amino acids of SEQ ID NO: 159.

The full-length cDNA sequence incorporating Contigs 17, 19, and 24, referred to as L762P, is provided in SEQ ID NO: 160, with the corresponding predicted amino acid sequence being provided in SEQ ID NO: 161. Further analysis of L762P has determined it to be a type I membrane protein and two additional variants have been sequenced. Variant 1 (SEQ ID NO: 167, with the corresponding amino acid sequence in SEQ ID NO: 169) is an alternatively spliced form of SEQ ID NO: 160 resulting in deletion of 503 nucleotides, as well as deletion of a short segment of the expressed protein. Variant 2 (SEQ ID NO: 168, with the corresponding amino acid sequence in SEQ ID NO: 170) has a two nucleotide deletion at the 3' coding region in comparison to SEQ ID NO: 160, resulting in a secreted form of the expressed protein. Real-time RT-PCR analysis of L762P revealed that is over-expressed in 3/4 lung squamous tumors and 4/4 head & neck tumors, with low level expression being observed in normal skin, soft pallet and trachea.

The full-length cDNA sequence for contig 56 (SEQ ID NO: 148), also referred to as L773P, is provided in SEQ ID NO: 171, with the predicted amino acid sequence in SEQ ID NO: 172. L773P was found to be identical to dihydroxyl dehydrogenase at the 3' portion of the gene, with divergent 5' sequence. As a result, the 69 N-terminal amino acids are unique. The cDNA sequence encoding the 69 N-terminal amino acids is provided in SEQ ID NO: 349, with the N-terminal amino acid sequence being provided in SEQ ID NO: 350. Real-time PCR revealed that L773P is highly expressed in lung squamous tumor and lung adenocarcinoma, with no detectable expression in normal tissues. Subsequent Northern blot analysis of L773P demonstrated that this transcript is differentially over-expressed in squamous tumors and detected at approximately 1.6 Kb in primary lung tumor tissue and approximately 1.3 Kb in primary head and neck tumor tissue.

Subsequent microarray analysis has shown Contig 58, also referred to as L769S (SEQ ID NO: 150), to be overexpressed in breast tumors in addition to lung squamous tumors.

Example 4

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

Example 5

Preparation of Antibodies Against Lung Cancer Antigens

Polyclonal antibodies against the lung cancer antigens L514S, L528S, and L531S (SEQ ID NO: 155, 225, and 112 respectively) were prepared as follows.

Rabbits were immunized with recombinant protein expressed in and purified from *E. coli* as described above. For the initial immunization, 400 μg of antigen combined with muramyl dipeptide (MDP) was injected subcutaneously (S.C.). Animals were boosted S.C. 4 weeks later with 200 μg of antigen mixed with incomplete Freund's Adjuvant (IFA). Subsequent boosts of 100 μg of antigen mixed with IFA were injected S.C. as necessary to induce high antibody titer responses. Serum bleeds from immunized rabbits were tested for antigen-specific reactivity using ELISA assays with purified protein. Polyclonal antibodies against L514S, L528S, and L531S were affinity purified from high titer polyclonal sera using purified protein attached to a solid support.

Immunohistochemical analysis using polyclonal antibodies against L514S was performed on a panel of 5 lung tumor samples, 5 normal lung tissue samples and normal colon, kidney, liver, brain and bone marrow. Specifically, tissue samples were fixed in formalin solution for 24 hours and embedded in paraffin before being sliced into 10 micron sections. Tissue sections were permeabilized and incubated with antibody for 1 hr. HRP-labeled anti-mouse followed by incubation with DAB chromogen was used to visualize L514S immunoreactivity. L514S was found to be highly expressed in lung tumor tissue with little or no expression being observed in normal lung, brain or bone marrow. Light staining was observed in colon and kidney. Staining was seen in normal liver but no mRNA has been detected in this tissue making this result suspect.

Generation of polyclonal anti-sera against L762P (SEQ ID NO: 169 and 170) was performed as follows. 400 micrograms of lung antigen was combined with 100 micrograms of muramyldipeptide (MDP). Equal volume of Incomplete Freund's Adjuvant (IFA) was added and then mixed until an emulsion was formed. Rabbits were injected subcutaneously (S.C.). After four weeks the animals were injected S.C. with 200 micrograms of antigen that was mixed with an equal volume of IFA. Every four weeks animals were boosted with 100 micrograms of antigen. Seven days following each boost the animal was bled. Sera was generated by incubating the blood at 4° C. for 12–24 hours followed by centrifugation.

Characterization of polyclonal antisera was carried out as follows. 96 well plates were coated with antigen by incubing with 50 microliters (typically 1 microgram) at 4° C. for 20 hrs. 250 microliters of BSA blocking buffer was added to the wells and incubated at RT for 2 hrs. Plates were washed 6 times with PBS/0.01% tween. Rabbit sera was diluted in PBS. Fifty microliters of diluted sera was added to each well and incubated at RT for 30 min. Plates were washed as described above before 50 microliters of goat anti-rabbit horse radish peroxidase (HRP) at a 1:10000 dilution was added and incubated at RT for 30 min. Plates were washed as described above and 100 μl of TMB Microwell Peroxidase Substrate was added to each well. Following a 15 minute incubation in the dark at room temperature the colorimetric reaction was stopped with 100 μl 1N H2SO4 and read immediately at 450 nm. Antisera showed strong reactivity to antigen L762P.

Example 6

Peptide Priming of Mice and Propagation of CTL Lines

Immunogenic peptides from the lung cancer antigen L762P (SEQ ID NO: 161) for HLA-A2/$K^b$-restricted CD8+ T cells were identified as follows.

The location of HLA-A2 binding peptides within the lung cancer antigen L762P (SEQ ID NO: 161) was predicted using a computer program which predicts peptides sequences likely to being to HLA-A*0201 by fitting to the known peptide binding motif for HLA-A*0201 (Rupert et al. (1993) *Cell* 74:929; Rammensee et al. (1995) *Immunogenetics* 41:178–228). A series of 19 synthetic peptides corresponding to a selected subset of the predicted HLA-A*0201 binding peptides was prepared as described above.

Mice expressing the transgene for human HLA A2/$K^b$ (provided by Dr L. Sherman, The Scripps Research Institute, La Jolla, Calif.) were immunized with the synthetic peptides, as described by Theobald et al., *Proc. Natl. Acad. Sci. USA* 92:11993–11997, 1995 with the following modifications. Mice were immunized with 50 μg of L726P peptide and 120 μg of an I-A$^b$ binding peptide derived from hepatitis B Virus protein emulsified in incomplete Freund's adjuvant. Three weeks later these mice were sacrificed and single cell suspensions prepared. Cells were then resuspended at 7×10$^6$ cells/ml in complete media (RPMI-1640; Gibco BRL, Gaithersburg, Md.) containing 10% FCS, 2 mM Glutamine (Gibco BRL), sodium pyruvate (Gibco BRL), non-essential amino acids (Gibco BRL), 2×10$^{-5}$ M 2-mercaptoethanol, 50 U/ml penicillin and streptomycin, and cultured in the presence of irradiated (3000 rads) L762P peptide-(5 kg/ml) and 10 mg/ml B$_2$-microglobulin-(3 μg/ml) LPS blasts (A2 transgenic spleens cells cultured in the presence of 7 μg/ml dextran sulfate and 25 μg/ml LPS for 3 days). After six days, cells (5×10$^5$ /ml) were restimulated with 2.5×10$^6$ /ml peptide pulsed irradiated (20,000 rads) EL4A2Kb cells (Sherman et al., *Science* 258:815–818, 1992) and 5×10$^6$ /ml irradiated (3000 rads) A2/K$^b$-transgenic spleen feeder cells. Cells were cultured in the presence of 10 U/ml IL-2. Cells were restimulated on a weekly basis as described, in preparation for cloning the line.

Peptide-specific cell lines were cloned by limiting dilution analysis with irradiated (20,000 rads) L762P peptide-pulsed EL4 A2Kb tumor cells (1×1 cells/well) as stimulators and irradiated (3000 rads) A2/K$^b$-transgenic spleen cells as feeders (5×10$^5$ cells/well) grown in the presence of 10 U/ml IL-2. On day 7, cells were restimulated as before. On day 14, clones that were growing were isolated and maintained in culture.

Cell lines specific for L762P-87 (SEQ ID NO: 226; corresponding to amino acids 87–95 of SEQ ID NO: 161), L762P-145 (SEQ ID NO: 227; corresponding to amino acids 145–153 of SEQ ID NO: 161), L762P-585 (SEQ ID NO: 228; corresponding to amino acids 585–593 of SEQ ID NO: 161), L762P-425 (SEQ ID NO: 229; corresponding to amino acids 425–433 of SEQ ID NO: 161), L762P(10)-424 (SEQ ID NO: 230; corresponding to amino acids 424–433 of SEQ ID NO: 161) and L762P(10)-458 (SEQ ID NO: 231; corresponding to amino acids 458–467 of SEQ ID NO: 161) demonstrated significantly higher reactivity (as measured by percent specific lysis) against L762P peptide-pulsed EL4-A2/K$^b$ tumor target cells than control peptide-pulsed EL4-A2/K$^b$ tumor target cells.

Example 7

Identification of CD4 Immunogenic T Cell Epitopes Derived from the Lung Cancer Antigen L762P CD4 T cell lines specific for the antigen L762P (SEQ ID NO: 161) were generated as follows.

A series of 28 overlapping peptides were synthesized that spanned approximately 50% of the L762P sequence. For priming, peptides were combined into pools of 4–5 peptides, pulsed at 20 micrograms/ml into dendritic cells for 24 hours. The dendritic cells were then washed and mixed with positively selected CD4+ T cells in 96 well U-bottomed plates. Forty cultures were generated for each peptide pool. Cultures were restimulated weekly with fresh dendritic cells loaded with peptide pools. Following a total of 3 stimulation cycles, cells were rested for an additional week and tested for specificity to antigen presenting cells (APC) pulsed with peptide pools using interferon-gamma ELISA and proliferation assays. For these assays, adherent monocytes loaded with either the relevant peptide pool or an irrelevant peptide were used as APC. T cell lines that appeared to specifically recognize L762P peptide pools both by cytokine release and proliferation were identified for each pool. Emphasis was placed on identifying T cells with proliferative responses. T cell lines that demonstrated either both L762P-specific cytokine secretion and proliferation, or strong proliferation alone were further expanded to be tested for recognition of individual peptides from the pools, as well as for recognition of recombinant L762P. The source of recombinant L762P was *E. coli*, and the material was partially purified and endotoxin positive. These studies employed 10 micrograms of individual peptides, 10 or 2 micrograms of an irrelevant peptide, and 2 or 0.5 micrograms of either L762P protein or an irrelevant, equally impure, *E. coli* generated recombinant protein. Significant interferon-gamma production and CD4 T cell proliferation was induced by a number of L762P-derived peptides in each pool. The amino acid sequences for these peptides are provided in SEQ ID NO: 232–251. These peptides correspond to amino acids 661–680, 676–696, 526–545, 874–893, 811–830, 871–891, 856–875, 826–845, 795–815, 736–755, 706–725, 706–725, 691–710, 601–620, 571–590, 556–575, 616–635, 646–665, 631–650, 541–560 and 586–605, respectively, of SEQ ID NO: 161.

CD4 T cell lines that demonstrated specificity for individual L762P-derived peptides were further expanded by stimulation with the relevant peptide at 10 micrograms/ml. Two weeks post-stimulation, T cell lines were tested using both proliferation and IFN-gamma ELISA assays for recognition of the specific peptide. A number of previously identified T cells continued to demonstrate L762P-peptide specific activity. Each of these lines was further expanded on the relevant peptide and, following two weeks of expansion, tested for specific recognition of the L762P-peptide in titration experiments, as well as for recognition of recombinant *E. coli*-derived L762P protein. For these experiments, autologous adherent monocytes were pulsed with either the relevant L762P-derived peptide, an irrelevant mammaglobin-derived peptide, recombinant *E. coli*-derived L762P (approx. 50% pure), or an irrelevant *E. coli*-derived protein. The majority of T cell lines were found to show low affinity for the relevant peptide, since specific proliferation and IFN-gamma ratios dramatically decreased as L762P peptide was diluted. However, four lines were identified that demonstrated significant activity even at 0.1 micrograms/ml peptide. Each of these lines (referred to as A/D5, D/F5, E/A7 and E/B6) also appeared to specifically proliferate in response to the *E. coli*-derived L762P protein preparation, but not in response to the irrelevant protein preparation. The amino acid sequences of the L762P-derived peptides recognized by these lines are provided in SEQ ID NO: 234, 249, 236 and 245, respectively. No protein specific IFN-gamma was detected for any of the lines. Lines A/D5, E/A7 and E/B6 were cloned on autologous adherent monocytes pulsed with the relevant peptide at 0.1 (A/D5 and E/A7) or 1 (D/F5) microgram/ml. Following growth, clones were tested for specificity for the relevant peptide. Numerous clones specific for the relevant peptide were identified for lines A/D5 and E/A7.

Example 8

Protein Expression of Lung Tumor-specific Antigens a) Expression of L514S in *E. coli*

The lung tumor antigen L514S (SEQ ID NO: 89) was subcloned into the expression vector pE32b at NcoI and NotI sites, and transformed into *E. coli* using standard techniques. The protein was expressed from residues 3–153 of SEQ ID NO: 89. The expressed amino acid sequence and the corresponding DNA sequence are provided in SEQ ID NO: 252 and 253, respectively.

b) Expression of L762P

Amino acids 32–944 of the lung tumor antigen L762P (SEQ ID NO: 161), with a 6×His Tag, were subcloned into a modified pET28 expression vector, using kanamycin resistance, and transformed into BL21 CodonPlus using standard techniques. Low to moderate levels of expression were observed. The determined DNA sequence of the L762P expression construct is provided in SEQ ID NO: 254.

Example 9

Identification of MHC Class II Restricting Allele for L-762 Peptide-specific Responses A panel of HLA mismatched antigen presenting cells (APC) were used to identify the MHC class II restricting allele for the L762-peptide specific responses of CD4 T cell clones derived from lines that recognized L762 peptide and recombinant protein. Clones from two lines, AD-5 and EA-7, were tested. The AD-5 derived clones were found to be restricted by the HLA-DRB-1101 allele, and an EA-7 derived clone was found to be restricted by the HLA DRB-0701 or DQB1-0202 allele. Identification of the restriction allele allows targeting of vaccine therapies using the defined peptide to individuals that express the relevant class II allele. Knowing the relevant restricting allele will also enable clinical monitoring for responses to the defined peptide since only individuals that express the relevant allele will be monitored.

CD4 T cell clones derived from line AD-5 and EA-7 were stimulated on autologous APC pulsed with the specific peptide at 10 g/ml, and tested for recognition of autologous APC (D72) as well as against a panel of APC partially matched with D72 at class II alleles. Table 1 shows the HLA class typing of the APC tested. Adherent monocytes (generated by 2 hour adherence) from D45, D187, D208, and D326 were used as APC in these experiments. Autologous APC (D72) were not included in the experiment. Each of the APC were pulsed with the relevant peptide (5a for AD-5 and 3e for 3A-7) or the irrelevant mammoglobin peptide at 10 g/ml, and cultures were established for 10,000 T cells and about 20,000 APC/well. As shown in Table 2, specific proliferation and cytokine production could be detected only when partially matched donor cells were used as APC. Based on the MHC typing analysis, these results strongly suggest that the restricting allele for the L762-specific response of the AD-5 derived clones is HLA-DRB-1101 and for the EA-7 derived clone the restricting allele is HLA DRB-0701 or DQB1-0202.

TABLE 1

HLA TYPING OF APC

| DONOR | DR | DR | DQ | DQ |
| --- | --- | --- | --- | --- |
| D72 | B1-1101 | B1-0701 | B1-0202 | B1-0301 |
| D45 | -3 | -15 | B1-0201 | B1-0602 |
| D187 | -4 | -15 | -1 | -7 |
| D208 | B1-1101 | B1-0407 | -3 | -3 |
| D326 | B1-0301 | B1-0701 | B1-0202 | B1-0201 |

TABLE 2

L762 PEPTIDE RESPONSES MAP TO HLA DR ALLELES

| | AD-5 | | | | | | | | | | | |
| --- | --- | --- | --- | --- | --- | --- | --- | --- | --- | --- | --- | --- |
| | A11 | | B10 | | C10 | | C11 | | E6 | | F1 | |
| Donor | Prol | γ-IFN | Prol | γ-IFN | Prol | γ-IFN | Prol | γ-IFN | Prol | γ-IFN | Prol | γ-IFN |
| D72 DR-0701, -1101, DQ-0202, -7 | 46 | | 31 | | 34 | | 24 | | 31 | | 40 | |
| D45 DR-3, -15, DQ-1, -0201 | 3.2 | 1.7 | 5.5 | 1.2 | 3.3 | 1 | 1.0 | 1.5 | 1.1 | 1.1 | 1.6 | 1.1 |
| D187 DR-4, -15, DQ-1, -7 | 1.4 | 1.2 | 1.3 | 1 | 1.4 | 1.1 | 1.4 | 1.7 | 1.0 | 1.1 | 1.4 | 1.2 |
| D208 DR-4, -1101, DQ-3 | 138 | 13 | 38 | 5.4 | 18.8 | 10 | 14.6 | 4.6 | 15.3 | 6.1 | 45.9 | 8.6 |
| D326 DR-3, -0701, DQ-0202 | 0.7 | 4 | 0.3 | 1 | 0.3 | 1.4 | 1.0 | 2 | 0.8 | 1.1 | 0.3 | 1.1 |

TABLE 2-continued

L762 PEPTIDE RESPONSES MAP TO HLA DR ALLELES

|  | AD-5 | | | | | | | | EA-7 | |
| --- | --- | --- | --- | --- | --- | --- | --- | --- | --- | --- |
|  | F9 | | G8 | | G9 | | G10 | | G12 | |
| Donor | Prol | γ-IFN | Prol | γ-IFN | Prol | γ-IFN | Prol | γ-IFN | Prol | γ-IFN |
| D72 DR-0701, -1101, DQ-0202, -7 | 55 | | 45 | | 43 | | 91 | | 10 | |
| D45 DR-3, -15, DQ-1, -0201 | 1.4 | 1.3 | 0.2 | 1.1 | 1.1 | 1.1 | 1.2 | 1.5 | 0.8 | 1.1 |
| D187 DR-4, -15, DQ-1, -7 | 1.2 | 1.1 | 0.9 | 1 | 1.0 | 1 | 1.0 | 1.6 | 0.5 | 1 |
| D208 DR-4, -1101, DQ-3 | 73.3 | 14.1 | 38.0 | 7.7 | 174.3 | 16.1 | 113.6 | 19.6 | 0.8 | 1 |
| D326 DR-3, -0701, DQ-0202 | 0.7 | 1.1 | 0.6 | 1.2 | 0.4 | 1 | 1.2 | 5 | 14.1 | 6.8 |

Example 10

Fusion Proteins of N-terminal and C-terminal Portions of L763P

In another embodiment, a Mycobacterium tuberculosis-derived Ra12 polynucleotide is linked to at least an immunogenic portion of a polynucleotide of this invention. Ra12 compositions and methods for their use in enhancing expression of heterologous polynucleotide sequences are described in U.S. Patent Application No. 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application No. 60/158,585; see also, Skeiky et al., *Infection and Immun.* (1999) 67:3998–4007, incorporated herein by reference). Surprisingly, it was discovered that a 14 KD C-terminal fragment of the MTB32A coding sequence expresses at high levels on its own and remains as a soluble protein throughout the purification process. Moreover, Ra12 may enhance the immunogenicity of heterologous antigenic polypeptides with which it is fused. This 14 KD C-terminal fragment of the MTB32A is referred herein as Ra12 and represents a fragment comprising some or all of amino acid residues 192 to 323 of MTB32A.

Recombinant nucleic acids, which encode a fusion polypeptide comprising a Ra12 polypeptide and a heterologous lung tumor polypeptide of interest, can be readily constructed by conventional genetic engineering techniques. Recombinant nucleic acids are constructed so that, preferably, a Ra12 polynucleotide sequence is located 5' to a selected heterologous lung tumor polynucleotide sequence. It may also be appropriate to place a Ra12 polynucleotide sequence 3' to a selected heterologous polynucleotide sequence or to insert a heterologous polynucleotide sequence into a site within a Ra12 polynucleotide sequence.

In addition, any suitable polynucleotide that encodes a Ra12 or a portion or other variant thereof can be used in constructing recombinant fusion polynucleotides comprising Ra12 and one or more lung tumor polynucleotides disclosed herein. Preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide.

Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Two specific embodiments of fusions between Ra12 and antigens of the present invention are described in this example.

A. N-Terminal Portion of L763P

A fusion protein of full-length Ra12 and the N-terminal portion of L763P (amino acid residues 1–130) was expressed as a single recombinant protein in *E. coli*. The cDNA for the N-terminal portion was obtained by PCR with a cDNA for the full length L763P and primers L763F3 5' CGGCGAATTCAT-GGATTGGGGGACGCTGC (SEQ ID NO: 355) and 1763RV3 5' CGGCCTCGAGTCACCCCTCTA-TCCGAACCTTCTGC (SEQ ID NO: 356). The PCR product with expected size was recovered from agarose gel, digested with restriction enzymes EcoRI and XhoI, and cloned into the corresponding sites in the expression vector pCRX1. The sequence for the fusion of full-length of Ra12 and L763P-N was confirmed by DNA sequencing (SEQ ID NO:351 and 352).

B. C-Terminal Portion of L763P

A fusion protein of full-length Ra12 and the C-terminal portion of L763P (amino acid residues 100–262) was expressed as a single recombinant protein in E. coli. The cDNA of the C-terminal portion of L763P was obtained by PCR with a cDNA for the full length of L763P and primers L763F4 5' CGGCGAATTCCACGAACCACTCGCAAGT-TCAG (SEQ ID NO: 357) and L763RV4 5' CGGCTCGAG-TTAGCTTGGGCCTGTGATTGC (SEQ ID NO: 358). The PCR product with expected size was recovered from agarose gel, digested with restriction enzymes EcoRI and XhoI, and cloned into the corresponding sites in the expression vector pCRX1. The sequence for the fusion of full-length Ra12 and L763P-C was confirmed by DNA sequencing (SEQ ID NO:353 and 354).

The recombinant proteins described in this example are useful for the preparation of vaccines, for antibody therapeutics, and for diagnosis of lung tumors.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. A method for stimulating or expanding T cells, or both, in vitro comprising, contact T cells with an amino acid sequence of SEQ ID No. 348, thereby stimulating or expanding said T cells, or both.

2. The method of claim 1 wherein said T cells are isolated from bone marrow, or a fraction thereof, of a patient.

3. The method of claim 1 wherein said T cells are isolated from peripheral blood, or a fraction thereof, of a patient.

4. The method of claim 1 wherein said T cells are stimulated or expanded, or both, by contacting said T cells with an antigen presenting cell pulsed with or that expresses an amino acid sequence of SEQ ID NO:348.

5. The method of claim 1 wherein said T cells are CD4+ T cells.

6. The method of claim 1 wherein said T cells are CD8+ T cells.

* * * * *